(12) United States Patent
Yan et al.

(10) Patent No.: US 7,947,809 B2
(45) Date of Patent: May 24, 2011

(54) COMPOSITIONS AND METHODS RELATING TO GLUCAGON RECEPTOR ANTIBODIES

(75) Inventors: Hai Yan, Newbury Park, CA (US); Shaw-Fen Sylvia Hu, Thousand Oaks, CA (US); Thomas C. Boone, Newbury Park, CA (US); Richard A. Lindberg, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 550 days.

(21) Appl. No.: 11/903,481

(22) Filed: Sep. 20, 2007

(65) Prior Publication Data

US 2009/0041784 A1    Feb. 12, 2009

Related U.S. Application Data

(60) Provisional application No. 60/846,202, filed on Sep. 20, 2006, provisional application No. 60/968,977, filed on Aug. 30, 2007.

(51) Int. Cl.
  *C12P 21/08*    (2006.01)
(52) U.S. Cl. ............ 530/387.3; 530/350; 530/388.1; 530/388.15; 530/388.2; 530/388.22
(58) Field of Classification Search ............ 530/350, 530/387.3, 388.1, 388.15, 388.2, 388.22
See application file for complete search history.

(56) References Cited

U.S. PATENT DOCUMENTS

| | | | |
|---|---|---|---|
| 5,889,167 A * | 3/1999 | Cascieri et al. | 536/23.1 |
| 6,864,069 B2 | 3/2005 | Pan et al. | |
| 6,909,031 B2 | 6/2005 | Allen et al. | |

FOREIGN PATENT DOCUMENTS

| | | |
|---|---|---|
| EP | 1 245 676 A1 | 10/2002 |
| EP | 1 514 932 A2 | 3/2005 |
| WO | WO 95/35374 | 12/1995 |
| WO | WO 2004/050683 A2 | 6/2004 |
| WO | WO 2006/005469 A2 | 1/2006 |
| WO | WO 2006/068953 A2 | 6/2006 |
| WO | WO 2006/081139 A2 | 8/2006 |

OTHER PUBLICATIONS

J. Buggy et al., "Human Glucagon Receptor Monoclonal Antibodies: Antagonism of Glucagon Action and Use in Receptor Characterization," *Horm. Metab. Res.* 28(5):215-219, 1996.
Q. Dallas-Yang et al., "Hepatic glucagon receptor binding and glucose-lowering in vivo by peptidyl and non-peptidyl glucagon receptor antagonists," *European Journal of Pharmacology* 501:225-234, 2004.
J. Davies et al., "Affinity improvement of single antibody VH domains: residues in all three hypervariable regions affect antigen binding," *Immunotechnology* 2:169-179, 1996.
R.W. Gelling et al., "Lower blood glucose, hyperglucagonemia, and pancreatic α cell hyperplasia in glucagon receptor knockout mice," *Proc. Natl. Acad. Sci. USA* 100(3):1438-1443, 2003.
L.J. Holt et al., "Domain antibodies: proteins for therapy," *TRENDS in Biotechnology* 21(11):484-490, 2003.
V. Iwanij et al., "Characterization of the Glucagon Receptor and Its Functional Domains Using Monoclonal Antibodies," *J. Biol. Chem.* 265(34):21302-21308, 1990.
S. Runge et al., "Three Distinct Epitopes on the Extracellular Face of the Glucagon Receptor Determine Specificity for the Glucagon Amino Terminus," *J. Biol. Chem.* 278(30):28005-28010, 2003.
L.M. Wright, "Structure of Fab hGR-2 F6, a competitive antagonist of the glucagon receptor," *Acta Cryst.* D56:573-580, 2000.

* cited by examiner

*Primary Examiner* — Stephen L Rawlings
*Assistant Examiner* — Brad Duffy

(57) ABSTRACT

The present disclosure provides compositions and methods relating to antigen binding proteins, in particular, antibodies which specifically bind to the human glucagon receptor. The disclosure provides nucleic acids encoding such antigen binding proteins and antibodies and methods of making and using such antibodies including methods of treating and preventing type 2 diabetes and related disorders by administering such antibodies to a subject in need of such treatment.

7 Claims, 7 Drawing Sheets

|  | A-18 | A-3 | A-21 | A-10 | Sequence derived from human GCGR |
|---|---|---|---|---|---|
| Chimera-4 | + | + | + | + | (1-142) |
| Chimera-4 1CA;3CA | – | + | – | – | (1-142) |
| Chimera-4 2CA;5CA | – | – | – | – | (1-142) |
| Chimera-4 4CA;6CA | – | – | – | – | (1-142) |
| Chimera-7 | – | – | – | – | (1-79) |
| Chimera-8 | – | + | – | – | (80-477) |
| Chimera-10 | – | + | – | – | (80-142) |
| Chimera-15 | – | + | – | – | (80-119) |
| Chimera-19 | – | + | – | – | (1-119; 143-477) |

FIGURE 7

COMPOSITIONS AND METHODS RELATING TO GLUCAGON RECEPTOR ANTIBODIES

REFERENCE TO RELATED APPLICATIONS

This application claims benefit of U.S. Provisional Application Ser. No. 60/846,202, filed on Sep. 20, 2006, and U.S. Provisional Application Ser. No. 60/968,977, filed Aug. 30, 2007, the entire disclosure of which is relied upon and incorporated by reference herein.

SEQUENCE LISTING APPENDIX ON COMPACT DISC

This application includes the sequence listing submitted on the enclosed three compact discs identified as "Compact Disc 1", and duplicate copies, "Copy 1", and "Copy 2". Each disc was created on Sep. 20, 2007, having a file named "A-1133-US-NP.txt" and having 150 K bytes of data, using an IBM-PC Compatible computer, MS-DOS/Windows NT, and Patentin software version 3.3. The content of each disc is identical, and all of which are incorporated by reference herein.

FIELD OF THE INVENTION

The field of this invention relates to compositions and methods related to glucagon receptor antibodies.

BACKGROUND OF THE INVENTION

Glucagon is a 29 amino acid hormone processed from its proform in the pancreatic alpha cells by cell specific expression of prohormone convertase 2 (Furuta et al., J. Biol. Chem. 276: 27197-27202 (2001)). During fasting, glucagon secretion increases in response to falling glucose levels. Increased glucagon secretion stimulates glucose production by promoting hepatic glycogenolysis and gluconeogenesis. Thus glucagon counterbalances the effects of insulin in maintaining normal levels of glucose in animals.

The glucagon receptor (GCGR) is a member of the secretin subfamily (family B) of G-protein-coupled receptors (GCGR). The glucagon receptor is predominantly expressed in the liver, where it regulates hepatic glucose output, and the kidney, reflecting its role in gluconeogenesis. The activation of the glucagon receptors in the liver stimulates the activity of adenyl cyclase and phosphoinositol turnover which subsequently results in increased expression of gluconeogenic enzymes including phosphoenolpyruvate carboxykinase (PEPCK), fructose-1,6-bisphosphatase (FBPase-1), and glucose-6-phosphatase (G-6-Pase). In addition, glucagon signalling activates glycogen phosphorylase and inhibits glycogen synthase.

Studies have shown that higher basal glucagon levels and lack of suppression of postprandial glucagon secretion contribute to diabetic conditions in humans (Muller et al., N Eng J Med 283: 109-115 (1970)). Targeting glucagon production or function may be one method of controlling and lowering blood glucose. There is a continuing need to provide effective treatments for type 2 diabetes. The present invention addresses this need by providing novel compositions and methods for treating type 2 diabetes and related diseases.

SUMMARY OF THE INVENTION

In one aspect, the present invention provides an isolated antigen binding protein comprising either: a. a light chain CDR3 comprising a sequence selected from the group consisting of: i. a light chain CDR3 sequence that differs by no more than a total of three amino acid additions, substitutions, and/or deletions from a CDR3 sequence selected from the group consisting of the light chain CDR3 sequences of L1-L23, SEQ ID NOs: 72; 74, 76, 78, 80, 83, 85, 87, 89, 91, 93, 95, 97, 100; ii. L Q $X_{21}$ N S $X_{22}$ P L T (SEQ ID NO: 208), iii. Q A W D S $X_{23}$ T V $X_{24}$ (SEQ ID NO: 209); b. a heavy chain CDR3 sequence comprising a sequence selected from the group consisting of: i. a heavy chain CDR3 sequence that differs by no more than a total of four amino acid additions, substitutions, and/or deletions from a CDR3 sequence selected from the group consisting of the heavy chain CDR3 sequences of H1-H23, SEQ ID NO: 165, 167, 169, 171, 173, 175, 177, 179, 181, 183, 185, 187, 189, 191, 193, 195, 197, 199; ii. E $X_{25}$ $X_{26}$ $X_{27}$ YD IL T G Y $X_{28}$ $X_{29}$ Y Y G $X_{30}$ D V (SEQ ID NO: 210) iii. $X_{31}$ G G G F D Y (SEQ ID NO: 211); or c. the light chain CDR3 sequence of (a) and the heavy chain CDR3 sequence of (b); wherein, $X_{21}$ is a histidine residue, or a glutamine residue, $X_{22}$ is an asparagine residue, an aspartate residue, or a tyrosine residue, $X_{23}$ is an asparagine residue or a serine residue, $X_{24}$ is an isoleucine residue or a valine residue, $X_{25}$ is a lysine residue, a glutamate residue, or a proline residue, $X_{26}$ is an aspartate residue, a threonine residue, a glutamine residue, or a proline residue, $X_{27}$ is a histidine residue or a tyrosine residue, $X_{28}$ is an asparagine residue, a histidine residue, an aspartate residue, or a phenylalanine residue, $X_{29}$ is a tyrosine residue, a histidine residue, or an asparagine residue, $X_{30}$ is a leucine residue or a methionine residue, $X_{31}$ is a leucine residue or a methionine residue, wherein said antigen binding protein specifically binds to the human glucagon receptor.

In one embodiment, the isolated binding protein further comprises an amino acid sequence selected from the group consisting of: a. a light chain CDR1 sequence selected from the group consisting of: i. a light chain CDR1 that differs by no more than three amino acids additions, substitutions, and/or deletions from a CDR1 sequence of L1-L23, SEQ ID NOs: 10, 12, 14, 16, 18, 20, 22, 24, 26, 28, 30, 32, 34, 36, 38 and 41; ii. R S $X_1$ Q S L L D $X_2$ $X_3$ D G T Y T L D (SEQ ID NO: 200); iii. R A S Q $X_4$ I R N D $X_5$ G (SEQ ID NO: 201); and iv. S G D K L G D K Y $X_6$ C (SEQ ID NO: 202); wherein $X_1$ is a serine residue or a threonine residue, $X_2$ is an arginine residue or a serine residue, $X_3$ is an aspartate residue or an alanine residue, $X_4$ is a glycine residue or an aspartate residue, $X_5$ is a leucine residue or a phenylalanine residue, $X_6$ is a valine residue or an alanine residue, b. a light chain CDR2 sequence selected from the group consisting of: i. a light chain CDR2 that differs by no more than two amino acid additions, substitutions, and/or deletions from a CDR2 sequence of L1-L23, SEQ ID NOs: 43, 45, 48, 50, 52, 54, 56, 58, 60, 62, 64, 66, 68, and 70; ii. A A S S L $X_9$ S (SEQ ID NO: 204); and iii. Q $X_{10}$ $X_{11}$ K R P S (SEQ ID NO: 205); wherein $X_9$ is a glutamine residue or a glutamate residue, $X_{10}$ is a serine residue or a threonine residue, $X_{11}$ is a threonine residue, or a serine residue; c. a heavy chain CDR1 sequence selected from the group consisting of: i. a heavy chain CDR1 that differs by no more than two amino acid additions, substitutions, and/or deletions from a CDR1 sequence of H1-H23, SEQ ID NOs: 102, 104, 106, 108, 111, 113, 115, 117, 118, 120 and 122, ii. $X_7$ Y $X_8$ M H (SEQ ID NO: 203) wherein $X_7$ is a serine residue or a threonine residue, $X_8$ is a glycine residue or an aspartate residue; and d. a heavy chain CDR2 selected from the group consisting of: i. a heavy sequence that differs by no more than three amino acid additions, substitutions, and/or deletions from a CDR2 sequence of H1-H23, SEQ ID NOs: 124, 126, 128, 130, 132, 134, 136, 138, 140, 143, 145, 147, 149, 151, 153, 155, 157, 159, 161, and 163; ii. $X_{12}$ I W $X_{13}$ D G S X$_{14}$ K Y Y X$_{15}$ D S V K G (SEQ ID NO: 206); and iii. X$_{16}$ I S X$_{17}$ D G S X$_{18}$ K Y X$_{19}$ X$_{20}$ D S V K G (SEQ ID NO: 207); wherein X$_{12}$ is a serine residue, a phenylalanine residue, a valine residue, or a glutamate residue, X$_{13}$ is a tyrosine residue or an asparagine residue, X$_{14}$ is an asparagine residue or a glutamate residue, X$_{15}$ is a valine residue or an alanine residue, X$_{16}$ is a valine residue or a phenylalanine residue, X$_{17}$ is a histidine residue, an aspartate residue, or a tyrosine residue, X$_{18}$ is an aspartate residue, an asparagine residue, or a histidine residue, X$_{19}$ is a tyrosine residue, or a serine residue, X$_{20}$ is an alanine residue or a glycine residue, wherein said antigen binding protein specifically binds to the human glucagon receptor.

In another embodiment, the antigen binding protein further comprises an amino acid sequence selected from the group consisting of: a. a light chain CDR1 sequence selected from the group consisting of: i. a light chain CDR1 that differs by no more than three amino acids additions, substitutions, and/or deletions from a CDR1 sequence of L1-L23, SEQ ID NOs: 10, 12, 14, 16, 18, 20, 22, 24, 26, 28, 30, 32, 34, 36, 38 and 41; ii. R S X$_1$ Q S L L D X$_2$ X$_3$ D G T Y T L D (SEQ ID NO: 200); iii. R A S Q X$_4$ I R N D X$_5$ G (SEQ ID NO: 201); or iv. S G D K L G D K Y X$_6$ C (SEQ ID NO: 202); wherein X$_1$ is a serine residue or a threonine residue, X$_2$ is an arginine residue or a serine residue, X$_3$ is an aspartate residue or an alanine residue, X$_4$ is a glycine residue or an aspartate residue, X$_5$ is a leucine residue or a phenylalanine residue, X$_6$ is a valine residue or an alanine residue; b. a light chain CDR2 sequence selected from the group consisting of: i. a light chain CDR2 that differs by no more than two amino acid additions, substitutions, and/or deletions from a CDR2 sequence of L1-L23, SEQ ID NOs: 43, 45, 48, 50, 52, 54, 56, 58, 60, 62, 64, 66, 68, and 70; ii. A A S S L X$_9$ S (SEQ ID NO: 204); or iii. Q X$_{10}$ X$_{11}$ K R P S (SEQ ID NO: 205); wherein X$_9$ is a glutamine residue or a glutamate residue, X$_{10}$ is a serine residue or a threonine residue, X$_{11}$ is a threonine residue, or a serine residue, c. a heavy chain CDR1 sequence selected from the group consisting of: i. a heavy chain CDR1 that differs by no more than two amino acid additions, substitutions, and/or deletions from a CDR1 sequence of H1-H23, SEQ ID NOs: 102, 104, 106, 108, 111, 113, 115, 117, 118, 120 and 122; ii. X$_7$ Y X$_8$ M H (SEQ ID NO: 203) wherein X$_7$ is a serine residue or a threonine residue, X$_8$ is a glycine residue or an aspartate residue; d. a heavy chain CDR2 selected from the group consisting of: i. a heavy chain sequence that differs by no more than three amino acid additions, substitutions, and/or deletions from a CDR2 sequence of H1-H23, SEQ ID NOs: 124, 126, 128, 130, 132, 134, 136, 138, 140, 143, 145, 147, 149, 151, 153, 155, 157, 159, 161, and 163; ii. X$_{12}$ I W X$_{13}$ D G S X$_{14}$ K Y Y X$_{15}$ D S V K G (SEQ ID NO: 206); iii. X$_{16}$ I S X$_{17}$ D G S X$_{18}$ K Y X$_{19}$ X$_{20}$ D S V K G (SEQ ID NO: 207); wherein X$_{12}$ is a serine residue, a phenylalanine residue, a valine residue, or a glutamate residue, X$_{13}$ is a tyrosine residue or an asparagine residue, X$_{14}$ is an asparagine residue or a glutamate residue, X$_{15}$ is a valine residue or an alanine residue, X$_{16}$ is a valine residue or a phenylalanine residue, X$_{17}$ is a histidine residue, an aspartate residue, or a tyrosine residue; X$_{18}$ is an aspartate residue, an asparagine residue, or a histidine residue; X$_{19}$ is a tyrosine residue, or a serine residue, X$_{20}$ is an alanine residue or a glycine residue; e. the light chain CDR1 of (a) and the light chain CDR2 of (b); the light chain CDR1 of (a) and the heavy chain CDR1 of (c); g. the light chain CDR1 of (a) and the heavy chain CDR2 of (d); h. the light chain CDR2 of (b) and the heavy chain CDR1 of (c); i. the heavy chain CDR1 of (c) and the heavy chain CDR2 of (d); j. the light chain CDR2 of (b) and the heavy chain CDR2 of (d); k. the light chain CDR1 of (a), the light chain CDR2 of (b), and the heavy chain CDR1 of (c); l. the light chain CDR2 of (b), the heavy chain CDR1 of (c), and the heavy chain CDR2 of (d); m. the light chain CDR1 of (a), the heavy chain CDR1 of (c), and the heavy chain CDR2 of (d); or n. the light chain CDR1 of (a), the light chain CDR2 of (b), the heavy chain CDR1 of (c), and the heavy chain CDR2 of (d), wherein said antigen binding protein specifically binds to the human glucagon receptor.

In another embodiment, the isolated binding protein comprises an amino acid sequence selected from the group consisting of: a. a light chain CDR1 sequence that differs by no more than two amino acids additions, substitutions, and/or deletions from a CDR1 sequence of L1-L23, SEQ ID NOs: 10, 12, 14, 16, 18, 20, 22, 24, 26, 28, 30, 32, 34, 36, 38 and 41; b. a light chain CDR2 sequence that differs by no more than one amino acid addition, substitution, and/or deletion from a CDR2 sequence of L1-L23, SEQ ID NOs: 43, 45, 48, 50, 52, 54, 56, 58, 60, 62, 64, 66, 68, and 70; c. a light chain CDR3 sequence that differs by no more than two amino acid additions, substitutions, and/or deletions from a CDR3 sequence of L1-L23, SEQ ID NOs: 72, 74, 76, 78, 80, 83, 85, 87, 89, 91, 93, 95, 97, and 100; d. a heavy chain CDR1 sequence that differs by no more than one amino acid addition, substitution, and/or deletion from a CDR1 sequence of H1-H23, SEQ ID NOs: 102, 104, 106, 108, 111, 113, 115, 117, 118, 120, and 122; e. a heavy chain CDR2 sequence that differs by no more than two amino acid additions, substitutions, and/or deletions from a CDR2 sequence of H1-H23, SEQ ID NOs: 124, 126, 128, 130, 132, 134, 136, 138, 140, 143, 145, 147, 149, 151, 153, 155, 157, 159, 161, and 163; and f. a heavy chain CDR3 sequence that differs by no more than three amino acid additions, substitutions, and/or deletions from a CDR3 sequence of H1-H23, SEQ ID NOs: 165, 167, 169, 171, 173, 175, 177, 179, 181, 183, 185, 187, 189, 191, 193, 195, 197, and 199, wherein the antigen binding protein specifically binds to the human glucagon receptor.

In another embodiment, the isolated binding protein comprises an amino acid sequence selected from the group consisting of: a. a light chain CDR1 sequence that differs by no more than one amino acid addition, substitution, and/or deletion from a CDR I sequence of L1-L23, SEQ ID NOs: 10, 12, 14, 16, 18, 20, 22, 24, 26, 28, 30, 32, 34, 36, 38, and 41; b. a light chain CDR2 sequence of L1-L23, SEQ ID NOs: 43, 45, 48, 50, 52, 54, 56, 58, 60, 62, 64, 66, 68, and 70; c. a light chain CDR3 sequence that differs by no more than one amino acid addition, substitution, and/or deletion from a CDR3 sequence of L1-L23, SEQ ID NOs: 72, 74, 76, 78, 80, 83, 85, 87, 89, 91, 93, 95, 97, and 100; d. a heavy chain CDR1 sequence of H1-H23, SEQ ID NOs: 102, 104, 106, 108, 111, 113, 115, 117, 118, 120, and 122; e. a heavy chain CDR2 sequence that differs by no more than one amino acid addition, substitution, and/or deletions from a CDR2 sequence of H1-H23, SEQ ID NOs: 124, 126, 128, 130, 132, 134, 136, 138, 140, 143, 145, 147, 149, 151, 153, 155, 157, 159, 161, and 163; and f. a heavy chain CDR3 sequence that differs by no more than two amino acid additions, substitutions, and/or deletions from a CDR3 sequence of H11-H23, SEQ ID NOs: 165, 167, 169, 171, 173, 175, 177, 179, 181, 183, 185, 187, 189, 191, 193, 195, 197, and 199, wherein the antigen binding protein specifically binds to the human glucagon receptor.

In a further embodiment, the isolated binding protein comprises an amino acid sequence selected from the group consisting of: a. a light chain CDR1 sequence of L1-L23, SEQ ID NOs: 10, 12, 14, 16, 18, 20, 22, 24, 26, 28, 30, 32, 34, 36, 38, and 41; b. a light chain CDR3 sequence of L1-L23, SEQ ID NOs: 72, 74, 76, 78, 80, 83, 85, 87, 89, 91, 93, 95, 97, and 100; c. a heavy chain CDR2 sequence of H11-H23, SEQ ID NOs: 124, 126, 128, 130, 132, 134, 136, 138, 140, 143, 145, 147, 149, 151, 153, 155, 157, 159, 161, and 163; and d. a heavy chain CDR3 sequence that differs by no more than one amino acid addition, substitution, and/or deletions from a CDR3 sequence of H1-H23, SEQ ID NOs: 165, 167, 169, 171, 173, 175, 177, 179, 181, 183, 185, 187, 189, 191, 193, 195, 197, and 199, wherein the antigen binding protein specifically binds to the human glucagon receptor.

In a further embodiment, the isolated binding protein comprises an amino acid sequence selected from the group consisting of: a heavy chain CDR3 sequence of H1-H23, SEQ ID NOs: 165, 167, 169, 171, 173, 175, 177, 179, 181, 183, 185, 187, 189, 191, 193, 195, 197, and 199, wherein the antigen binding protein specifically binds to the human glucagon receptor.

In a further embodiment, the isolated binding protein comprises two amino acid sequences selected from the group consisting of: a. a light chain CDR1 sequence that differs by no more than three amino acids additions, substitutions, and/or deletions from a CDR I sequence of L1-L23, SEQ ID NOs: 10, 12, 14, 16, 18, 20, 22, 24, 26, 28, 30, 32, 34, 36, 38, and 41; b. a light chain CDR2 sequence that differs by no more than two amino acid additions, substitutions, and/or deletions from a CDR2 sequence of L1-L23, SEQ ID NOs: 43, 45, 48, 50, 52, 54, 56, 58, 60, 62, 64, 66, 68, and 70; c. a light chain CDR3 sequence that differs by no more than three amino acid additions, substitutions, and/or deletions from a CDR3 sequence of L1-L23, SEQ ID NOs: 72, 74, 76, 78, 80, 83, 85, 87, 89, 91, 93, 95, 97, and 100; d. a heavy chain CDR1 sequence that differs by no more than two amino acid additions, substitutions, and/or deletions from a CDR1 sequence of H1-H23, SEQ ID NOs: 102, 104, 106, 108, 111, 113, 115, 117, 118, 120, and 122; e. a heavy chain CDR2 sequence that differs by no more than three amino acid additions, substitutions, and/or deletions from a CDR2 sequence of H1-H23, SEQ ID NOs: 124, 126, 128, 130, 132, 134, 136, 138, 140, 143, 145, 147, 149, 151, 153, 155, 157, 159, 161, and 163; and f. a heavy chain CDR3 sequence that differs by no more than four amino acid additions, substitutions, and/or deletions from a CDR3 sequence of H1-H23, SEQ ID NOs: 165, 167, 169, 171, 173, 175, 177, 179, 181, 183, 185, 187, 189, 191, 193, 195, 197, and 199, wherein the antigen binding protein specifically binds to the human glucagon receptor.

In further embodiment, the isolated binding protein comprises three amino acid sequences selected from the group consisting of: a. a light chain CDR1 sequence that differs by no more than three amino acids additions, substitutions, and/or deletions from a CDR1 sequence of L1-L23, SEQ ID NOs: 10, 12, 14, 16, 18, 20, 22, 24, 26, 28, 30, 32, 34, 36, 38, and 41; b. a light chain CDR2 sequence that differs by no more than two amino acid additions, substitutions, and/or deletions from a CDR2 sequence of L1-L23, SEQ ID NOs: 43, 45, 48, 50, 52, 54, 56, 58, 60, 62, 64, 66, 68, and 70; c. a light chain CDR3 sequence that differs by no more than three amino acid additions, substitutions, and/or deletions from a CDR3 sequence of L1-L23, SEQ ID NOs: 72, 74, 76, 78, 80, 83, 85, 87, 89, 91, 93, 95, 97, and 100; d. a heavy chain CDR1 sequence that differs by no more than two amino acid additions, substitutions, and/or deletions from a CDR1 sequence of H1-H23, SEQ ID NOs: 102, 104, 106, 108, 111, 113, 115, 117, 118, 120, and 122; e. a heavy chain CDR2 sequence that differs by no more than three amino acid additions, substitutions, and/or deletions from a CDR2 sequence of H1-H23, SEQ ID NOs: 124, 126, 128, 130, 132, 134, 136, 138, 140, 143, 145, 147, 149, 151, 153, 155, 157, 159, 161, and 163; and f. a heavy chain CDR3 sequence that differs by no more than four amino acid additions, substitutions, and/or deletions from a CDR3 sequence of H1-H23, SEQ ID NOs: 165, 167, 169, 171, 173, 175, 177, 179, 181, 183, 185, 187, 189, 191, 193, 195, 197, and 199, wherein the antigen binding protein specifically binds to the human glucagon receptor.

In a further embodiment, the isolated binding protein comprises four amino acid sequences selected from the group consisting of: a. a light chain CDR1 sequence that differs by no more than three amino acids additions, substitutions, and/or deletions from a CDR1 sequence of L1-L23, SEQ ID NOs: 10, 12, 14, 16, 18, 20, 22, 24, 26, 28, 30, 32, 34, 36, 38, and 41; b. a light chain CDR2 sequence that differs by no more than two amino acid additions, substitutions, and/or deletions from a CDR2 sequence of L1-L23, SEQ ID NOs: 43, 45, 48, 50, 52, 54, 56, 58, 60, 62, 64, 66, 68, and 70; c. a light chain CDR3 sequence that differs by no more than three amino acid additions, substitutions, and/or deletions from a CDR3 sequence of L1-L23, SEQ ID NOs: 72, 74, 76, 78, 80, 83, 85, 87, 89, 91, 93, 95, 97, and 100; d. a heavy chain CDR1 sequence that differs by no more than two amino acid additions, substitutions, and/or deletions from a CDR1 sequence of H1-H23, SEQ ID NOs: 102, 104, 106, 108, 111, 113, 115, 117, 118, 120, and 122; e. a heavy chain CDR2 sequence that differs by no more than three amino acid additions, substitutions, and/or deletions from a CDR2 sequence of H1-H23, SEQ ID NOs: 124, 126, 128, 130, 132, 134, 136, 138, 140, 143, 145, 147, 149, 151, 153, 155, 157, 159, 161, and 163; and f. a heavy chain CDR3 sequence that differs by no more than four amino acid additions, substitutions, and/or deletions from a CDR3 sequence of H1-H23, SEQ ID NOs: 165, 167, 169, 171, 173, 175, 177, 179, 181, 183, 185, 187, 189, 191, 193, 195, 197, and 199, wherein the antigen binding protein specifically binds to the human glucagon receptor. In another embodiment, the isolated binding protein comprises five amino acid sequences selected from the group consisting of: a. a light chain CDR1 sequence that differs by no more than three amino acids additions, substitutions, and/or deletions from a CDR1 sequence of L1-L23, SEQ ID NOs: 10, 12, 14, 16, 18, 20, 22, 24, 26, 28, 30, 32, 34, 36, 38, and 41; b. a light chain CDR2 sequence that differs by no more than two amino acid additions, substitutions, and/or deletions from a CDR2 sequence of L1-L23, SEQ ID NOs: 43, 45, 48, 50, 52, 54, 56, 58, 60, 62, 64, 66, 68, and 70; c. a light chain CDR3 sequence that differs by no more than three amino acid additions, substitutions, and/or deletions from a CDR3 sequence of L1-L23, SEQ ID NOs: 72, 74, 76, 78, 80, 83, 85, 87, 89, 91, 93, 95, 97, and 100; d. a heavy chain CDR1 sequence that differs by no more than two amino acid additions, substitutions, and/or deletions from a CDR1 sequence of H1-H23, SEQ ID NOs: 102, 104, 106, 108, 111, 113, 115, 117, 118, 120, and 122; e. a heavy chain CDR2 sequence that differs by no more than three amino acid additions, substitutions, and/or deletions from a CDR2 sequence of H1-H23, SEQ ID NOs: 124, 126, 128, 130, 132, 134, 136, 138, 140, 143, 145, 147, 149, 151, 153, 155, 157, 159, 161, and 163; and f. a heavy chain CDR3 sequence that differs by no more than four amino acid additions, substitutions, and/or deletions from a CDR3 sequence of H1-H23, SEQ ID NOs: 165, 167, 169, 171, 173, 175, 177, 179, 181, 183, 185, 187, 189, 191, 193, 195, 197, and 199, wherein the antigen binding protein specifically binds to the human glucagon receptor.

In a further embodiment, the isolated binding protein comprises: a. a light chain CDR1 sequence that differs by no more than three amino acids additions, substitutions, and/or deletions from a CDR1 sequence of L1-L23, SEQ ID NOs: 10, 12, 14, 16, 18, 20, 22, 24, 26, 28, 30, 32, 34, 36, 38, and 41; b. a light chain CDR2 sequence that differs by no more than two amino acid additions, substitutions, and/or deletions from a CDR2 sequence of L1-L23, SEQ ID NOs: 43, 45, 48, 50, 52, 54, 56, 58, 60, 62, 64, 66, 68, and 70; c. a light chain CDR3 sequence that differs by no more than three amino acid additions, substitutions, and/or deletions from a CDR3 sequence of L1-L23, SEQ ID NOs: 72, 74, 76, 78, 80, 83, 85, 87, 89, 91, 93, 95, 97, and 100; d. a heavy chain CDR1 sequence that differs by no more than two amino acid additions, substitutions, and/or deletions from a CDR1 sequence of H1-H23, SEQ ID NOs: 102, 104, 106, 108, 111, 113, 115, 117, 118, 120, and 122; e. a heavy chain CDR2 sequence that differs by no more than three amino acid additions, substitutions, and/or deletions from a CDR2 sequence of H1-H23, SEQ ID NOs: 124, 126, 128, 130, 132, 134, 136, 138, 140, 143, 145, 147, 149, 151, 153, 155, 157, 159, 161, and 163; and f. a heavy chain CDR3 sequence that differs by no more than four amino acid additions, substitutions, and/or deletions from a CDR3 sequence of H1-H23, SEQ ID NOs: 165, 167, 169, 171, 173, 175, 177, 179, 181, 183, 185, 187, 189, 191, 193, 195, 197, and 199, wherein the antigen binding protein specifically binds to the human glucagon receptor.

In another embodiment, the isolated antigen binding protein comprises either: a. a light chain variable domain comprising i. a light chain CDR1 sequence selected from SEQ ID NOs: 10, 12, 14, 16, 18, 20, 22, 24, 26, 28, 30, 32, 34, 36, 38, and 41; ii a light chain CDR2 sequence selected from SEQ ID NOs: 43, 45, 48, 50, 52, 54, 56, 58, 60, 62, 64, 66, 68, and 70; and iii. a light chain CDR3 sequence selected from SEQ ID NOs: 72, 74, 76, 78, 80, 83, 85, 87, 89, 91, 93, 95, 97, and 100; b. a heavy chain variable domain comprising: i. a heavy chain CDR1 sequence selected from SEQ ID NOs: 102, 104, 106, 108, 111, 113, 115, 117, 118, 120, and 122; ii. a heavy chain CDR2 sequence selected from SEQ ID NOs: 124, 126, 128, 130, 132, 134, 136, 138, 140, 143, 145, 147, 149, 151, 153, 155, 157, 159, 161, and 163; and iii. a heavy chain CDR3 sequence selected from SEQ ID NOs: 165, 167, 169, 171, 173, 175, 177, 179, 181, 183, 185, 187, 189, 191, 193, 195, 197, and 199; or c. the light chain variable domain of (a) and the heavy chain variable domain of (b), wherein the antigen binding protein specifically binds to the human glucagon receptor.

In another embodiment, the isolated antigen binding protein comprises either: a. a light chain variable domain sequence selected from the group consisting of: i. amino acids having a sequence at least 80% identical to a light chain variable domain sequence selected from L1-L23, SEQ ID NOs: 213, 215, 217, 219, 221, 223, 225, 227, 229, 231, 233, 235, 237, 239, 241, 243, 245, 247, 249, 251, 253, 255, and 257; ii. a sequence of amino acids encoded by a polynucleotide sequence that is at least 80% identical to a polynucleotide sequence encoding the light chain variable domain sequence of L1-L23, SEQ ID NOs: 212, 214, 216, 218, 220, 222, 224, 226, 228, 230, 232, 234, 236, 238, 240, 242, 244, 246, 248, 250, 252, 254, and 256; iii. a sequence of amino acids encoded by a polynucleotide sequence that hybridizes under moderately stringent conditions to the complement of a polynucleotide consisting of a light chain variable domain sequence of L1-L23 of SEQ ID NOs: 212, 214, 216, 218, 220, 222, 224, 226, 228, 230, 232, 234, 236, 238, 240, 242, 244, 246, 248, 250, 252, 254, and 256; b. a heavy chain variable domain sequence selected from the group consisting of: i. a sequence of amino acids that is at least 80% identical to a heavy chain variable domain sequence of H1-H23 of SEQ ID NOs: 259, 261, 263, 265, 267, 269, 271, 273, 275, 277, 279, 281, 283, 285, 287, 289, 291, 293, 295, 297, 299, 301, and 303; ii. a sequence of amino acids encoded by a polynucleotide sequence that is at least 80% identical to a polynucleotide sequence encoding the heavy chain variable domain sequence of H1-H23, SEQ ID NOs: 258, 260, 262, 264, 266, 268, 270, 272, 274, 276, 278, 280, 282, 284, 286, 288, 290, 292, 294, 296, 298, 300, and 302; iii. a sequence of amino acids encoded by a polynucleotide sequence that hybridizes under moderately stringent conditions to the complement of a polynucleotide consisting of a heavy chain variable domain sequence of H1-H23, SEQ ID NOs: 258, 260, 262, 264, 266, 268, 270, 272, 274, 276, 278, 280, 282, 284, 286, 288, 290, 292, 294, 296, 298, 300, and 302; or c. the light chain variable domain of (a) and the heavy chain variable domain of (b), wherein said antigen binding protein specifically binds to the human glucagon receptor.

In another embodiment, the isolated antigen binding protein comprises either: a. a light chain variable domain sequence selected from the group consisting of: L1-L23 of SEQ ID NOs: 213, 215, 217, 219, 221, 223, 225, 227, 229, 231, 233, 235, 237, 239, 241, 243, 245, 247, 249, 251, 253, 255, and 257; b. a heavy chain variable domain sequence selected from the group consisting of: H1-H23 of SEQ ID NOs: 259, 261, 263, 265, 267, 269, 271, 273, 275, 277, 279, 281, 283, 285, 287, 289, 291, 293, 295, 297, 299, 301, and 303; or c. the light chain variable domain of (a) and the heavy chain variable domain of (b), wherein the antigen binding protein specifically binds to the human glucagon.

In another embodiment the isolated antigen binding protein comprises a combination of a light chain variable domain and a heavy chain variable domain selected from the group of combinations consisting of: L1H1, L2H2, L3H3, L4H4, L5H5, L6H6, L7H7, L8H8, L9H9, L10H10, L11H111, L12H12, L13H13, L14H14, L15H15, L16H16, L17H17, L18H18, L19H19, L20H20, L21H21, L22H22, and L23H23 wherein the antigen binding protein specifically binds to the human glucagon receptor. In one embodiment, the isolated antigen binding protein further comprises: the light chain constant sequence of SEQ ID NO: 305; the light chain constant sequence of SEQ ID NO: 307; the heavy chain constant sequence of SEQ ID NO: 309; the light chain constant sequence of SEQ ID NO: 305 and the heavy chain constant sequence of SEQ ID NO: 309; or the light chain constant sequence of SEQ ID NO: 307 and the heavy chain constant sequence of SEQ ID NO: 309.

In another embodiment, the isolated antigen binding protein is selected from the group consisting of a human antibody, a humanized antibody, chimeric antibody, a monoclonal antibody, a polyclonal antibody, a recombinant antibody, an antigen-binding antibody fragment, a single chain antibody, a diabody, a triabody, a tetrabody, a Fab fragment, an $F(fa')_x$ fragment, a domain antibody, an IgD antibody, an IgE antibody, and IgM antibody, and IgG1 antibody, and IgG2 antibody, and IgG3 antibody, and IgG4 antibody, and IgG4 antibody having at least one mutation in the hinge region that alleviates a tendency to form intra H-chain disulfide bonds. In one embodiment, the antigen binding protein is a human antibody.

In another aspect, the isolated antigen binding protein, when bound to the human glucagon receptor: a. binds to the human glucagon receptor with substantially the same Kd as a reference antibody; b. inhibits glucagon stimulation of the human glucagon receptor with substantially the same $IC_{50}$ as said reference antibody, or c. competes for binding with said reference antibody, wherein said reference antibody comprises a combination of light chain and heavy chain variable domain sequences selected from the group consisting of L1H1, L2H2, L3H3, L4H4, L5H5, L6H6, L7H7, L8H8, L9H9, L11H11, L12H12, L13H13, L15H15, L21H21, and L22H22.

In another aspect, provided is an isolated human antibody, when bound to the human glucagon receptor: a. binds to the human glucagon receptor with substantially the same Kd as a reference antibody; b. inhibits glucagon stimulation of the human glucagon receptor with substantially the same $IC_{50}$ as said reference antibody, or c. competes for binding with said reference antibody, wherein said reference antibody comprises a combination of light chain and heavy chain variable domain sequences selected from the group consisting of A-1, A-2, A-3, A-4, A-5, A-6, A-7, A-8, A-9, A-11, A-12, A-13, A-15, A-21, and A-22.

In another aspect, provided is an isolated human antibody, that, when bound to the human glucagon receptor: a. specifically binds to Ser80 to Ser119 of the human glucagon receptor; b. reduces glucagon signalling with an IC50 value of 90 nM or less; c. lowers blood glucose in an animal model; d. both a. and b., or e. both a., b., and c. In one embodiment, the animal model is the ob/ob animal model.

In another aspect, provided is a pharmaceutical composition comprising the antigen binding protein in admixture with a pharmaceutically acceptable carrier. In another embodiment, the pharmaceutical composition comprises an isolated human antibody in admixture with a pharmaceutically acceptable carrier.

In another aspect, provided is an isolated nucleic acid comprising the polynucleotide sequence that encodes either the light chain variable domain, the heavy chain variable domain, or both, of an antigen binding protein of the invention. In one embodiment, the polynucleotide comprises a light chain variable domain polynucleotide sequence L1-L23, SEQ ID NOs: 212, 214, 216, 218, 220, 222, 224, 226, 228, 230, 232, 234, 236, 238, 240, 242, 244, 246, 248, 250, 252, 254, and 256, a heavy chain variable domain polynucleotide sequence H1-H23, SEQ ID NO: 258, 260, 262, 264, 266, 270, 272, 274, 276, 278, 280, 282, 284, 286, 288, 290, 292, 294, 296, 298, 300, 302, or both.

Also provided are vectors comprising the nucleic acid of the present invention. In one embodiment the vector is an expression vector. Also provided is an isolated cell comprising the nucleic acid of the invention. In one embodiment, the cell is a host cell comprising the expression vector of the invention. In another embodiment, the cell is a hybridoma, wherein the chromosome of the cell comprises nucleic acid of the invention. Further provided is a method of making the antigen binding protein of the present invention comprising culturing or incubating the cell under conditions that allow the cell to express the antigen binding protein of the invention.

Also provided is a method of lowering blood glucose in a subject in need thereof comprising administering a therapeutically effective amount of the pharmaceutical compositions to the subject. Also provided is a method of improving glucose tolerance in a subject in need thereof comprising administering a therapeutically effective dosage of the pharmaceutical compositions to the subject. Also provided is a method of preventing or treating type 2 diabetes or related disorders in a subject in need thereof by administering a therapeutically effective amount of the pharmaceutical compositions to the subject. In one embodiment, the subject is a human subject. In another embodiment, the related disorder is selected from hyperglycemia, hyperinsulinemia, impaired fasting glucose, impaired glucose tolerance, dyslipodemia, and metabolic syndrome. Also provided is a method of treating a condition in a subject in need of such treatment comprising administering a therapeutically effective amount of the pharmaceutical composition to the subject, wherein the condition is treatable by lowering blood glucose. In one embodiment, the condition is selected from hyperglycemia, hyperinsulinemia, impaired fasting glucose, impaired glucose tolerance, dyslipodemia, and type 2 diabetes.

BRIEF DESCRIPTION OF THE FIGURES

FIG. 7 shows the results of binding studies for four anti-GCGR antibodies to chimeric receptors constructed from human GCGR and human GLP-1 receptors as indicted.

DETAILED DESCRIPTION OF THE INVENTION

Figure 1:
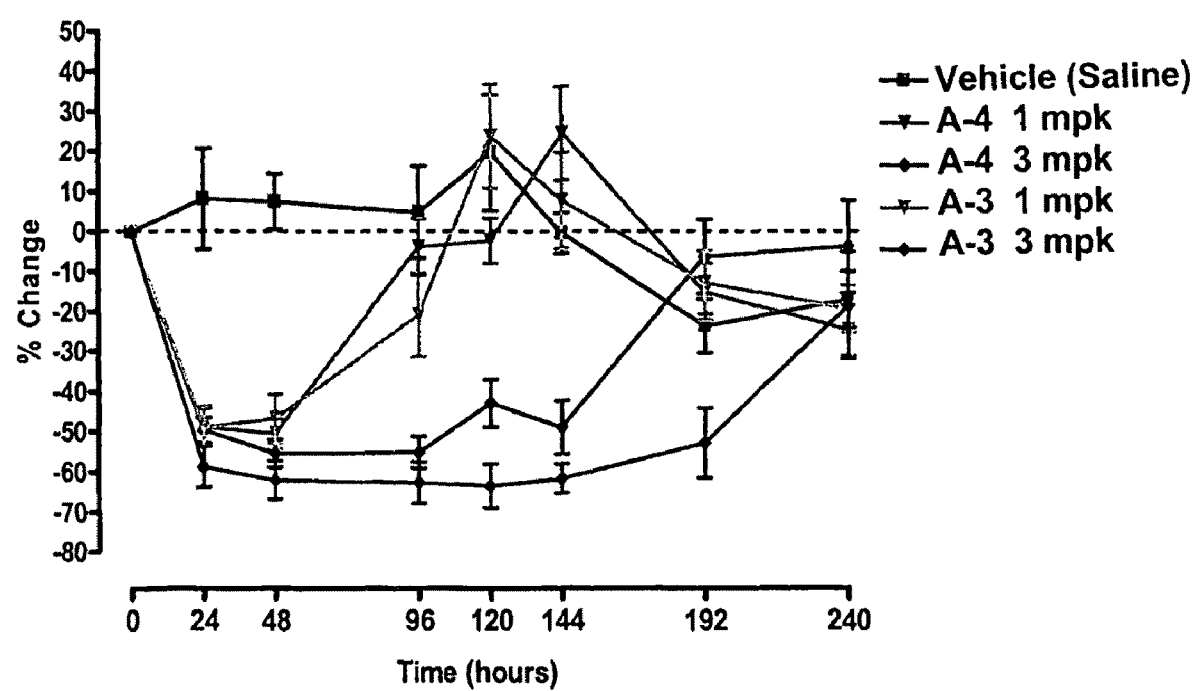
FIG. 1 shows blood glucose levels of 14-week old male ob/ob mice after a single injection of antibody A-3 or antibody A-4 compared with buffer, at a dose of 1 or 3 mg/kg (n=10 animals/group). Blood glucose was measured at time 0 and at 24, 48, 96, 120, 144, 192 and 240 hours after injection.

The present invention relates to antigen binding proteins such as antibodies that specifically bind to the human glucagon receptor (GCGR). These include antigen binding proteins that inhibit or block the binding of glucagon to human GCGR, and reduce glucagon signalling through the receptor. In one embodiment, provided are human antibodies including antagonistic antibodies capable lower blood glucose in animal models. The antigen binding proteins are useful for treating diabetes and related diseases.

The present invention further provides compositions, kits, and methods relating to antigen binding proteins that specifically bind to the human glucagon receptor. Also provided are nucleic acid molecules, and derivatives and fragments thereof, comprising a sequence of polynucleotides that encode all or a portion of a polypeptide that binds to the glucagon receptor, such as a nucleic acid encoding all or part of an anti-glucagon receptor antibody, antibody fragment, or antibody derivative. The present invention further provides vectors and plasmids comprising such nucleic acids, and cells or cell lines comprising such nucleic acids and/or vectors and plasmids. The provided methods include, for example, methods of making, identifying, or isolating antigen binding proteins that bind to human GCGR, such as anti-GCGR antibodies, methods of determining whether an antigen binding protein binds to GCGR, methods of making compositions, such as pharmaceutical compositions, comprising an antigen binding protein that binds to human GCGR, and methods for administering an antigen binding protein that binds GCGR to a subject, for example, methods for treating a condition mediated by GCGR, and for modulating a biological activity associated with glucagon signalling in vivo or in vitro.

Definitions

Polynucleotide and polypeptide sequences are indicated using standard one- or three-letter abbreviations. Unless otherwise indicated, polypeptide sequences have their amino termini at the left and their carboxy termini at the right, and single-stranded nucleic acid sequences, and the top strand of double-stranded nucleic acid sequences, have their 5' termini at the left and their 3' termini at the right. A particular section of a polypeptide can be designated by amino acid residue number such as amino acids 80 to 119, or by the actual residue at that site such as Ser80 to Ser119. A particular polypeptide or polynucleotide sequence also can be described by explaining how it differs from a reference sequence. Polynucleotide and polypeptide sequences of particular light and heavy chain variable domains are designated L1 ("light chain variable domain 1") and H1 ("heavy chain variable domain 1"). Antigen binding proteins or antibodies comprising a light chain and heavy chain are indicated by combining the name of the light chain and the name of the heavy chain variable domains. For example, "L4H7," indicates, for example, an antibody comprising the light chain variable domain of L4 and the heavy chain variable domain of H7.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The following terms, unless otherwise indicated, shall be understood to have the following meanings: The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The terms "glucagon inhibitor", and "glucagon antagonist" are used interchangeably. Each is a molecule that detectably inhibits glucagon signalling. The inhibition caused by an inhibitor need not be complete so long as it is detectable using an assay. For example, the cell-based assay described in Example 4 below, demonstrates an assay useful for determining glucagon signalling inhibition.

The terms "peptide" "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

The term "polypeptide fragment" as used herein refers to a polypeptide that has an amino-terminal and/or carboxy-terminal deletion as compared to a corresponding full-length protein. Fragments can be, for example, at least 5, 6, 7, 8, 9, 10, 11, 12, 13, 14, 15, 20, 50, 70, 80, 90, 100, 150 or 200 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

Polypeptides of the invention include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (4) confer or modify other physicochemical or functional properties. Analogs include muteins of a polypeptide. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

The present invention also provides non-peptide analogs of GCGR antigen binding proteins. Non-peptide analogs are commonly used to provide drugs with properties analogous to those of the template peptide. These types of non-peptide compound are termed "peptide mimetics" or "peptidomimetics". Fauchere, J. Adv. Drug Res. 15:29 (1986); Veber and Freidinger TINS p. 392 (1985); and Evans et al. J. Med. Chem. 30:1229 (1987), which are incorporated herein by reference. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage selected from the group consisting of: —CH$_2$NH—, —CH$_2$S—, —CH$_2$—CH$_2$—, —CH=CH-(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992), incorporated herein by reference), for example, by adding internal cysteine residues capable of forming intramolecular disulfide bridges which cyclize the peptide.

A "variant" of a polypeptide (e.g., an antibody) comprises an amino acid sequence wherein one or more amino acid residues are inserted into, deleted from and/or substituted into the amino acid sequence relative to another polypeptide sequence. Variants of the invention include fusion proteins.

A "derivative" of a polypeptide is a polypeptide (e.g., an antibody) that has been chemically modified, e.g., via conjugation to another chemical moiety such as, for example, polyethylene glycol, albumin (e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129 (2003); Roque et al., Biotechnol. Prog. 20:639-654 (2004). In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5th Ed., US Dept. of Health and Human Services, PHS, NIH, NIH Publication no. 91-3242, 1991.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), fragments including complementarity determining regions (CDRs), single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_H1$ domains; a F(ab')$_2$ fragment is a bivalent fragment having two Fab fragments linked by a disulfide bridge at the hinge region; a Fd fragment has the $V_H$ and $C_H1$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634, 6,696,245, US App. Pub. No. 05/0202512, 04/0202995, 04/0038291, 04/0009507, 03/0039958, Ward et al., Nature 341:544-546 (1989)).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., Science 242:423-26 (1988) and Huston et al., 1988, Proc. Natl. Acad. Sci. USA 85:5879-83 (1988)). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48 (1993), and Poljak et al., Structure 2:1121-23 (1994)). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242, 1991. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-GCGR antibody. In another embodiment, all of the CDRs are derived from a human anti-GCGR antibody. In another embodiment, the CDRs from more than one human anti-GCGR antibodies are mixed and matched in a chimeric antibody. For instance, a chimeric antibody may comprise a CDR1 from the light chain of a first human anti-GCGR antibody, a CDR2 and a CDR3 from the light chain of a second human anti-GCGR antibody, and the CDRs from the heavy chain from a third anti-GCGR antibody. Further, the framework regions may be derived from one of the same anti-GCGR antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody or antibodies from another species or belonging to another antibody class or subclass. Also included are fragments of such antibodies that exhibit the desired biological activity (i.e., the ability to specifically bind the human glucagon receptor).

A "neutralizing antibody" or "inhibitory antibody" refers to an antibody that inhibits the binding of glucagon to the human glucagon receptor, and/or inhibits or reduces glucagon signalling, as determined, for example, by the cell-based assay described in Example 4 below. The inhibition need not be complete and may be, in one embodiment, reduces binding or signalling by at least 20%. In further embodiments, the reduction in binding or signalling is at least 30%, 40%, 50%, 60%, 70%, 80%, 85%, 90%, 95%, 97%, 99% and 99.9%.

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al., Science 253:164 (1991).

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein including an antibody "specifically binds" to an antigen, such as the human glucagon receptor if it binds to the antigen with a high binding affinity as determined by a dissociation constant (Kd, or corresponding Kb, as defined below) value of $10^{-7}$ M or less. An antigen binding protein that specifically binds to the human glucagon receptor may be able to bind to glucagon receptors from other species as well with the same or different affinities.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06.

A "host cell" is a cell that can be used to express a nucleic acid, e.g., a nucleic acid of the invention. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Glucagon Receptors

The glucagon receptor (GCGR) belongs to the family of 7-transmembrane receptors that are coupled to one or more intracellular signalling pathways via heterotrimeric guanine nucleotide-binding proteins (G proteins) (Jelinek et al., Science 259: 1614-1616 (1993), Segre et al., Trends Endocrinol. Metab 4:309-314 (1993)). As used herein, "glucagon receptor" and "GCGR" are used interchangeably. Other members of this group include receptors for secretin, glucagon-like peptide (GLP-1), vasoactive intestinal protein (VIP), and growth hormone releasing factor. These receptors have similar structural features including a relatively large extracellular N-terminal domain, and a series of transmembrane, intracellular and extracellular domains.

In one embodiment, the antigen binding agents of the present invention may be selected to bind to membrane-bound glucagon receptors as expressed on cells, and inhibit or block glucagon signalling through the glucagon receptor. In one embodiment, the antigen binding agents of the present invention specifically bind to the human glucagon receptor. In a further embodiment, the antigen binding proteins binding to the human glucagon receptor may also bind to the glucagon receptors of other species. The Examples below provide one method of generating fully human antibodies which bind to human membrane-bound glucagon receptors, and in a further embodiment, bind to glucagon receptors of other species.

The polynucleotide and polypeptide sequences for several species of glucagon receptor are known. Table 1 presents sequences for human, mouse, and rat. The cynomolgus glucagon receptor sequences are identified herein and are presented below.

TABLE 1

Glucagon Receptors

Human (*Homo sapiens*) polynucleotides (SEQ ID NO: 1)
accession number BC104854

```
  1 gtgcagcccc tgccagatgt gggaggcagc tagctgccca gaggcatgcc ccctgccag
 61 ccacagcgac ccctgctgct gttgctgctg ctgctggcct gccagccaca ggtcccctcc
121 gctcaggtga tggacttcct gtttgagaag tggaagctct acggtgacca gtgtcaccac
181 aacctgagcc tgctgccccc tcccacggag ctggtgtgca acagaacctt cgacaagtat
```

TABLE 1-continued

Glucagon Receptors

```
 241 tcctgctggc cggacacccc cgccaatacc acggccaaca tctcctgccc ctggtacctg
 301 ccttggcacc acaaagtgca cacccgcttc gtgttcaaga gatgcgggcc cgacggtcag
 361 tgggtgcgtg gaccccgggg gcagccttgg cgtgatgcct cccagtgcca gatggatggc
 421 gaggagattg aggtccagaa ggaggtggcc aagatgtaca gcagcttcca ggtgatgtac
 481 acagtgggct acagcctgtc cctgggggcc ctgctcctcg ccttggccat cctgggggc
 541 ctcagcaagc tgcactgcac ccgcaatgcc atccacgcga atctgtttgc gtccttcgtg
 601 ctgaaagcca gctccgtgct ggtcattgat gggctgctca ggacccgcta cagccagaaa
 661 attggcgacg acctcagtgt cagcacctgg ctcagtgatg gagcggtggc tggctgccgt
 721 gtggccgcgg tgttcatgca atatggcatc gtggccaact actgctggct gctggtggag
 781 ggcctgtacc tgcacaacct gctgggcctg gccaccctcc ccgagaggag cttcttcagc
 841 ctctacctgg gcatcggctg gggtgccccc atgctgttcg tcgtcccctg ggcagtggtc
 901 aagtgtctgt tcgagaacgt ccagtgctgg accagcaatg acaacatggg cttctggtgg
 961 atcctgcggt tccccgtctt cctggccatc ctgatcaact tcttcatctt cgtccgcatc
1021 gttcagctgc tcgtggccaa gctgcgggca cggcagatgc accacacaga ctacaagttc
1081 cggctggcca gtccacgct gaccctcatc cctctgctgg cgtccacga agtggtcttc
1141 gccttcgtga cggacgagca cgcccaggg accctgcgct ccgccaagct cttcttcgac
1201 ctcttcctca gctccttcca gggctgctg tgctgtcc tctactgctt cctcaacaag
1261 gaggtgcagt cggagctgcg gcggcgttgg caccgctggc gcctgggcaa agtgctatgg
1321 gaggagcgga acaccagcaa ccacagggcc tcatcttcgc ccggccacga ccctcccagc
1381 aaggagctgc agtttgggag gggtggtggc agccaggatt catctgcgga ccccccttg
1441 gctggtggcc tccctagatt ggctgagagc cccttctgaa ccctgctggg accccagcta
1501 gggctggact ctggcaccc
```

Human (Homo sapiens) amino acid (SEQ ID NO: 2)
477 aa; accession no. EAW89684

```
Met Pro Pro Cys Gln Pro Gln Arg Pro Leu Leu Leu Leu Leu Leu Leu Ala Cys Gln Pro Gln
Val Pro Ser Ala Gln Val Met Asp Phe Leu Phe Glu Lys Trp Lys Leu Tyr Gly Asp Gln Cys His
His Asn Leu Ser Leu Leu Pro Pro Pro Thr Glu Leu Val Cys Asn Arg Thr Phe Asp Lys Tyr Ser
Cys Trp Pro Asp Thr Pro Ala Asn Thr Thr Ala Asn Ile Ser Cys Pro Trp Tyr Leu Pro Trp His His
Lys Val Gln His Arg Phe Val Phe Lys Arg Cys Gly Pro Asp Gly Gln Trp Val Arg Gly Pro Arg
Gly Gln Pro Trp Arg Asp Ala Ser Gln Cys Gln Met Asp Gly Glu Glu Ile Glu Val Gln Lys Glu
Val Ala Lys Met Tyr Ser Ser Phe Gln Val Met Tyr Thr Val Gly Tyr Ser Leu Ser Leu Gly Ala
Leu Leu Leu Ala Leu Ala Ile Leu Gly Gly Leu Ser Lys Leu His Cys Thr Arg Asn Ala Ile His
Ala Asn Leu Phe Ala Ser Phe Val Leu Lys Ala Ser Ser Val Leu Val Ile Asp Gly Leu Leu Arg
Thr Arg Tyr Ser Gln Lys Ile Gly Asp Asp Leu Ser Val Ser Thr Trp Leu Ser Asp Gly Ala Val
Ala Gly Cys Arg Val Ala Ala Val Phe Met Gln Tyr Gly Ile Val Ala Asn Tyr Cys Trp Leu Leu
Val Glu Gly Leu Tyr Leu His Asn Leu Leu Gly Leu Ala Thr Leu Pro Glu Arg Ser Phe Phe Ser
Leu Tyr Leu Gly Ile Gly Trp Gly Ala Pro Met Leu Phe Val Val Pro Trp Ala Val Val Lys Cys
Leu Phe Glu Asn Val Gln Cys Trp Thr Ser Asn Asp Asn Met Gly Phe Trp Trp Ile Leu Arg Phe
Pro Val Phe Leu Ala Ile Leu Ile Asn Phe Phe Ile Phe Val Arg Ile Val Gln Leu Leu Val Ala Lys
Leu Arg Ala Arg Gln Met His His Thr Asp Tyr Lys Phe Arg Leu Ala Lys Ser Thr Leu Thr Leu
Ile Pro Leu Leu Gly Val His Glu Val Val Phe Ala Phe Val Thr Asp Glu His Ala Gln Gly Thr
Leu Arg Ser Ala Lys Leu Phe Phe Asp Leu Phe Leu Ser Ser Phe Gln Gly Leu Leu Val Ala Val
Leu Tyr Cys Phe Leu Asn Lys Glu Val Gln Ser Glu Leu Arg Arg Arg Trp His Arg Trp Arg Leu
Gly Lys Val Leu Trp Glu Glu Arg Asn Thr Ser Asn His Arg Ala Ser Ser Ser Pro Gly His Gly
Pro Pro Ser Lys Glu Leu Gln Phe Gly Arg Gly Gly Gly Ser Gln Asp Ser Ser Ala Glu Thr Pro
Leu Ala Gly Gly Leu Pro Arg Leu Ala Glu Ser Pro Phe
```

Mouse (Mus musculus) polynucleotide (SEQ ID NO: 3)
accession number BC5057988

```
   1 cgcgaggagc gcagccctag ccccggcgac tgagcacacc tgaggagagg tgcacacact
  61 ctgaggacct aggtgtgcaa cctctgccag atgtggggcg tggctaccca gaggcatgcc
 121 cctcacccag ctccactgtc cccacctgct gctgctgctg ttggtgctgt catgtctgcc
 181 agaggcaccc tctgcccagg taatggactt tttgtttgag aagtggaagc tctatagtga
 241 ccaatgccac cacaacctaa gcctgctgcc cccacctact gagctggtct gtaacagaac
 301 cttcgacaag tactcctgct ggcctgacac ccctcccaac accactgcca acatttcctg
 361 cccctggtac ctaccttggt accacaaagt gcagcaccgc ctagtgttca gaggtgtgg
 421 gcccgatggg cagtgggttc gagggccacg ggggcagccg tggcgcaacg cctcccaatg
 481 tcagttggat gatgaagaga tcgaggtcca gaaggggtg gccaagatgt atagcagcca
 541 gcaggtgatg tacaccgtgg gctacagtct gtccctgggg gccttgctcc ttgcgctggt
 601 catcctgctg ggcctcagga agctgcactg cacccgaaac tacatccatg ggaacctgtt
 661 tgcgtccttt gtgctcaagg ctggctctgt gttggtcatc gattggctgc tgaagacacg
 721 gtacagccag aagattggcg atgacctcag tgtgagcgtc tggctcagtg acggggcgat
 781 ggccggctgc agagtggcca cagtgatcat gcagtacggc atcatagcca actattgctg
 841 gttgctggta gagggcgtgt acctgtacag cctgctgagc cttgccacct ctctgagag
 901 gagcttcttt tccctctacc tgggcattgg ctgggtgcg ccctgctgt tgtcatccc
 961 ctgggtggtg gtcaagtgtc tgtttgagaa tgttcagtgc tggaccagca atgacaacat
1021 gggattctgg tggatcctgc gtattcctgc ttcctggcc ttactgatca atttttttcat
1081 cttttgtccac atcattacc ttcttgtggc caagctgcgt gcccatcaga tgcactatgc
1141 tgactataag ttccggctgg ccaggtccac gctgaccctc atccctctgc tgggggtcca
1201 cgaggtggtc tttgccttg tgactgacga ggtgcccaa ggcactgccgc gctccaccaa
1261 gctctttttt gacctgttcc tcagctcctt ccagggtctg ctggtgctg ttctctactg
1321 tttcctcaac aaggaggtgc aggcagagct gatgcggcgt tggaggcaat ggcaagaagg
1381 caaagctctt caggaggaaa ggttggccag cagccatggc agccacatgg ccccagcagg
1441 gccttgtcat ggtgatccct gtgagaaact tcagccttatg agtgcaggca gcagcagtgg
1501 gactggctgt gtgccctcta tggagacctc gctggccagt agtctcccaa ggttggctga
```

TABLE 1-continued

Glucagon Receptors

```
1561 cagccccacc tgaatctcca ctggagccta gccaggctgc gttcagaaag ggcctcagag
1621 gacaacccag agccagatgc ccggccaagg ctgaagagac aaagcagcaa gacagcagct
1681 tgtactgtgc acactcccct aacctgtcct agcctggcac aggccacagt gacagagtag
1741 gggttggata tgatggagaa gccatgttat ctatgaactc tgagtgttcc catgtgtgtt
1801 gacatggtcc ctgtacccag atatgtcctt cagtaaaaag ctcgagtggg agctgctgca
1861 caaaaaaaaa aaaaaaaaaa
```

Mouse (*Mus musculus*) amino acid (SEQ ID NO: 4)
485 aa accession number AAH57988

```
Met Pro Leu Thr Gln Leu His Cys Pro His Leu Leu Leu Leu Leu Val Leu Ser Cys Leu Pro
Glu Ala Pro Ser Ala Gln Val Met Asp Phe Leu Phe Glu Lys Trp Lys Leu Tyr Ser Asp Gln Cys
His His Asn Leu Ser Leu Leu Pro Pro Pro Thr Glu Leu Val Cys Asn Arg Thr Phe Asp Lys Tyr
Ser Cys Trp Pro Asp Thr Pro Pro Asn Thr Thr Ala Asn Ile Ser Cys Pro Trp Tyr Leu Pro Trp Tyr
His Lys Val Gln His Arg Leu Val Phe Lys Arg Cys Gly Pro Asp Gly Gln Trp Val Arg Gly Pro
Arg Gly Gln Pro Trp Arg Asn Ala Ser Gln Cys Gln Leu Asp Asp Glu Glu Ile Glu Val Gln Lys
Gly Val Ala Lys Met Tyr Ser Ser Gln Gln Val Met Tyr Thr Val Gly Tyr Ser Leu Ser Leu Gly
Ala Leu Leu Leu Ala Leu Val Ile Leu Leu Gly Leu Arg Lys Leu His Cys Thr Arg Asn Tyr Ile
His Gly AsnLeu Phe Ala Ser Phe Val Leu Lys Ala Gly Ser Val Leu Val Ile Asp Trp Leu Leu
Lys Thr Arg Tyr Ser Gln Lys Ile Gly Asp Asp Leu Ser Val Ser Val Trp Leu Ser Asp Gly Ala
Met Ala Gly Cys Arg Val Ala Thr Val Ile Met Gln Tyr Gly Ile Ile Ala Asn Tyr Cys Trp Leu Leu
Val Glu Gly Val Tyr Leu Tyr Ser Leu Leu Ser Leu Ala Thr Phe Ser Glu Arg Ser Phe Phe Ser
Leu Tyr Leu GlyIle Gly Tyr Gly Ala Pro Leu Gly Ile Leu Pro Trp Trp Val Val Lys Cys Leu
Phe Glu Asn Val Gln Cys Trp Thr Ser Asn Asp Asn Met Gly Phe Trp Trp Ile Leu Arg Ile Pro
Val Phe Leu Ala Leu Leu Ile Asn Phe Phe Ile Phe Val His Ile Ile His Leu Leu Val Ala Lys Leu
Arg Ala His Gln Met His Tyr Ala Asp Tyr Lys Phe Arg Leu Ala Arg Ser Thr Leu Thr Leu Ile
Pro Leu Leu GlyVal His Glu Val Val Phe Ala Phe Val Thr Asp Glu His Ala Gln Gly Thr Leu
Arg Ser Thr Lys Leu Phe Phe Asp Leu Phe Leu Ser Ser Phe Gln Gly Leu Leu Val Ala Val Leu
Tyr Cys Phe Leu Asn Lys Glu Val Gln Ala Glu Leu Met Arg Arg Trp Arg Gln Trp Gln Glu Gly
Lys Ala Leu Gln Glu Glu Arg Leu Ala Ser Ser His Gly Ser His Met Ala Pro Ala Gly Pro Cys
His Gly Asp Pro Cys GluLys Leu Gln Leu Met Ser Ala Gly Ser Ser Ser Gly Thr Gly Cys Val
Pro Ser Met Glu Thr Ser Leu Ala Ser Ser Leu Pro Arg Leu Ala Asp Ser Pro Thr
```

Rat (*Rattus norvegicus*) polynucleotide (SEQ ID NO: 5)
accession no. NM 172092

```
   1 gaattcgcgg ccgccgccgg gccccagatc ccagtgcgcg aggagcccag tcctagaccc
  61 agcaacctga ggagaggtgc acacacccccc aaggacccag gcacccaacc tctgccagat
 121 gtggggggt ggctaccag aggcatgctc ctcacccagc tccactgtcc ctacctgctg
 181 ctgctgctgg tggtgctgtc atgtctgcca aaggcaccct ctgcccagtg aatgacttt
 241 ttgttttgaga agtggaagct ctatagtgac cagtgccacc acaacctaag cctgctgccc
 301 ccacctactg agctggtctg caacagaact ttcgacaagt actcctgctg gcctgacacc
 361 cctcccaaca ccactgccaa catttcctgc ccctggtacc taccttggta ccacaaagtg
 421 cagcaccgcc tagtgttcaa gaggtgtggg cctgatgggc agtgggttcg agggccacgg
 481 gggcagtcat ggcgcgacgc ctcccaatgt cagatgggat atgacgagat cgaggtccag
 541 aaggggggtag ccaagatgta tagcagctac caggtgatgt acactgtggg ctacagtctg
 601 tccctggggg ccttgctcct ggcgctggtc atcctgctgg gcctcaggaa gctgcactgc
 661 acccggaact acatccacgg gaacctgttc gcgtccttcg tgctcaaggc tggctctgtg
 721 ctggtcattg attggctgct caagacacgc tataggccaga agattggaga tgacctcagt
 781 gtgagcgtct ggctcagtga tggggcggtg gctggctgca gagtggccac agtgatcatg
 841 cagtacggca tcatagccaa ctactgctgg ttgctggtgg aggtgtgta cctgtacagc
 901 ctgctgagca tcaccaccct tcggagaag agcttcttct ccctctatct gtgcatcggc
 961 tggggatctc ccctgctgtt tgtcatcccc tgggtggtg tcaagtgtct gtttgagaat
1021 gtccagtgct ggaccagcaa tgacaatatg ggattcggt ggatcctgcg tatccctgta
1081 ctcctggcca tactgatcaa tttttttcatc tttgtccgca tcattcatct tcttgtggcc
1141 aagctgcgtg cccatcgat gcactatgct gattacaagt tccggctagc caggtccacg
1201 ctgaccctca ttcctctgct gggagtccac gaagtggtct ttgcctttgt gactgatgag
1261 catgcccagg gcaccctgcg ctccaccaag ctctttttg acctgttctt cagctccttt
1321 cagggtctgc tggtggctgt tctctactgt ttcctcaaca aggaggtgca ggcagagcta
1381 ctgcggcgtt ggaggcgatg gcaagaaggc aaagctcttc aggaggaaag gatggccagc
1441 agccatggca gccacatggc cccagcaggg acttgtgtg gtgatccctg tgagaaactt
1501 cagcttatga gtgcaggcag cagcagtggg actggctgtg agccctctgc gaagacctca
1561 ttggccagta gtctcccaag gctggctgac agcccacct gaatctccac tggactccag
1621 ccaagttgga ttcagaaagg gcctcacaag acaacccaga aacagatgcc tggccaaggc
1681 tgaagaggca aagcagcaag acagcagctt gtactatcca cactcccta acctgtcctg
1741 gccgggtaca ggccacattg atgagtagg ggctggatat gatggagtag ccatgctatg
1801 aactatgggt gttcccatga tgtgttgccat gttccatgca cacagatatg accttcagta
1861 aagagctccc gtagg
```

Rat (*Rattus norvegicus*) amino acid (SEQ ID NO: 6)
489 aa, accession no. NM 172092

```
Met Leu Leu Thr Gln Leu His Cys Pro TyrLeu Leu Leu Leu Leu Val Val Leu Ser Cys Leu Pro
Lys Ala Pro Ser Ala Gln Val Met Asp Phe Leu Phe Glu Lys Trp Lys Leu Tyr Ser Asp Gln Cys
His His Asn Leu Ser Leu Leu Pro Pro Pro Thr Glu Leu Val Cys Asn Arg Thr Phe Asp Lys Tyr
Ser Cys Trp Pro Asp Thr Pro Pro Asn Thr Thr Ala Asn Ile Ser Cys Pro Trp Tyr Leu Pro Trp Tyr
His Lys Val Gln His Arg Leu Val Phe Lys Arg Cys Gly Pro Asp Gly Gln Trp Val Arg Gly Pro
Arg Gly Gln Ser Trp Arg Asp Ala Ser Gln Cys Gln Met Asp Asp Asp Glu Ile Glu Val Gln Lys
```

TABLE 1-continued

Glucagon Receptors

```
Gly Val Ala Lys Met Tyr Ser Ser Tyr Gln Val Met Tyr Thr Val Gly Tyr Ser Leu Ser Leu Gly
Ala Leu Leu Leu Ala Leu Val Ile Leu Leu Gly Leu Arg Lys Leu His Cys Thr Arg Asn Tyr Ile
His Gly Asn Leu Phe Ala Ser Phe Val Leu Lys Ala Gly Ser Val Leu Val Ile Asp Trp Leu Leu
Lys Thr Arg Tyr Ser Gln Lys Ile Gly Asp Asp Leu Ser Val Ser Val Trp Leu Ser Asp Gly Ala
Val Ala Gly Cys Arg Val Ala Thr Val Ile Met Gln Tyr Gly Ile Ile Ala Asn Tyr Cys Trp Leu Leu
Val Glu Gly Val Tyr Leu Tyr Ser Leu Leu Ser Ile Thr Thr Ser Glu Lys Ser Phe Phe Ser Leu
Tyr Leu Cys Ile Gly Trp Gly Ser Pro Leu Leu Phe Val Ile Pro Trp Val Val Val Lys Cys Leu Phe
Glu Asn Val Gln Cys Trp Thr Ser Asn Asp Asn Met Gly Phe Trp Trp Ile Leu Arg Ile Pro Val
Leu Leu Ala Ile Leu Ile Asn Phe Phe Ile Phe Val Arg Ile Ile His Leu Leu Val Ala Lys Leu Arg
Ala His Gln Met His Tyr Ala Asp Tyr Lys Phe Arg Leu Ala Arg Ser Thr Leu Thr Leu Ile Pro
Leu Leu Gly Val His Glu Val Val Phe Ala Phe Val Thr Asp Glu His Ala Gln Gly Thr Leu Arg
Ser Thr Lys Leu Phe Phe Asp Leu Phe Phe Ser Ser Phe Gln Gly Leu Leu Val Ala Val Leu Tyr
Cys Phe Leu Asn Lys Glu Val Gln Ala Glu Leu Leu Arg Arg Trp Arg Arg Trp Gln Glu Gly Lys
Ala Leu Gln Glu Glu Arg Met Ala Ser Ser His Gly Ser His Met Ala Pro Ala Gly Thr Cys His
Gly Asp Pro Cys Glu Lys Leu Gln Leu Met Ser Ala Gly Ser Ser Ser Gly Thr Gly Cys Glu Pro
Ser Ala Lys Thr Ser Leu Ala Ser Ser Leu Pro Arg Leu Ala Asp Ser Pro Thr
```

Cynomolgus (*Macaca fascicularis*) polynucleotides 1434 bp (SEQ ID NO: 7)

```
atgccccctgtcagccacgtcgaccctgctactgttgctgctgctgctggcctgccagccacaggcccctccgctcaggtgatggact
tcctgtttgagaagtggaaactctacggtgaccagtgtcaccacaacctgagcctgctgccccccccacggagctggtctgtaacagaac
cttcgacaagtattcctgctggccagacaccccgccaataccacagccaacatctcctgccctggtacctgccttggcaccacaaagtg
caacaccgcttcgtgttcaaggagatgcgggcccgatggtcagtgggtgcgtggaacccgggggcagcctggcgtgacgcctctcagtg
ccagatgacggcgaggagcttgaggtccagaaggaggtggctaagatgtacagcagcttccaggtgatgtacacggtgggctacagc
ctgtccctgggggccctgctcctcgccttggccatcctgggggggcatcagcaagctgcactgcaccgcaacgccatccacgcgaacct
gtttgtgtccttcgtgctgaaggccagctccgtgctggtcatcgatgggctgctcaggacccgctacagccagaagattggcgacgacctc
agtgtcagcatctggctcagtgatggagcggtggccggctgccgtgtggccgcggtgttcatgcaatatggcgtcgtggccaactactgct
ggctgctggtggagggcctgtacctgcacaacctgctgggccctggccactcccctgagaggagcttcttcagcctctacctgggcatcg
gctggggtgcccccatgctgttcatcatccctgggtggtggtcaggtgtctgttcgagaacatccagtgctggaccagcaatgacaacatg
ggcttctggtggatcctgcggttcccccgtcttcctggccatcctgatcaacttcttcatcttcatccgcattgttcacctgcttgtggccaagctg
cgggcgcgggagatgcaccacacagactacaagttccgactggccaagtccacactgaccctcatccccctgctgggtgtccacgaagt
gatcttcgccttcgtgacggacgagcacgcccagggcaccctgcgcttcgccaagctcttcttcgacctcttcctcagctccttccagggcc
tgctggtggctgtcctctactgcttcctcaacaaggaggtgcagtcggaacttcggcggcattggcaccgctggcgcctgggcaaagtgct
gcaggaggagcggggcaccagcaaccacaagacccatctgcgcctggccaaggccttcctggcaagaagctgcagtctgggaggg
gtggtggcagccaggactcatctgcggagatccccttggctggtggcctccctaggttggctgagagccccttctga
```

Cynomolgus (*Macaca fascicularis*) amino acids (SEQ ID NO: 8)
478 aa

```
Met Pro Pro Cys Gln Pro Arg Arg Pro Leu Leu Leu Leu Leu Leu Leu Leu Ala Cys Gln
Pro Gln Ala Pro Ser Ala Gln Val Met Asp Phe Leu Phe Glu Lys Trp Lys Leu Tyr Gly
Asp Gln Cys His His Asn Leu Ser Leu Leu Pro Pro Pro Thr Glu Leu Val Cys Asn Arg
Thr Phe Asp Lys Tyr Ser Cys Trp Pro AspThr Pro Ala Asn Thr Thr Ala Asn Ile Ser
Cys Pro Trp Tyr Leu Pro Trp His His LysVal Gln His Arg Phe Val Phe Lys Arg Cys
Gly Pro Asp Gly Gln Trp Val Arg Gly ProArg Gly Gln Pro Trp Arg Asp Ala Ser Gln
Cys Gln Met Asp Gly Glu Glu Leu Glu ValGln Lys Glu Val Ala Lys Met Tyr Ser Ser
Phe Gln Val Met Tyr Thr Val Gly Tyr SerLeu Ser Leu Gly Ala Leu Leu Leu Ala Leu
Ala Ile Leu Gly Ile Ser Lys Leu His Cys Thr Arg Asn Ala Ile His Ala Asn Leu
Phe Val Ser Phe Val Leu Lys Ala Ser SerVal Leu Val Ile Asp Gly Leu Leu Arg Thr
Arg Tyr Ser Gln Lys Ile Gly Asp Asp Leu Ser Val Ser Ile Trp Leu Ser Asp Gly Ala
Val Ala Gly Cys Arg Val Ala Ala Val Phe Met Gln Tyr Gly Val Val Ala Asn Tyr Cys
Trp Leu Leu Val Glu Gly Leu Tyr Leu His Asn Leu Gly Leu Ala Thr Leu Pro Glu
Arg Ser Phe Phe Ser Leu Tyr Leu Gly Ile Gly Trp Gly Ala Pro Met Leu Phe Ile Ile
Pro Trp Val Val Val Arg Cys Leu Phe Glu Asn Ile Gln Cys Trp Thr Ser Asn Asp Asn
Met Gly Phe Trp Trp Ile Leu Arg Phe Pro Val Phe Leu Ala Ile Leu Ile Asn Phe Phe
Ile Phe Ile Arg Ile Val His Leu Leu Val Ala Lys Leu Arg Ala Arg Glu Met His His
Thr Asp Tyr Lys Phe Arg Leu Ala Lys Ser Thr Leu Thr Leu Ile Pro Leu Leu Gly Val
His Glu Val Ile Phe Ala Phe Val Thr Asp Glu His Ala Gln Gly Thr Leu Arg Phe Ala
Lys Leu Phe Phe Asp Leu Phe Leu Ser Ser Phe Gln Gly Leu Leu Val Ala Val Leu Tyr
Cys Phe Leu Asn Lys Glu Val Gln Ser Glu Leu Arg Arg His Trp His Arg Trp Arg Leu
Gly Lys Val Leu Gln Glu Gly Arg Gly Thr Ser His Lys His Thr Pro Ser Ala Pro Gly
Gln Gly Leu Pro Gly Lys Lys Leu Gln Ser Gly Arg Gly Gly Ser Gln Asp Ser Ser
Ala Glu Ile Pro Leu Ala Gly Gly Leu Pro Arg Leu Ala Glu Ser Pro Phe
```

Antigen Binding Proteins

In one aspect, the present invention provides antigen binding proteins (e.g., antibodies, antibody fragments, antibody derivatives, antibody muteins, and antibody variants), that specifically bind to the human glucagon receptor. In one embodiment the antigen binding protein is a human antibody.

Antigen binding proteins in accordance with the present invention include antigen binding proteins that specifically bind to the human glucagon receptor and inhibit glucagon signalling through the glucagon receptor. In one embodiment, the IC50 value of the antigen binding protein is 90 nM or less. In another aspect, the antigen binding proteins specifically bind the glucagon receptor, inhibit signalling, and exhibit therapeutic biological effects, such as lowering blood glucose in animal models, or improving glucose clearance (tolerance) in animal models. In one embodiment, the antigen binding proteins are human antibodies that specifically bind the glucagon receptor, and inhibit signalling through the glucagon receptor. In another embodiment, the antigen binding proteins are human antibodies that specifically bind to the human glucagon receptor, inhibit signalling through the glucagon receptor, and are capable of lowering blood glucose or improving glucose clearance (tolerance) in animal models.

In one embodiment, the antigen binding protein (e.g., antibody) comprises sequences that each independently differ by 5, 4, 3, 2, 1, or 0 single amino acid additions, substitutions, and/or deletions from a CDR sequence of A1-A23 in Table 2 below. As used herein, a CDR sequence that differs by no more than a total of, for example, four amino acid additions, substitutions and/or deletions from a CDR sequence shown in Table 2 below refers to a sequence with 4, 3, 2, 1 or 0 single amino acid additions, substitutions, and/or deletions compared with the sequences shown in Table 2.

In another embodiment, the antigen binding protein comprises one or more CDR consensus sequences shown below. Consensus sequences are provided for light chain CDR1, CDR2, CDR3, and heavy chain CDR1, CDR2, and CDR3 below.

The light chain CDRs of antigen binding proteins (antibodies) A1-A23 and the heavy chain CDRs of exemplary antigen binding proteins (antibodies) A1-A23 are shown below in Table 2. A-1 to A-23 corresponds to L1 to L23 below, and H1 to H23 below. Also shown are polynucleotide sequences which encode the amino acid sequences of the CDRs.

TABLE 2

| Ab | CDR 1 | CDR 2 | CDR 3 |
|---|---|---|---|
| | | LIGHT CHAINS L1 to L23 | |
| A-1 NA | aggtctagtcagagcctcttggatagag atgatggagacacctatttggac (SEQ ID NO: 9) | Acgctttcctatcgggcctct (SEQ ID NO: 42) | atgcaacgtatagagtttc cattcact (SEQ ID NO: 71) |
| AA | RSSQSLLDRDDGDTYLD (SEQ ID NO: 10) | TLSYRAS (SEQ ID NO: 43) | MQRIEFPFT (SEQ ID NO: 72) |
| A-2 NA | aggtctagtcagagcctcttggatagtgc tgatggagacacctatttggac (SEQ ID NO: 11) | acgctttcctatcgggcctct (SEQ ID NO: 42) | atgcaacgtatagagtttc cattcact (SEQ ID NO: 71) |
| AA | RSSQSLLDSADGDTYLD (SEQ ID NO: 12) | TLSYRAS (SEQ ID NO: 43) | MQRIEFPFT (SEQ ID NO: 72) |
| A-3 NA | cgggcaagtcagggcattagaaatgatt taggc (SEQ ID NO: 13) | gctgcatccagtttgcaaagt (SEQ ID NO: 44) | ctacagcataatagtaacc ctctcact (SEQ ID NO: 73) |
| AA | RASQGIRNDLG (SEQ ID NO: 14) | AASSLQS (SEQ ID NO: 45) | LQHNSNPLT (SEQ ID NO: 74) |
| A-4 NA | cgggcaagtcagggcattagaaatgatt taggc (SEQ ID NO: 13) | gctgcatccagtttgcaaagt (SEQ ID NO: 44) | ctacagcataatagtaacc ctctcact (SEQ ID NO: 73) |
| AA | RASQGIRNDLG (SEQ ID NO: 14) | AASSLQS (SEQ ID NO: 45) | LQHNSNPLT (SEQ ID NO: 74) |
| A-5 NA | cgggcaagtcagggcattagaaatgatt taggc (SEQ ID NO: 13) | gctgcctccagtttgcaaagt (SEQ ID NO: 46) | ctacagcataatagtgacc cgctcacc (SEQ ID NO: 75) |
| AA | RASQGIRNDLG (SEQ ID NO: 14) | AASSLQS (SEQ ID NO: 45) | LQHNSDPLT (SEQ ID NO: 76) |
| A-6 NA | agggccagtcagagtgttagcagcaac tacttagcc (SEQ ID NO: 15) | ggtgcatccagcagggccact (SEQ ID NO: 47) | caacaatatggtaactcac cattcact (SEQ ID NO: 77) |
| AA | RASQSVSSNYLA (SEQ ID NO: 16) | GASSRAT (SEQ ID NO: 48) | QQYGNSPFT (SEQ ID NO: 78) |
| A-7 NA | cgggcaagtcaggacattagaaatgatt ttggc (SEQ ID NO: 17) | gctgcatccagtttacaaagt (SEQ ID NO: 44) | ctacagcaaaatagttacc cgctcact (SEQ ID NO: 79) |
| AA | RASQDIRNDFG (SEQ ID NO: 18) | AASSLQS (SEQ ID NO: 45) | LQQNSYPLT (SEQ ID NO: 80) |
| A-8 NA | gggtctactcagagcctcttggatagtga tgatggagacacctatttggac (SEQ ID NO: 19) | acgctttcctatcgggcctct (SEQ ID NO: 42) | atgcaacgtatagagtttc cattcact (SEQ ID NO: 71) |
| AA | RSTQSLLDSDDGDTYLD (SEQ ID NO: 20) | TLSYRAS (SEQ ID NO: 43) | MQRIEFPFT (SEQ ID NO: 72) |
| A-9 NA | cgggcaagtcagggcattagaaatgatt taggc (SEQ ID NO: 13) | gctgcatccagtttggaaagt (SEQ ID NO: 49) | ctacagcataatagtaacc ctctcact (SEQ ID NO: 73) |

TABLE 2-continued

| | | | |
|---|---|---|---|
| AA | RASQGIRNDLG<br>(SEQ ID NO: 14) | AASSLES<br>(SEQ ID NO: 50) | LQHNSNPLT<br>(SEQ ID NO: 74) |
| A-10<br>NA | caggcgagtcaggacattagtaagtattt<br>aaat<br>(SEQ ID NO: 21) | gatgcatccaatttggaaaca<br>(SEQ ID NO: 51) | caacagtatggtaatctcc<br>cgatcacc<br>(SEQ ID NO: 75) |
| AA | QASQDISKYLN<br>(SEQ ID NO: 22) | DASNLET<br>(SEQ ID NO: 52) | QQYGNLPIT<br>(SEQ ID NO: 76) |
| A-11<br>NA | tctggagataaattgggggataaatatgt<br>ttgc<br>(SEQ ID NO: 23) | caaacttccaagcggccctca<br>(SEQ ID NO: 53) | caggcgtgggacagcaa<br>cactgtgatt<br>(SEQ ID NO: 77) |
| AA | SGDKLGDKYVC<br>(SEQ ID NO: 24) | QTSKRPS<br>(SEQ ID NO: 54) | QAWDSNTVI<br>(SEQ ID NO: 78) |
| A-12<br>NA | tctggagataaattgggggataaatatgt<br>ttgc<br>(SEQ ID NO: 23) | caaacttccaagcggccctca<br>(SEQ ID NO: 53) | caggcgtgggacagcag<br>cactgtggtt<br>(SEQ ID NO: 79) |
| AA | SGDKLGDKYVC<br>(SEQ ID NO: 24) | QTSKRPS<br>(SEQ ID NO: 54) | QAWDSSTVV<br>(SEQ ID NO: 80) |
| A-13<br>NA | tctggagataaattgggggataaatatgc<br>ttgc<br>(SEQ ID NO: 25) | caatctaccaagcggccctca<br>(SEQ ID NO: 55) | caggcgtgggacagcag<br>cactgtggta<br>(SEQ ID NO: 81) |
| AA | SGDKLGDKYAC<br>(SEQ ID NO: 26) | QSTKRPS<br>(SEQ ID NO: 56) | QAWDSSTVV<br>(SEQ ID NO: 80) |
| A-14<br>NA | acccgcagcagtggcagcattgtcagc<br>aactttgtgcaa<br>(SEQ ID NO: 27) | gaggataaccaaagaccctct<br>(SEQ ID NO: 57) | cagtcttatgataccagca<br>atcaggtg<br>(SEQ ID NO: 82) |
| AA | TRSSGSIVSNFVQ<br>(SEQ ID NO: 28) | EDNQRPS<br>(SEQ ID NO: 58) | QSYDTSNQV<br>(SEQ ID NO: 83) |
| A-15<br>NA | actggaatcacctccaacatcggaagca<br>atactgtacac<br>(SEQ ID NO: 29) | agtaataatcagcggccctca<br>(SEQ ID NO: 59) | gcagcatgggatgacag<br>cctgaatggtccggtg<br>(SEQ ID NO: 84) |
| AA | TGITSNIGSNTVH<br>(SEQ ID NO: 30) | SNNQRPS<br>(SEQ ID NO: 60) | AAWDDSLNGPV<br>(SEQ ID NO: 85) |
| A-16<br>NA | tctggaagcaggtccaacatcggaagta<br>attatgtatac<br>(SEQ ID NO: 31) | aggaataatcagcggccctca<br>(SEQ ID NO: 61) | gcagcatgggatgacag<br>cctgagtaggccggta<br>(SEQ ID NO: 86) |
| AA | SGSRSNIGSNYVY<br>(SEQ ID NO: 32) | RNNQRPS<br>(SEQ ID NO: 62) | AAWDDSLSRPV<br>(SEQ ID NO: 87) |
| A-17<br>NA | actgggagcagctccaacatcggggca<br>ggttatgctgtacac<br>(SEQ ID NO: 33) | gataacaacaatcggccctca<br>(SEQ ID NO: 63) | cagtcctatgacagcagc<br>ctgagtgctata<br>(SEQ ID NO: 88) |
| AA | TGSSSNIGAGYAVH<br>(SEQ ID NO: 34) | DNNNRP<br>(SEQ ID NO: 64) | QSYDSSLSAI<br>(SEQ ID NO: 89) |
| A-18<br>NA | aagtctagtcagagcctcctgcatagtg<br>atggaaagaactatttgttt<br>(SEQ ID NO: 35) | gaagtttcctaccggttctct<br>(SEQ ID NO: 65) | atgcaaaatatacagcctc<br>ctctcacc<br>(SEQ ID NO: 90) |
| AA | KSSQSLLHSDGKNYLF<br>(SEQ ID NO: 36) | EVSYRFS<br>(SEQ ID NO: 66) | MQNIQPPLT<br>(SEQ ID NO: 91) |
| A-19<br>NA | aggtctagtcagagcctcctgcatagta<br>atggatacaactatttggat<br>(SEQ ID NO: 37) | ttgggttctaatcgggcctcc<br>(SEQ ID NO: 67) | atggaagctcttcaaacta<br>tgtgcagt<br>(SEQ ID NO: 92) |
| AA | RSSQSLLHSNGYNYLD<br>(SEQ ID NO: 38) | LGSNRAS<br>(SEQ ID NO: 68) | MEALQTMCS<br>(SEQ ID NO: 93) |
| A-20<br>NA | cgggcaagtcagggcattagaaatgatt<br>taggc<br>(SEQ ID NO: 39) | gctgcatccagtttgcaaagt<br>(SEQ ID NO: 44) | ctacagcataatagttacc<br>ctcgcagt<br>(SEQ ID NO: 94) |
| AA | RASQGIRNDLG<br>(SEQ ID NO: 14) | AASSLQS<br>(SEQ ID NO: 45) | LQHNSYPRS<br>(SEQ ID NO: 95) |

TABLE 2-continued

| | | | |
|---|---|---|---|
| A-21 NA | cgggcgagtcagggtattagcagctgg ttagcc (SEQ ID NO: 40) | gctgcatccagtttgcaaagt (SEQ ID NO: 44) | caacaggctaacagtttcc cgctcact (SEQ ID NO: 96) |
| AA | RASQGISSWLA (SEQ ID NO: 41) | AASSLQS (SEQ ID NO: 45) | QQANSFPLT (SEQ ID NO: 97) |
| A-22 NA | aggtctagtcagagcctcttggatagag atgatggagacacctatttggac (SEQ ID NO: 9) | acgctttcctatcgggcctct (SEQ ID NO: 42) | atgcaacgtatagagtttc cattcactt (SEQ ID NO: 98) |
| AA | RSSQSLLDRDDGDTYLD (SEQ ID NO: 10) | TLSYRAS (SEQ ID NO: 43) | MQRIEFPFT (SEQ ID NO: 72) |
| A-23 NA | cgggcgagtcagggtattagcagctgg ttagcc (SEQ ID NO: 40) | actgcatccactttgcaaagt (SEQ ID NO: 69) | caacagtctaacagtttcc cgctcact (SEQ ID NO: 99) |
| AA | RASQGISSWLA (SEQ ID NO: 41) | TASTLQS (SEQ ID NO: 70) | QQSNSFPLT (SEQ ID NO: 100) |
| HEAVY CHAINS H1 to H23 | | | |
| A-1 NA | agctatggcatgcac (SEQ ID NO: 101) | tctatatggtatgatggaagtaataaatatt atgtagactccgtgaagggc (SEQ ID NO: 123) | cttggtggtggttttgactac (SEQ ID NO: 164) |
| AA | SYGMH (SEQ ID NO: 102) | SIWYDGSNKYYVDSVKG (SEQ ID NO: 124) | LGGGFDY (SEQ ID NO: 165) |
| A-2 NA | agctatggcatgcac (SEQ ID NO: 101) | tttatatggtatgatggaagtgaaaaatat tatgtagactccgtgaagggc (SEQ ID NO: 125) | atgggaggcggctttgactac (SEQ ID NO: 166) |
| AA | SYGMH (SEQ ID NO: 102) | FIWYDGSEKYYVDSVKG (SEQ ID NO: 126) | MGGGFDY (SEQ ID NO: 167) |
| A-3 NA | agctatggcatgcac (SEQ ID NO: 101) | gttatgtggtatgatggaagtaataaaga ctatgtagactccgtgaagggc (SEQ ID NO: 127) | gaaaaagatcattacgacattttgactggttata actactactacggtctggacgtc (SEQ ID NO: 168) |
| AA | SYGMH (SEQ ID NO: 102) | VMWYDGSNKDYVDSVK G (SEQ ID NO: 128) | EKDHYDILTGYNYYYGLDV (SEQ ID NO: 169) |
| A-4 NA | agctatggcatgcac (SEQ ID NO: 101) | gttatgtggtatgatggaagtaataaaga ctatgtagactccgtgaagggc (SEQ ID NO: 127) | gaaaaagatcattacgacattttgactggttata actactactacggtctggacgtc (SEQ ID NO: 168) |
| AA | SYGMH (SEQ ID NO: 102) | VMWYDGSNKDYVDSVK G (SEQ ID NO: 128) | EKDHYDILTGYNYYYGLDV (SEQ ID NO: 169) |
| A-5 NA | acctatgggatgcac (SEQ ID NO: 103) | gttatatcagatgatggaagtcataaata ctctgcagactccgtgaagggc (SEQ ID NO: 129) | gaggagacgtattacgatattttgactggctat catcactactacggtatggacgtc (SEQ ID NO: 170) |
| AA | TYGMH (SEQ ID NO: 104) | VISDDGSHKYSADSVKG (SEQ ID NO: 130) | EETYYDILTGYHHYYGMDV (SEQ ID NO: 171) |
| A-6 NA | agctatggcatgcac (SEQ ID NO: 101) | gaaatatggaatgatggaagtaataaata ctatgcagactccgtgaagggc (SEQ ID NO: 131) | gagcctcagtattacgatattttgactggttatg ataactactacggtatggacgtc (SEQ ID NO: 172) |
| AA | SYGMH (SEQ ID NO: 102) | EIWNDGSNKYYADSVKG (SEQ ID NO: 132) | EPQYYDlLTGYDNYYGMDV (SEQ ID NO: 173) |
| A-7 NA | agctatggcatgcac (SEQ ID NO: 105) | gtgatatcacatgatggaagtgataaata ctatgcagactccgtgaagggc (SEQ ID NO: 133) | gaaaaaccgtattacgatattttgactggttattt ctactactatggtatggacgtc (SEQ ID NO: 174) |
| AA | SYDMH (SEQ ID NO: 106) | VISHDGSDKYYADSVKG (SEQ ID NO: 134) | EKPYYDILTGYFYYYGMDV (SEQ ID NO: 175) |
| A-8 NA | agctatggcatgcac (SEQ ID NO: 101) | ggtatatggtatgatggaaggaataaata ctatgtagactccgtgaagggc (SEQ ID NO: 135) | ttagcagtggcctttgactac (SEQ ID NO: 176) |

TABLE 2-continued

| | | | |
|---|---|---|---|
| AA | SYGMH (SEQ ID NO: 102) | GIWYDGRNKYYVDSVKG (SEQ ID NO: 136) | LAVAFDY (SEQ ID NO: 177) |
| A-9 NA | agctatggcatgcac (SEQ ID NO: 101) | gttatgtggtatgatggaagtaataaagactatgtagactccgtgaagggc (SEQ ID NO: 127) | gaaaaagatcattacgacattttgactggttataactactactacggtctggacgtc (SEQ ID NO: 168) |
| AA | SYGMH (SEQ ID NO: 102) | VMWYDGSNKDYVDSVKG (SEQ ID NO: 128) | EKDHYDILTGYNYYYGLDV (SEQ ID NO: 169) |
| A-10 NA | agcaactatgctgcttggaac (SEQ ID NO: 107) | aggacatactacaggtccaagtggtataatgattatgcagtatctgtgagaagt (SEQ ID NO: 137) | gaagatggcagtggctggtacggtgcttttgacatc (SEQ ID NO: 178) |
| AA | SNYAAWN (SEQ ID NO: 108) | RTYYRSKWYNDYAVSVRS (SEQ ID NO: 138) | EDGSGWYGAFDI (SEQ ID NO: 179) |
| A-11 NA | agctatgacatgcac (SEQ ID NO: 109) | tttatatcagatgatggaagtaataaatactatggagactccgtgaagggc (SEQ ID NO: 139) | gatcaatacgatattttgactggttattcttctgatgcttttgatatc (SEQ ID NO: 180) |
| AA | SYDMH (SEQ ID NO: 106) | FISDDGSNKYYGDSVKG (SEQ ID NO: 140) | DQYDILTGYSSDAFDI (SEQ ID NO: 181) |
| A-12 NA | agctatgacatgcac (SEQ ID NO: 109) | tttatatcagatgatggaagtaataaatattatggagactccgtgaagggc (SEQ ID NO: 141) | gatcaatacgatattttgactggttattcttctgatgcttttgatatc (SEQ ID NO: 180) |
| AA | SYDMH (SEQ ID NO: 106) | FISDDGSNKYYGDSVKG (SEQ ID NO: 140) | DQYDILTGYSSDAFDI (SEQ ID NO: 181) |
| A-13 NA | agctatgacatgcac (SEQ ID NO: 109) | gttatatcatatgatggaagtaataaatactatggagactccgtgaagggc (SEQ ID NO: 142) | gatcaatacgatattttgactggttattcttctgatgcttttgatatc (SEQ ID NO: 180) |
| AA | SYDMH (SEQ ID NO: 106) | VISYDGSNKYYGDSVKG (SEQ ID NO: 143) | DQYDILTGYSSDAFDI (SEQ ID NO: 181) |
| A-14 NA | aactatggcatgcac (SEQ ID NO: 110) | gttatatggtatgatggaagtaataaatactatgcagactccgtgaagggc (SEQ ID NO: 144) | gcctattacgatattttgactgattaccccagtatgactactactacggtatggacgtc (SEQ ID NO: 182) |
| AA | NYGMH (SEQ ID NO: 111) | VIWYDGSNKYYADSVKG (SEQ ID NO: 145) | AYYDILTDYPQYDYYYGMDV (SEQ ID NO: 183) |
| A-15 NA | agctatggcatgcac (SEQ ID NO: 101) | cttatatcatttgatggaagtaataaatactatgcagactccgtgaagggc (SEQ ID NO: 146) | gatgggtattacgatattttgactggttatgaggatgatgcttttgatatc (SEQ ID NO: 184) |
| AA | SYGMH (SEQ ID NO: 102) | LISFDGSNKYYADSVKG (SEQ ID NO: 147) | DGYYDILTGYEDDAFDI (SEQ ID NO: 185) |
| A-16 NA | ggctactatttgcac (SEQ ID NO: 112) | tggatcatccctgacagtggtggcacaaagtatgcacagaagtttcagggc (SEQ ID NO: 148) | gaagggtttcattacgatattttgactggttcctacttctactactacggtatggacgtc (SEQ ID NO: 186) |
| AA | GYYLH (SEQ ID NO: 113) | WIIPDSGGTKYAQKFQG (SEQ ID NO: 149) | EGFHYDILTGSYFYYYGMDV (SEQ ID NO: 187) |
| A-17 NA | agctatggtatcagt (SEQ ID NO: 114) | tggatcggcgtttacaatggtcacacaaaatatgcacagaagttccagggc (SEQ ID NO: 150) | agggtagcagtggctgggtactttgactac (SEQ ID NO: 188) |
| AA | SYGIS (SEQ ID NO: 115) | WIGVYNGHTKYAQKFQG (SEQ ID NO: 151) | RVAVAGYFDY (SEQ ID NO: 189) |
| A-18 NA | aagtctagtcagagcctcctgcatagtgatggaagaactatttgttt (SEQ ID NO: 116) | gaagtttcctaccggttctct (SEQ ID NO: 152) | atgcaaaatatacagcctcctctcacc (SEQ ID NO: 190) |
| AA | KSSQSLLHSDGKNYLF (SEQ ID NO: 117) | VIWYDGSHKYYEDSVKG (SEQ ID NO: 153) | VGYGSGWYEYYYHYGMDV (SEQ ID NO: 191) |

TABLE 2-continued

| | | | | |
|---|---|---|---|---|
| A-19 NA | agctatggcatgcac (SEQ ID NO: 101) | attatatggtctgatggaattaacaaatac tatgcagactccgtgaagggc (SEQ ID NO: 154) | gagagaggcctctacgatattttgactggttatt ataactactacggtattgacgtc (SEQ ID NO: 192) | |
| AA | SYGMH (SEQ ID NO: 102) | IIWSDGINKYYADSVKG (SEQ ID NO: 155) | ERGLYDILTGYYNYYGIDV (SEQ ID NO: 193) | |
| A-20 NA | ggctataccttgaac (SEQ ID NO: 117) | aacattaatagtaggagtagtctcatatac tacacagactctgtgaagggc (SEQ ID NO: 156) | gatcagtataactggaactactactacggtatg gacgtc (SEQ ID NO: 194) | |
| AA | GYTLN (SEQ ID NO: 118) | NINSRSSLIYYTDSVKG (SEQ ID NO: 157) | DQYNWNYYYGMDV (SEQ ID NO: 195) | |
| A-21 NA | agctatgccatgaac (SEQ ID NO: 119) | tacattggtagtagtagtagtgccatatac tacggagactctgtgaagggc (SEQ ID NO: 158) | tatagaagtggctggtcccccctctttgacttc (SEQ ID NO: 196) | |
| AA | SYAMN (SEQ ID NO: 120) | YIGSSSSAIYYGDSVKG (SEQ ID NO: 159) | YRSGWSPLFDF (SEQ ID NO: 197) | |
| A-22 NA | agctatggcatgcac (SEQ ID NO: 101) | tctatatggtatgatggaagtaataaatatt atgtagactccgtgaagggc (SEQ ID NO: 160) | cttggtggtggttttgactac (SEQ ID NO: 164) | |
| AA | SYGMH (SEQ ID NO: 102) | SIWYDGSNKYYVDSVKG (SEQ ID NO: 161) | LGGGFDY (SEQ ID NO: 165) | |
| A-23 NA | agatatgccatgaac (SEQ ID NO: 121) | tacattggtagtagtagtagtgccatatac tacgcagactctgtgaagggc (SEQ ID NO: 162) | tatagcagtggctggtcccccctctttgactac (SEQ ID NO: 198) | |
| AA | RYAMN (SEQ ID NO: 122) | YIGSSSSAIYYADSVKG (SEQ ID NO: 163) | YSSGWSPLFDY (SEQ ID NO: 199) | |

CDR Consensus Sequences

Light Chain CDR1
Group 1

RSSQSLLDRDDGDTYLD    (SEQ ID NO: 10)

RSSQSLLDSADGDTYLD    (SEQ ID NO: 12)

RSTQSLLDSDDGDTYLD    (SEQ ID NO: 20)

```
    X1           X2  X3
R S S   Q S L L D R  D  D G T Y T L D
    T           S    A
``` i.  R S $X_1$ Q S L L D $X_2$ $X_3$ D G T Y T L D    (SEQ ID NO: 200)

$X_1$ is a serine residue or a threonine residue, $X_2$ is an arginine residue or a serine residue, $X_3$ is an aspartate residue or an alanine residue, Group 2

RASQDIRNDFG    (SEQ ID NO: 18)

RASQGIRNDLG    (SEQ ID NO: 14)

```
      X4       X5
R A S Q G  I R N D L  G
      D          F
``` ii.  R A S Q $X_4$ I R N D $X_5$ G    (SEQ ID NO: 201)

$X_4$ is a glycine residue or an aspartate residue, $X_5$ is a leucine residue or a phenylalanine residue.

Group 3

SGDKLGDKYVC    (SEQ ID NO: 24)

SGDKLGDKYAC    (SEQ ID NO 26)

TABLE 2-continued

```
              X₆
S G D K L G D K Y V  C
                  A
``` iii. S G D K L G D K Y X₆ C                (SEQ ID NO: 202)

X₆ is a valine residue or an alanine residue

Heavy Chain CDR1
Group 1

TYGMH-         (SEQ ID NO: 104)

SYGMH-         (SEQ ID NO: 102)

SYDMH-         (SEQ ID NO: 106)

```
X₇   X₈
S  Y G  M H
T    D
``` i.  X₇ Y X₈ M H                            (SEQ ID NO: 203)

X₇ is a serine residue or a threonine residue,

X₈ is a glycine residue, or an aspartate residue,

Light Chain CDR2
Group 1

AASSLQS        (SEQ ID NO: 45)

AASSLES        (SEQ ID NO: 50)

```
           X₉
A A S S L Q  S
           E
``` i.  A A S S L X₉ S                         (SEQ ID NO: 204)

X₉ is a glutamine residue or a glutamate residue,

Group 2

QTSKRPS        (SEQ ID NO: 54)

QSTKRPS        (SEQ ID NO: 56)

```
  X₁₀ X₁₁
Q  T   S   K R P S
   S   T
``` ii.  Q X₁₀ X₁₁ K R P S                     (SEQ ID NO: 205)

X₁₀ is a serine residue or a threonine residue,

X₁₁ is a threonine residue or a serine residue,

Heavy Chain CDR2
Group 1

SIWYDGSNKYYVDSVKG    (SEQ ID NO: 124)

FIWYDGSEKYYVDSVKG    (SEQ ID NO: 126)

VIWYDGSNKYYADSVKG    (SEQ ID NO: 145)

EIWNDGSNKYYADSVKG    (SEQ ID NO: 132)

```
X₁₂    X₁₃    X₁₄    X₁₅
S  I W Y  D G S N  K Y Y V  D S V K G
F      N         E      A
V
E
``` i.  X₁₂ I W X₁₃ D G S X₁₄ K Y Y X₁₅ D S V K G    (SEQ ID NO: 206)

X₁₂ is a serine residue, a phenylalanine residue, a valine residue, or a glutamate residue, TABLE 2-continued $X_{13}$ is a tyrosine residue or an asparagine residue, $X_{14}$ is an asparagine residue or a glutamate residue, $X_{15}$ is a valine residue or an alanine residue, Group 2

VISHDGSDKYYADSVKG    (SEQ ID NO: 134)

FISDDGSNKYYGDSVKG    (SEQ ID NO: 140)

VISYDGSNKYYGDSVKG    (SEQ ID NO: 143)

VISDDGSHKYSADSVKG    (SEQ ID NO: 130)

```
     X16   X17    X18    X19 X20
     V  I S H  D G S D  K Y Y  A  D S V K G
     F      D        N      S  G
            Y        H
``` ii.  $X_{16}$ I S $X_{17}$ D G S $X_{18}$ K Y $X_{19}$ $X_{20}$ D S V K G    (SEQ ID NO: 207)

$X_{16}$ is a valine residue or a phenylalanine residue, $X_{17}$ is a histidine residue, an aspartate residue, or a tyrosine residue, $X_{18}$ is an aspartate residue, an asparagine residue, or a histidine residue, $X_{19}$ is a tyrosine residue or a serine residue, $X_{20}$ is an alanine residue or a glycine residue, Light Chain CDR3
Group 1

LQHNSDPLT    (SEQ ID NO: 76)

LQQNSYPLT    (SEQ ID NO: 80)

LQHNSNPLT    (SEQ ID NO: 74)

```
        X21    X22
    L Q H  N S N  P L T
        Q      D
               Y
``` i.   L Q $X_{21}$ N S $X_{22}$ P L T    (SEQ ID NO: 208)

$X_{21}$ is a histidine residue, or a glutamine residue, $X_{22}$ is an asparagine residue, an aspartate residue, or a tyrosine residue, Group 2

QAWDSNTVI    (SEQ ID NO: 78)

QAWDSSTVV    (SEQ ID NO: 80)

```
            X23     X24
    Q A W D S N   T V I
              S       V
``` ii.  Q A W D S $X_{23}$ T V $X_{24}$    (SEQ ID NO: 209)

$X_{23}$ is an asparagine residue or a serine residue, $X_{24}$ is an isoleucine residue or a valine residue, Heavy Chain CDR3
Group 1

EKDHYDILTGYNYYYGLDV (SEQ ID NO: 169)

EETYYDILTGYHHYYGMDV (SEQ ID NO: 171)

EPQYYDILTGYDNYYGMDV (SEQ ID NO: 173)

EKPYYDILTGYFYYYGMDV (SEQ ID NO: 175)

TABLE 2-continued

```
         X25 X26 X27        X28 X29     X30
       E  K   D   H   YDILTGY N   Y   Y Y G L   D V
          E   T   Y            H   H           M
          P   Q                D   N
              P                F
``` i.   E X$_{25}$ X$_{26}$ X$_{27}$ Y D I L T G Y X$_{28}$ X$_{29}$ Y Y G X$_{30}$ D V    (SEQ ID NO: 210)

X$_{25}$ is a lysine residue, a glutamate residue, or a proline residue,

X$_{26}$ is an aspartate residue, a threonine residue, a glutamine residue, or a proline residue, X$_{27}$ is a histidine residue or a tyrosine residue, X$_{28}$ is an asparagine residue, a histidine residue, an aspartate residue, or a phenylalanine residue, .

X$_{29}$ is a tyrosine residue, a histidine residue, or an asparagine residue,

X$_{30}$ is a leucine residue or a methionine residue,

Group 2

LGGGFDY              (SEQ ID NO: 165)

MGGGFDY              (SEQ ID NO: 167)

```
X31
L     G G G F D Y
M
``` ii.  X$_{31}$ G G G F D Y                (SEQ ID NO: 211)

X$_{31}$ is a leucine residue or a methionine residue.

In another aspect, the present invention provides antigen binding proteins that comprise a light chain variable region selected from the group consisting of L1-L23 or a heavy chain variable region selected from the group consisting of H1-H23, and fragments, derivatives, muteins, and variants thereof. Such an antigen binding protein can be denoted using the nomenclature "LxHy", wherein "x" corresponds to the number of the light chain variable region and "y" corresponds to the number of the heavy chain variable region. For example, L2H1 refers to an antigen binding protein with a light chain variable region comprising the amino acid sequence of L2 and a heavy chain variable region comprising the amino acid sequence of H1 as shown in Table 3 below. The CDR and framework regions of each of these variable domain sequences are also identified in Table 3 below. Antigen binding proteins of the invention include, for example, antibodies having a combination of light chain and heavy chain variable domains selected from the group of combinations consisting of L1H1, L2H2, L3H3, L4H4, L5H5, L6H6, L7H7, L8H8, L9H9, L10H10, L11H11, L12H12, L13H13, L14H14, L15H15, L16H16, H17H17, L18H18, L19H19, L20H20, L21H21, L22H22, and L23H23. In one embodiment, the antibodies are human antibodies.

Table 3 below also provides the polynucleotide (DNA) sequences encoding the amino acid sequences of the variable light and variable heavy domains for exemplary GCGR antibodies.

TABLE 3

Anti-GCGR Variable Region Polynucleotide Sequences and Amino Acid Sequences

Light Chain Variable Region Polynucleotide and Amino acid sequences

L1 (A-1)                                                                    (SEQ ID NO: 212)

```
gatattgtgctgacccagactccactctccctgcccgtcacccctggagagccggcctccatctcctgcaggtctagtcagagcctcttg
gatagagatgatggagacacctatttggactggtacctgcagaagccagggcagtctccacagctcctgatctatacgctttcctatcgg
gcctctggagtcccagacaggttcagtggcagtgggtcaggcactgatttctcactgaaaatcagcagggtggaggctgaggatgttg
gagtttattactgcatgcaacgtatagagtttccattcactttcggccctgggaccaaagtggatatcaaa
```

(SEQ ID NO: 213)

```
DIVLTQTPLSLPVTPGEPASISCRSSQSLLDRDDGDTYLDWYLQKPGQSPQLLIYTLSY
RASGVPDRFSGSGSGTDFSLKISRVEAEDVGVYYCMQRIEFPFTFGPGTKVDIK
```

L2 (A-2)                                                                    (SEQ ID NO: 214)

```
agactccactctccctgcccgtcacccctggagagccggcctccatctcctgcaggtctagtcagagcctcttggatagtgctgatgga
gacacctatttggactggtacctgcagaagccagggcagtctccacagctcctgatctatacgctttcctatcgggcctctggagtccca
gacaggttcagtggcagtgggtcagacactgatttctcactgaaaatcagcagggtggaggctgaggatgttggagtttattactgcatg
caacgtatagagtttccattcactttcggccctgggaccaaagtggatatcaaa
```

TABLE 3-continued

Anti-GCGR Variable Region Polynucleotide Sequences and Amino Acid Sequences (SEQ ID NO: 215)

DIVMTQTPLSLPVTPGEPASISCRSSQSLLDSADGDTYLDWYLQKPGQSPQLLIYTLSY
RASGVPDRFSGSGSDTDFSLKISRVEAEDVGVYYCMQRIEFPFTFGPGTKVDIK

L3 (A-3) (SEQ ID NO: 216)

gacatccagatgacccagtctccatcctccctgtctgcatctgtaggagacagagtcaccatcacttgccgggcaagtcagggcattag
aaatgatttaggctggtatcagcagaaaccagggaaagcccctaagcgcctgatctatgctgcatccagtttgcaaagtggggtcccat
caaggttcagcggcagtggatctgggacagaattcactctcacaatcagcagtgtgcagcctgaagattttgtaacttattactgtctaca
gcataatagtaaccctctcactttcggcggagggaccaaggtggagatcaaa (SEQ ID NO: 217)

DIQMTQSPSSLSASVGDRVTITCRASQGIRNDLGWYQQKPGKAPKRLIYAASSLQSGV
PSRFSGSGSGTEFTLTISSVQPEDFVTYYCLQHNSNPLTFGGGTKVEIK

L4 (A-4) (SEQ ID NO: 218)

gacatccagatgacccagtctccatcctccctgtctgcatctgtaggagacagagtcaccatcacttgccgggcaagtcagggcattag
aaatgatttaggctggtatcagcagaaaccagggaaagcccctaagcgcctgatctatgctgcatccagtttgcaaagtggggtcccat
caaggttcagcggcagtggatctgggacagaattcactctcacaatcagcagtctgcagcctgaagattttgcaacttattactgtctaca
gcataatagtaaccctctcactttcggcggagggaccaaggtggagatcaaa (SEQ ID NO: 219)

DIQMTQSPSSLSASVGDRVTITCRASQGIRNDLGWYQQKPGKAPKRLIYAASSLQSGV
PSRFSGSGSGTEFTLTISSLQPEDFATYYCLQHNSNPLTFGGGTKVEIK

L5 (A-5) (SEQ ID NO: 220)

gacatccagatgacccagtctccatcctccctgtctgcatttgtaggagacagagtcaccatcacttgccgggcaagtcagggcattag
aaatgatttaggctggtatcagcagaaaccagggaaagcccctaagcgcctgctctatgctgcctccagtttgcaaagtggggtcccat
caaggttcagcggcagtgggtctgggtcagaattcactctcacaatcagcagcctgcagcctgaagattttgcaacttattactgtctaca
gcataatgtgacccgctcacttcggccaagggacacgactggagattaaa (SEQ ID NO: 221)

DIQMTQSPSSLSAFVGDRVTITCRASQGIRNDLGWYQQKPGKAPKRLLYAASSLQSG
VPSRFSGSGSGSEFTLTISSLQPEDFATYYCLQHNSDPLTFGQGTRLEIK

L6 (A-6) (SEQ ID NO: 222)

gaaattgtgttgacgcagtctccaggcaccctgtctttgtttccaggggaaagagccaccctctcctgcagggccagtcagagtgttagc
agcaactacttagcctggtaccagcagaaatctggccaggctcccaggctcctcatctatggtgcatccagcagggccactggcatcc
cagacaggttcagtggcagtgggtctgggacagacttcactctcaccatcagcagactggagcctgaagattttgcagtgtattactgtc
aacaatatggtaactcaccattcactttcggccctgggaccaatgtggatatcaaa (SEQ ID NO: 223)

EIVLTQSPGTLSLFPGERATLSCRASQSVSSNYLAWYQQKSGQAPRLLIYGASSRATGI
PDRFSGSGSGTDFTLTISRLEPEDFAVYYCQQYGNSPFTFGPGTNVDIK

L7 (A-7) (SEQ ID NO: 224)

gacatccagatgacccagtctccatcctccctgtctgcatctgtaggagacagagtcaccgtcacttgccgggcaagtcaggacattag
aaatgattttggctggtatcagcaaaaaccagggaaagcccctaagcgcctgatctatgctgcatccagtttacaaagtggggtcccatc
aaggttcagcggcagtggatctgggacagaattcactctcacaatcagcagcctgcagcctgaagattttgcaacttattactgtctacag
caaaatagttacccgctcactttcgggggagggaccaaggtggaaatcaaa (SEQ ID NO: 225)

DIQMTQSPSSLSASVGDRVTVTCRASQDIRNDFGWYQQKPGKAPKRLIYAASSLQSG
VPSRFSGSGSGTEFTLTISSLQPEDFATYYCLQQNSYPLTFGGGTKVEIK

L8 (A-8) (SEQ ID NO: 226)

gatattgtgatgacccagactccactctccctgcccgtcacccctggagagccggcctccatctcctgcaggtctactcagagcctcttg
gatagtgatgatggagacacctatttggactggtacctgcagaagccggggcagtctccacagctcctgatctatacgctttcctatcgg
gcctctggagtcccagacaggttcagtggcagtgggtcaggcactgatttcacactgaaaatcagcagggtggaggctgaggatgttg
gagtttattactgcatgcaacgtatagagtttccattcactttcggccctgggaccaaagtggatatcaaa (SEQ ID NO: 227)

DIVMTQTPLSLPVTPGEPASISCRSTQSLLDSDDGDTYLDWYLQKPGQSPQLLIYTLSY
RASGVPDRFSGSGSGTDFTLKISRVEAEDVGVYYCMQRIEFPFTFGPGTKVDIK

L9 (A-9) (SEQ ID NO: 228)

gacatccagatgacccagtctccatcctccctgtctgcatctgtaggagacagagtcaccatcacttgccgggcaagtcagggcattag
aaatgatttaggctggtatcagcagaaaccagggaaagcccctaagcgcctgatctatgctgcatccagtttggaaagtggggtcccat
caaggttcagcggcagtggatctgggacagaattcactctcacaatcagcagtgtgcagcctgaagattttgtaacttattactgtctaca
gcataatagtaaccctctcactttcggcggagggaccaaggtggagatcaaa (SEQ ID NO: 229)

DIQMTQSPSSLSASVGDRVTITCRASQGIRNDLGWYQQKPGKAPKRLIYAASSLESGV
PSRFSGSGSGTEFTLTISSVQPEDFVTYYCLQHNSNPLTFGGGTKVEIK

TABLE 3-continued

Anti-GCGR Variable Region Polynucleotide Sequences and Amino Acid Sequences

L10 (A-10) (SEQ ID NO: 230)
```
gacatccagatgacccagtctccatcctccctgtctgcatctgtgggagacagagtcaccatcacttgccaggcgagtcaggacattag
taagtatttaaattggtatcagcagaaaccagggaaagcccctaagctcctcatctacgatgcatccaatttggaaacagggtcccatc
aaggttcagtggaagtggatctgggacagattttactttcaccatcagcagcctgcagcctgaagatattgcaacatattactgtcaacag
tatggtaatctcccgatcaccttcggccaagggacacgactggagagtaaa
```

(SEQ ID NO: 231)
DIQMTQSPSSLSASVGDRCTITCQASQDISKYLNWYQQKPGKAPKLLIYDASNLETGV
PSRFSGSGSGTDFTFTISSLQPEDIATYYCQQYGNLPITFGQGTRLESK

L11 (A-11) (SEQ ID NO: 232)
```
tcctatgagctgactcagccaccctcagtgtccgtgtccccaggacagacagccagcatcacctgctctggagataaattgggggataa
atatgtttgctggtatcagcagaagccaggccagtcccctgtgctggtcatctatcaaacttccaagcggccctcagggatccctgagcg
gttctctggctccaactctgggaacacagccactctgaccatcagcgggacccaggctatggatgaggctgactattactgtcaggcgt
gggacagcaacactgtgattttcggcggagggaccaagctgaccgtccta
```

(SEQ ID NO: 233)
SYELTQPPSVSVSPGQTASITCSGDKLGDKYVCWYQQKPGQSPVLVIYQTSKRPSGIP
ERFSGSNSGNTATLTISGTQAMDEADYYCQAWDSNTVIFGGGTKLTVL

L12 (A-12) (SEQ ID NO: 234)
```
tcctatgagctgactcagccaccctcagtgtccgtgtccccaggacagacagccagcatcacctgctctggagataaattgggggataa
atatgtttgctggtatcagcagaagccaggccagtcccctgtgctggtcatctatcaaacttccaagcggccctcagggatccctgagcg
gttctctggctccaactctgggaacacagccactctgaccatcagcgggacccaggctatggatgaggctgactattactgtcaggcgt
gggacagcagcactgtggttttcggcggagggaccaagctgaccgtccta
```

(SEQ ID NO: 235)
SYELTQPPSVSVSPGQTASITCSGDKLGDKYVCWYQQKPGQSPVLVIYQTSKRPSGIP
ERFSGSNSGNTATLTISGTQAMDEADYYCQAWDSSTVVFGGGTKLTVL

L13 (A-13) (SEQ ID NO: 236)
```
tcctatgagctgactcagccaccctcagtgtccgtgtccccaggacagacagccagcatcacctgctctggagataaattgggggataa
atatgcttgctggtatcagcagaagccaggccagtcccctgtactggtcatctatcaatctaccaagcggccctcagggatccctgagc
gtttctctggctccaactctgggaacacagccactctgaccatcagcgggacccaggctatggatgaggctgactattactgtcaggcg
tgggacagcagcactgtggtattcggcggagggaccaagctgaccgtccta
```

(SEQ ID NO: 237)
SYELTQPPSVSVSPGQTASITCSGDKLGDKYACWYQQKPGQSPVLVIYQSTKRPSGIP
ERFSGSNSGNTATLTISGTQAMDEADYYCQAWDSSTVVFGGGTKLTVL

L14 (A-14) (SEQ ID NO: 238)
```
aattttatgctgactcagccccactctgtgtcggagtctccggggaagacggtaaccatctcctgcacccgcagcagtggcagcattgtc
agcaactttgtgcaatggtaccagcagcgcccgggcagttcccccaccactgtgatctatgaggataaccaaagaccctctgggtcc
ctgatcggttctctggctccatcgacagctcctccaactctgcctccctcaccatctctggactgaagactgaggacgaggctgactact
actgtcagtcttatgataccagcaatcaggtgttcggcggagggaccaagctgaccgtcctg
```

(SEQ ID NO: 239)
NFMLTQPHSVSESPGKTVTISCTRSSGSIVSNFVQWYQQRPGSSPTTVIYEDNQRPSGV
PDRFSGSIDSSSNSASLTISGLKTEDEADYYCQSYDTSNQVFGGGTKLTVL

L15 (A-15) (SEQ ID NO: 240)
```
cagtctgtcctgactcagccaccccagcgtctgggaccccgggcagaggtcaccatctcgtgtactggaatcacctccaacatcg
gaagcaatactgtacactggtaccagcagttcccaggaacggcccccaaactcctcatctatagtaataatcagcggccctcagggtc
cctgaccgattctctggctccaagtctggcacctcagcctcctggccatcagtgggctccagtctgaggatgaggctgattattactgtg
cagcatgggatgacagcctgaatggtccggtgttcggcggagggaccaagctgaccgtccta
```

(SEQ ID NO: 241)
QSVLTQPPPASGTPGQRVTISCTGITSNIGSNTVHWYQQFPGTAPKLLIYSNNQRPSGV
PDRFSGSKSGTSASLAISGLQSEDEADYYCAAWDDSLNGPVFGGGTKLTVL

L16 (A-16) (SEQ ID NO: 242)
```
cagtctgtgctgactcagccaccctcagcgtctgggaccccgggcagaggtcaccatctcttgttctggaagcaggtccaacatcg
gaagtaattatgtatactggtaccaacagctcccaggaacggcccccaaactcctcatctataggaataatcagcggccctcagggtc
cctgaccgattctctggctccaagtctggcacctcagcctcctggccatcagtgggctccggtccgaggatgaggctgattattactgt
gcagcatgggatgacagcctgagtaggccggtattcggcggagggaccaagctgaccgtccta
```

(SEQ ID NO: 243)
QSVLTQPPSASGTPGQRVTISCSGSRSNIGSNYVYWYQQLPGTAPKLLIYRNNQRPSG
VPDRFSGSKSGTSASLAISGLRSEDEADYYCAAWDDSLSRPVFGGGTKLTVL

L17 (A-17) (SEQ ID NO: 244)
```
cagtctgtgctgacgcagccgccctcagtgtctggggccccagggcagagggtcaccatctcctgcactgggagcagctccaacatc
ggggcaggttatgctgtatacactggtaccagcagcttccaggaacagcccccaaactcctcatctatgataacaacaatcggccctcag
gggtccctgaccgattctctggctccaagtctggcacctcagcctcctggccatcactgggctccaggctgaggatgaggctgattatt
actgccagtcctatgacagcagcctgagtgctatattcggcggagggaccaagctgaccgtccta
```

TABLE 3-continued

Anti-GCGR Variable Region Polynucleotide Sequences and Amino Acid Sequences (SEQ ID NO: 245)

QSVLTQPPSVSGAPGQRVTISC<u>TGSSSNIGAGYAVH</u>WYQQLPGTAPKLLIY<u>DNNNRPS</u>
GVPDRFSGSKSGTSASLAITGLQAEDEADYYC<u>QSYDSSLSAI</u>FGGGTKLTVL

L18 (A-18) (SEQ ID NO: 246)

```
aatattgtgatgacccagactccactctctctgtccgtcaccc ctggacagccggcctccatctcctgcaagtctagtcagagcctcctgc
atagtgatggaaagaactatttgttttggtacctacagaagccaggccagtctccacagctcctgatctatgaagtttcctaccggttctctg
gagtgccagataggttcagtggcagcgggtcagggacagatttctcattgaaaatcagccgggtggaggctgaggatgttggggtttat
tactgcatgcaaaatatacagcctcctctcaccttcggccaagggacacgactggagattaaa
```

(SEQ ID NO: 247)

NIVMTQTPLSLSVTPGQPASISC<u>KSSQSLLHSDGKNYLF</u>WYLQKPGQSPQLLIY<u>EVSYR</u>
<u>FS</u>GVPDRFSGSGSGTDFSLKISRVEAEDVGVYYC<u>MQNIQPPLT</u>FGQGTRLEIK

L19 (A-19) (SEQ ID NO: 248)

```
ggtattgtgctgactcagtctccactctccctgcccgtcacccctggagagccggcctccatctcctgcaggtctagtcagagcctcctg
catagtaatggatacaactatttggattggtacttgcagaagccagggcagtctccgcagctcctgatctatttgggttctaatcgggcctc
cggggtccctgacaggttcagtggcagtggatcaggcacagattttacactgaaaatcagcagagtggaggctgaggatgttggggtt
tattactgcatggaagctcttcaaactatgtgcagttttggccaggggaccaagctggagatcaag
```

(SEQ ID NO: 249)

GIVLTQSPLSLPVTPGEPASISC<u>RSSQSLLHSNGYNYLD</u>WYLQKPGQSPQLLIY<u>LGSNR</u>
<u>AS</u>GVPDRFSGSGSGTDFTLKISRVEAEDVGVYYC<u>MEALQTMCS</u>FGQGTKLEIK

L20 (A-20) (SEQ ID NO: 250)

```
gacatccagatgacccagtctccatcctccctgtctgcatctgtaggagacagagtcaccatcacttgccgggcaagtcagggcattag
aaatgatttaggctggtatcagcagaaaccagggaaagcccctaagcgcctgatctatgctgcatccagtttgcaaagtggggtcccat
ctaggttcagcggcagtggatctgggacagaattcactctcacaatcagcaacctgcagcctgaagattttgcaacttattactgtctaca
gcataatagttaccctcgcagttttggccaggggaccaagctggagatcaaa
```

L21 (A-21) (SEQ ID NO: 251)

DIQMTQSPSSLSASVGDRVTITC<u>RASQGIRNDLG</u>WYQQKPGKAPKRLIY<u>AASSLQS</u>GV
PSRFSGSGSGTEFTLTISNLQPEDFATYYC<u>LQHNSYPRS</u>FGQGTKLEIK (SEQ ID NO: 252)

```
gacatccagatgacccagtctccatcttccgtgtctgcatctgtaggagacagagtcaccatcacttgtcgggcgagtcagggtattagc
agctggttagcctggtatcagcagaaaccagggaaagcccctaagctcctaatctatgctgcatccagtttgcaaagtgggtcccatc
acggttcagcggcagtgggtctgggacagattttcactctcaccatcagcagcctgcagcctgaagattttgcaacttactattgtcaaca
ggctaacagtttcccgctcactttcggcggagggaccaaggtggagatcaaa
```

(SEQ ID NO: 253)

DIQMTQSPSSVSASVGDRVTITC<u>RASQGISSWLA</u>WYQQKPGKAPKLLIY<u>AASSLQS</u>GV
PSRFSGSGSGTDFTLTISSLQPEDFATYYC<u>QQANSFPLT</u>FGGGTKVEIK

L22 (A-22) (SEQ ID NO: 254)

```
gatattgtgctgacccagactccactctccctgcccgtcacccctggagagccggcctccatctcctgcaggtctagtcagagcctcttg
gatagagatgatggagacacctatttggactggtacctgcagaagccagggcagtctccacagctcctgatctatacgctttcctatcgg
gcctctggagtcccagacaggttcagtggcagtgggtcaggcactgatttctcactgaaaatcagcagggtggaggctgaggatgttg
gagtttattactgcatgcaacgtatagagtttccattcacttcggcccctgggaccaaagtggatatcaaa
```

(SEQ ID NO: 255)

DIVLTQTPLSLPVTPGEPASISC<u>RSSQSLLDRDDGDTYLD</u>WYLQKPGQSPQLLIY<u>TLSY</u>
<u>RAS</u>GVPDRFSGSGSGTDFSLKISRVEAEDVGVYYC<u>MQRIEFPFT</u>FGPGTKVDIK

L23 (A-23) (SEQ ID NO: 256)

```
gacatccagatgacccagtctccatcttccgtgtctgcgtctgtaggggacagagtcaccatcacttgtcgggcgagtcagggtattagc
agctggttagcctggtatcagcagaaaccagggaaagcccctaagctcctgatctatactgcatccactttgcaaagtgggtcccatc
aaggttcagcggcagtggatctgggacagattttcactctcaccatcagcagcctgcagcctgaagattttgcaacttactattgtcaacag
tctaacagtttcccgctcactttcggcggagggaccaaggtggagatcaaa
```

(SEQ ID NO: 257)

DIQMTASPSSVSASVGDRVTITC<u>RASQGISSWLA</u>WYQQKPGKAPKLLIYTASTLQSGV
PSRFSGSGSGTDFTLTISSLQPEDFATYYC<u>QQSNSFPLT</u>FGGGTKVEIK

Heavy Chain Variable Region Polynucleotide and Amino acid Sequences

H1 (A-1) (SEQ ID NO: 258)

```
caggtgcagctggtggagtctgggggaggcgtggtccagcctgggaggtccctgagactctcctgtgcagcgtctggaatcaccttca
gtagctatggcatgcactgggtccgccaggctccaggcaaggggctggagtgggtggcatctatatggtatgatggaagtaataaatat
tatgtagactccgtgaagggccgattcaccatcttcagagacaattccaagaaaacgctgtatctgcaaatgaacaggctgagagcga
ggacacggctgtgtattactgtgcgagacttggtggtggttttgactactggggccagggaaccctggtcaccgtctcctca
```

(SEQ ID NO: 259)

QVQLVESGGGCQPGRSLRLSCAASGITFS<u>SYGMH</u>WVRQAPGKGLEWVA<u>SIWYDGS</u>
<u>NKYYVDSVKG</u>RFTIFRDNSKKTLYLQMNRLRAEDTAVYYCAR<u>LGGGFDY</u>WGQGTL
VTVSS

TABLE 3-continued

Anti-GCGR Variable Region Polynucleotide Sequences and Amino Acid Sequences

H2 (A-2) (SEQ ID NO: 260)
caggtgcaactggtggagtctgggggaggcgtggtccagcctgggaggtccctgagactctcctgtgcagcgtctggaatcaccttca
gtagctatggcatgcactgggtccgccagggtccaggcaaggggctggagtgggtggcatttatatggtatgatggaagtgaaaaata
ttatgtagactccgtgaagggccgattcaccatctccagagacaattccaagaacacgctgtatctgcaaatgaacagtctgagagccg
aggacacggctgtgtattactgtgcgagaatgggaggcggctttgactactggggccagggaaccctggtcaccgtctcctca (SEQ ID NO: 261)
QVQLVESGGGVVQPGRSLRLSCAASGITFSSYGMHWVRQGPGKGLEWVAFIWYDGS
EKYYVDSVKGRFTISRDNSKNTLYLQMNSLRAEDTAVYYCARMGGGFDYWGQGTL
VTVSS H3 (A-3) (SEQ ID NO: 262)
caggtgcagctggtggagtctgggggaggcgtggtccagcctgggaggtccctgagactctcctgtgcagcgtctggattcaccttca
gtagctatggcatgcactgggtccgccaggctccaggcaaggggctggagtgggtggcagttatgtggtatgatggaagtaataaag
actatgtagactccgtgaagggccgattcaccatctccagagacaattccaagaacacgctgtatctgcaaatgaaccgcctgagagcc
gaggacacggctgtgtattactgtgcgagagaaaaagatcattacgacattttgactggttataactactactacggtctggacgtctggg
gccaagggaccacggtcaccgtctcctca (SEQ ID NO: 263)
QVQLVESGGGVVQPGRSLRLSCAASGFTFSSYGMHWVRQAPGKGLEWVAVMWYD
GSNKDYVDSVKGRFTISRDNSKNTLYLQMNSLRAEDTAVYYCAREKDHYDILTGYN
YYYGLDVWGQGTTVTVSS H4 (A-4) (SEQ ID NO: 264)
caggtgcagctggtggagtctgggggaggcgtggtccagcctgggaggtccctgagactctcctgtgcagcgtctggattcaccttca
gtagctatggcatgcactgggtccgccaggctccaggcaaggggctggagtgggtggcagttatgtggtatgatggaagtaataaag
actatgtagactccgtgaagggccgattcaccatctccagagacaattccaagaacacgctgtatctgcaaatgaaccgcctgagagcc
gaggacacggctgtgtattactgtgcgagagaaaaagatcattacgacattttgactggttataactactactacggtctggacgtctggg
gccaagggaccacggtcaccgtctcctcagcctccaccaagggcccatcggtcttccccctggcgccctgctccaggagcacctccg
agagcacagcggccctgggctgcct (SEQ ID NO: 265)
QVQLVESGGGVVQPGRSLRLSCAASGFTFSSYGMHWVRQAPGKGLEQVAVMWYD
GSNKDYVDSVKGRFTISRDNSKNTLYLQMNSLRAEDTAVYYCAREKDHYDILTGYN
YYYGLDVWGQGTTVTVSS H5 (A-5) (SEQ ID NO: 266)
caggtgcagctggtggagtctgggggaggcgtggtccagcctgggaggtccctgagactctcctgtgcagcctctggattcaccttca
gtacctatgggatgcactgggtccgccaggctccaggcaagggtctggagtgggtggcagttatatcagatgatggaagtcataaata
ctctgcagactccgtgaagggccgattcaccatctccagagacaattccaagaacacgctgtatctgcaaatgaacagcctgagaactg
aggactcggctgtgtattactgtgcgagagaggagacgtattacgatattttgactggctatcatcactacggtatggacgtctggg
ccaagggaccacggtcaccgtctcctca (SEQ ID NO: 267)
QVQLVESGGGVVQPGRSLRLSCAASGFTFSTYGMHWVRQAPGKGLEWVAVISDDGS
HKYSADSVKGRFTISRDNSKNTLYLQMNSLRTEDSAVYYCAREETYYDILTGYHHY
YGMDVWGQGTTVTVSS H6 (A-6) (SEQ ID NO: 268)
caggtgcagctggtggagtctgggggaggcgtggtccagcctgggaggtccctgagactctcctgtgcagcgtctggattcaccttca
gtagctatggcatgcactgggtccgccaggctccaggcaaggggctggagtgggtggcagaaatatggaatgatggaagtaataaat
actatgcagactccgtgaagggccgattcaccatctccagagacaatcccaagaacacgctgtatctgcaaatgaacagcctgagagc
cgaggacacggctgtgtattattgtgcgagagagcctcagtattacgatattttgactggttatgataactactacggtatggacgtctggg
gccaagggaccacggtcaccgtctcctca (SEQ ID NO: 269)
QVQLVESGGGVVQPGRSLRLSCAASGFTFSSYGMHWVRQAPGKGLEWVAEIWNDG
SNKYYADSVKGRFTISRDNPKNTLYLQMNSLRAEDTAVYYCAREPQYYDILTGYDN
YYGMDVWGQGTTVTVSS H7 (A-7) (SEQ ID NO: 270)
caggtgcagctggtggagtctgggggaggcgtggtccagcctgggaggtccctgagactctcctgtgcagcctctggattcaccttca
gtagctatgacatgcactgggtccgccaggctccaggcaaggggctggagtgggtggcagtgatatcacatgatggaagtgataaat
actatgcagactccgtgaagggccgattcaccatctccagagacaattccaagaacacgctgtatctgcaaatgagcagtttgagagct
gaggacacggctgtgtattactgtgcgagagaaaaaccgtattacgatattttgactggttatttctactactatggtatggacgtctggg
ccaagggaccacggtcaccgtctcctca (SEQ ID NO: 271)
QVQLVESGGGVVQPGRSLRLSCAASGFTFSSYDMHWVRQAPGKGLEWVAVISHDGS
DKYYADSVKGRFTISRDNSKNTLYLQMSSLRAEDTAVYYCAREKPYYDILTGYFYY
YGMDVWGQGTTVTVSS H8 (A-8) (SEQ ID NO: 272)
caggtgcagttggcggagtctgggggaggcgtggtccagcctgggaggtccctgagactctcctgtacagcgtctggaatcaccttca
gtagctatggcatgcactgggtccgccaggctccaggcaaggggctggagtgggtggcaggtatatggtatgatggaaggaataaat
actatgtagactccgtgaagggccgattcaccatctccagagacaattccaagaaaacgctgtatctgcaaatgaacagcctgagagcc
gaggacacggctgtgtattactgtgcgaggttagcagtggcctttgactactggggccagggaacttggtcaccgtctcctca TABLE 3-continued Anti-GCGR Variable Region Polynucleotide Sequences and Amino Acid Sequences (SEQ ID NO: 273)

QVQLAESGGGVVQPGRSLRLSCTASGITFSSYGMHWVRAQPGKGLEWVAGIWYDG
RNKYYVDSVKGRFTISRDNSKKTLYLQMNSLRAEDTAVYYCARLAVAFDYWGQGT
LVTVSS

H9 (A-9)

(SEQ ID NO: 274)

caggtgcagctggtggagtctgggggaggcgtggtccagcctgggaggtccctgagactctcctgtgcagcgtctggattcaccttca
gtagctatggcatgcactgggtccgccaggctccaggcaaggggctggagtgggtggcagttatgtggtatgatggaagtaataaag
actatgtagactccgtgaagggccgattcaccatctccagagacaattccaagaacacgctgtatctgcaaatgaaccgcctgagagcc
gaggacacggctgtgtattactgtgcgagagaaaaagatcattacgacattttgactggttataactactactacggtctggacgtctggg
gccaagggaccacggtcaccgtctcctca (SEQ ID NO: 275)

QVQLVESGGGVVQPGRSLRLSCAASGFTFSSYGMHWVRQAPGKGLEWVAVMWYD
GSNKDYVDSVKGRFTISRDNSKNTLYLQMNRLRAEDTAVYYCAREKDHYDILTGYN
YYYGLDVWGQGTTVTVSS

H10 (A-10)

(SEQ ID NO: 276)

caggtacagctgcagcagtcaggtccaggactggtgaggccctcgcagaccctctcactcacctgtgccatctccggggacagtgtct
ctagcaactatgctgcttggaactggatcaggcagtccccatcgagaggccttgagtggctgggaaggacatactacaggtccaagtg
gtataatgattatgcagtatctgtgagaagtcgaacaaccatcaacccagacacatccaagaaccagttctccctgcagttgaactctgtg
actcccgaggacacggctgtgtattactgtacaagagaagatggcagtggctggtacggtgcttttgacatctggggccaagggacaa
tggtcaccgtctcttca (SEQ ID NO: 277)

QVQLQQSGPGLVRPSQTLSLTCAISGDSVSSNYAAWNWIRQSPSRGLEWLGRTYYRS
KWYNDYAVSVRSRTTINPDTSKNQFSLQLNSVTPEDTAVYYCTREDGSGWYGAFDI
WGQGTMVTVSS

H11 (A-11)

(SEQ ID NO: 278)

caggtgcaactggtggagtctgggggaggcgtggtccagcctgggaggtccctgagactctcctgtgcagcctctgggagcaccttc
agaagctatgacatgcactgggtccgccaggctccaggcaaggggctggagtgggtggcagttatatcagatgatggaagtaataaat
actatggagactccgtgaagggccgattgaccatctccagagacaattccaagaacacgctgtatctgcaaatgaacagcctgagagc
tgaggacacggctgtgtattactgtgcgagagatcaatacgatattttgactggttattcttctgatgcttttgatatctggggccaagggac
aatggtcaccgtctcttc (SEQ ID NO: 279)

QVQLVESGGGVVQPGRSLRLSCAASGSTFRSYDMHWVRQAPGKGLEWVAFISDDGS
NKYYGDSVKGRLTISRDNSKNTLYLQMNSLRAEDTAVYYCARDQYDILTGYSSDAF
DIWGQGTMVTVSS

H12 (A-12)

(SEQ ID NO: 280)

caggtgcaactggtggagtctgggggaggcgtggtccagcctgggaggtccctgagactctcctgtgcagcctctgggagcaccttc
agaagctatgacatgcactgggtccgccaggctccaggcaaggggctggagtgggtggcatttatatcagatgatgaagtaataaat
attatggagactccgtgaagggccgattgaccatctccagagacaattccaagaacacgctgtatctgcaaatgaacagcctgagagct
gaggacacggctgtgtattattgtgcgagagatcaatacgatattttgactggttattcttctgatgcttttgatatctggggccaagggaca
atggtcaccgtctcttca (SEQ ID NO: 281)

QVQLVESGGGVVQPGRSLRLSCAASGSTFRSYDMHWVRQAPGKGLEWVAFISDDGS
NKYYGDSVKGRLTISRDNSKNTLYLQMNSLRAEDTAVYYCARDQYDILTGYSSDAF
DIWGQGTMVTVSS

H13 (A-13)

(SEQ ID NO: 282)

caggtgcagctggtggagtctgggggaggcgtggtccagcctgggaggtccctgagactctcctgtgcagcctctggaagcaccttc
agaagctatgacatgcactgggtccgccaggctccaggcaaggggctggagtgggtggcagttatatcatatgatggaagtaataaat
actatggagactccgtgaagggccgattgaccatctccagagacaattccaagaacacgctgtatctgcaaatgaacagcctgagagc
tgaggacacggctgtgtattactgtgcgagagatcaatacgatattttgactggttattcttctgatgcttttgatatctggggccaagggac
aatggtcaccgtctcttca (SEQ ID NO: 283)

QVQLVESGGGVVQPGRSLRLSCAASGSTFRSYDMHWVRQAPGKGLEWVAVISYDG
SNKYYGDSVKGRLTISRDNSKNTLYLQMNSLRAEDTAVYYCARDQYDILTGYSSDA
FDIWGQGTMVTVSS

H14 (A-14)

(SEQ ID NO: 284)

caggtgcagctggtggagtctgggggaggcgtggtccagcctgggaggtccctgagactctcctgtgcagcgtctggattcaccttca
gtaactatggcatgcactgggtccgccaggctccaggcaaggggctggagtgggtggcagttatatggtatgatggaagtaataaata
ctatgcagactccgtgaagggccgattcaccatctccagagacaattccaagaacacgctgtatctgcaaatgaacagcctgagagcc
gaggacacggctgtgtattactgtgcgagagcctattacgatattttgactgattaccccagtatgactactacggtatggacgtctg
gggccaagggaccacggtcaccgtctcctca (SEQ ID NO: 285)

QVQLVESGGGVVQPGRSLRLSCAASGFTFSNYGMHWVRQAPGKGLEWVAVIWYDG
SNKYYADSVKGRFTISRDNSKNTLYLQMNSLRAEDTAVYYCARAYYDILTDYPQYD
YYYGMDVWGQGTTVTVSS

TABLE 3-continued

Anti-GCGR Variable Region Polynucleotide Sequences and Amino Acid Sequences

H15 (A-15) (SEQ ID NO: 286)
caggtgcagctggtggagtctgggggaggcgtggtccagcctgggaagtccctgagactctcctgtgcagtctctggattcatcttcag
tagctatggcatgcactgggtccgccaggctccaggcaagggctggagtgggtggcacttatatcatttgatggaagtaataaatact
atgcagactccgtgaagggccgattcaccatctccagagacaattccaagaacacgctgtatctgcaaatgaacagcctgagagctga
ggacacggctgtgtattactgtgcgagagatgggtattacgatattttgactggttatgaggatgatgcttttgatatctggggccaaggga
caatggtcaccgtctcttca (SEQ ID NO: 287)
QVQLVESGGGVVQPGKSLRLSCAVSGFIFSSYGMHWVRQAPGKGLEWVALISFDGS
NKYYADSVKGRFTISRDNSKNTLYLQMNSLRAEDTAVYYCARDGYYDILTGYEDDA
FDIWGQGTMVTVSS H16 (A-16) (SEQ ID NO: 288)
caggtgcagctggtgcagtctggggctgaggtgaagaagcctggggcctcagtgaaggtctcctgcaaggcttctggatacaccttca
ccggctactatttgcactgggtgcgacaggcccctggacaagggcttgagtggatggatggatggatcatcctgacagtggtggcacaaa
gtatgcacagaagtttcagggcagggtcaccatgaccagggacacgtccatcagcacagcctacttggagctgagcaggctgagatc
tgacgacacggccgtgtattactgtgcgagagaagggtttcattacgatattttgactggttcctacttctactactacggtatggacgtctg
gggccaagggaccacggtcaccgtctcctca (SEQ ID NO: 289)
QVQLVQSGAEVKKPGASVKVSCKASGYTFTGYYLHWVRQAPGQGLEWMGWIIPDS
GGTKYAQKFQGRVTMTRDTSISTAYLELSRLRSDDTAVYYCAREGFHYDILTGSYFY
YYGMDVWGQGTTVTVSS H17 (A-17) (SEQ ID NO: 290)
caggttcagctggtgcagtctggagctgaggtgaagaagcctggggcctcagtgaaggtctcctgcaaggcttctggttacacctttac
cagctatggtatcagttgggcgcgacaggcccctggacaagggcttgagtggatgggatggatcggcgtttacaatggtcacacaaaa
tatgcacagaagttccagggcagagtcaccatgaccacagacacatccacgagcacagcctacatggagctgaggagcctgagatct
gacgacacggccatatttactgtgcgagaagggtagcagtggctgggtactttgactactggggccagggaaccctggtcaccgtctcctca (SEQ ID NO: 291)
QVQLVQSGAEVKKPGASVKVSCKASGYTFTSYGISWARQAPGQGLEWMGWIGVYN
GHTKYAQKFQGRVTMTTDTSTSTAYMELRSLRSDDTAIFYCARRVAVAGYFDYWG
QGTLVTVSS H18 (A-18) (SEQ ID NO: 292)
caggtgcagctggtggagtctgggggaggcgtggtccagcctgggaggtccctgagactctcctgtgcagcgtctggattcaccttca
gtagatatggcatgcactgggtccgccaggctccaggcaagggctggagtgggtggcagttatatggtatgatgaagtcataaata
ctatgaagactccgtgaagggccgattcaccatctccagagacaattctaagaacacgctgtatctgcaaatgaacagcctgagagcc
gacgacacgggtgtgtattactgtgcgagagtcgggtatggcagtggctggtacgagtactattaccactacggtatggacgtctgggg
ccaagggaccacggtcaccgtctcctca (SEQ ID NO: 293)
QVQLVESGGGVVQPGRSLRLSCAASGFTFSRYGMHWVRQAPGKGLEWVAVIWYDG
SHKYYEDSVKGRFTISRDNSKNTLYLQMNSLRADDTGVYYCARVGYGSGWYEYYY
HYGMDVWGQGTTVTVSS H19 (A-19) (SEQ ID NO: 294)
caggtgcagctggtggagtctgggggaggcgtggtccagcctggggaggtccctgagactctcctgtgcagcgtctggattcaccttca
gtagctatggcatgcactgggtccgccaggctccaggcaagggctggagtgggtgacaattatatggtctgatggaattaacaaata
ctatgcagactccgtgaagggccgattcaccatatccagagacaattccaagaacacgctgaatctgcaaatgaacagtttgagagcc
gaggacacggctgtgtattactgtgcgagagagagaggcctctacgatattttgactggttattataactactacggtattgacgtctggg
gccaagggaccacggtcaccgtctcctca (SEQ ID NO: 295)
QVQLVESGGGVVQPGRSLRLSCAASGFTFSSYGMHWVRQAPGKGLEWVTIIWSDGI
NKYYADSVKGRFTISRDNSKNTLNLQMNSLRAEDTAVYYCARERGLYDILTGYYNY
YGIDVWGQGTTVTVSS H20 (A-20) (SEQ ID NO: 296)
gaggtgcagctggtggagtctgggggagacttggtacagcctgggggtccctgagactctcctgtgcagcctctggattcaccttca
gtggctataccttgaactgggtccgccaggctccagggaaggggctggagtgggtttcaaacattaatagtaggagtagtctcatatact
acacagactctgtgaagggccgattcaccatctccagagacaatgccaagaactcactgtatctgcaaatgaacagcctgagagacga
ggacacggctgtgtatttctgtgcgagagatcagtataactggaactactactacggtatggacgtctggggccaagggaccacggtca
ccgtctcctca (SEQ ID NO: 297)
EVQLVESGGDLVQPGGSLRLSCAASGFTFSGYTLNWVRQAPGKGLEWVSNINSRSSL
IYYTDSVKGRFTISRDNAKNSLYLQMNSLRDEDTAVYFCARDQYNWNYYYGMDVW
GQGTTVTVSS H21 (A-21) (SEQ ID NO: 298)
gaggtgcggctggtggagtctgggggagacttggtacagcctgggggtccctgagactctcctgtgcagcctctggattcaccttca
gtagctatgccatgaactgggtccgccaggctccagggaaggggctggagttttcatacattggtagtagtagtagtgccatatact
acggagactctgtgaagggccgattcaccatctccagagacaatgccaagaactcactgtatctgcaaatgaacagcctgagagacga
ggacacggctgtgtattactgtgcgagatatagaagtggctggtcccccctctttgacttctggggccagggaagcctggtcaccgtctc
ctca

TABLE 3-continued

Anti-GCGR Variable Region Polynucleotide Sequences and Amino Acid Sequences (SEQ ID NO: 299)

EVRLVESGGDLVQPGGSLRLSCAASGFTFSSYAMNWVRQAPGKGLEWISYIGSSSSAI
YYGDSVKGRFTISRDNAKNSLYLQMNSLRDEDTAVYYCARYRSGWSPLFDFWGQGS
LVTVSS

H22 (A-22) (SEQ ID NO: 300)

caggtgcagctggtggagtctgggggaggcgtggtccagcctggggaggtccctgagactctcctgtgcagcgtctggaatcaccttca
gtagctatggcatgcactgggtccgccaggctccaggcaaggggctggagtgggtggcatctatatggtatgatggaagtaataaatat
tatgtagactccgtgaagggccgattcaccatcttcagagacaattccaagaaaacgctgtatctgcaaatgaacaggctgagagccga
ggacacggctgtgtattactgtgcgagacttggtggtggttttgactactgggccagggaaccctggtcaccgtctcctca (SEQ ID NO: 301)

QVQLVESGGGVVQPGRSLRLSCAASGITFSSYGMHWVRQAPGKGLEWVASIWYDGS
NKYYVDSVKGRFTIFRDNSKKTLYLQMNRLRAEDTAVYYCARLGGGFDYWGQGTL
VTVSS

H23 (A-23) (SEQ ID NO: 302)

gaggtgcggctggtggagtctgggggaggcttggtacagcctgggggtccctgagactctcctgtacagcctctggattcccttca
atagatatgccatgaactgggtccgccaggctccagggaagggctggagtgggtttcatacattggtagtagtagtagtgccatatact
acgcagactctgtgaagggccgattcaccatctccagagacaatgccaagaactcactgtatctgcaaatgaacagcctgagagatga
agacacggctgtgtattactgtgcgagatatagcagtggctggtccccccctctttgactactggggccagggaaccctggtcaccgtctc
ctca (SEQ ID NO: 303)

EVRLVESGGGLVQPGGSLRLSCTASGFPFNRYAMNWVRQAPGKGLEWVSYIGSSSS
AIYYADSVKGRFTISRDNAKNSLYLQMNSLRDEDTAVYYCARYSSGWSPLFDYWGQ
GTLVTVSS

Particular embodiments of antigen binding proteins of the present invention comprise one or more amino acid sequences that are identical to the amino acid sequences of one or more of the CDRs and/or FRs (framework regions) illustrated above. In one embodiment, the antigen binding protein comprises a light chain CDR1 sequence illustrated above. In another embodiment, the antigen binding protein comprises a light chain CDR2 sequence illustrated above. In another embodiment, the antigen binding protein comprises a light chain CDR3 sequence illustrated in above. In another embodiment, the antigen binding protein comprises a heavy chain CDR1 sequence illustrated in above. In another embodiment, the antigen binding protein comprises a heavy chain CDR2 sequence illustrated above. In another embodiment, the antigen binding protein comprises a heavy chain CDR3 sequence illustrated above. In another embodiment, the antigen binding protein comprises a light chain FR1 sequence illustrated above. In another embodiment, the antigen binding protein comprises a light chain FR2 sequence illustrated above. In another embodiment, the antigen binding protein comprises a light chain FR3 sequence illustrated above. In another embodiment, the antigen binding protein comprises a light chain FR4 sequence illustrated above. In another embodiment, the antigen binding protein comprises a heavy chain FR1 sequence illustrated above. In another embodiment, the antigen binding protein comprises a heavy chain FR2 sequence illustrated above. In another embodiment, the antigen binding protein comprises a heavy chain FR3 sequence illustrated above. In another embodiment, the antigen binding protein comprises a heavy chain FR4 sequence illustrated above.

In another embodiment, at least one of the antigen binding protein's CDR3 sequences differs by no more than 6, 5, 4, 3, 2, 1 or 0 single amino acid addition, substitution, and/or deletion from a CDR3 sequence from A1-A23, as shown in Tables 2 and 3 above. In another embodiment, the antigen binding protein's light chain CDR3 sequence differs by no more than 6, 5, 4, 3, 2, 1 or 0 single amino acid addition, substitution, and/or deletion from a light chain CDR3 sequence from A1-A23 as shown above and the antigen binding protein's heavy chain CDR3 sequence differs by no more than 6, 5, 4, 3, 2, 1 or 0 single amino acid addition, substitution, and/or deletion from a heavy chain CDR3 sequence from A1-A23 as shown above. In another embodiment, the antigen binding protein further comprises 1, 2, 3, 4, or 5 CDR sequences that each independently differs by 6, 5, 4, 3, 2, 1, or 0 single amino acid additions, substitutions, and/or deletions from a CDR sequence of A1-A23. In another embodiment, the antigen binding protein comprises the CDRs of the light chain variable region and the CDRs of the heavy chain variable region set forth above. In another embodiment, the antigen binding protein comprises 1, 2, 3, 4, 5, and/or 6 consensus CDR sequences shown above. In a further embodiment, the antigen binding protein comprises the CDRs of any one of L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, and L23H23. In one embodiment, the antigen binding protein is a human antibody.

In one embodiment, the antigen binding protein (such as an antibody or antibody fragment) comprises a light chain variable domain comprising a sequence of amino acids that differs from the sequence of a light chain variable domain selected from the group consisting of L1 through L23 only at 15, 14, 13, 12, 11, 10, 9, 8, 7, 6, 5, 4, 3, 2, 1 or 0 residues, wherein each such sequence difference is independently either a deletion, insertion, or substitution of one amino acid residue. In another embodiment, the light-chain variable domain comprises a sequence of amino acids that is at least 70%, 75%, 80%, 85%, 90%, 95%, 97%, or 99% identical to the sequence of a light chain variable domain selected from the group consisting of L1-L23. In another embodiment, the light chain variable domain comprises a sequence of amino acids that is encoded by a nucleotide sequence that is at least 70%, 75%, 80%, 85%, 90%, 95%, 97%, or 99% identical to a L1-L23 polynucleotide sequence listed below. In another embodiment, the light chain variable domain comprises a sequence of amino acids that is encoded by a polynucleotide that hybridizes under moderately stringent conditions to the complement of a polynucleotide that encodes a light chain variable domain selected from the group consisting of L1-L23. In another embodiment, the light chain variable domain comprises a sequence of amino acids that is encoded by a polynucleotide that hybridizes under stringent conditions to the complement of a polynucleotide that encodes a light chain variable domain selected from the group consisting of L1-L23.

In another embodiment, the present invention provides an antigen binding protein comprising a heavy chain variable domain comprising a sequence of amino acids that differs from the sequence of a heavy chain variable domain selected from the group consisting of H1-H23 only at 15, 14, 13, 12, 11, 10, 9, 8, 7, 6, 5, 4, 3, 2, 1 or 0 residue(s), wherein each such sequence difference is independently either a deletion, insertion, or substitution of one amino acid residue. In another embodiment, the heavy chain variable domain comprises a sequence of amino acids that is at least 70%, 75%, 80%, 85%, 90%, 95%, 97%, or 99% identical to the sequence of a heavy chain variable domain selected from the group consisting of H1-H23. In another embodiment, the heavy chain variable domain comprises a sequence of amino acids that is encoded by a nucleotide sequence that is at least 70%, 75%, 80%, 85%, 90%, 95%, 97%, or 99% identical to a nucleotide sequence that encodes a heavy chain variable domain selected from the group consisting of H1-H23. In another embodiment, the heavy chain variable domain comprises a sequence of amino acids that is encoded by a polynucleotide that hybridizes under moderately stringent conditions to the complement of a polynucleotide that encodes a heavy chain variable domain selected from the group consisting of H1-H23. In another embodiment, the heavy chain variable domain comprises a sequence of amino acids that is encoded by a polynucleotide that hybridizes under stringent conditions to the complement of a polynucleotide that encodes a heavy chain variable domain selected from the group consisting of H1-H23.

Additional embodiments include antigen binding proteins comprising the combinations L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22 and L23H23.

Antigen binding proteins (e.g., antibodies, antibody fragments, and antibody derivatives) of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lanitto et al., Methods Mol. Biol. 178:303-16 (2002).

In one embodiment, an antigen binding protein of the invention further comprises the constant light chain kappa or lambda domains or a fragment of these. Sequences of the light chain constant regions and polynucleotides encoding them are provided in Table 4 below. In another embodiment, an antigen binding protein of the invention further comprises a heavy chain constant domain, or a fragment thereof, such as the IgG2 heavy chain constant region provided in Table 4.

In one embodiment, an IgG2 form of the human light chain and heavy chain amino acid sequences for antibody A-9 and A-3 are presented in SEQ ID NO: 310, SEQ ID NO: 311, SEQ ID NO: 312, and SEQ ID NO: 311 below.

TABLE 4

Light chain constant region
polynucleotide (kappa)

(SEQ ID NO: 304)
cgaactgtggctgcaccatctgtcttcatcttcccgccatctgatgagcagttgaaatctggaactgcctctgttgtgtgcctgctgaataa
cttctatcccagagaggccaaagtacagtggaaggtggataacgccctccaatcgggtaactcccaggagagtgtcacagagcagga
cagcaaggacagcacctacagcctcagcagcaccctgacgctgagcaaagcagactacgagaaacacaaagtctacgcctgcgaa
gtcacccatcagggcctgagctcgcccgtcacaaagagcttcaacaggggagagtgt amino acid (kappa)

(SEQ ID NO: 305)
RTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC polynucleotide (lambda)

(SEQ ID NO: 306)
ggtcagcccaaggctgcccctcggtcactctgttcccgccctcctctgaggagcttcaagccaacaaggccacactggtgtgtctcat
aagtgacttctaccgggagccgtgacagtggcctggaaggcagatagcagcccgtcaaggcgggagtggagaccaccacaccc
tccaaacaaagcaacaacaagtacgcggccagcagctatctgagcctgacgcctgagcagtggaagtcccacagaagctacagctg
ccaggtcacgcatgaagggagcaccgtggagaagacagtggcccctacagaatgttca amino acid (lambda)

(SEQ ID NO: 307)
GQPKAAPSVTLFPPSSEELQANKATLVCLISDFYPGAVTVAWKADSSPVKAGVETTTP
SKQSNNKYAASSYLSLTPEQWKSHRSYSCQVTHEGSTVEKTVAPTECS

TABLE 4-continued heavy chain constant region
polynucleotide (SEQ ID NO: 308)
```
gcctccaccaagggcccatcggtcttccccctggcgccctgctccaggagcacctccgagagcacagcggccctgggctgcctggt
caaggactacttccccgaaccggtgacggtgtcgtggaactcaggcgctctgaccagcggcgtgcacaccttcccagctgtcctacag
tcctcaggactctactccctcagcagcgtggtgaccgtgccctccagcaacttcggcacccagacctacacctgcaacgtagatcaca
agcccagcaacaccaaggtggacaagacagttgagcgcaaatgttgtgtcgagtgcccaccgtgcccagcacccacctgtggcagga
ccgtcagtcttcctcttccccccaaaacccaaggacaccctcatgatctcccggacccctgaggtcacgtgcgtggtggtggacgtgag
ccacgaagaccccgaggtccagttcaactggtacgtggacggcgtggaggtgcataatgccaagacaaagccacgggaggagcag
ttcaacagcacgttccgtgtggtcagcgtcctcaccgttgtgcaccaggactggctgaacggcaaggagtacaagtgcaaggtctcca
acaaaggcctcccagcccccatcgagaaaaccatctccaaaaccaaagggcagccccgagaaccacaggtacaccctgccccc
atcccgggaggagatgaccaagaaccaggtcagcctgacctgcctggtcaaaggcttctaccccagcgacatcgccgtggagtggg
agagcaatgggcagccggagaacaactacaagaccacacctcccatgctggactccgacggctccttcttcctctacagcaagctcac
cgtggacaagagcaggtggcagcaggggaacgtcttctcatgctccgtgatgcatgaggctctgcacaaccactacacgcagaaga
gcctctccctgtctccgggtaaa
```

Amino acid (SEQ ID NO: 309)
```
ASTKGPSVFPLAPCSRSTSESTAALGCLVKDYFPEPVTVSWNSGALTSGVHTFPAVLQ
SSGLYSLSSVVTVPSSNFGTQTYTCNVDHKPSNTKVDKTVERKCCVECPPCPAPPVA
GPSVFLFPPKPKDTLMISRTPEVTCVVVDVSHEDPEVQFNWYVDGVEVHNAKTKPRE
EQFNSTFRVVSVLTVVHQDWLNGKEYKCKVSNKGLPAPIEKTISKTKGQPREPQVYT
LPPSREEMTKNQVSLTCLVKGFYPSDIAVEWESNGQPENNYKTTPPMLDSDGSFFLYS
KLTVDKSRWQQGNVFSCSVMHEALHNHYTQKSLSLSPGK
```

IgG2 form light chain A-9

(SEQ ID NO: 310)
```
MDMRVPAQLLGLLLLWFPGARCDIQMTQSPSSLSASVGDRVTITCRASQGIRNDLGW
YQQKPGKAPKRLIYAASSLESGVPSRFSGSGSGTEFTLTISSVQPEDFVTYYCLQHNSN
PLTFGGGTKVEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGLSSPVTKS
FNRGEC
```

IgG2 form heavy chain A-9

(SEQ ID NO: 311)
```
MEFGLSWVFLVALLRGVQCQVQLVESGGGVVQPGRSLRISCAASGFTFSSYGMHW
VRQAPGKGLEWVAVMWYDGSNKDYVDSVKGRFTISRDNSKNTLYLQMNRLRAED
TAVYYCAREKDHYDILTGYNYYYGLDVWGQGTTVTVSSASTKGPSVFPLAPCSRSTS
ESTAALGCLVKDYFPEPVTVSWNSGALTSGVHTFPAVLQSSGLYSLSSVVTVPSSNFG
TQTYTCNVDHKPSNTKVDKTVERKCCVECPPCPAPPVAGPSVFLFPPKPKDTLMISRT
PEVTCVVVDVSHEDPEVQFNWYVDGVEVHNAKTKPREEQFNSTFRVVSVLTVVHQ
DWLNGKEYKCKVSNKGLPAPIEKTISKTKGQPREPQVYTLPPSREEMTKNQVSLTCL
VKGFYPSDIAVEWESNGQPENNYKTTPPMLDSDQSFFLYSKLTVDKSRWQQGNVFS
CSVMHEALHNHYTQKSLSLSPGK
```

IgG2 form light chain A-3

(SEQ ID NO: 312)
```
MDMRVPAQLLGLLLLWFPGARCDIQMTQSPSSLSASVGDRVTITCRASQGIRNDLGW
YQQKPGKAPKRLIYAASSLQSGVPSRFSGSGSGTEFTLTISSVQPEDFVTYYCLQHNSN
PLTFGGGTKVEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGLSSPVTKS
FNRGEC
```

IgG2 form heavy chain A-3

(SEQ ID NO: 311)
```
MEFGLSWVFLVALLRGVQCQVQLVESGGGVVQPGRSLRLSCAASGFTFSSYGMHW
VRQAPGKGLEWVAVMWYDGSNKDYVDSVKGRFTISRDNSKNTLYLQMNRLRAED
TAVYYCAREKDHYDILTGYNYYYGLDVWGQGTTVTVSSASTKGPSVFPLAPCSRSTS
ESTAALGCLVKDYFPEPVTVSWNSGALTSGVHTFPAVLQSSGLYSLSSVVTVPSSNFG
TQTYTCNVDHKPSNTKVDKTVERKCCVECPPCPAPPVAGPSVFLFPPKPKDTLMISRT
PEVTCVVVDVSHEDPEVQFNWYVDGVEVHNAKTKPREEQFNSTFRVVSVLTVVHQ
DWLNGKEYKCKVSNKGLPAPIEKTISKTKGQPREPQVYTLPPSREEMTKNQVSLTCL
VKGFYPSDIAVEWESNGQPENNYKTTPPMLDSDGSFFLYSKLTVDKSRWQQGNVFS
CSVMHEALHNHYTQKSLSLSPGK
```

The antigen binding proteins (for example, antibodies) of the present invention include those comprising, for example, the variable domain combinations L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, and L23H23 having a desired isotype (for example, IgA, IgG1, IgG2, IgG3, IgG4, IgM, IgE, and IgD) as well as Fab or F(ab')$_2$ fragments thereof. Moreover, if an IgG4 is desired, it may also be desired to introduce a point mutation in the hinge region as described in Bloom et al., 1997, Protein Science 6:407, (incorporated by reference herein) to alleviate a tendency to form intra-H chain disulfide bonds that can lead to heterogeneity in the IgG4 antibodies.

Antibodies and Antibody Fragments

In one embodiment the antigen binding proteins are antibodies. The term "antibody" refers to an intact antibody, or an antigen binding fragment thereof, as described extensively in the definition section. An antibody may comprise a complete antibody molecule (including polyclonal, monoclonal, chimeric, humanized, or human versions having full length heavy and/or light chains), or comprise an antigen binding fragment thereof. Antibody fragments include F(ab')$_2$, Fab, Fab', Fv, Fc, and Fd fragments, and can be incorporated into single domain antibodies, single-chain antibodies, maxibodies, minibodies, intrabodies, diabodies, triabodies, tetrabodies, v-NAR and bis-scFv (see e.g., Hollinger and Hudson, 2005, Nature Biotechnology, 23, 9, 1126-1136). Also included are antibody polypeptides such as those disclosed in U.S. Pat. No. 6,703,199, including fibronectin polypeptide monobodies. Other antibody polypeptides are disclosed in U.S. Patent Publication 2005/0238646, which are single-chain polypeptides. In one embodiment, the antibodies of the present invention comprise at least one CDR or consensus CDR set forth in Table 2 above. In another aspect, the present invention provides hybridomas capable of producing the antibodies of the invention, and methods of producing antibodies from hybridomas, as described further below.

Chimeric antibodies and humanized antibodies are defined in the definition section and may be prepared by known techniques. In one embodiment, a humanized monoclonal antibody comprises the variable domain of a murine antibody (or all or part of the antigen binding site thereof) and a constant domain derived from a human antibody. Alternatively, a humanized antibody fragment may comprise the antigen binding site of a murine monoclonal antibody and a variable domain fragment (lacking the antigen-binding site) derived from a human antibody. Procedures for the production of engineered monoclonal antibodies include those described in Riechmann et al., 1988, Nature 332:323, Liu et al., 1987, Proc. Nat. Acad. Sci. USA 84:3439, Larrick et al., 1989, Bio/Technology 7:934, and Winter et al., 1993, TIPS 14:139. In one embodiment, the chimeric antibody is a CDR grafted antibody. Techniques for humanizing antibodies are discussed in, e.g., U.S. Pat. Nos. 5,869,619; 5,225,539; 5,821, 337; 5,859,205; 6,881,557, Padlan et al., 1995, FASEB J. 9:133-39, Tamura et al., 2000, J. Immunol. 164:1432-41, Zhang, W., et al., Molecular Immunology. 42(12):1445-1451, 2005; Hwang W. et al., Methods. 36(1):3542, 2005; Dall'Acqua W F, et al., Methods 36(1):43-60, 2005; and Clark, M., Immunology Today. 21(8):397-402, 2000.

An antibody of the present invention may also be a fully human monoclonal antibody. Fully human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B-cells, fusion of spleen cells from immunized transgenic mice carrying inserted human immunoglobulin genes, isolation from human immunoglobulin V region phage libraries, or other procedures as known in the art and based on the disclosure herein.

Procedures have been developed for generating human monoclonal antibodies in non-human animals. For example, mice in which one or more endogenous immunoglobulin genes have been inactivated by various means have been prepared. Human immunoglobulin genes have been introduced into the mice to replace the inactivated mouse genes. In this technique, elements of the human heavy and light chain locus are introduced into strains of mice derived from embryonic stem cell lines that contain targeted disruptions of the endogenous heavy chain and light chain loci (see also Bruggemann et al., Curr. Opin. Biotechnol. 8:455-58 (1997)). For example, human immunoglobulin transgenes may be mini-gene constructs, or transloci on yeast artificial chromosomes, which undergo B-cell-specific DNA rearrangement and hypermutation in the mouse lymphoid tissue.

Antibodies produced in the animal incorporate human immunoglobulin polypeptide chains encoded by the human genetic material introduced into the animal. In one embodiment, a non-human animal, such as a transgenic mouse, is immunized with a suitable GCGR immunogen. One example of a suitable GCGR immunogen are receptor enriched cell membrane fractions such as is described in the Examples below. Another example is the extracellular domain of SEQ ID NO: 2.

Examples of techniques for production and use of transgenic animals for the production of human or partially human antibodies are described in U.S. Pat. Nos. 5,814,318, 5,569, 825, and 5,545,806, Davis et al., Production of human antibodies from transgenic mice in Lo, ed. Antibody Engineering: Methods and Protocols, Humana Press, NJ: 191-200 (2003), Kellermann et al., 2002, Curr Opin Biotechnol. 13:593-97, Russel et al., 2000, Infect Immun. 68:1820-26, Gallo et al., 2000, Eur J. Immun. 30:534-40, Davis et al., 1999, Cancer Metastasis Rev. 18:421-25, Green, 1999, J Immunol Methods. 231:11-23, Jakobovits, 1998, Advanced Drug Delivery Reviews 31:3342, Green et al., 1998, J Exp Med. 188:483-95, Jakobovits A, 1998, Exp. Opin. Invest. Drugs. 7:607-14, Tsuda et al., 1997, Genomics. 42:413-21, Mendez et al., 1997, Nat. Genet. 15:146-56, Jakobovits, 1994, Curr Biol. 4:761-63, Arbones et al., 1994, Immunity. 1:247-60, Green et al., 1994, Nat. Genet. 7:13-21, Jakobovits et al., 1993, Nature. 362:255-58, Jakobovits et al., 1993, Proc Natl Acad Sci USA. 90:2551-55. Chen, J., M. Trounstine, F. W. Alt, F. Young, C. Kurahara, J. Loring, D. Huszar. "Immunoglobulin gene rearrangement in B-cell deficient mice generated by targeted deletion of the JH locus." International Immunology 5 (1993): 647-656, Choi et al., 1993, Nature Genetics 4: 117-23, Fishwild et al., 1996, Nature Biotechnology 14: 845-51, Harding et al., 1995, Annals of the New York Academy of Sciences, Lonberg et al., 1994, Nature 368: 856-59, Lonberg, 1994, Transgenic Approaches to Human Monoclonal Antibodies in Handbook of Experimental Pharmacology 113: 49-101, Lonberg et al., 1995, Internal Review of Immunology 13: 65-93, Neuberger, 1996, Nature Biotechnology 14: 826, Taylor et al., 1992, Nucleic Acids Research 20: 6287-95, Taylor et al., 1994, International Immunology 6: 579-91, Tomizuka et al., 1997, Nature Genetics 16: 133-43, Tomizuka et al., 2000, Proceedings of the National Academy of Sciences USA 97: 722-27, Tuaillon et al., 1993, Proceedings of the National Academy of Sciences USA 90: 3720-24, and Tuaillon et al., 1994, Journal of Immunology 152: 2912-20; Lonberg et al., Nature 368:856, 1994; Taylor et al., Int. Immun. 6:579, 1994; U.S. Pat. No. 5,877,397; Bruggemann et al., 1997 Curr. Opin. Biotechnol. 8:455-58; Jakobovits et al., 1995 Ann. N.Y. Acad. Sci. 764:525-35. In addition, protocols involving the XenoMouse® (Abgenix, now Amgen, Inc.) are described, for example in U.S. 05/0118643 and WO 05/694879, WO 98/24838, WO 00/76310, and U.S. Pat. No. 7,064,244.

Lymphoid cells from the immunized transgenic mice are fused with myeloma cells for example to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in such fusions include Sp-20, P3-X63/Ag8, P3-X63-Ag8.653, NS1/1.Ag 41, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

The lymphoid (e.g., spleen) cells and the myeloma cells may be combined for a few minutes with a membrane fusion-promoting agent, such as polyethylene glycol or a nonionic detergent, and then plated at low density on a selective medium that supports the growth of hybridoma cells but not unfused myeloma cells. One selection media is HAT (hypoxanthine, aminopterin, thymidine). After a sufficient time, usually about one to two weeks, colonies of cells are observed. Single colonies are isolated, and antibodies produced by the cells may be tested for binding activity to human GCGR using any one of a variety of immunoassays known in the art and described herein. The hybridomas are cloned (e.g., by limited dilution cloning or by soft agar plaque isolation) and positive clones that produce an antibody specific to human GCGR are selected and cultured. The monoclonal antibodies from the hybridoma cultures may be isolated from the supernatants of hybridoma cultures. Thus the present invention provides hybridomas that comprise polynucleotides encoding the antigen binding proteins of the invention in the chromosomes of the cell. These hybridomas can be cultured according to methods described herein and known in the art.

Another method for generating human antibodies of the invention includes immortalizing human peripheral blood cells by EBV transformation. See, e.g., U.S. Pat. No. 4,464,456. Such an immortalized B-cell line (or lymphoblastoid cell line) producing a monoclonal antibody that specifically binds to human GCGR can be identified by immunodetection methods as provided herein, for example, an ELISA, and then isolated by standard cloning techniques. The stability of the lymphoblastoid cell line producing an anti-GCGR antibody may be improved by fusing the transformed cell line with a murine myeloma to produce a mouse-human hybrid cell line according to methods known in the art (see, e.g., Glasky et al., Hybridoma 8:377-89 (1989)). Still another method to generate human monoclonal antibodies is in vitro immunization, which includes priming human splenic B-cells with human GCGR, followed by fusion of primed B-cells with a hetero-hybrid fusion partner. See, e.g., Boerner et al., 1991 J. Immunol. 147:86-95.

In certain embodiments, a B-cell that is producing an anti-human GCGR antibody is selected and the light chain and heavy chain variable regions are cloned from the B-cell according to molecular biology techniques known in the art (WO 92/02551; U.S. Pat. No. 5,627,052; Babcook et al., Proc. Natl. Acad. Sci. USA 93:7843-48 (1996)) and described herein. B-cells from an immunized animal may be isolated from the spleen, lymph node, or peripheral blood sample by selecting a cell that is producing an antibody that specifically binds to GCGR. B-cells may also be isolated from humans, for example, from a peripheral blood sample. Methods for detecting single B-cells that are producing an antibody with the desired specificity are well known in the art, for example, by plaque formation, fluorescence-activated cell sorting, in vitro stimulation followed by detection of specific antibody, and the like. Methods for selection of specific antibody-producing B-cells include, for example, preparing a single cell suspension of B-cells in soft agar that contains human GCGR. Binding of the specific antibody produced by the B-cell to the antigen results in the formation of a complex, which may be visible as an immunoprecipitate. After the B-cells producing the desired antibody are selected, the specific antibody genes may be cloned by isolating and amplifying DNA or mRNA according to methods known in the art and described herein.

An additional method for obtaining antibodies of the invention is by phage display. See, e.g., Winter et al., 1994 Annu. Rev. Immunol. 12:433-55; Burton et al., 1994 Adv. Immunol. 57:191-280. Human or murine immunoglobulin variable region gene combinatorial libraries may be created in phage vectors that can be screened to select Ig fragments (Fab, Fv, sFv, or multimers thereof) that bind specifically to TGF-beta binding protein or variant or fragment thereof. See, e.g., U.S. Pat. No. 5,223,409; Huse et al., 1989 Science 246: 1275-81; Sastry et al., Proc. Natl. Acad. Sci. USA 86:5728-32 (1989); Alting-Mees et al., Strategies in Molecular Biology 3:1-9 (1990); Kang et al., 1991 Proc. Natl. Acad. Sci. USA 88:4363-66; Hoogenboom et al., 1992 J. Molec. Biol. 227: 381-388; Schlebusch et al., 1997 Hybridoma 16:47-52 and references cited therein. For example, a library containing a plurality of polynucleotide sequences encoding Ig variable region fragments may be inserted into the genome of a filamentous bacteriophage, such as M13 or a variant thereof, in frame with the sequence encoding a phage coat protein. A fusion protein may be a fusion of the coat protein with the light chain variable region domain and/or with the heavy chain variable region domain. According to certain embodiments, immunoglobulin Fab fragments may also be displayed on a phage particle (see, e.g., U.S. Pat. No. 5,698,426).

Heavy and light chain immunoglobulin cDNA expression libraries may also be prepared in lambda phage, for example, using λImmunoZap™(H) and λImmunoZap™(L) vectors (Stratagene, La Jolla, Calif.). Briefly, mRNA is isolated from a B-cell population, and used to create heavy and light chain immunoglobulin cDNA expression libraries in the λImmunoZap(H) and λImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid that allows high level expression of monoclonal antibody fragments from E. coli.

In one embodiment, in a hybridoma the variable regions of a gene expressing a monoclonal antibody of interest are amplified using nucleotide primers. These primers may be synthesized by one of ordinary skill in the art, or may be purchased from commercially available sources. (See, e.g., Stratagene (La Jolla, Calif.), which sells primers for mouse and human variable regions including, among others, primers for $V_{Ha}$, $V_{Hb}$, $V_{Hc}$, $V_{Hd}$, $C_{H1}$, $V_L$ and $C_L$ regions.) These primers may be used to amplify heavy or light chain variable regions, which may then be inserted into vectors such as ImmunoZAP™H or ImmunoZAP™L (Stratagene), respectively. These vectors may then be introduced into E. coli, yeast, or mammalian-based systems for expression. Large amounts of a single-chain protein containing a fusion of the $V_H$ and $V_L$ domains may be produced using these methods (see Bird et al., Science 242:423-426, 1988).

Once cells producing antibodies according to the invention have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described previously to generate other antibodies according to the invention.

Antigen binding proteins of the present invention preferably modulate glucagon signalling in the cell-based assay described herein and/or the in vivo assay described herein described herein and/or cross-block the binding of one of the antibodies described in this application and/or are cross-blocked from binding GCGR by one of the antibodies described in this application. Accordingly such binding agents can be identified using the assays described herein.

In certain embodiments, antibodies are generated by first identifying antibodies that bind to cells overexpressing GCGRs and/or neutralize in the cell-based and/or in vivo assays described herein and/or cross-block the antibodies described in this application and/or are cross-blocked from binding GCGRs by one of the antibodies described in this application.

It will be understood by one skilled in the art that some proteins, such as antibodies, may undergo a variety of post-translational modifications. The type and extent of these modifications often depends on the host cell line used to express the protein as well as the culture conditions. Such modifications may include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in Harris, R. J. Journal of Chromatography 705:129-134, 1995).

An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in Methods in Molecular Biology, Vol. 10, pages 79-104 (The Humana Press, Inc. 1992)). Monoclonal antibodies may be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anticonstant region (light chain or heavy chain) antibody, an anti-idiotype antibody, and a TGF-beta binding protein, or fragment or variant thereof.

Molecular evolution of the complementarity determining regions (CDRs) in the center of the antibody binding site also has been used to isolate antibodies with increased affinity, for example, antibodies having increased affinity for c-erbB-2, as described by Schier et al., 1996, J. Mol. Biol. 263:551. Accordingly, such techniques are useful in preparing antibodies to human glucagon receptor.

Antigen binding proteins directed against human glucagon receptor can be used, for example, in assays to detect the presence of the glucagon receptor, either in vitro or in vivo.

Although human, partially human, or humanized antibodies will be suitable for many applications, particularly those involving administration of the antibody to a human subject, other types of antigen binding proteins will be suitable for certain applications. The non-human antibodies of the invention can be, for example, derived from any antibody-producing animal, such as mouse, rat, rabbit, goat, donkey, or non-human primate (for example, monkey such as cynomolgus or rhesus monkey) or ape (e.g., chimpanzee)). Non-human antibodies of the invention can be used, for example, in in vitro and cell-culture based applications, or any other application where an immune response to the antibody of the invention does not occur, is insignificant, can be prevented, is not a concern, or is desired. Example 2 below describes the generation of a mouse antibody. In one embodiment, a non-human antibody of the invention is administered to a non-human subject. In another embodiment, the non-human antibody does not elicit an immune response in the non-human subject. In another embodiment, the non-human antibody is from the same species as the non-human subject, e.g., a mouse antibody of the invention is administered to a mouse. An antibody from a particular species can be made by, for example, immunizing an animal of that species with the desired immunogen or using an artificial system for generating antibodies of that species (e.g., a bacterial or phage display-based system for generating antibodies of a particular species), or by converting an antibody from one species into an antibody from another species by replacing, e.g., the constant region of the antibody with a constant region from the other species, or by replacing one or more amino acid residues of the antibody so that it more closely resembles the sequence of an antibody from the other species. In one embodiment, the antibody is a chimeric antibody comprising amino acid sequences derived from antibodies from two or more different species.

Antibodies also may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988). This is discussed in the nucleic acid section below.

Where it is desired to improve the affinity of antibodies according to the invention containing one or more of the above-mentioned CDRs can be obtained by a number of affinity maturation protocols including maintaining the CDRs (Yang et al., J. Mol. Biol., 254, 392-403, 1995), chain shuffling (Marks et al., Bio/Technology, 10, 779-783, 1992), use of mutation strains of E. coli. (Low et al., J. Mol. Biol., 250, 350-368, 1996), DNA shuffling (Patten et al., Curr. Opin. Biotechnol., 8, 724-733, 1997), phage display (Thompson et al., J. Mol. Biol., 256, 7-88, 1996) and additional PCR techniques (Crameri, et al., Nature, 391, 288-291, 1998). All of these methods of affinity maturation are discussed by Vaughan et al. (Nature Biotechnology, 16, 535-539, 1998).

Antibody Fragments

In another aspect, the present invention provides fragments of an anti-glucagon receptor antibody of the invention. Such fragments can consist entirely of antibody-derived sequences or can comprise additional sequences. Examples of antigen-binding fragments include Fab, F(ab')2, single chain antibodies, diabodies, triabodies, tetrabodies, and domain antibodies. Other examples are provided in Lunde et al., 2002, Biochem. Soc. Trans. 30:500-06.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol. Biol. 178:379-87. Single chain antibodies derived from antibodies provided herein include, but are not limited to, scFvs comprising the variable domain combinations L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, and L23H23 are encompassed by the present invention.

Antigen binding fragments derived from an antibody can also be obtained, for example, by proteolytic hydrolysis of the antibody, for example, pepsin or papain digestion of whole antibodies according to conventional methods. By way of example, antibody fragments can be produced by enzymatic cleavage of antibodies with pepsin to provide a 5S fragment termed F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoff et al., Arch. Biochem. Biophys. 89:230, 1960; Porter, Biochem. J. 73:119, 1959; Edelman et al., in Methods in Enzymology 1:422 (Academic Press 1967); and by Andrews, S. M. and Titus, J. A. in Current Protocols in Immunology (Coligan J. E., et al., eds), John Wiley & Sons, New York (2003), pages 2.8.1-2.8.10 and 2.10A.1-2.10A.5. Other methods for cleaving antibodies, such as separating heavy chains to form monovalent light-heavy chain fragments (Fd), further cleaving of fragments, or other enzymatic, chemical, or genetic techniques may also be used, so long as the fragments bind to the antigen that is recognized by the intact antibody.

Another form of an antibody fragment is a peptide comprising one or more complementarity determining regions (CDRs) of an antibody. CDRs can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., Methods: A Companion to Methods in Enzymology 2:106, 1991; Courtenay-Luck, "Genetic Manipulation of Monoclonal Antibodies," in Monoclonal Antibodies: Production, Engineering and Clinical Application, Ritter et al. (eds.), page 166 (Cambridge University Press 1995); and Ward et al., "Genetic Manipulation and Expression of Antibodies," in Monoclonal Antibodies: Principles and Applications, Birch et al., (eds.), page 137 (Wiley-Liss, Inc. 1995)). The antibody fragment further may comprise at least one variable region domain of an antibody described herein. Thus, for example, the V region domain may be monomeric and be a $V_H$ or $V_L$ domain, which is capable of independently binding human glucagon receptor with an affinity at least equal to $10^{-7}$M or less as described below.

The variable region domain may be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly a $V_L$ domain may be linked to a $C_K$ domain or a fragment thereof. In this way, for example, the antibody may be a Fab fragment wherein the antigen binding domain contains associated $V_H$ and $V_L$ domains covalently linked at their C-termini to a CH1 and $C_K$ domain, respectively. The CH1 domain may be extended with further amino acids, for example to provide a hinge region or a portion of a hinge region domain as found in a Fab' fragment, or to provide further domains, such as antibody CH2 and CH3 domains.

Derivatives and Variants of Antigen Binding Proteins

The nucleotide sequences of L1-L23 and H1-H23, encoding the corresponding amino acid sequences of A1-A23, can be altered, for example, by random mutagenesis or by site-directed mutagenesis (e.g., oligonucleotide-directed site-specific mutagenesis) to create an altered polynucleotide comprising one or more particular nucleotide substitutions, deletions, or insertions as compared to the non-mutated polynucleotide. Examples of techniques for making such alterations are described in Walder et al., 1986, Gene 42:133; Bauer et al. 1985, Gene 37:73; Craik, BioTechniques, January 1985, 12-19; Smith et al., 1981, Genetic Engineering: Principles and Methods, Plenum Press; and U.S. Pat. Nos. 4,518,584 and 4,737,462. These and other methods can be used to make, for example, derivatives of anti-glucagon receptor antibodies that have a desired property, for example, increased affinity, avidity, or specificity for glucagon receptor increased activity or stability in vivo or in vitro, or reduced in vivo side-effects as compared to the underivatized antibody.

Other derivatives of anti-glucagon receptor antibodies within the scope of this invention include covalent or aggregative conjugates of anti-glucagon receptor antibodies, or fragments thereof, with other proteins or polypeptides, such as by expression of recombinant fusion proteins comprising heterologous polypeptides fused to the N-terminus or C-terminus of an anti-glucagon receptor antibody polypeptide. For example, the conjugated peptide may be a heterologous signal (or leader) polypeptide, e.g., the yeast alpha-factor leader, or a peptide such as an epitope tag. Antigen binding protein-containing fusion proteins can comprise peptides added to facilitate purification or identification of antigen binding protein (e.g., poly-His). An antigen binding protein also can be linked to the FLAG peptide as described in Hopp et al., Bio/Technology 6:1204, 1988, and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.). In another embodiment, oligomers that contain one or more antigen binding proteins may be employed as glucagon receptor antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have glucagon receptor binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins", in Current Protocols in Immunology, Suppl. 4, pages 10.19.1-10.19.11. One embodiment of the present invention is directed to a dimer comprising two fusion proteins created by fusing a glucagon receptor binding fragment of an anti-glucagon receptor antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. In other embodiments, the variable portion of the heavy and/or light chains of an anti-glucagon receptor antibody may be substituted for the variable portion of an antibody heavy and/or light chain.

Alternatively, the oligomer is a fusion protein comprising multiple antigen binding proteins, with or without peptide linkers (spacer peptides). Among the suitable peptide linkers are those described in U.S. Pat. Nos. 4,751,180 and 4,935,233.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising an anti-glucagon receptor antibody fragment or derivative fused to a leucine zipper peptide are expressed in suitable host cells, and the soluble oligomeric anti-glucagon receptor antibody fragments or derivatives that form are recovered from the culture supernatant.

In another embodiment, the antibody derivatives can comprise at least one of the CDRs disclosed herein. For example, one or more CDR may be incorporated into known antibody framework regions (IgG1, IgG2, etc.), or conjugated to a suitable vehicle to enhance the half-life thereof. Suitable vehicles include, but are not limited to Fc, albumin, transferrin, and the like. These and other suitable vehicles are known in the art. Such conjugated CDR peptides may be in monomeric, dimeric, tetrameric, or other form. In one embodiment, one or more water-soluble polymer is bonded at one or more specific position, for example at the amino terminus, of a binding agent. In an example, an antibody derivative comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

It will be appreciated that an antibody of the present invention may have at least one amino acid substitution, providing that the antibody retains binding specificity. Therefore, modifications to the antibody structures are encompassed within the scope of the invention. These may include amino acid substitutions, which may be conservative or non-conservative, that do not destroy the human glucagon receptor binding capability of an antibody. Conservative amino acid substitutions may encompass non-naturally occurring amino acid residues, which are typically incorporated by chemical peptide synthesis rather than by synthesis in biological systems.

These include peptidomimetics and other reversed or inverted forms of amino acid moieties. A conservative amino acid substitution may also involve a substitution of a native amino acid residue with a normative residue such that there is little or no effect on the polarity or charge of the amino acid residue at that position. Non-conservative substitutions may involve the exchange of a member of one class of amino acids or amino acid mimetics for a member from another class with different physical properties (e.g. size, polarity, hydrophobicity, charge). Such substituted residues may be introduced into regions of the human antibody that are homologous with non-human antibodies, or into the non-homologous regions of the molecule.

Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure. Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2):211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Curr. Opin. Struct. Biol., 7(3): 377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-4358 (1987)), and "evolutionary linkage" (See Holm, supra (1999), and Brenner, supra (1997)). In certain embodiments, variants of antibodies include glycosylation variants wherein the number and/or type of glycosylation site has been altered compared to the amino acid sequences of a parent polypeptide. In certain embodiments, variants comprise a greater or a lesser number of N-linked glycosylation sites than the native protein. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Desired amino acid substitutions (whether conservative or non-conservative) can be determined by those skilled in the art at the time such substitutions are desired. In certain embodiments, amino acid substitutions can be used to identify important residues of antibodies to human glucagon receptor, or to increase or decrease the affinity of the antibodies to human glucagon receptor described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

In certain embodiments, antibodies of the invention may be chemically bonded with polymers, lipids, or other moieties.

The antigen binding agents may comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendamistat domains may be used (See e.g., Nygren and Uhlen, 1997, Current Opinion in Structural Biology, 7, 463-469).

Additionally, one skilled in the art will recognize that suitable binding agents include portions of these antibodies, such as one or more of heavy chain CDR1, CDR2, CDR3, light chain CDR1, CDR2 and CDR3 as specifically disclosed herein. At least one of the regions of heavy chain CDR1, CDR2, CDR3, CDR1, CDR2 and CDR3 may have at least one amino acid substitution, provided that the antibody retains the binding specificity of the non-substituted CDR. The non-CDR portion of the antibody may be a non-protein molecule, wherein the binding agent cross-blocks the binding of an antibody disclosed herein to human GCGR and/or inhibits the activity of glucagon signalling through the receptor. The non-CDR portion of the antibody may be a non-protein molecule in which the antibody exhibits a similar binding pattern to human GCGR peptides in a competition binding assay as that exhibited by at least one of antibodies A1-A23, and/or neutralizes the activity of glucagon. The non-CDR portion of the antibody may be composed of amino acids, wherein the antibody is a recombinant binding protein or a synthetic peptide, and the recombinant binding protein cross-blocks the binding of an antibody disclosed herein to human GCGR and/or neutralizes glucagon activity in vitro or in vivo. The non-CDR portion of the antibody may be composed of amino acids, wherein the antibody is a recombinant antibody, and the recombinant antibody exhibits a similar binding pattern to human GCGR peptides in a competition binding assay as exhibited by at least one of the antibodies A1-A23, and/or neutralizes glucagon signalling.

Nucleic Acids

In one aspect, the present invention provides isolated nucleic acid molecules that encode the antigen binding agents of the present invention. In addition, provided are vectors comprising the nucleic acids, cell comprising the nucleic acids, and methods of making the antigen binding proteins of the invention. The nucleic acids comprise, for example, polynucleotides that encode all or part of an antigen binding protein, for example, one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids encoding antibody polypeptides (e.g., heavy or light chain, variable domain only, or full length) may be isolated from B-cells of mice that have been immunized with GCGR antigen. The nucleic acid may be isolated by conventional procedures such as polymerase chain reaction (PCR).

Nucleic acid sequences encoding the variable regions of the heavy and light chain variable regions are shown above. The skilled artisan will appreciate that, due to the degeneracy of the genetic code, each of the polypeptide sequences disclosed herein is encoded by a large number of other nucleic acid sequences. The present invention provides each degenerate nucleotide sequence encoding each antigen binding protein of the invention.

The invention further provides nucleic acids that hybridize to other nucleic acids (e.g., nucleic acids comprising a nucleotide sequence of any of A1-A14) under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, for example, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1× SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA. Changes can be introduced by mutation into a nucleic acid, thereby leading to changes in the amino acid sequence of a polypeptide (e.g., an antigen binding protein) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. In one embodiment, a nucleotide sequence provided herein for L-1-L-23 and H-1 to H-23, or a desired fragment, variant, or derivative thereof, is mutated such that it encodes an amino acid sequence comprising one or more deletions or substitutions of amino acid residues that are shown herein for L-1 to L-23 and H-1 to H-23 to be residues where two or more sequences differ. In another embodiment, the mutagenesis inserts an amino acid adjacent to one or more amino acid residues shown herein for L-1 to L-23 and H-1 to H-23 to be residues where two or more sequences differ. Alternatively, one or more mutations can be introduced into a nucleic acid that selectively change the biological activity. (e.g., binding to GCGR) of a polypeptide that it encodes. For example, the mutation can quantitatively or qualitatively change the biological activity. Examples of quantitative changes include increasing, reducing or eliminating the activity. Examples of qualitative changes include changing the antigen specificity of an antigen binding protein.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., a GCGR binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide.

In another aspect, the present invention provides vectors comprising a nucleic acid encoding a polypeptide of the invention or a portion thereof. Examples of vectors include, but are not limited to, plasmids, viral vectors, non-episomal mammalian vectors and expression vectors, for example, recombinant expression vectors.

The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell or eukaryotic cell. Prokaryotic host cells include gram negative or gram positive organisms, for example E. coli or bacilli. Higher eukaryotic cells include insect cells, yeast cells, and established cell lines of mammalian origin. Examples of suitable mammalian host cell lines include Chinese hamster ovary (CHO) cells or their derivatives such as Veggie CHO and related cell lines which grow in serum-free media (see Rasmussen et al., 1998, Cytotechnology 28:31) or CHO strain DXB-11, which is deficient in DHFR (see Urlaub et al., 1980, Proc. Natl. Acad. Sci. USA 77:4216-20). Additional CHO cell lines include CHO-K1 (ATCC#CCL-61), EM9 (ATCC# CRL-1861), and W20 (ATCC# CRL-1862). Additional host cells include the COS-7 line of monkey kidney cells (ATCC CRL 1651) (see Gluzman et al., 1981, Cell 23:175), L cells, C127 cells, 3T3 cells (ATCC CCL 163), AM-1/D cells (described in U.S. Pat. No. 6,210,924), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Appropriate cloning and expression vectors for use with bacterial, fungal, yeast, and mammalian cellular hosts are described by Pouwels et al. (Cloning Vectors: A Laboratory Manual, Elsevier, N.Y., 1985).

Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

The transformed cells can be cultured under conditions that promote expression of the polypeptide, and the polypeptide recovered by conventional protein purification procedures. One such purification procedure is described in the Examples below. Polypeptides contemplated for use herein include substantially homogeneous recombinant mammalian anti-glucagon receptor antibody polypeptides substantially free of contaminating endogenous materials.

Cells containing the nucleic acid encoding the antigen binding proteins of the present invention also include hybridomas. The production and culturing of hybridomas are discussed in the antibody section above.

Activity of Antigen Binding Proteins

In one aspect, the present invention provides antigen binding proteins, in particular human, humanized, or chimeric antibodies, that specifically bind to the human glucagon receptor. Such antibodies include antagonizing or neutralizing antibodies capable of reducing or neutralizing glucagon signalling, as determined, for example, by the cell based functional assay described in Example 4. In one embodiment, the antigen binding proteins, such as the human antibodies of the present invention have an IC50 value of 90 nM or less, in another embodiment, an IC50 value of 80 nM or less, in another embodiment, 70 nM or less, in another embodiment, 60 nM or less, in another embodiment, 50 nM or less, in another embodiment, 40 nM or less, in another embodiment, 30 nM or less, in another embodiment 25 nM or less. In another embodiment, the antigen binding proteins such as the human antibodies of the present invention are capable of specifically binding to the human glucagon receptor, and have an IC50 value that is substantially similar to that of a reference antibody. In another embodiment, the antigen binding proteins have a Kb (or Kd) as measured by the assay described in the Examples below (or similar assays), that is substantially similar to that of a reference antibody. As used herein, the term "substantially similar" means comparable to, or about 100%, 99%, 98%, 97%, 95%, 90%, 85%, 80%, 75%, 70%, 65% or 50% identical to the IC50 or Kb (or Kd) value of the reference antibody. Reference antibodies include, for example, antibodies having a combination of heavy chain and light chains L1H1, L2H2, L3H3, L4H4, L5H5, L6H6, L7H7, L8H8, L9H9, L11H11, L12H12, L13H13, L15H15, L21H21, and L22H22. In one embodiment, the reference antibodies include A-1, A-2, A-3, A4, A-5, A-6, A-7, A-8, A-9, A-11, A-12, A-13, A-15, A-21, and A-22. In another embodiment, the antigen binding proteins such as the human antibodies of the present invention are capable of specifically binding to the human glucagon receptor, and lowering blood glucose in an animal model. In one embodiment, the blood glucose is lowered by 2% compared with untreated animals, in another embodiment the blood glucose is lowered by 5% compared with untreated animals, in another embodiment, the blood glucose is lowered by 10% compared to untreated animal, in another embodiment, the blood glucose is lowered by 15%, in another embodiment, by 20%, in another embodiment, by 25% or more, compared with untreated animals. The amount of reduction of blood glucose is controlled by dosage. A therapeutically effective dosage is the dosage required to reduce blood glucose into the normal range for the animal or human patient. An exemplary animal model is the ob/ob mouse, as described in Example 6 below. In another embodiment, the human antibodies of the present invention are capable of specifically binding to the human glucagon receptor, and improving glucose clearance in an animal model. An exemplary animal model is the cynomolgus monkey, as described in Example 7 below. Improving glucose clearance refers to the amount of time it takes to reduce blood glucose after an oral glucose challenge given to the animal or human patient, and is a measure of glucose tolerance. This is measured by standard tests such as oral glucose tolerance test (OGTT), as described in the example below. The antigen binding proteins of the present invention can improve glucose tolerance in the animal model. In addition, the antigen binding proteins can improve other in vivo indicators associated with type 2 diabetes and hyperglycemia, including but not limited to fasting glucose tolerance, dyslipodemia, and metabolic syndrome.

Binding to Human Glucagon Receptor

In one embodiment, the present invention provides antigen binding proteins that cross-competes for binding with a reference antibody, wherein the reference antibody comprises a combination of light chain and heavy chain variable domain sequences selected from the group consisting of L1H1, L2H2, L3H3, L4H4, L5H5, L6H6, L7H7, L8H8, L9H9, L11H11, L12H12, L13H13, L15H15, L17H17, L21H21 and L22H22. In another embodiment, the present invention provides human antibodies that cross-competes for binding with a reference antibody, wherein the reference antibody is A-1, A-2, A-3, A4, A-5, A-6, A-7, A-8, A-9, A-11, A-12, A-13, A-15, A-21, and A-22. In another aspect, the present invention provides human antibodies that bind to the Ser80 to Ser119 region of the human glucagon receptor. In another embodiment, the present invention provides human antibodies that cross-compete for binding with a reference antibody, wherein the reference antibody binds to the Ser80 to Ser119 region of the human glucagon receptor. In another embodiment, the present invention provides human antibodies that bind to Ser80 to Ser119 region of the glucagon receptor, and have an IC50 value of 90 nM or less, in another embodiment 80 nM or less, in another embodiment, 70 nM or less, in another embodiment, 60 nM or less, in another embodiment, 50 nM or less, in another embodiment, 40 nM or less, in another embodiment, 30 nM or less, in another embodiment, 25 nM or less, as determined, for example, in the assay set out in Example 4. In another embodiment, the present invention provides human antibodies that cross-competes for binding to the human glucagon receptor with a reference antibody, wherein the reference antibody is A-3.

In a further embodiment, the antigen binding proteins, when bound to the human glucagon receptor binds to the human glucagon receptor with substantially the same Kd as a reference antibody; inhibits glucagon stimulation of the human glucagon receptor with substantially the same $IC_{50}$ as said reference antibody; and/or cross-competes for binding with said reference antibody on human glucagon receptor, wherein said reference antibody comprises a combination of light chain and heavy chain variable domain sequences selected from the group consisting of L1H1, L2H2, L3H3, L4H4, L5H5, L6H6, L7H7, L8H8, L9H9, L11H11, L12H12, L13H13, L15H15, L21H21, and L22H22.

In a further embodiment, an isolated human antibody is provided that, when bound to the human glucagon receptor: binds to the human glucagon receptor with substantially the same Kd as a reference antibody; inhibits glucagon stimulation of the human glucagon receptor with substantially the same $IC_{50}$ as said reference antibody; and/or cross-competes for binding with said reference antibody on human glucagon receptor, wherein said reference antibody is selected from the group consisting of A-1, A-2, A-3, A4, A-5, A-6, A-7, A-8, A-9, A-11, A-12, A-13, A-15, A-21, and A-22.

In a further embodiment, an isolated human antibody is provided that, when bound to the human glucagon receptor: a. specifically binds to the amino acid Ser80 to Ser119 portion of the human glucagon receptor; b. reduces glucagon signalling with an IC50 value of 90 nM or less; c. lowers blood glucose in an animal model; (a) and (b); or (a), (b) and (c).

Figure 4:
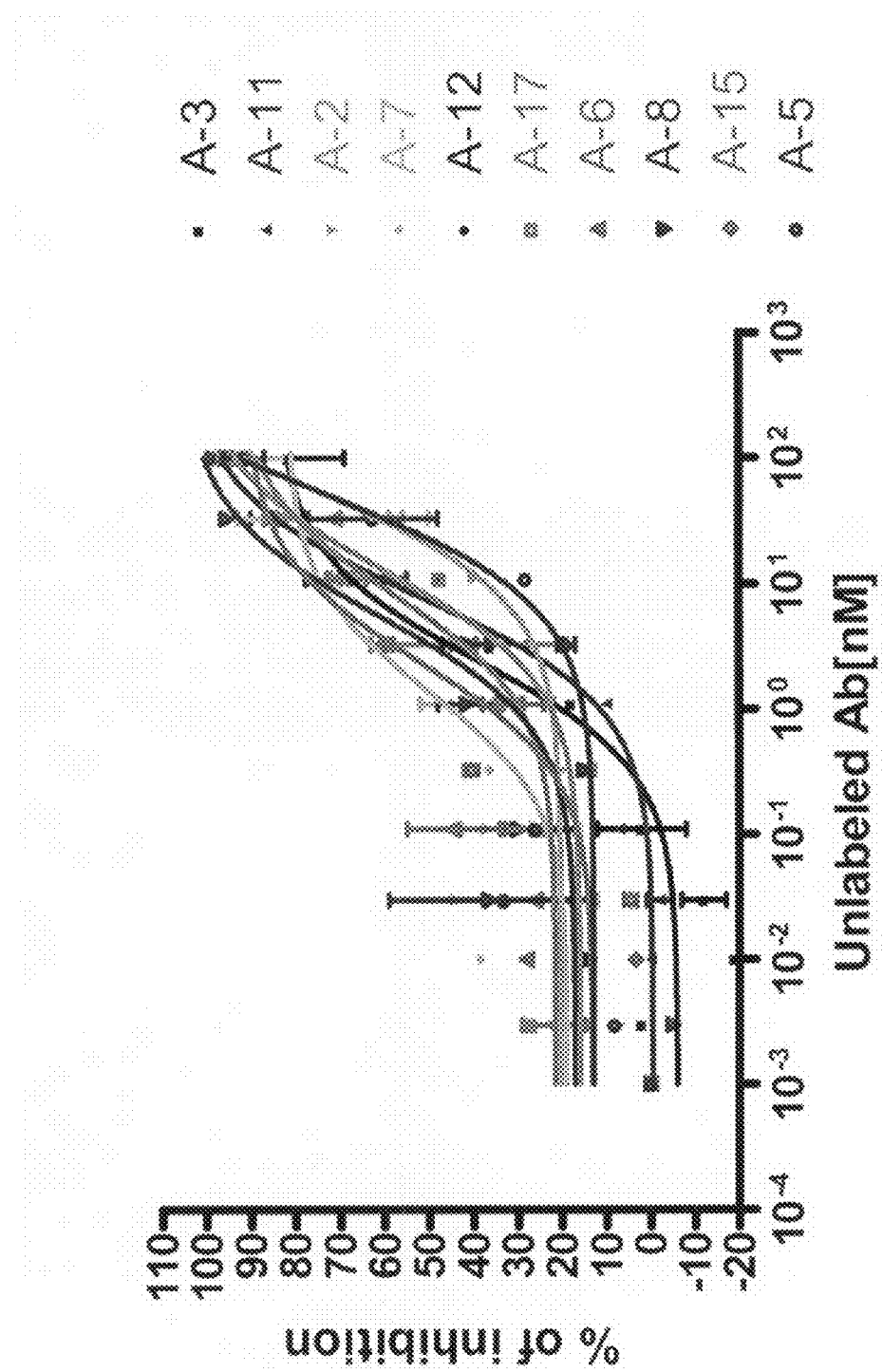
FIG. 4 shows unlabeled antibodies capable of competing for binding with labeled antibody A-3 (surmountable antibodies).
Figure 5:
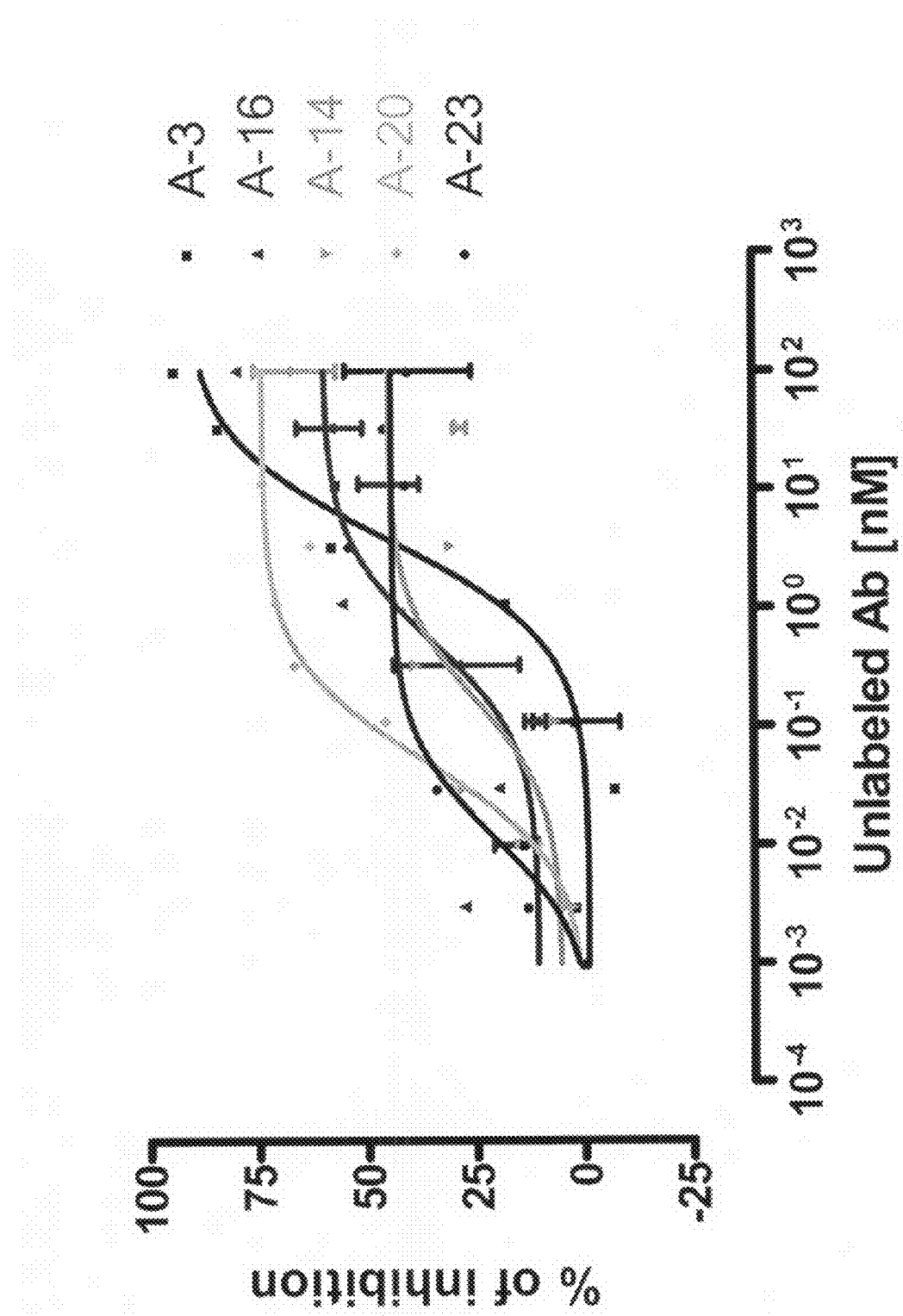
FIG. 5 shows unlabeled antibodies capable of partially competing for binding with labeled antibody A-3 (partially surmountable antibodies).
Figure 6:
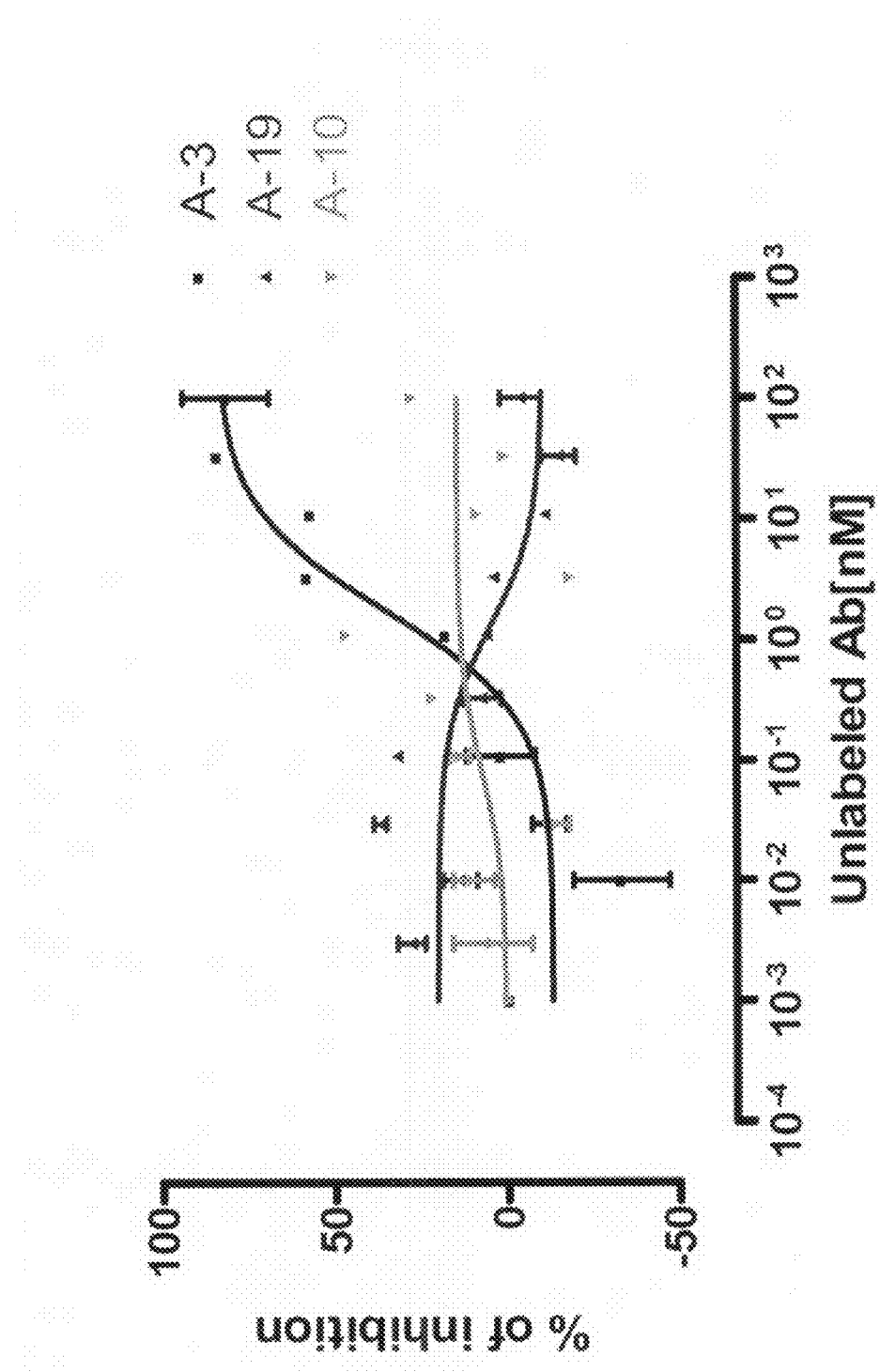
FIG. 6 shows unlabeled antibodies not capable of competing for binding with labeled antibody A-3 (unsurmountable antibodies).

The ability to cross-compete with an antibody can be determined using any suitable assay, such as that described in Example 8, an exemplary competitive binding assay using A-3 as the reference antibody. The antibodies tested were surmountable, those that could compete for binding with A-3, partially surmountable, those that could only partially compete for binding, and the unsurmountable antibodies, those that did not compete for binding with A-3. The results are shown in FIGS. 4-6.

In addition, site of binding on the human glucagon receptor of human antibody A-3 and other human antibodies were determining by constructing chimeric receptors using human GCGR and human GLP-1 receptors, as described in Example 9 below. Using the chimeric receptors, as described below, and as shown in FIG. 7, it was determined that for antibody A-3, the region of the human glucagon receptor amino acids Ser80 to Ser117 were necessary and sufficient for binding. In addition, the human GCGR contains 3 pairs of cysteines. For antibody A-3, the second and third pairs of cysteines but not the first pair was needed for binding. This was in contrast to antibodies A-18, A-21 and A-10, which bound only when the 3 pairs of cysteines were intact.

Indications

Diabetes, in particular type 2 diabetes, and its complications are a growing problem for populations world-wide. Generally, this disease results from impaired insulin production from pancreatic β-cells. In type 2 diabetes, the most common form of the disease, a combination of genetic and environmental factors is thought to bring about β-cell failure, which results in impaired insulin secretion and activity, and insulin resistance in many individuals. Obesity is one condition thought to contribute to the increase in type 2 diabetes in adults and even children. It is also known that dyslipodemia, or abnormal HDL (high density lipoprotein), and LDL (low density lipoprotein) is related to type 2 diabetes.

Type 2 diabetes is characterized by the failure of muscles and other organs to respond to normal circulating concentrations of insulin. This is followed by an increase in insulin secretion from pancreatic beta cells, a condition known as hyperinsulinemia. Ultimately, the beta cells can no longer compensate, leading to impaired glucose tolerance, impaired fasting glucose levels, chronic hyperglycemia and tissue damage. In addition, type 2 diabetes is known to be related to dyslipodemia, or abnormal HDL (high density lipoprotein), and LDL (low density lipoprotein). Both dyslipodemia and hyperglycemia are present in patients suffering from metabolic syndrome.

The present invention provides antigen binding proteins, in particular, human antibodies that can bind to the glucagon receptor in vivo and reduce blood glucose levels in animal models. The antigen binding proteins can also improve glucose tolerance. In one embodiment, the present invention provides fully human antibodies having in vivo efficacy. The effect of single antibody injection in ob/ob mice, for example, lowers blood glucose for several days after injection, providing an effective, long-lasting treatment for hyperglycemia, type 2 diabetes, and related disorders. A single antibody injection also improved glucose clearance (improved glucose tolerance) from the blood in glucose tolerance tests (GTT) performed on cynomolgus monkeys as described below. The antigen binding proteins, and in particular, the human antibodies of the present invention are useful for lowering blood or serum glucose, improving impaired glucose tolerance, improving fasting glucose levels, improving dyslipodemia. Thus the antigen binding proteins, in particular the human antibodies of the present invention are useful for treating hyperglycemia, type 2 diabetes, metabolic syndrome, dyslipodemia, impaired glucose tolerance, impaired fasting glucose, and hyperinsulinemia. In addition, lowering blood glucose has been shown to be useful in some circumstances in the prevention and treatment of certain cancers such as colorectal cancers, as discussed in Richardson et al, Nature Clin Pract Oncol 2: 48-53 (2005), Giovannucci et al. Gastroenterology 132: 2208-2225 (2007), Krone et al, Integrative Cancer Ther 4(1): 25-31 (2005), Chang et al., Diabetologia 46(5): 595-607 (2003), Jee et al, Yonsei Med J 46(4): 449-55 (2005).

Methods of Treatment

In another aspect, a method of treating a subject, comprising administering a therapeutic dosage of the antigen binding proteins of the present invention is provided. In one embodiment, the antigen binding proteins are human antibodies. As used herein the term "subject" refers to a mammal, including humans, and is used interchangeably with the term "patient". The human antibodies, can be used to treat, control or prevent a disorder or condition characterized by excessive levels of glucagon and/or blood glucose in a subject. These disorders include hyperglycemia, impaired fasting glucose, impaired glucose tolerance, hyperinsulinemia, metabolic syndrome, and type 2 diabetes. The term "treatment" encompasses alleviation or prevention of at least one symptom or other aspect of a disorder, or reduction of disease severity, and the like. An antigen binding protein, in particular a human antibody according to the present invention, need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient an antigen binding protein such as a human antibody in an amount and for a time sufficient to induce a sustained improvement over baseline of an indicator that reflects the severity of the particular disorder.

As is understood in the pertinent field, pharmaceutical compositions comprising the antigen binding proteins of the invention are administered to a subject in a manner appropriate to the indication and the composition. In one embodiment, pharmaceutical compositions comprise the human antibodies of the present invention. Pharmaceutical compositions may be administered by any suitable technique, including but not limited to parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Delivery by inhalation includes, for example, nasal or oral inhalation, use of a nebulizer, inhalation of the antigen binding protein in aerosol form, and the like. Other alternatives include oral preparations including pills, syrups, or lozenges.

Advantageously, the antigen binding proteins of the invention, are administered in the form of a composition comprising one or more additional components such as a physiologically acceptable carrier, excipient or diluent. Optionally, the composition additionally comprises one or more physiologically active agents, for example, as described below. In various particular embodiments, the composition comprises one, two, three, four, five, or six physiologically active agents in addition to one or more antigen binding proteins (e.g, human antibodies) of the present invention.

In one embodiment, the pharmaceutical composition comprises a human antibody of the invention together with one or more substances selected from the group consisting of a buffer suitable for antibodies at a suitable pH, an antioxidant such as ascorbic acid, a low molecular weight polypeptide (such as those having fewer than 10 amino acids), a protein, an amino acid, a carbohydrate such as dextrin, a chelating agent such as EDTA, glutathione, a stabilizer, and an excipient. In accordance with appropriate industry standards, preservatives may also be added. The composition may be formulated as a lyophilizate using appropriate excipient solutions as diluents. Suitable components are nontoxic to recipients at the dosages and concentrations employed. Further examples of components that may be employed in pharmaceutical formulations are presented in Remington's Pharmaceutical Sciences, 16$^{th}$ Ed. (1980) and 20$^{th}$ Ed. (2000), Mack Publishing Company, Easton, Pa.

Kits for use by medical practitioners are provided including one or more antigen binding proteins of the invention and a label or other instructions for use in treating any of the conditions discussed herein. In one embodiment, the kit includes a sterile preparation of one or more human antibodies, which may be in the form of a composition as disclosed above, and may be in one or more vials.

Dosages and the frequency of administration may vary according to such factors as the route of administration, the particular antibodies employed, the nature and severity of the disease to be treated, whether the condition is acute or chronic, and the size and general condition of the subject. Appropriate dosages can be determined by procedures known in the pertinent art, e.g. in clinical trials that may involve dose escalation studies.

An antigen binding protein, in particular, the human antibodies, of the invention may be administered, for example, once or more than once, e.g., at regular intervals over a period of time. In particular embodiments, a human antibody is administered over a period of at least once a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the human antibody is administered until the patient manifests a medically relevant degree of improvement over baseline for the chosen indicator or indicators.

One example of therapeutic regimens provided herein comprise subcutaneous injection of an antigen binding protein such as a human antibody once a week, or once every two weeks, at an appropriate dosage, to treat a condition in which blood glucose levels play a role. Weekly or monthly administration of antigen binding protein would be continued until a desired result is achieved, e.g., the subject's symptoms subside. Treatment may resume as needed, or, alternatively, maintenance doses may be administered.

A subject's levels of blood glucose may be monitored before, during and/or after treatment with an antigen binding protein such as a human antibody, to detect changes, if any, in their levels. For some disorders, the incidence of elevated blood glucose may vary according to such factors as the stage of the disease. Known techniques may be employed for measuring glucose levels. Glucagon levels may also be measured in the patient's blood using know techniques, for example, ELISA.

Particular embodiments of methods and compositions of the invention involve the use of an antigen binding protein such as a human antibody and one or more glucagon antagonists for example, two or more antigen binding proteins of the invention, or an antigen binding protein of the invention and one or more other glucagon antagonists. In further embodiments, antigen binding protein are administered alone or in combination with other agents useful for treating the condition with which the patient is afflicted. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but also include treatment regimens in which an antigen binding protein is administered at least once during a course of treatment that involves administering at least one other therapeutic agent to the patient.

Combination Therapies

In another aspect, the present invention provides a method of treating a subject for diabetes with a therapeutic antigen binding protein of the present invention, such as the fully human therapeutic antibodies described herein, together with one or more other treatments. In one embodiment, such a combination therapy achieves a synergistic effect. The antigen binding proteins may be in combination with one or more of the following type 2 diabetes treatments currently available. These include biguanide (metaformin), and sulfonylureas (such as glyburide, glipizide). Additional treatments directed at maintaining glucose homeostasis including PPAR gamma antagonists (pioglitazone, rosiglitazone); and alpha glucosidase inhibitors (acarbose, voglibose). Additional treatments include injectable treatments such as Exenatide® (glucagon-like peptide), and Symlin® (pramlintide).

The invention having been described, the following examples are offered by way of illustration, and not limitation.

EXAMPLES

Example 1

Preparation of Antigen

Human GCGR cDNA encoding the full-length 477 amino acid glucagon receptor (SEQ ID NO: 2) was subcloned into the pDC312 expression vector and transfected into AM1D cells. After selection and single cell cloning, a single clone (clone 1004) was chosen for further characterization based on cell surface expression of the receptor. The receptor expression level ($B_{max}$) as determined by saturation binding analysis was 11.4 pmole of glucagon receptor/mg membrane protein.

In addition, a cDNA sequence coding an N-terminal GCGR (amino acid 1 to 142 of SEQ ID NO: 2) was in frame fused to cDNA of human IgG1 Fc and subcloned into pDsRa21 vector (described in U.S. 2005/0118643). A stable pool of cells was selected after transfection into AM1D cell. GCGR N-terminal Fc was purified from concentrated conditioned media by recombinant Protein A Fast flow column (GE Healthcare) and followed by Source 30Q anion exchange column (GE Healthcare).

Example 2

Mouse Anti-Human Hybridoma Generation

Crude cell membrane fractions from clone 1004 as described above were used as the antigen for both conventional and RIMMS (Rapid Immunization with Multiple sites injection) immunization of C57BL/6 or DBF1 mice (Jackson Laboratories, Bar Harbor, Me.). After several rounds of immunization, lymphocytes were released from the lymph nodes (RIMMS immunization) or spleen (conventional immunization) and were fused with mouse myeloma cells, Sp2/0-Ag14 (ATCC) by electrofusion. The fused cells were seeded in 96-well plates at the density of $2\times10^4$ cells/well in 100 ul of BD media supplemented with 10% FBS, 5% Origen Cloning Factor (BioVeris™), 1× Penicillin-Streptomycin-Glutamine (Gibco), and 1×OPI (oxaloacetate, pyruvate, and insulin, Sigma). After 24 hrs in culture, 100 ul of 2×HAT (0.1 mM hypoxanthine, 0.16 mM thymidine, 4 mM aminopterin, Sigma) was added to each well. Medium was changed 7 days and 10 days post fusion respectively and the conditioned media were collected two days after the $2^{nd}$ media change and sent for primary screening as described below.

Hybridoma supernatants were subjected for the cell based ELISA (Enzyme-Linked ImmunoSorbent Assay) or FMAT (Fluorometric Microvolume Assay Technology) with 1004 cell and in parallel with parental AM1D cells. The hybridoma clones containing GCGR-specific antibodies were selected based on the specific binding to 1004 but not AM1D.

Monoclonal antibodies were partially purified from the expanded hybridoma cultures as described below and assayed using the both binding (ELISA or FMAT) and functional cell-based assays for neutralization of glucagon-induced cAMP production, as described below. Positive clones were expanded, single-cell cloned, and further confirmed by multiple assays Example 3

Fully Human Antibody Generation

The human GCGR high expresser cell line 1004 derived crude cell membrane preparation was used as the antigen for immunizing IgG2 and IgG4 XenoMouse® (Abgenix, now Amgen, Inc.) according to protocols described, for example in U.S. 05/0118643 and WO 05/694879, WO 98/24838, WO 00/76310, and U.S. Pat. No. 7,064,244, all of which are herein incorporated by reference. A total of two campaigns were conducted. After the initial immunization, subsequent rounds of booster immunizations were administered until a suitable antibody titer was achieved. Animals exhibiting a suitable titer were identified, and lymphocytes were obtained from draining lymph nodes and if necessary, pooled from each cohort. In some instances, lymphocytes were dissociated from lymphoid tissue by grinding with a suitable media (for example, DMEM, Invitrogen, Carlsbad, Calif.) to release the cells from the tissue. B cells were selected and fused with a suitable fusion partners, for example such as nonsecretory myelomas P3X63Ag8.653 cells (American Type Culture Collection CRL 1580, Kerney et al, J. Immunol. 123, 1548-1550 (1979)), as described in the references above. Other suitable fusion partners include Sp2/0-Ag14 (ATCC) cells. Fused cells were pelleted and resuspended in selection media (typically, DMEM containing azaserine and hypozanthine and other supplemental materials), incubated for 20-30 minutes and then resuspended in selection media and cultured prior to plating. Cells were then distributed into wells to maximize clonality and cultured using standard techniques. After culturing, hybridoma supernatants were screened against enriched glucagon receptor cell clone 1004 and parental cell lines AM1D using FMAT. The GCGR specific binders were subsequently confirmed by FACS analysis with FITC-labeled (fluoroescein isothiocynate conjugated) anti-human IgG antibody. The hybridoma clones containing receptor specific monoclonal antibodies were expanded according to the protocols described in U.S 2005/0118643 and other references cited above. Supernatants were tested for the inhibition of glucagon-induced cAMP production as described below. The hybridoma clones containing the antagonizing antibody were single-cell cloned and expanded for further testing. The antibodies were then purified as described below and purified antibodies from these single clones were then tested again for neutralizing activity.

Antibodies were purified from conditioned media of the hybridomas using Mab Select (GE Healthcare) resin. 100 ul of a 1:2 slurry of Mab Select resin equilibrated in PBS was added to between 7 and 10 ml of conditioned media (CM). The tubes were placed on rotators at 4-8° C. overnight. The tubes were centrifuged at 1,000×g for 5 minutes and the non-bound fraction was decanted. The resin was washed with 5 ml of PBS, and centrifuged and decanted as above. The resin was then transferred to a SPIN-X, 0.45 um, 2 ml tube. The resin was washed an additional two times with 0.5 ml of PBS and centrifuged. The monoclonal antibodies were eluted with 0.2 ml of 0.1M acetic acid by incubating at room temperature with occasional mixing for 10 minutes. The tubes were centrifuged, and 30 ul of 1M Tris buffer Ph 8.0 is added to the eluate. Purified antibodies were stored 4-8° C.

Example 4

In vitro Characterization of Antibodies
Antibody/Receptor Binding Assays: Whole Cell Based ELISA GCGR over-expressing CHO cells (clone 1004) and parental cells (AM1D) were seeded on microplates up to 90% confluence. Cells were blocked with BSA and incubated with the supernatants of hybridomas at 4° C. for 90 mins. After intensive washing, cells were incubated with detection antibody goat anti-murine IgG Fc-HRP (Pierce) and washed for three times. 50 ul/well of TMB substrate (KPL) was added and allowed to incubate at RT for 5-10 min. The reaction was stopped with the addition of 50 ul of 0.5N H2SO4 and the plate was read at 450 nm in a SpectraMax (Molecular Devices). The sera of GCGR membrane immunized mouse were used as positive controls and media alone as background control.

Antibody/Receptor Binding Assays: FMAT

GCGR over-expressing CHO cells (clone 1004) were seeded in 96 well clear bottom, black wall microplates (Applied Biosystems) at sub-confluent density (50-60%) and incubated with the hybridoma supernatants at room temperature for 60 mins. The cell images and quantities of cell binding fluorescence were recorded after incubating with FMAT blue labeled secondary antibody (goat anti-human IgG, Applied Biosystems) using 8200 Cellular Detection System (Applied Biosystems).

Cell Based Functional Assay

Anti-glucagon receptor antibodies were tested for their neutralizing activity in a cell-based functional assay using stable functional cell lines. Expression constructs (pcDNA3.1, Invitrogen) containing GCGR cDNAs from human, mouse, rat, cynomolgus or rat (cDNAs encoding SEQ ID NO: 2, 4, 6, 8 respectively) were transfected into CHO K1 cells respectively establishing stable cell lines. The final functional cell lines expressing GCGR from abovementioned species were single cell cloned from the transfected pools and tested for glucagon stimulated cAMP production. Based on $EC_{50}$ of each individual line, the final assay cell lines were selected and banked for future uses.

The following protocol was used to determine Kb, or the dissociation constant of antibody binding as calculated by Schild analysis based on the shift of a dose-response curve in the presence of an antagonist, in a competition binding assay.

The use of the Schild analysis is described Lazaeno et al, Br. J. Pharmacol. 109(4):1110-9 (1993), which is hereby incorporated by reference. This assay is adapted from use for small molecules to use with antibodies herein. Both hybridoma supernatant and purified antibodies were tested using the protocol below.

HTRF (Homogeneous Time-Resolved Fluorescence)-cAMP Dynamic kit from Cisbio was used for the functional assay. The hybridoma supernatants from the clones shown specific binding to human GCGR in the binding assay were first screened using functional assay. Antibodies were then purified from hybridoma conditioned media and retested for Kb and $IC_{50}$ values. Antibodies that are glucagon antagonists, capable of inhibition of cAMP production upon glucagon stimulation can be identified using this process.

The selected stable functional cell line as described above were seeded into 96-half well plate. The GCGR antibody was added into the wells and incubated at 37° C. for 20 minutes followed by addition of glucagon (Calbiochem) and incubation at 37° C. for additional 15 minutes. After adding the cAMP-conjugate in lysis buffer and then anti-cAMP-cryptate (antibody against cAMP conjugated to cryptate) into the wells, the plate was incubated at room temperature for 1 hour before being read with RubyStar (fluorescence microplate reader from BMG Labtech).

The purified antibodies were initially tested at 2 uM concentration with the functional human GCGR cell line. The cells were stimulated with 50 pM glucagon and antibodies showed strong inhibitory activity were selected for the determination of $IC_{50}$ which is defined as concentration of antibody required to inhibit half of maximum response over the base line. The antibodies were tested from 1 uM concentration and followed by a sequential 2-fold of serial dilution. The dose response curve was plotted and $IC_{50}$ was determined using GraphPad Prism software. Antibodies with the low $IC_{50}$ to human GCGR were selected and further tested for cross-species receptor activities using the appropriate cell lines.

$IC_{50}$ of Human Antibodies in Functional Assays

| Antibody | Human | Cynomolgus Monkey | Murine | Rat |
|---|---|---|---|---|
| | | $IC_{50}$ (nM) | | |
| A-3 | 9.1 | 22.5 | 4.9 | 13.5 |
| A-4 | 18.1 | 52.1 | 10.1 | 17.2 |
| A-9 | 7.4 | 26.6 | 4.1 | 9.9 |

To determine the relative potency of human anti-GCGR antibodies across different species, Schild analysis was performed for each of selected human antibodies. Briefly, the antibodies at different concentrations were tested in the presence of a serial dilution of glucagons, from 100 nM to 10 fM. The glucagon dose-response curves at different concentration of antibodies were plotted using GraphPad Prism software. pA2, which is the negative logarithm of the concentration of antibody required to cause a 2-fold rightward shift of the glucagon dose-response curve, was calculated for the antibody. When the Schild slope equals to 1, pA2 equals to pKb, the dissociation constant of the antibody binding. Then, Kb is derived by anti-log of pKb and can be used directly to compare the relative potency of individual antibody across the species.

Additional antibodies were tested for activity against the human GCGR.

| Antibody | IC50 (nM) |
|---|---|
| A-1 | 15.0 |
| A-2 | 10.1 |
| A-5 | 13.3 |
| A-6 | 32.2 |
| A-7 | 8.8 |
| A-8 | 10.4 |
| A-10 | No activity |
| A-11 | 16.7 |
| A-12 | 21.3 |
| A-13 | 72.6 |
| A-14 | 457.5 |
| A-15 | 11.3 |
| A-16 | No activity |
| A-17 | No activity |
| A-18 | 203.7 |
| A-19 | No activity |
| A-20 | No activity |
| A-21 | 47.2 |
| A-22 | 7.2 |
| A-23 | No activity |

Kb Values Determined by Schild Analysis

| | Kb (nM) | | | |
|---|---|---|---|---|
| | Human | Cynomolgus Monkey | Murine | Rat |
| A-3 | 1.6 | 5.0 | 0.5 | 3.2 |
| A-4 | 1.76 | 5.7 | 0.88 | ND |

Example 5

Recombinant Expression and Purification of Antibodies

Development of Stable Cell Line Expressing Antibodies

PCR primers were designed to capture the complete light chain open reading frame and signal peptide and variable region of the heavy chain open reading frame based on the DNA sequences of each antibody provided by Abgenix. The complete light chain and heavy chain signal peptide and variable region plus the human IgG2 constant region were ligated into the expression vectors pDC323 and pDC324 respectively.

As example of the PCR primer sets; the 5' A-9 light chain primer was 4337-12 (5'-AAG CTC GAG GTC GAC TAG ACC ACC ATG GAC ATG AGG GTC CCC GCT CAG CTC CTG-3') (SEQ ID NO: 313) which contains the SalI restriction enzyme site, an in-frame termination codon, the Kozak sequence and codes for the amino acids MDMRVPAQLL (SEQ ID NO: 314) and the 3' primer 3250-80 (5'-AAC CGT TTA AAC GCG GCC GCT CAA CAC TCT CCC CTG TTG AA-3') (SEQ ID NO: 315) which contains the NotI restriction enzyme site, the termination codon and codes for the amino acids FNRGEC (SEQ ID NO: 316). The 5' A-9 heavy chain primer was 3444-34 (5'-AAG CTC GAG GTC GAC TAG ACC ACC ATG GAG TTT GGG CTG AGC TGG GTT TTC-3') (SEQ ID NO: 317) which contains the SalI restriction enzyme site, an in-frame termination codon, the Kozak sequence and codes for the amino acids MEFGLSWVF (SEQ ID NO: 318), the A-9 heavy chain variable region/IgG2 (+) strand junction primer 4341-29 (5'-GAC CAC GGT CAC CGT CTC CTC AGC CTC CAC CAA GGG CCC ATC GGT CTT-3') (SEQ ID NO: 319) and its complimentary (−) strand primer 4341-30 (5'-AAG ACC GAT GGG CCC TTG GTG GAG GCT GAG GAG ACG GTG ACC GTG GTC-3') (SEQ ID NO: 320) which code for the amino acids GTTVTVSSAS-TKGPSVF (SEQ ID NO: 321) and the 3' primer 3250-79 (5'-AAC CGT TTA AAC GCG GCC GCT CAT TTA CCC GGA GAC AGG GA-3') (SEQ ID NO: 322) which contains the NotI restriction enzyme site, the termination codon and codes for the amino acids SLSPGK (SEQ ID NO: 323).

The CHO host cells used for transfection of the anti-GCGR expression plasmid(s) are a CHO cell line derived from DXB-11 cells (Urlaub et al, PNAS US 77:4126-4220, (1980)) through adaptation to serum-free medium (Rasmussen et al, Cytotechnology 28:3142, 1998).

The anti-GCGR cell lines were created by transfecting host cells with the expression plasmids pDC323-anti-GCGR kappa and pDC324-[anti-GCGR-IgG2] using a standard electroporation procedure. After transfection of the host cell line with the expression plasmids the cells were grown in selection medium (without GHT) containing 4% dialysed fetal bovine serum (ds or dfFBS) for 2-3 weeks to allow for selection of the plasmid and recovery of the cells. Serum was then removed from the medium and the cells were grown in −GHT selective medium until they achieved >85% viability. This pool of transfected cells was then cultured in medium containing 150 nM of MTX.

Cell Line Cloning

A cell bank was made of selected clones according to the following procedure. The cloning step ensures that clonal populations and cell banks were generated enabling a reproducible performance in commercial manufacturing. An amplified pool of antibody-expressing cells was seeded under limiting dilution in 96-well plates, and candidate clones were evaluated for growth and productivity performance in small-scale studies Example 6

In vivo Activity in ob/ob Mice 12-week old male ob/ob mice (Jackson Laboratories, Bar Harbor, Me.) were injected IP with a buffer or antibody 3 or 4 at the dose of 1 or 3 mg/kg (n=8-10/group). Blood glucose was measured at time 0 and at 24, 48, 72, 96, 120, 144, 192 and 240 hours after a single injection of antibody. Blood glucose was lowered with antibody 3 for 8 days at a dose of 3 mg/kg antibody as shown in FIG. 1.

Figure 2:
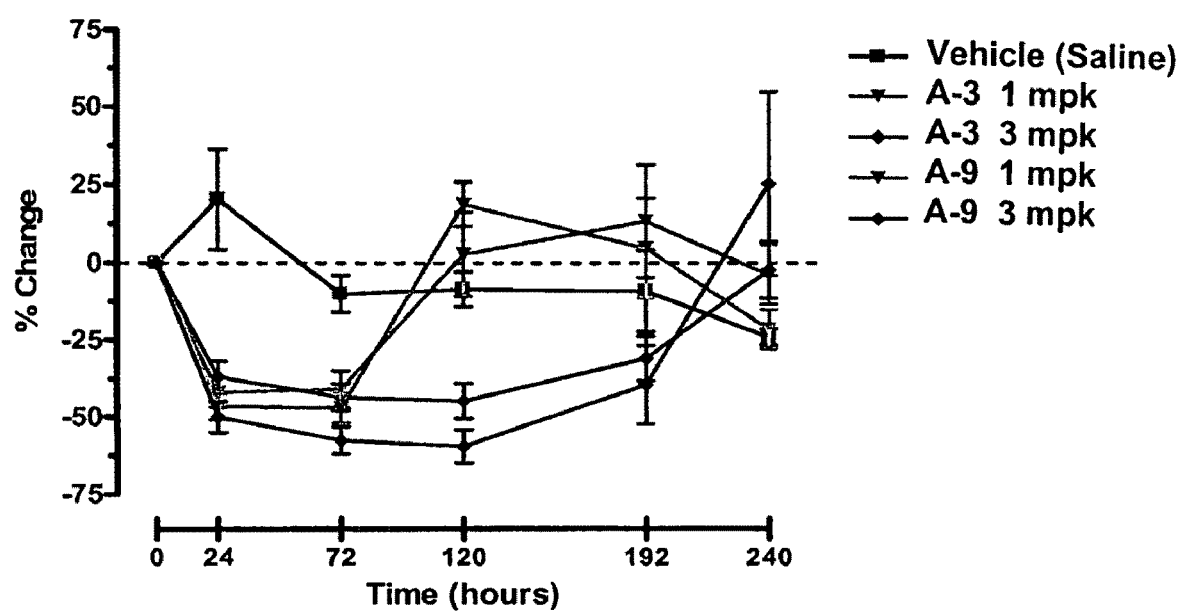
FIG. 2 shows blood glucose levels of 14-week old male ob/ob mice after a single injection of antibody A-3, or antibody A-9 compared with buffer at a dose of 1 or 3 mg/kg (n=10 animals/group). Blood glucose was measured at time 0 and at 24, 72, 120, 192, and 240 hours after injection.

Similarly, 12-week old male ob/ob mice (Jackson Laboratories, Bar Harbor, Me.) were injected IP with a buffer or antibody 3 or 9 at the dose of 1 or 3 mg/kg (n=8-10/group). Blood glucose was measured at time 0 and at 24, 72, 120, 192 and 240 hours after a single injection of antibody. Blood glucose was lowered with antibody 3 and 9 for 8 days at a dose of 3 mg/kg antibody as shown in FIG. 2.

Example 7

In vivo Efficacy in Normal Male Cynomolgus Monkeys

Figure 3:
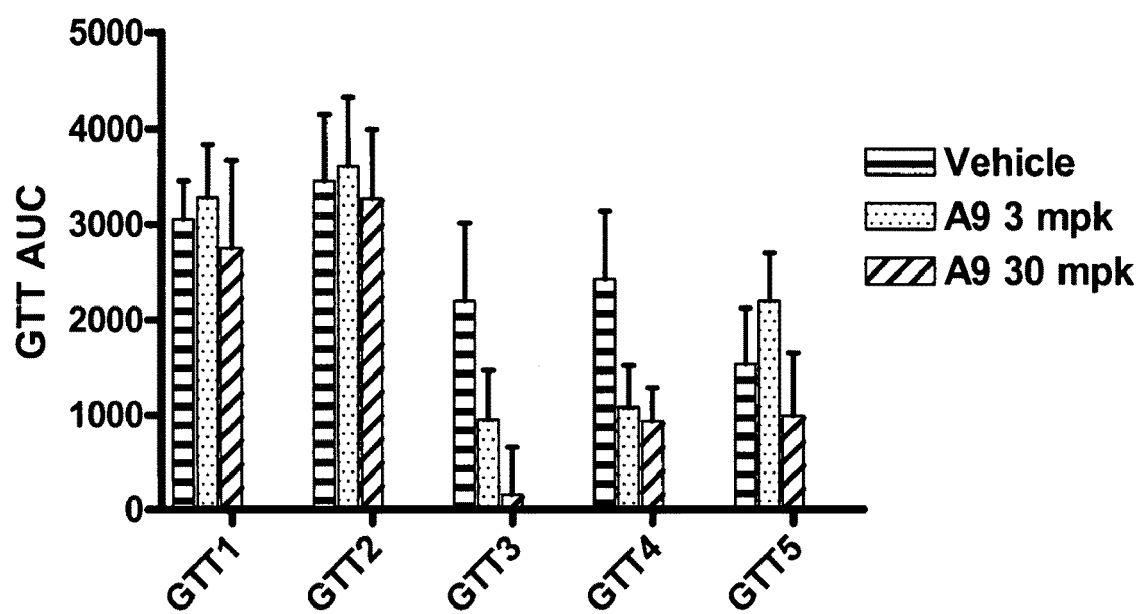
FIG. 3 shows the results of an oral glucose tolerance test (GTT) showing the glucose levels under the curve (AUC) before (GTT1 and GTT2) and after (GTT3, 4, and 5) a single subcutaneous injection of vehicle or antibody 9 (A9).

The efficacy of a single subcutaneous (SC) dose of antibody A-9 was evaluated in male cynomolgus monkeys at the Yunnan Primate Center (Yunnan, China). Glucose tolerance tests (GTT) were performed on the monkeys by testing for glucose clearance from the blood after challenging them with an oral dose of glucose. The GTT data is presented as AUC (area under the curve), as seen in FIG. 3, representing the glucose clearance by measuring amount of blood glucose at 0, 30 and 90 minutes post challenge. As shown in FIG. 3, pre-dose GTT1 was administered in a staggered fashion starting 24 days prior to the antibody administration, pre-dose GTT2 was administered in a staggered manner starting 17 days prior to a single dose. The antibody was administered as a single subcutaneous (SC) injection of a total of 3 or 30 mg/kg of antibody A-9 or a control to 30 male cynomolgus monkeys. GTT3 was administered to the monkeys at 3 days post injection, GTT4 was administered 8 days post injection, and GTT5 was administered 17 days post injection. The results, shown in FIG. 3, were that a single SC injection of either 3 or 30 mg/kg of antibody 9 improved glucose clearance during a glucose tolerance test.

Example 8

Competitive Binding Assays

Several of the antibodies of the present invention were binned using a competition binding assay to determine what antibodies cross-competed for binding with a labeled reference anti-GCGR antibody. The A-3 antibody was labeled with Alexa fluorescent dye (Molecular Probes/Invitrogen, Carlsbad, Calif.) as a tracer, prepared according to manufacturer's instructions. Each antibody was assayed across a dose range for its ability to compete with labeled A-3 antibody fixed at 1 nM concentration for binding to human GCGR receptor expressed on CHO cells (as described above). The fluorescent intensity was measured by FMAT as described in Example 4, and the extent of inhibition of Alexa A-3 binding to the receptor was calculated. Three groups of antibodies can be categorized based on these analyses. They are surmountable, partially surmountable or non-surmountable antibodies when competing with Alexa-A-3. The surmountable antibodies are able to compete for binding with A-3, while the non-surmountable antibodies cannot cross-compete and appear to have different sites of binding on the human GCGR. The partially surmountable antibodies have some overlap of binding site with A-3. These are shown in FIGS. 4-6. The antibodies tested and found to be capable of competing for binding with Alexa A-3 (surmountable) are A-11, A-2, A-7, A-12, A-17, A-6, A-8, A-15 and A-S. The antibodies tested and found to be only partially capable of competing for binding with Alexa A-3 (partially surmountable) are A-16, A-14, A-20, and A-23. The antibodies tested and found to be not capable of competing for binding with Alexa A-3 are A-19 and A-10. It is noted that all or most of the surmountable antibodies show inhibitory activity in the cell based assay (IC50) whereas the partially surmountable and unsurmountable antibodies did not show activity using this assay.

Example 9

Construction of Chimeric Receptors

Human GCGR is most homologous to human GLP-1 receptor and both belong to family B GPCR with 3 pairs of cysteines in the N-terminal section of the receptors. In order to determine the region or site on the human GCGR to which the human antibodies being tested will bind, and determine the importance of conformation maintained by the three pairs of cysteines that form disulfide bonds with each other, multiple chimeric receptor constructs between human GCGR and human GLP-1R (GLP-1R, accession number NP_002053) were generated and expressed in cells. These are shown in FIG. 7. The sequences of the chimera from human GCGR are indicated in FIG. 7. For example, in chimera 4 shown at the top of the figure amino acids 1-142 are from human GCGR and the remainder from GLP-1 receptor. Chimera 4 contains the three pairs of cysteines intact. Point mutations in paired cysteines (Cys 1-3, Cys 2-5 or Cys 4-6) were introduced in chimera 4 so that the three subsequent chimeras, chimera-4 1CA, 3CA; 4 2CA, 5CA, and 4 4CA, 6CA each have one of the cysteine pairs disrupted. Chimera-7 has amino acids 1-79 from the human GCGR; chimera-8 has amino acids 80-477 from human GCGR; chimera-10 has amino acids 80-142 from human GCGR; chimera-15 has amino acids 80-119 from human GCGR; chimera-19 has amino acids 1-119 and 143-477 from human GCGR. The cell surface receptor expression were monitored by in frame C-terminal fusion of fluorescent protein. The binding of the antibody to specific chimera receptor was directly measured by FMAT with Alexa-labeled reference antibody A-3. As shown in FIG. 7, all antibodies tested here require N-terminus of human GCGR (amino acid 1-142) for binding. Antibodies A-18, A-21, and A-10 behaved similarly in that they exhibited binding only the chimera-4 with all three cysteine pairs intact. This indicates a conformational epitope for these antibodies. For antibody A-3, amino acid sequence from 80 to 119 of human GCGR is necessary and sufficient enough for antibody binding. In addition, it was demonstrated that amino acids 120-142 of human GCGR are not needed for A-3 binding. Furthermore, for antibody A-3, conformation is maintained by $2^{nd}$ and $3^{rd}$ pairs (Cys 2-5, Cys 4-6), but not $1^{st}$ pair of cysteines. Therefore, the area of the receptor that antibody A-3 and all antibodies that cross-react with A-3 bind to the human GCGR within amino acids Ser80 to Ser119 of human GCGR.

Each reference cited herein is incorporated by reference in its entirety for all that it teaches and for all purposes.

The present invention is not to be limited in scope by the specific embodiments described herein, which are intended as single illustrations of individual aspects of the invention, and functionally equivalent methods and components are invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An isolated antibody or antigen-binding fragment thereof that specifically binds to human glucagon receptor, wherein said antibody or said antigen-binding fragment thereof comprises: a light chain variable domain comprising a complementarity determining region 1 (CDR1) comprising the amino acid sequence of SEQ ID NO: 14, a CDR2 comprising the amino acid sequence of SEQ ID NO: 45 and a CDR3 comprising the amino acid sequence of SEQ ID NO: 74 and a heavy chain variable domain comprising a CDR1 comprising the amino acid sequence of SEQ ID NO: 102, a CDR2 comprising the amino acid sequence of SEQ ID NO: 128, a CDR3 comprising the amino acid sequence of SEQ ID NO: 169.

2. The isolated antibody or antigen-binding fragment thereof of claim 1, wherein the light chain variable domain and the heavy chain variable domain are selected from the group of combinations consisting of: a light chain variable domain comprising the sequence of SEQ ID NO: 217 and a heavy chain variable domain comprising the sequence of SEQ ID NO: 263 and a light chain variable domain comprising the sequence of SEQ ID NO: 219 and a heavy chain variable domain comprising the sequence of SEQ ID NO: 265.

3. The isolated antibody or antigen-binding fragment thereof of claim 2, further comprising: a. the light chain constant sequence of SEQ ID NO: 305; b. the light chain constant sequence of SEQ ID NO: 307; c. the heavy chain constant sequence of SEQ ID NO: 309; d. the light chain constant sequence of SEQ ID NO: 305 and the heavy chain constant sequence of SEQ ID NO: 309, or e. the light chain constant sequence of SEQ ID NO: 307 and the heavy chain constant sequence of SEQ ID NO: 309.

4. The isolated antibody or antigen-binding fragment thereof of claim 1, wherein said antibody or antigen-binding fragment thereof is selected from the group consisting of a human antibody, a chimeric antibody, a monoclonal antibody, a polyclonal antibody, a recombinant antibody, a single chain antibody, a diabody, a triabody, a tetrabody, a Fab fragment, an IgD antibody, an IgE antibody, and IgM antibody, and IgG1 antibody, and IgG2 antibody, and IgG3 antibody, and IgG4 antibody, and an IgG4 antibody having at least one mutation in the hinge region.

5. The isolated antibody of claim 1, wherein said antibody is a human antibody.

6. The isolated human antibody of claim 5, wherein the antibody comprises a light chain comprising the amino acid sequence of SEQ ID NO: 312 and a heavy chain comprising the amino acid sequence of SEQ ID NO: 311.

7. A composition comprising the isolated antibody or antigen-binding fragment thereof of claim 1 in admixture with a pharmaceutically acceptable carrier.

* * * * *

SEQUENCE LISTING

```
<160> NUMBER OF SEQ ID NOS: 324

<210> SEQ ID NO 1
<211> LENGTH: 1519
<212> TYPE: DNA
<213> ORGANISM: Homo sapiens

<400> SEQUENCE: 1
gtgcagcccc tgccagatgt gggaggcagc tagctgccca gaggcatgcc cccctgccag      60
ccacagcgac ccctgctgct gttgctgctg ctgctggcct gccagccaca ggtcccctcc     120
gctcaggtga tggacttcct gtttgagaag tggaagctct acggtgacca gtgtcaccac     180
aacctgagcc tgctgccccc tcccacggag ctggtgtgca acagaacctt cgacaagtat     240
tcctgctggc cggacacccc cgccaatacc acggccaaca tctcctgccc ctggtacctg     300
ccttggcacc acaaagtgca acaccgcttc gtgttcaaga gatgcgggcc cgacggtcag     360
tgggtgcgtg gaccccgggg gcagccttgg cgtgatgcct cccagtgcca gatggatggc     420
gaggagattg aggtccagaa ggaggtggcc aagatgtaca gcagcttcca ggtgatgtac     480
acagtgggct acagcctgtc cctgggggcc ctgctcctcg ccttggccat cctgggggc      540 ctcagcaagc tgcactgcac ccgcaatgcc atccacgcga atctgtttgc gtccttcgtg     600
ctgaaagcca gctccgtgct ggtcattgat gggctgctca ggacccgcta cagccagaaa     660
attggcgacg acctcagtgt cagcacctgg ctcagtgatg gagcggtggc tggctgccgt     720
gtggccgcgg tgttcatgca atatggcatc gtggccaact actgctggct gctggtggag     780
ggcctgtacc tgcacaacct gctgggcctg gccaccctcc ccgagaggag cttcttcagc     840
ctctacctgg gcatcggctg gggtgccccc atgctgttcg tcgtcccctg ggcagtggtc     900
aagtgtctgt tcgagaacgt ccagtgctgg accagcaatg acaacatggg cttctggtgg     960
atcctgcggt tccccgtctt cctggccatc ctgatcaact tcttcatctt cgtccgcatc    1020
gttcagctgc tcgtggccaa gctgcgggca cggcagatgc accacacaga ctacaagttc    1080
cggctggcca agtccacgct gaccctcatc cctctgctgg gcgtccacga agtggtcttc    1140
gccttcgtga cggacgagca cgcccagggc accctgcgct ccgccaagct cttcttcgac    1200
ctcttcctca gctccttcca gggcctgctg gtggctgtcc tctactgctt cctcaacaag    1260
```

-continued

```
gaggtgcagt cggagctgcg gcggcgttgg caccgctggc gcctgggcaa agtgctatgg    1320
gaggagcgga acaccagcaa ccacagggcc tcatcttcgc ccggccacgg ccctcccagc    1380
aaggagctgc agtttgggag gggtggtggc agccaggatt catctgcgga gaccccttg     1440 gctggtggcc tccctagatt ggctgagagc cccttctgaa ccctgctggg accccagcta    1500
gggctggact ctggcaccc                                                 1519

<210> SEQ ID NO 2
<211> LENGTH: 477
<212> TYPE: PRT
<213> ORGANISM: Homo sapiens

<400> SEQUENCE: 2

Met Pro Pro Cys Gln Pro Gln Arg Pro Leu Leu Leu Leu Leu Leu Leu
1               5                   10                  15

Leu Ala Cys Gln Pro Gln Val Pro Ser Ala Gln Val Met Asp Phe Leu
            20                  25                  30

Phe Glu Lys Trp Lys Leu Tyr Gly Asp Gln Cys His His Asn Leu Ser
        35                  40                  45

Leu Leu Pro Pro Thr Glu Leu Val Cys Asn Arg Thr Phe Asp Lys
    50                  55                  60

Tyr Ser Cys Trp Pro Asp Thr Pro Ala Asn Thr Thr Ala Asn Ile Ser
65                  70                  75                  80

Cys Pro Trp Tyr Leu Pro Trp His His Lys Val Gln His Arg Phe Val
                85                  90                  95

Phe Lys Arg Cys Gly Pro Asp Gly Gln Trp Val Arg Gly Pro Arg Gly
            100                 105                 110

Gln Pro Trp Arg Asp Ala Ser Gln Cys Gln Met Asp Gly Glu Glu Ile
        115                 120                 125

Glu Val Gln Lys Glu Val Ala Lys Met Tyr Ser Ser Phe Gln Val Met
    130                 135                 140

Tyr Thr Val Gly Tyr Ser Leu Ser Leu Gly Ala Leu Leu Ala Leu
145                 150                 155                 160

Ala Ile Leu Gly Gly Leu Ser Lys Leu His Cys Thr Arg Asn Ala Ile
                165                 170                 175

His Ala Asn Leu Phe Ala Ser Phe Val Leu Lys Ala Ser Ser Val Leu
            180                 185                 190

Val Ile Asp Gly Leu Leu Arg Thr Arg Tyr Ser Gln Lys Ile Gly Asp
        195                 200                 205

Asp Leu Ser Val Ser Thr Trp Leu Ser Asp Gly Ala Val Ala Gly Cys
    210                 215                 220

Arg Val Ala Ala Val Phe Met Gln Tyr Gly Ile Val Ala Asn Tyr Cys
225                 230                 235                 240

Trp Leu Leu Val Glu Gly Leu Tyr Leu His Asn Leu Leu Gly Leu Ala
                245                 250                 255

Thr Leu Pro Glu Arg Ser Phe Phe Ser Leu Tyr Leu Gly Ile Gly Trp
            260                 265                 270

Gly Ala Pro Met Leu Phe Val Val Pro Trp Ala Val Val Lys Cys Leu
        275                 280                 285

Phe Glu Asn Val Gln Cys Trp Thr Ser Asn Asp Asn Met Gly Phe Trp
    290                 295                 300

Trp Ile Leu Arg Phe Pro Val Phe Leu Ala Ile Leu Ile Asn Phe Phe
305                 310                 315                 320

Ile Phe Val Arg Ile Val Gln Leu Leu Val Ala Lys Leu Arg Ala Arg
```

|  |  |  | 325 |  |  |  | 330 |  |  |  | 335 |  |
| --- | --- | --- | --- | --- | --- | --- | --- | --- | --- | --- | --- | --- |
| Gln | Met | His | His | Thr | Asp | Tyr | Lys | Phe | Arg | Leu | Ala | Lys | Ser | Thr | Leu |
|  |  |  | 340 |  |  |  | 345 |  |  |  | 350 |  |

Thr Leu Ile Pro Leu Leu Gly Val His Glu Val Val Phe Ala Phe Val
            355                 360                 365

Thr Asp Glu His Ala Gln Gly Thr Leu Arg Ser Ala Lys Leu Phe Phe
        370                 375                 380

Asp Leu Phe Leu Ser Ser Phe Gln Gly Leu Leu Val Ala Val Leu Tyr
385                 390                 395                 400

Cys Phe Leu Asn Lys Glu Val Gln Ser Glu Leu Arg Arg Arg Trp His
                405                 410                 415

Arg Trp Arg Leu Gly Lys Val Leu Trp Glu Glu Arg Asn Thr Ser Asn
            420                 425                 430

His Arg Ala Ser Ser Ser Pro Gly His Gly Pro Ser Lys Glu Leu
        435                 440                 445

Gln Phe Gly Arg Gly Gly Ser Gln Asp Ser Ser Ala Glu Thr Pro
    450                 455                 460

Leu Ala Gly Gly Leu Pro Arg Leu Ala Glu Ser Pro Phe
465                 470                 475

<210> SEQ ID NO 3
<211> LENGTH: 1880
<212> TYPE: DNA
<213> ORGANISM: Mus musculus

<400> SEQUENCE: 3

| cgcgaggagc gcagccctag ccccggcgac tgagcacacc tgaggagagg tgcacacact | 60 |
| --- | --- |
| ctgaggacct aggtgtgcaa cctctgccag atgtggggcg tggctaccca gaggcatgcc | 120 |
| cctcacccag ctccactgtc cccacctgct gctgctgctg ttggtgctgt catgtctgcc | 180 |
| agaggcaccc tctgcccagg taatggactt tttgtttgag aagtggaagc tctatagtga | 240 |
| ccaatgccac cacaacctaa gcctgctgcc cccacctact gagctggtct gtaacagaac | 300 |
| cttcgacaag tactcctgct ggcctgacac ccctcccaac accactgcca acatttcctg | 360 |
| cccctggtac ctaccttggt accacaaagt gcagcaccgc ctagtgttca agaggtgtgg | 420 |
| gcccgatggg cagtgggttc gagggccacg ggggcagccg tggcgcaacg cctcccaatg | 480 |
| tcagttggat gatgaagaga tcgaggtcca gaaggggtg gccaagatgt atagcagcca | 540 |
| gcaggtgatg tacaccgtgg gctacagtct gtccctgggg gccttgctcc ttgcgctggt | 600 |
| catcctgctg ggcctcagga agctgcactg cacccgaaac tacatccatg ggaacctgtt | 660 |
| tgcgtccttt gtgctcaagg ctggctctgt gttggtcatc gattggctgc tgaagacacg | 720 |
| gtacagccag aagattggcg atgaccctca gtgtgagcgtc tggctcagtg acggggcgat | 780 |
| ggccggctgc agagtggcca cagtgatcat gcagtacggc atcatagcca actattgctg | 840 |
| gttgctggta gagggcgtgt acctgtacag cctgctgagc cttgccacct tctctgagag | 900 |
| gagcttcttt tccctctacc tgggcattgg ctggggtgcg ccctgctgt tgtcatccc | 960 |
| ctgggtggtg gtcaagtgtc tgtttgagaa tgttcagtgc tggaccagca atgacaacat | 1020 |
| gggattctgg tggatcctgc gtattcctgt cttcctggcc ttactgatca attttttcat | 1080 |
| ctttgtccac atcattcacc ttcttgtggc caagctgcgt gcccatcaga tgcactatgc | 1140 |
| tgactataag ttccggctgg ccaggtccac gctgaccctc atccctctgc tgggggtcca | 1200 |
| cgaggtggtc tttgccttg tgactgacga gcatgcccaa ggcaccctgc gctccaccaa | 1260 |
| gctctttttt gacctgttcc tcagctcctt ccagggtctg ctggtggctg ttctctactg | 1320 |

```
tttcctcaac aaggaggtgc aggcagagct gatgcggcgt tggaggcaat ggcaagaagg    1380
caaagctctt caggaggaaa ggttggccag cagccatggc agccacatgg ccccagcagg    1440
gccttgtcat ggtgatccct gtgagaaact tcagcttatg agtgcaggca gcagcagtgg    1500
gactggctgt gtgccctcta tggagacctc gctggccagt agtctcccaa ggttggctga    1560
cagccccacc tgaatctcca ctggagccta gccaggctgc gttcagaaag gcctcagag     1620 gacaacccag agccagatgc ccggccaagg ctgaagagac aaagcagcaa gacagcagct    1680
tgtactgtgc acactcccct aacctgtcct agcctggcac aggccacagt gacagagtag    1740
gggttggata tgatggagaa gccatgttat ctatgaactc tgagtgttcc catgtgtgtt    1800
gacatggtcc ctgtacccag atatgtcctt cagtaaaaag ctcgagtggg agctgctgca    1860
caaaaaaaaa aaaaaaaaa                                                 1880
```

<210> SEQ ID NO 4
<211> LENGTH: 485
<212> TYPE: PRT
<213> ORGANISM: Mus musculus
<400> SEQUENCE: 4

```
Met Pro Leu Thr Gln Leu His Cys Pro His Leu Leu Leu Leu Leu
1               5                   10                  15

Val Leu Ser Cys Leu Pro Glu Ala Pro Ser Ala Gln Val Met Asp Phe
            20                  25                  30

Leu Phe Glu Lys Trp Lys Leu Tyr Ser Asp Gln Cys His His Asn Leu
        35                  40                  45

Ser Leu Leu Pro Pro Pro Thr Glu Leu Val Cys Asn Arg Thr Phe Asp
    50                  55                  60

Lys Tyr Ser Cys Trp Pro Asp Thr Pro Pro Asn Thr Thr Ala Asn Ile
65                  70                  75                  80

Ser Cys Pro Trp Tyr Leu Pro Trp Tyr His Lys Val Gln His Arg Leu
                85                  90                  95

Val Phe Lys Arg Cys Gly Pro Asp Gly Gln Trp Val Arg Gly Pro Arg
            100                 105                 110

Gly Gln Pro Trp Arg Asn Ala Ser Gln Cys Gln Leu Asp Asp Glu Glu
        115                 120                 125

Ile Glu Val Gln Lys Gly Val Ala Lys Met Tyr Ser Ser Gln Gln Val
    130                 135                 140

Met Tyr Thr Val Gly Tyr Ser Leu Ser Leu Gly Ala Leu Leu Leu Ala
145                 150                 155                 160

Leu Val Ile Leu Leu Gly Leu Arg Lys Leu His Cys Thr Arg Asn Tyr
                165                 170                 175

Ile His Gly Asn Leu Phe Ala Ser Phe Val Leu Lys Ala Gly Ser Val
            180                 185                 190

Leu Val Ile Asp Trp Leu Leu Lys Thr Arg Tyr Ser Gln Lys Ile Gly
        195                 200                 205

Asp Asp Leu Ser Val Ser Val Trp Leu Ser Asp Gly Ala Met Ala Gly
    210                 215                 220

Cys Arg Val Ala Thr Val Ile Met Gln Tyr Gly Ile Ile Ala Asn Tyr
225                 230                 235                 240

Cys Trp Leu Leu Val Glu Gly Val Tyr Leu Tyr Ser Leu Leu Ser Leu
                245                 250                 255

Ala Thr Phe Ser Glu Arg Ser Phe Phe Ser Leu Tyr Leu Gly Ile Gly
            260                 265                 270
```

```
Trp Gly Ala Pro Leu Leu Phe Val Ile Pro Trp Val Val Lys Cys
            275                 280                 285
Leu Phe Glu Asn Val Gln Cys Trp Thr Ser Asn Asp Asn Met Gly Phe
    290                 295                 300
Trp Trp Ile Leu Arg Ile Pro Val Phe Leu Ala Leu Leu Ile Asn Phe
305                 310                 315                 320
Phe Ile Phe Val His Ile Ile His Leu Leu Val Ala Lys Leu Arg Ala
                325                 330                 335
His Gln Met His Tyr Ala Asp Tyr Lys Phe Arg Leu Ala Arg Ser Thr
            340                 345                 350
Leu Thr Leu Ile Pro Leu Leu Gly Val His Glu Val Val Phe Ala Phe
            355                 360                 365
Val Thr Asp Glu His Ala Gln Gly Thr Leu Arg Ser Thr Lys Leu Phe
    370                 375                 380
Phe Asp Leu Phe Leu Ser Ser Phe Gln Gly Leu Leu Val Ala Val Leu
385                 390                 395                 400
Tyr Cys Phe Leu Asn Lys Glu Val Gln Ala Glu Leu Met Arg Arg Trp
                405                 410                 415
Arg Gln Trp Gln Glu Gly Lys Ala Leu Gln Glu Arg Leu Ala Ser
            420                 425                 430
Ser His Gly Ser His Met Ala Pro Ala Gly Pro Cys His Gly Asp Pro
    435                 440                 445
Cys Glu Lys Leu Gln Leu Met Ser Ala Gly Ser Ser Gly Thr Gly
450                 455                 460
Cys Val Pro Ser Met Glu Thr Ser Leu Ala Ser Ser Leu Pro Arg Leu
465                 470                 475                 480
Ala Asp Ser Pro Thr
                485

<210> SEQ ID NO 5
<211> LENGTH: 1875
<212> TYPE: DNA
<213> ORGANISM: Rattus norvegicus

<400> SEQUENCE: 5
gaattcgcgg ccgccgccgg gccccagatc ccagtgcgcg aggagcccag tcctagaccc      60
agcaacctga ggagaggtgc acacaccccc aaggacccag gcaccaaacc tctgccagat     120 gtggggggggt ggctacccag aggcatgctc ctcacccagc tccactgtcc ctacctgctg     180
ctgctgctgt tggtgctgtc atgtctgcca aaggcaccct gcccaggta atggactttt    240 ttgtttgaga agtggaagct ctatagtgac cagtgccacc acaacctaag cctgctgccc     300
ccacctactg agctggtctg caacagaact ttcgacaagt actcctgctg gcctgacacc     360
cctcccaaca ccactgccaa catttcctgc cctggtacc taccttggta ccacaaagtg      420
cagcaccgcc tagtgttcaa gaggtgtggg cctgatgggc agtgggttcg agggccacgg     480
gggcagtcat ggcgcgacgc ctcccaatgt cagatggatg atgacgagat cgaggtccag    540
aagggggtag ccaagatgta tagcagctac caggtgatgt acactgtggg ctacagtctg    600
tccctggggg ccttgctcct ggcgctggtc atcctgctgg gcctcaggaa gctgcactgc    660
acccggaact acatccacgg gaacctgttc gcgtccttcg tgctcaaggc tggctctgtg    720
ctggtcattg attggctgct caagacacgc tatagccaga agattggaga tgacctcagt    780
gtgagcgtct ggctcagtga tgggcggtg gctggctgca gagtggccac agtgatcatg     840
cagtacggca tcatagccaa ctactgctgg ttgctggtgg agggtgtgta cctgtacagc    900
```

```
ctgctgagca tcaccacctt ctcggagaag agcttcttct ccctctatct gtgcatcggc      960
tggggatctc ccctgctgtt tgtcatcccc tgggtggtgg tcaagtgtct gtttgagaat     1020
gtccagtgct ggaccagcaa tgacaatatg ggattctggt ggatcctgcg tatccctgta     1080
ctcctggcca tactgatcaa ttttttcatc tttgtccgca tcattcatct tcttgtggcc     1140
aagctgcgtg cccatcagat gcactatgct gattacaagt tccggctagc caggtccacg     1200 ctgacccctca ttcctctgct gggagtccac gaagtggtct ttgcctttgt gactgatgag     1260
catgcccagg gcaccctgcg ctccaccaag ctcttttttg acctgttctt cagctccttt     1320
cagggtctgc tggtggctgt tctctactgt ttcctcaaca aggaggtgca ggcagagcta     1380
ctgcggcgtt ggaggcgatg caagaaggc aaagctcttc aggaggaaag gatggccagc       1440
agccatggca gccacatggc cccagcaggg acttgtcatg gtgatccctg tgagaaactt     1500
cagcttatga gtgcaggcag cagcagtggg actggctgtg agccctctgc gaagacctca     1560
ttggccagta gtctcccaag gctggctgac agccccacct gaatctccac tggactccag     1620
ccaagttgga ttcagaaagg gcctcacaag acaacccaga acagatgcc tggccaaggc       1680 tgaagaggca aagcagcaag acagcagctt gtactatcca cactccccta acctgtcctg     1740
gccgggtaca ggccacattg atggagtagg ggctggatat gatggagtag ccatgctatg     1800
aactatgggt gttcccatga gtgttgccat gttccatgca cacagatatg accttcagta     1860
aagagctccc gtagg                                                      1875
```

<210> SEQ ID NO 6
<211> LENGTH: 485
<212> TYPE: PRT
<213> ORGANISM: Rattus norvegicus

<400> SEQUENCE: 6

```
Met Leu Leu Thr Gln Leu His Cys Pro Tyr Leu Leu Leu Leu Val
1               5                   10                  15

Val Leu Ser Cys Leu Pro Lys Ala Pro Ser Ala Gln Val Met Asp Phe
            20                  25                  30

Leu Phe Glu Lys Trp Lys Leu Tyr Ser Asp Gln Cys His His Asn Leu
        35                  40                  45

Ser Leu Leu Pro Pro Pro Thr Glu Leu Val Cys Asn Arg Thr Phe Asp
    50                  55                  60

Lys Tyr Ser Cys Trp Pro Asp Thr Pro Pro Asn Thr Thr Ala Asn Ile
65                  70                  75                  80

Ser Cys Pro Trp Tyr Leu Pro Trp Tyr His Lys Val Gln His Arg Leu
                85                  90                  95

Val Phe Lys Arg Cys Gly Pro Asp Gly Gln Trp Val Arg Gly Pro Arg
            100                 105                 110

Gly Gln Ser Trp Arg Asp Ala Ser Gln Cys Gln Met Asp Asp Asp Glu
        115                 120                 125

Ile Glu Val Gln Lys Gly Val Ala Lys Met Tyr Ser Ser Tyr Gln Val
    130                 135                 140

Met Tyr Thr Val Gly Tyr Ser Leu Ser Leu Gly Ala Leu Leu Leu Ala
145                 150                 155                 160

Leu Val Ile Leu Leu Gly Leu Arg Lys Leu His Cys Thr Arg Asn Tyr
                165                 170                 175

Ile His Gly Asn Leu Phe Ala Ser Phe Val Leu Lys Ala Gly Ser Val
            180                 185                 190

Leu Val Ile Asp Trp Leu Leu Lys Thr Arg Tyr Ser Gln Lys Ile Gly
        195                 200                 205
```

Asp Asp Leu Ser Val Ser Val Trp Leu Ser Asp Gly Ala Val Ala Gly
        210                 215                 220

Cys Arg Val Ala Thr Val Ile Met Gln Tyr Gly Ile Ile Ala Asn Tyr
225                 230                 235                 240

Cys Trp Leu Leu Val Glu Gly Val Tyr Leu Tyr Ser Leu Leu Ser Ile
                245                 250                 255

Thr Thr Phe Ser Glu Lys Ser Phe Phe Ser Leu Tyr Leu Cys Ile Gly
            260                 265                 270

Trp Gly Ser Pro Leu Leu Phe Val Ile Pro Trp Val Val Lys Cys
        275                 280                 285

Leu Phe Glu Asn Val Gln Cys Trp Thr Ser Asn Asp Asn Met Gly Phe
    290                 295                 300

Trp Trp Ile Leu Arg Ile Pro Val Leu Leu Ala Ile Leu Ile Asn Phe
305                 310                 315                 320

Phe Ile Phe Val Arg Ile Ile His Leu Leu Val Ala Lys Leu Arg Ala
                325                 330                 335

His Gln Met His Tyr Ala Asp Tyr Lys Phe Arg Leu Ala Arg Ser Thr
            340                 345                 350

Leu Thr Leu Ile Pro Leu Leu Gly Val His Glu Val Val Phe Ala Phe
        355                 360                 365

Val Thr Asp Glu His Ala Gln Gly Thr Leu Arg Ser Thr Lys Leu Phe
370                 375                 380

Phe Asp Leu Phe Phe Ser Ser Phe Gln Gly Leu Leu Val Ala Val Leu
385                 390                 395                 400

Tyr Cys Phe Leu Asn Lys Glu Val Gln Ala Glu Leu Leu Arg Arg Trp
                405                 410                 415

Arg Arg Trp Gln Glu Gly Lys Ala Leu Gln Glu Arg Met Ala Ser
            420                 425                 430

Ser His Gly Ser His Met Ala Pro Ala Gly Thr Cys His Gly Asp Pro
        435                 440                 445

Cys Glu Lys Leu Gln Leu Met Ser Ala Gly Ser Ser Ser Gly Thr Gly
    450                 455                 460

Cys Glu Pro Ser Ala Lys Thr Ser Leu Ala Ser Ser Leu Pro Arg Leu
465                 470                 475                 480

Ala Asp Ser Pro Thr
            485

<210> SEQ ID NO 7
<211> LENGTH: 1434
<212> TYPE: DNA
<213> ORGANISM: Macaca fascicularis

<400> SEQUENCE: 7 atgccccct gtcagccacg tcgacccctg ctactgttgc tgctgctgct ggcctgccag        60
ccacaggccc cctccgctca ggtgatggac ttcctgtttg agaagtggaa actctacggt       120
gaccagtgtc accacaacct gagcctgctg ccccccccca cggagctggt ctgtaacaga       180
accttcgaca gtattcctg ctggccagac accccgcca ataccacagc aacatctcc          240 tgccctggt acctgccttg caccacaaa gtgcaacacc gcttcgtgtt caagagatgc         300
gggcccgatg tcagtgggt gcgtggaccc cgggggcagc cttggcgtga cgcctctcag        360
tgccagatgg acggcgagga gcttgaggtc cagaaggagg tggctaagat gtacagcagc       420
ttccaggtga tgtacacggt gggctacagc ctgtccctgg ggccctgct cctcgccttg        480 gccatcctgg ggggcatcag caagctgcac tgcacccgca acgccatcca cgcgaacctg      540

-continued

```
tttgtgtcct tcgtgctgaa ggccagctcc gtgctggtca tcgatgggct gctcaggacc    600
cgctacagcc agaagattgg cgacgacctc agtgtcagca tctggctcag tgatggagcg    660
gtggccggct gccgtgtggc cgcggtgttc atgcaatatg cgtcgtggc caactactgc     720 tggctgctgg tggagggcct gtacctgcac aacctgctgg gcctggccac cctccctgag    780
aggagcttct tcagcctcta cctgggcatc ggctggggtg cccccatgct gttcatcatc    840
ccctgggtgg tggtcaggtg tctgttcgag aacatccagt gctggaccag caatgacaac    900
atgggcttct ggtggatcct gcggttcccc gtcttcctgg ccatcctgat caacttcttc    960
atcttcatcc gcattgttca cctgcttgtg gccaagctgc gggcgcggga gatgcaccac   1020
acagactaca agttccgact ggccaagtcc acactgaccc tcatcccct gctgggtgtc    1080 cacgaagtga tcttcgcctt cgtgacggac gagcacgccc agggcaccct gcgcttcgcc   1140
aagctcttct tcgacctctt cctcagctct ttccagggcc tgctggtggc tgtcctctac   1200
tgcttcctca acaaggaggt gcagtcggaa cttcggcggc attggcaccg ctggcgcctg   1260
ggcaaagtgc tgcaggagga gcggggcacc agcaaccaca agaccccatc tgcgcctggc   1320
caaggccttc ctggcaagaa gctgcagtct gggaggggtg gtggcagcca ggactcatct   1380
gcggagatcc ccttggctgg tggcctccct aggttggctg agagccccct ctga         1434
```

<210> SEQ ID NO 8
<211> LENGTH: 477
<212> TYPE: PRT
<213> ORGANISM: Macaca fascicularis

<400> SEQUENCE: 8

```
Met Pro Pro Cys Gln Pro Arg Arg Pro Leu Leu Leu Leu Leu Leu Leu
1               5                   10                  15

Leu Ala Cys Gln Pro Gln Ala Pro Ser Ala Gln Val Met Asp Phe Leu
            20                  25                  30

Phe Glu Lys Trp Lys Leu Tyr Gly Asp Gln Cys His His Asn Leu Ser
        35                  40                  45

Leu Leu Pro Pro Thr Glu Leu Val Cys Asn Arg Thr Phe Asp Lys
    50                  55                  60

Tyr Ser Cys Trp Pro Asp Thr Pro Ala Asn Thr Thr Ala Asn Ile Ser
65                  70                  75                  80

Cys Pro Trp Tyr Leu Pro Trp His His Lys Val Gln His Arg Phe Val
                85                  90                  95

Phe Lys Arg Cys Gly Pro Asp Gly Gln Trp Val Arg Gly Pro Arg Gly
            100                 105                 110

Gln Pro Trp Arg Asp Ala Ser Gln Cys Gln Met Asp Gly Glu Glu Leu
        115                 120                 125

Glu Val Gln Lys Glu Val Ala Lys Met Tyr Ser Ser Phe Gln Val Met
    130                 135                 140

Tyr Thr Val Gly Tyr Ser Leu Ser Leu Gly Ala Leu Leu Leu Ala Leu
145                 150                 155                 160

Ala Ile Leu Gly Gly Ile Ser Lys Leu His Cys Thr Arg Asn Ala Ile
                165                 170                 175

His Ala Asn Leu Phe Val Ser Phe Val Leu Lys Ala Ser Ser Val Leu
            180                 185                 190

Val Ile Asp Gly Leu Leu Arg Thr Arg Tyr Ser Gln Lys Ile Gly Asp
        195                 200                 205

Asp Leu Ser Val Ser Ile Trp Leu Ser Asp Gly Ala Val Ala Gly Cys
    210                 215                 220
```

```
Arg Val Ala Ala Val Phe Met Gln Tyr Gly Val Ala Asn Tyr Cys
225                 230                 235                 240

Trp Leu Leu Val Glu Gly Leu Tyr Leu His Asn Leu Gly Leu Ala
                245                 250                 255

Thr Leu Pro Glu Arg Ser Phe Phe Ser Leu Tyr Leu Gly Ile Gly Trp
            260                 265                 270

Gly Ala Pro Met Leu Phe Ile Ile Pro Trp Val Val Arg Cys Leu
        275                 280                 285

Phe Glu Asn Ile Gln Cys Trp Thr Ser Asn Asp Asn Met Gly Phe Trp
290                 295                 300

Trp Ile Leu Arg Phe Pro Val Phe Leu Ala Ile Leu Ile Asn Phe Phe
305                 310                 315                 320

Ile Phe Ile Arg Ile Val His Leu Leu Val Ala Lys Leu Arg Ala Arg
                325                 330                 335

Glu Met His His Thr Asp Tyr Lys Phe Arg Leu Ala Lys Ser Thr Leu
                340                 345                 350

Thr Leu Ile Pro Leu Leu Gly Val His Glu Val Ile Phe Ala Phe Val
                355                 360                 365

Thr Asp Glu His Ala Gln Gly Thr Leu Arg Phe Ala Lys Leu Phe Phe
370                 375                 380

Asp Leu Phe Leu Ser Ser Phe Gln Gly Leu Leu Val Ala Val Leu Tyr
385                 390                 395                 400

Cys Phe Leu Asn Lys Glu Val Gln Ser Glu Leu Arg Arg His Trp His
                405                 410                 415

Arg Trp Arg Leu Gly Lys Val Leu Gln Glu Arg Gly Thr Ser Asn
                420                 425                 430

His Lys Thr Pro Ser Ala Pro Gly Gln Gly Leu Pro Gly Lys Lys Leu
                435                 440                 445

Gln Ser Gly Arg Gly Gly Ser Gln Asp Ser Ala Glu Ile Pro
                450                 455                 460

Leu Ala Gly Gly Leu Pro Arg Leu Ala Glu Ser Pro Phe
465                 470                 475

<210> SEQ ID NO 9
<211> LENGTH: 51
<212> TYPE: DNA
<213> ORGANISM: Homo sapiens

<400> SEQUENCE: 9
aggtctagtc agagcctctt ggatagagat gatggagaca cctatttgga c            51

<210> SEQ ID NO 10
<211> LENGTH: 17
<212> TYPE: PRT
<213> ORGANISM: Homo sapiens

<400> SEQUENCE: 10

Arg Ser Ser Gln Ser Leu Leu Asp Arg Asp Asp Gly Asp Thr Tyr Leu
1               5                   10                  15

Asp

<210> SEQ ID NO 11
<211> LENGTH: 51
<212> TYPE: DNA
<213> ORGANISM: Homo sapiens

<400> SEQUENCE: 11
```

```
aggtctagtc agagcctctt ggatagtgct gatggagaca cctatttgga c          51
```

<210> SEQ ID NO 12
<211> LENGTH: 17
<212> TYPE: PRT
<213> ORGANISM: Homo sapiens

<400> SEQUENCE: 12

```
Arg Ser Ser Gln Ser Leu Leu Asp Ser Ala Asp Gly Asp Thr Tyr Leu
1               5                   10                  15

Asp
```

<210> SEQ ID NO 13
<211> LENGTH: 33
<212> TYPE: DNA
<213> ORGANISM: Homo sapiens

<400> SEQUENCE: 13

```
cgggcaagtc agggcattag aaatgattta ggc                              33
```

<210> SEQ ID NO 14
<211> LENGTH: 11
<212> TYPE: PRT
<213> ORGANISM: Homo sapiens

<400> SEQUENCE: 14

```
Arg Ala Ser Gln Gly Ile Arg Asn Asp Leu Gly
1               5                   10
```

<210> SEQ ID NO 15
<211> LENGTH: 36
<212> TYPE: DNA
<213> ORGANISM: Homo sapiens

<400> SEQUENCE: 15

```
agggccagtc agagtgttag cagcaactac ttagcc                           36
```

<210> SEQ ID NO 16
<211> LENGTH: 12
<212> TYPE: PRT
<213> ORGANISM: Homo sapiens

<400> SEQUENCE: 16

```
Arg Ala Ser Gln Ser Val Ser Ser Asn Tyr Leu Ala
1               5                   10
```

<210> SEQ ID NO 17
<211> LENGTH: 33
<212> TYPE: DNA
<213> ORGANISM: Homo sapiens

<400> SEQUENCE: 17

```
cgggcaagtc aggacattag aaatgatttt ggc                              33
```

<210> SEQ ID NO 18
<211> LENGTH: 11
<212> TYPE: PRT
<213> ORGANISM: Homo sapiens

<400> SEQUENCE: 18

```
Arg Ala Ser Gln Asp Ile Arg Asn Asp Phe Gly
1               5                   10
```

<210> SEQ ID NO 19

-continued

```
<211> LENGTH: 51
<212> TYPE: DNA
<213> ORGANISM: Homo sapiens

<400> SEQUENCE: 19
gggtctactc agagcctctt ggatagtgat gatggagaca cctatttgga c          51

<210> SEQ ID NO 20
<211> LENGTH: 17
<212> TYPE: PRT
<213> ORGANISM: Homo sapiens

<400> SEQUENCE: 20

Arg Ser Thr Gln Ser Leu Leu Asp Ser Asp Asp Gly Asp Thr Tyr Leu
1               5                   10                  15

Asp

<210> SEQ ID NO 21
<211> LENGTH: 33
<212> TYPE: DNA
<213> ORGANISM: Homo sapiens

<400> SEQUENCE: 21
caggcgagtc aggacattag taagtattta aat                              33

<210> SEQ ID NO 22
<211> LENGTH: 11
<212> TYPE: PRT
<213> ORGANISM: Homo sapiens

<400> SEQUENCE: 22

Gln Ala Ser Gln Asp Ile Ser Lys Tyr Leu Asn
1               5                   10

<210> SEQ ID NO 23
<211> LENGTH: 33
<212> TYPE: DNA
<213> ORGANISM: Homo sapiens

<400> SEQUENCE: 23
tctggagata aattggggga taaatatgtt tgc                              33

<210> SEQ ID NO 24
<211> LENGTH: 11
<212> TYPE: PRT
<213> ORGANISM: Homo sapiens

<400> SEQUENCE: 24

Ser Gly Asp Lys Leu Gly Asp Lys Tyr Val Cys
1               5                   10

<210> SEQ ID NO 25
<211> LENGTH: 33
<212> TYPE: DNA
<213> ORGANISM: Homo sapiens

<400> SEQUENCE: 25
tctggagata aattggggga taaatatgct tgc                              33

<210> SEQ ID NO 26
<211> LENGTH: 11
<212> TYPE: PRT
<213> ORGANISM: Homo sapiens

<400> SEQUENCE: 26
```

-continued

Ser Gly Asp Lys Leu Gly Asp Lys Tyr Ala Cys
1               5                   10

<210> SEQ ID NO 27
<211> LENGTH: 39
<212> TYPE: DNA
<213> ORGANISM: Homo sapiens

<400> SEQUENCE: 27
acccgcagca gtggcagcat tgtcagcaac tttgtgcaa                            39

<210> SEQ ID NO 28
<211> LENGTH: 13
<212> TYPE: PRT
<213> ORGANISM: Homo sapiens

<400> SEQUENCE: 28

Thr Arg Ser Ser Gly Ser Ile Val Ser Asn Phe Val Gln
1               5                   10

<210> SEQ ID NO 29
<211> LENGTH: 39
<212> TYPE: DNA
<213> ORGANISM: Homo sapiens

<400> SEQUENCE: 29
actggaatca cctccaacat cggaagcaat actgtacac                            39

<210> SEQ ID NO 30
<211> LENGTH: 13
<212> TYPE: PRT
<213> ORGANISM: Homo sapiens

<400> SEQUENCE: 30

Thr Gly Ile Thr Ser Asn Ile Gly Ser Asn Thr Val His
1               5                   10

<210> SEQ ID NO 31
<211> LENGTH: 39
<212> TYPE: DNA
<213> ORGANISM: Homo sapiens

<400> SEQUENCE: 31
tctggaagca ggtccaacat cggaagtaat tatgtatac                            39

<210> SEQ ID NO 32
<211> LENGTH: 13
<212> TYPE: PRT
<213> ORGANISM: Homo sapiens

<400> SEQUENCE: 32

Ser Gly Ser Arg Ser Asn Ile Gly Ser Asn Tyr Val Tyr
1               5                   10

<210> SEQ ID NO 33
<211> LENGTH: 42
<212> TYPE: DNA
<213> ORGANISM: Homo sapiens

<400> SEQUENCE: 33
actgggagca gctccaacat cggggcaggt tatgctgtac ac                        42

<210> SEQ ID NO 34
<211> LENGTH: 14

```
<212> TYPE: PRT
<213> ORGANISM: Homo sapiens

<400> SEQUENCE: 34

Thr Gly Ser Ser Ser Asn Ile Gly Ala Gly Tyr Ala Val His
1               5                   10

<210> SEQ ID NO 35
<211> LENGTH: 48
<212> TYPE: DNA
<213> ORGANISM: Homo sapiens

<400> SEQUENCE: 35
aagtctagtc agagcctcct gcatagtgat ggaaagaact atttgttt                    48

<210> SEQ ID NO 36
<211> LENGTH: 16
<212> TYPE: PRT
<213> ORGANISM: Homo sapiens

<400> SEQUENCE: 36

Lys Ser Ser Gln Ser Leu Leu His Ser Asp Gly Lys Asn Tyr Leu Phe
1               5                   10                  15

<210> SEQ ID NO 37
<211> LENGTH: 48
<212> TYPE: DNA
<213> ORGANISM: Homo sapiens

<400> SEQUENCE: 37
aggtctagtc agagcctcct gcatagtaat ggatacaact atttggat                    48

<210> SEQ ID NO 38
<211> LENGTH: 16
<212> TYPE: PRT
<213> ORGANISM: Homo sapiens

<400> SEQUENCE: 38

Arg Ser Ser Gln Ser Leu Leu His Ser Asn Gly Tyr Asn Tyr Leu Asp
1               5                   10                  15

<210> SEQ ID NO 39
<211> LENGTH: 33
<212> TYPE: DNA
<213> ORGANISM: Homo sapiens

<400> SEQUENCE: 39
cgggcaagtc agggcattag aaatgattta ggc                                    33

<210> SEQ ID NO 40
<211> LENGTH: 33
<212> TYPE: DNA
<213> ORGANISM: Homo sapiens

<400> SEQUENCE: 40
cgggcgagtc agggtattag cagctggtta gcc                                    33

<210> SEQ ID NO 41
<211> LENGTH: 11
<212> TYPE: PRT
<213> ORGANISM: Homo sapiens

<400> SEQUENCE: 41

Arg Ala Ser Gln Gly Ile Ser Ser Trp Leu Ala
1               5                   10
```

<210> SEQ ID NO 42
<211> LENGTH: 21
<212> TYPE: DNA
<213> ORGANISM: Homo sapiens

<400> SEQUENCE: 42
acgctttcct atcgggcctc t                                              21

<210> SEQ ID NO 43
<211> LENGTH: 7
<212> TYPE: PRT
<213> ORGANISM: Homo sapiens

<400> SEQUENCE: 43

Thr Leu Ser Tyr Arg Ala Ser
1               5

<210> SEQ ID NO 44
<211> LENGTH: 21
<212> TYPE: DNA
<213> ORGANISM: Homo sapiens

<400> SEQUENCE: 44
gctgcatcca gtttgcaaag t                                              21

<210> SEQ ID NO 45
<211> LENGTH: 7
<212> TYPE: PRT
<213> ORGANISM: Homo sapiens

<400> SEQUENCE: 45

Ala Ala Ser Ser Leu Gln Ser
1               5

<210> SEQ ID NO 46
<211> LENGTH: 21
<212> TYPE: DNA
<213> ORGANISM: Homo sapiens

<400> SEQUENCE: 46
gctgcctcca gtttgcaaag t                                              21

<210> SEQ ID NO 47
<211> LENGTH: 21
<212> TYPE: DNA
<213> ORGANISM: Homo sapiens

<400> SEQUENCE: 47
ggtgcatcca gcagggccac t                                              21

<210> SEQ ID NO 48
<211> LENGTH: 7
<212> TYPE: PRT
<213> ORGANISM: Homo sapiens

<400> SEQUENCE: 48

Gly Ala Ser Ser Arg Ala Thr
1               5

<210> SEQ ID NO 49
<211> LENGTH: 21
<212> TYPE: DNA
<213> ORGANISM: Homo sapiens

```
<400> SEQUENCE: 49
gctgcatcca gtttggaaag t                                          21

<210> SEQ ID NO 50
<211> LENGTH: 7
<212> TYPE: PRT
<213> ORGANISM: Homo sapiens

<400> SEQUENCE: 50

Ala Ala Ser Ser Leu Glu Ser
1               5

<210> SEQ ID NO 51
<211> LENGTH: 21
<212> TYPE: DNA
<213> ORGANISM: Homo sapiens

<400> SEQUENCE: 51
gatgcatcca atttggaaac a                                          21

<210> SEQ ID NO 52
<211> LENGTH: 7
<212> TYPE: PRT
<213> ORGANISM: Homo sapiens

<400> SEQUENCE: 52

Asp Ala Ser Asn Leu Glu Thr
1               5

<210> SEQ ID NO 53
<211> LENGTH: 21
<212> TYPE: DNA
<213> ORGANISM: Homo sapiens

<400> SEQUENCE: 53
caaacttcca agcggccctc a                                          21

<210> SEQ ID NO 54
<211> LENGTH: 7
<212> TYPE: PRT
<213> ORGANISM: Homo sapiens

<400> SEQUENCE: 54

Gln Thr Ser Lys Arg Pro Ser
1               5

<210> SEQ ID NO 55
<211> LENGTH: 21
<212> TYPE: DNA
<213> ORGANISM: Homo sapiens

<400> SEQUENCE: 55
caatctacca agcggccctc a                                          21

<210> SEQ ID NO 56
<211> LENGTH: 7
<212> TYPE: PRT
<213> ORGANISM: Homo sapiens

<400> SEQUENCE: 56

Gln Ser Thr Lys Arg Pro Ser
1               5

<210> SEQ ID NO 57
```

```
<211> LENGTH: 21
<212> TYPE: DNA
<213> ORGANISM: Homo sapiens

<400> SEQUENCE: 57
gaggataacc aaagaccctc t                                              21

<210> SEQ ID NO 58
<211> LENGTH: 7
<212> TYPE: PRT
<213> ORGANISM: Homo sapiens

<400> SEQUENCE: 58

Glu Asp Asn Gln Arg Pro Ser
1               5

<210> SEQ ID NO 59
<211> LENGTH: 21
<212> TYPE: DNA
<213> ORGANISM: Homo sapiens

<400> SEQUENCE: 59
agtaataatc agcggccctc a                                              21

<210> SEQ ID NO 60
<211> LENGTH: 7
<212> TYPE: PRT
<213> ORGANISM: Homo sapiens

<400> SEQUENCE: 60

Ser Asn Asn Gln Arg Pro Ser
1               5

<210> SEQ ID NO 61
<211> LENGTH: 21
<212> TYPE: DNA
<213> ORGANISM: Homo sapiens

<400> SEQUENCE: 61
aggaataatc agcggccctc a                                              21

<210> SEQ ID NO 62
<211> LENGTH: 7
<212> TYPE: PRT
<213> ORGANISM: Homo sapiens

<400> SEQUENCE: 62

Arg Asn Asn Gln Arg Pro Ser
1               5

<210> SEQ ID NO 63
<211> LENGTH: 21
<212> TYPE: DNA
<213> ORGANISM: Homo sapiens

<400> SEQUENCE: 63
gataacaaca atcggccctc a                                              21

<210> SEQ ID NO 64
<211> LENGTH: 6
<212> TYPE: PRT
<213> ORGANISM: Homo sapiens

<400> SEQUENCE: 64

Asp Asn Asn Asn Arg Pro
```

-continued

<210> SEQ ID NO 65
<211> LENGTH: 21
<212> TYPE: DNA
<213> ORGANISM: Homo sapiens

<400> SEQUENCE: 65
gaagtttcct accggttctc t                                              21

<210> SEQ ID NO 66
<211> LENGTH: 7
<212> TYPE: PRT
<213> ORGANISM: Homo sapiens

<400> SEQUENCE: 66

Glu Val Ser Tyr Arg Phe Ser
1               5

<210> SEQ ID NO 67
<211> LENGTH: 21
<212> TYPE: DNA
<213> ORGANISM: Homo sapiens

<400> SEQUENCE: 67
ttgggttcta atcgggcctc c                                              21

<210> SEQ ID NO 68
<211> LENGTH: 7
<212> TYPE: PRT
<213> ORGANISM: Homo sapiens

<400> SEQUENCE: 68

Leu Gly Ser Asn Arg Ala Ser
1               5

<210> SEQ ID NO 69
<211> LENGTH: 21
<212> TYPE: DNA
<213> ORGANISM: Homo sapiens

<400> SEQUENCE: 69
actgcatcca ctttgcaaag t                                              21

<210> SEQ ID NO 70
<211> LENGTH: 7
<212> TYPE: PRT
<213> ORGANISM: Homo sapiens

<400> SEQUENCE: 70

Thr Ala Ser Thr Leu Gln Ser
1               5

<210> SEQ ID NO 71
<211> LENGTH: 27
<212> TYPE: DNA
<213> ORGANISM: Homo sapiens

<400> SEQUENCE: 71
atgcaacgta tagagtttcc attcact                                        27

<210> SEQ ID NO 72
<211> LENGTH: 9
<212> TYPE: PRT
<213> ORGANISM: Homo sapiens

```
<400> SEQUENCE: 72

Met Gln Arg Ile Glu Phe Pro Phe Thr
1               5

<210> SEQ ID NO 73
<211> LENGTH: 27
<212> TYPE: DNA
<213> ORGANISM: Homo sapiens

<400> SEQUENCE: 73
ctacagcata atagtaaccc tctcact                                           27

<210> SEQ ID NO 74
<211> LENGTH: 9
<212> TYPE: PRT
<213> ORGANISM: Homo sapiens

<400> SEQUENCE: 74

Leu Gln His Asn Ser Asn Pro Leu Thr
1               5

<210> SEQ ID NO 75
<211> LENGTH: 27
<212> TYPE: DNA
<213> ORGANISM: Homo sapiens

<400> SEQUENCE: 75
ctacagcata atagtgaccc gctcacc                                           27

<210> SEQ ID NO 76
<211> LENGTH: 9
<212> TYPE: PRT
<213> ORGANISM: Homo sapiens

<400> SEQUENCE: 76

Leu Gln His Asn Ser Asp Pro Leu Thr
1               5

<210> SEQ ID NO 77
<211> LENGTH: 27
<212> TYPE: DNA
<213> ORGANISM: Homo sapiens

<400> SEQUENCE: 77
caacaatatg gtaactcacc attcact                                           27

<210> SEQ ID NO 78
<211> LENGTH: 9
<212> TYPE: PRT
<213> ORGANISM: Homo sapiens

<400> SEQUENCE: 78

Gln Gln Tyr Gly Asn Ser Pro Phe Thr
1               5

<210> SEQ ID NO 79
<211> LENGTH: 27
<212> TYPE: DNA
<213> ORGANISM: Homo sapiens

<400> SEQUENCE: 79
ctacagcaaa atagttaccc gctcact                                           27
```

<210> SEQ ID NO 80
<211> LENGTH: 9
<212> TYPE: PRT
<213> ORGANISM: Homo sapiens

<400> SEQUENCE: 80

Leu Gln Gln Asn Ser Tyr Pro Leu Thr
1               5

<210> SEQ ID NO 81
<211> LENGTH: 27
<212> TYPE: DNA
<213> ORGANISM: Homo sapiens

<400> SEQUENCE: 81
caggcgtggg acagcagcac tgtggta                                           27

<210> SEQ ID NO 82
<211> LENGTH: 27
<212> TYPE: DNA
<213> ORGANISM: Homo sapiens

<400> SEQUENCE: 82
cagtcttatg ataccagcaa tcaggtg                                           27

<210> SEQ ID NO 83
<211> LENGTH: 9
<212> TYPE: PRT
<213> ORGANISM: Homo sapiens

<400> SEQUENCE: 83

Gln Ser Tyr Asp Thr Ser Asn Gln Val
1               5

<210> SEQ ID NO 84
<211> LENGTH: 33
<212> TYPE: DNA
<213> ORGANISM: Homo sapiens

<400> SEQUENCE: 84
gcagcatggg atgacagcct gaatggtccg gtg                                    33

<210> SEQ ID NO 85
<211> LENGTH: 11
<212> TYPE: PRT
<213> ORGANISM: Homo sapiens

<400> SEQUENCE: 85

Ala Ala Trp Asp Asp Ser Leu Asn Gly Pro Val
1               5                   10

<210> SEQ ID NO 86
<211> LENGTH: 33
<212> TYPE: DNA
<213> ORGANISM: Homo sapiens

<400> SEQUENCE: 86
gcagcatggg atgacagcct gagtaggccg gta                                    33

<210> SEQ ID NO 87
<211> LENGTH: 11
<212> TYPE: PRT
<213> ORGANISM: Homo sapiens

<400> SEQUENCE: 87

Ala Ala Trp Asp Asp Ser Leu Ser Arg Pro Val
1               5                   10

<210> SEQ ID NO 88
<211> LENGTH: 30
<212> TYPE: DNA
<213> ORGANISM: Homo sapiens

<400> SEQUENCE: 88
cagtcctatg acagcagcct gagtgctata                                        30

<210> SEQ ID NO 89
<211> LENGTH: 10
<212> TYPE: PRT
<213> ORGANISM: Homo sapiens

<400> SEQUENCE: 89

Gln Ser Tyr Asp Ser Ser Leu Ser Ala Ile
1               5                   10

<210> SEQ ID NO 90
<211> LENGTH: 27
<212> TYPE: DNA
<213> ORGANISM: Homo sapiens

<400> SEQUENCE: 90
atgcaaaata tacagcctcc tctcacc                                           27

<210> SEQ ID NO 91
<211> LENGTH: 9
<212> TYPE: PRT
<213> ORGANISM: Homo sapiens

<400> SEQUENCE: 91

Met Gln Asn Ile Gln Pro Pro Leu Thr
1               5

<210> SEQ ID NO 92
<211> LENGTH: 27
<212> TYPE: DNA
<213> ORGANISM: Homo sapiens

<400> SEQUENCE: 92
atggaagctc ttcaaactat gtgcagt                                           27

<210> SEQ ID NO 93
<211> LENGTH: 9
<212> TYPE: PRT
<213> ORGANISM: Homo sapiens

<400> SEQUENCE: 93

Met Glu Ala Leu Gln Thr Met Cys Ser
1               5

<210> SEQ ID NO 94
<211> LENGTH: 27
<212> TYPE: DNA
<213> ORGANISM: Homo sapiens

<400> SEQUENCE: 94
ctacagcata atagttaccc tcgcagt                                           27

<210> SEQ ID NO 95
<211> LENGTH: 9
<212> TYPE: PRT

<213> ORGANISM: Homo sapiens

<400> SEQUENCE: 95

Leu Gln His Asn Ser Tyr Pro Arg Ser
1               5

<210> SEQ ID NO 96
<211> LENGTH: 27
<212> TYPE: DNA
<213> ORGANISM: Homo sapiens

<400> SEQUENCE: 96
caacaggcta acagtttccc gctcact                                          27

<210> SEQ ID NO 97
<211> LENGTH: 9
<212> TYPE: PRT
<213> ORGANISM: Homo sapiens

<400> SEQUENCE: 97

Gln Gln Ala Asn Ser Phe Pro Leu Thr
1               5

<210> SEQ ID NO 98
<211> LENGTH: 28
<212> TYPE: DNA
<213> ORGANISM: Homo sapiens

<400> SEQUENCE: 98
atgcaacgta tagagtttcc attcactt                                         28

<210> SEQ ID NO 99
<211> LENGTH: 27
<212> TYPE: DNA
<213> ORGANISM: Homo sapiens

<400> SEQUENCE: 99
caacagtcta acagtttccc gctcact                                          27

<210> SEQ ID NO 100
<211> LENGTH: 9
<212> TYPE: PRT
<213> ORGANISM: Homo sapiens

<400> SEQUENCE: 100

Gln Gln Ser Asn Ser Phe Pro Leu Thr
1               5

<210> SEQ ID NO 101
<211> LENGTH: 15
<212> TYPE: DNA
<213> ORGANISM: Homo sapiens

<400> SEQUENCE: 101
agctatggca tgcac                                                       15

<210> SEQ ID NO 102
<211> LENGTH: 5
<212> TYPE: PRT
<213> ORGANISM: Homo sapiens

<400> SEQUENCE: 102

Ser Tyr Gly Met His
1               5

```
<210> SEQ ID NO 103
<211> LENGTH: 15
<212> TYPE: DNA
<213> ORGANISM: Homo sapiens

<400> SEQUENCE: 103
acctatggga tgcac                                                    15

<210> SEQ ID NO 104
<211> LENGTH: 5
<212> TYPE: PRT
<213> ORGANISM: Homo sapiens

<400> SEQUENCE: 104

Thr Tyr Gly Met His
1               5

<210> SEQ ID NO 105
<211> LENGTH: 15
<212> TYPE: DNA
<213> ORGANISM: Homo sapiens

<400> SEQUENCE: 105
agctatggca tgcac                                                    15

<210> SEQ ID NO 106
<211> LENGTH: 5
<212> TYPE: PRT
<213> ORGANISM: Homo sapiens

<400> SEQUENCE: 106

Ser Tyr Asp Met His
1               5

<210> SEQ ID NO 107
<211> LENGTH: 21
<212> TYPE: DNA
<213> ORGANISM: Homo sapiens

<400> SEQUENCE: 107
agcaactatg ctgcttggaa c                                             21

<210> SEQ ID NO 108
<211> LENGTH: 7
<212> TYPE: PRT
<213> ORGANISM: Homo sapiens

<400> SEQUENCE: 108

Ser Asn Tyr Ala Ala Trp Asn
1               5

<210> SEQ ID NO 109
<211> LENGTH: 15
<212> TYPE: DNA
<213> ORGANISM: Homo sapiens

<400> SEQUENCE: 109
agctatgaca tgcac                                                    15

<210> SEQ ID NO 110
<211> LENGTH: 15
<212> TYPE: DNA
<213> ORGANISM: Homo sapiens

<400> SEQUENCE: 110
```

```
aactatggca tgcac                                              15

<210> SEQ ID NO 111
<211> LENGTH: 5
<212> TYPE: PRT
<213> ORGANISM: Homo sapiens

<400> SEQUENCE: 111

Asn Tyr Gly Met His
1               5

<210> SEQ ID NO 112
<211> LENGTH: 15
<212> TYPE: DNA
<213> ORGANISM: Homo sapiens

<400> SEQUENCE: 112
ggctactatt tgcac                                              15

<210> SEQ ID NO 113
<211> LENGTH: 5
<212> TYPE: PRT
<213> ORGANISM: Homo sapiens

<400> SEQUENCE: 113

Gly Tyr Tyr Leu His
1               5

<210> SEQ ID NO 114
<211> LENGTH: 15
<212> TYPE: DNA
<213> ORGANISM: Homo sapiens

<400> SEQUENCE: 114
agctatggta tcagt                                              15

<210> SEQ ID NO 115
<211> LENGTH: 5
<212> TYPE: PRT
<213> ORGANISM: Homo sapiens

<400> SEQUENCE: 115

Ser Tyr Gly Ile Ser
1               5

<210> SEQ ID NO 116
<211> LENGTH: 48
<212> TYPE: DNA
<213> ORGANISM: Homo sapiens

<400> SEQUENCE: 116
aagtctagtc agagcctcct gcatagtgat ggaaagaact atttgttt           48

<210> SEQ ID NO 117
<211> LENGTH: 16
<212> TYPE: PRT
<213> ORGANISM: Homo sapiens

<400> SEQUENCE: 117

Lys Ser Ser Gln Ser Leu Leu His Ser Asp Gly Lys Asn Tyr Leu Phe
1               5                   10                  15

<210> SEQ ID NO 118
<211> LENGTH: 5
```

```
-continued

<212> TYPE: PRT
<213> ORGANISM: Homo sapiens

<400> SEQUENCE: 118

Gly Tyr Thr Leu Asn
1               5

<210> SEQ ID NO 119
<211> LENGTH: 15
<212> TYPE: DNA
<213> ORGANISM: Homo sapiens

<400> SEQUENCE: 119
agctatgcca tgaac                                                      15

<210> SEQ ID NO 120
<211> LENGTH: 5
<212> TYPE: PRT
<213> ORGANISM: Homo sapiens

<400> SEQUENCE: 120

Ser Tyr Ala Met Asn
1               5

<210> SEQ ID NO 121
<211> LENGTH: 15
<212> TYPE: DNA
<213> ORGANISM: Homo sapiens

<400> SEQUENCE: 121
agatatgcca tgaac                                                      15

<210> SEQ ID NO 122
<211> LENGTH: 5
<212> TYPE: PRT
<213> ORGANISM: Homo sapiens

<400> SEQUENCE: 122

Arg Tyr Ala Met Asn
1               5

<210> SEQ ID NO 123
<211> LENGTH: 51
<212> TYPE: DNA
<213> ORGANISM: Homo sapiens

<400> SEQUENCE: 123
tctatatggt atgatggaag taataaatat tatgtagact ccgtgaaggg c              51

<210> SEQ ID NO 124
<211> LENGTH: 17
<212> TYPE: PRT
<213> ORGANISM: Homo sapiens

<400> SEQUENCE: 124

Ser Ile Trp Tyr Asp Gly Ser Asn Lys Tyr Tyr Val Asp Ser Val Lys
1               5                   10                  15

Gly

<210> SEQ ID NO 125
<211> LENGTH: 51
<212> TYPE: DNA
<213> ORGANISM: Homo sapiens

<400> SEQUENCE: 125
```

```
tttatatggt atgatggaag tgaaaaatat tatgtagact ccgtgaaggg c          51
```

<210> SEQ ID NO 126
<211> LENGTH: 17
<212> TYPE: PRT
<213> ORGANISM: Homo sapiens

<400> SEQUENCE: 126

```
Phe Ile Trp Tyr Asp Gly Ser Glu Lys Tyr Tyr Val Asp Ser Val Lys
1               5                   10                  15
Gly
```

<210> SEQ ID NO 127
<211> LENGTH: 51
<212> TYPE: DNA
<213> ORGANISM: Homo sapiens

<400> SEQUENCE: 127

```
gttatgtggt atgatggaag taataaagac tatgtagact ccgtgaaggg c          51
```

<210> SEQ ID NO 128
<211> LENGTH: 17
<212> TYPE: PRT
<213> ORGANISM: Homo sapiens

<400> SEQUENCE: 128

```
Val Met Trp Tyr Asp Gly Ser Asn Lys Asp Tyr Val Asp Ser Val Lys
1               5                   10                  15
Gly
```

<210> SEQ ID NO 129
<211> LENGTH: 51
<212> TYPE: DNA
<213> ORGANISM: Homo sapiens

<400> SEQUENCE: 129

```
gttatatcag atgatggaag tcataaatac tctgcagact ccgtgaaggg c          51
```

<210> SEQ ID NO 130
<211> LENGTH: 17
<212> TYPE: PRT
<213> ORGANISM: Homo sapiens

<400> SEQUENCE: 130

```
Val Ile Ser Asp Asp Gly Ser His Lys Tyr Ser Ala Asp Ser Val Lys
1               5                   10                  15
Gly
```

<210> SEQ ID NO 131
<211> LENGTH: 51
<212> TYPE: DNA
<213> ORGANISM: Homo sapiens

<400> SEQUENCE: 131

```
gaaatatgga atgatggaag taataaatac tatgcagact ccgtgaaggg c          51
```

<210> SEQ ID NO 132
<211> LENGTH: 17
<212> TYPE: PRT
<213> ORGANISM: Homo sapiens

<400> SEQUENCE: 132

Glu Ile Trp Asn Asp Gly Ser Asn Lys Tyr Tyr Ala Asp Ser Val Lys
1               5                   10                  15
Gly

<210> SEQ ID NO 133
<211> LENGTH: 51
<212> TYPE: DNA
<213> ORGANISM: Homo sapiens

<400> SEQUENCE: 133
gtgatatcac atgatggaag tgataaatac tatgcagact ccgtgaaggg c          51

<210> SEQ ID NO 134
<211> LENGTH: 17
<212> TYPE: PRT
<213> ORGANISM: Homo sapiens

<400> SEQUENCE: 134

Val Ile Ser His Asp Gly Ser Asp Lys Tyr Tyr Ala Asp Ser Val Lys
1               5                   10                  15
Gly

<210> SEQ ID NO 135
<211> LENGTH: 51
<212> TYPE: DNA
<213> ORGANISM: Homo sapiens

<400> SEQUENCE: 135
ggtatatggt atgatggaag gaataaatac tatgtagact ccgtgaaggg c          51

<210> SEQ ID NO 136
<211> LENGTH: 17
<212> TYPE: PRT
<213> ORGANISM: Homo sapiens

<400> SEQUENCE: 136

Gly Ile Trp Tyr Asp Gly Arg Asn Lys Tyr Tyr Val Asp Ser Val Lys
1               5                   10                  15
Gly

<210> SEQ ID NO 137
<211> LENGTH: 54
<212> TYPE: DNA
<213> ORGANISM: Homo sapiens

<400> SEQUENCE: 137
aggacatact acaggtccaa gtggtataat gattatgcag tatctgtgag aagt       54

<210> SEQ ID NO 138
<211> LENGTH: 18
<212> TYPE: PRT
<213> ORGANISM: Homo sapiens

<400> SEQUENCE: 138

Arg Thr Tyr Tyr Arg Ser Lys Trp Tyr Asn Asp Tyr Ala Val Ser Val
1               5                   10                  15
Arg Ser

<210> SEQ ID NO 139
<211> LENGTH: 51
<212> TYPE: DNA
<213> ORGANISM: Homo sapiens

```
<400> SEQUENCE: 139
tttatatcag atgatggaag taataaatac tatggagact ccgtgaaggg c          51

<210> SEQ ID NO 140
<211> LENGTH: 17
<212> TYPE: PRT
<213> ORGANISM: Homo sapiens

<400> SEQUENCE: 140

Phe Ile Ser Asp Asp Gly Ser Asn Lys Tyr Tyr Gly Asp Ser Val Lys
1               5                   10                  15
Gly

<210> SEQ ID NO 141
<211> LENGTH: 51
<212> TYPE: DNA
<213> ORGANISM: Homo sapiens

<400> SEQUENCE: 141
tttatatcag atgatggaag taataaatat tatggagact ccgtgaaggg c          51

<210> SEQ ID NO 142
<211> LENGTH: 51
<212> TYPE: DNA
<213> ORGANISM: Homo sapiens

<400> SEQUENCE: 142
gttatatcat atgatggaag taataaatac tatggagact ccgtgaaggg c          51

<210> SEQ ID NO 143
<211> LENGTH: 17
<212> TYPE: PRT
<213> ORGANISM: Homo sapiens

<400> SEQUENCE: 143

Val Ile Ser Tyr Asp Gly Ser Asn Lys Tyr Tyr Gly Asp Ser Val Lys
1               5                   10                  15
Gly

<210> SEQ ID NO 144
<211> LENGTH: 51
<212> TYPE: DNA
<213> ORGANISM: Homo sapiens

<400> SEQUENCE: 144
gttatatggt atgatggaag taataaatac tatgcagact ccgtgaaggg c          51

<210> SEQ ID NO 145
<211> LENGTH: 17
<212> TYPE: PRT
<213> ORGANISM: Homo sapiens

<400> SEQUENCE: 145

Val Ile Trp Tyr Asp Gly Ser Asn Lys Tyr Tyr Ala Asp Ser Val Lys
1               5                   10                  15
Gly

<210> SEQ ID NO 146
<211> LENGTH: 51
<212> TYPE: DNA
<213> ORGANISM: Homo sapiens

<400> SEQUENCE: 146
```
cttatatcat tgatggaag taataaatac tatgcagact ccgtgaaggg c        51

<210> SEQ ID NO 147
<211> LENGTH: 17
<212> TYPE: PRT
<213> ORGANISM: Homo sapiens

<400> SEQUENCE: 147

Leu Ile Ser Phe Asp Gly Ser Asn Lys Tyr Tyr Ala Asp Ser Val Lys
1               5                   10                  15

Gly

<210> SEQ ID NO 148
<211> LENGTH: 51
<212> TYPE: DNA
<213> ORGANISM: Homo sapiens

<400> SEQUENCE: 148
tggatcatcc ctgacagtgg tggcacaaag tatgcacaga agtttcaggg c        51

<210> SEQ ID NO 149
<211> LENGTH: 17
<212> TYPE: PRT
<213> ORGANISM: Homo sapiens

<400> SEQUENCE: 149

Trp Ile Ile Pro Asp Ser Gly Gly Thr Lys Tyr Ala Gln Lys Phe Gln
1               5                   10                  15

Gly

<210> SEQ ID NO 150
<211> LENGTH: 51
<212> TYPE: DNA
<213> ORGANISM: Homo sapiens

<400> SEQUENCE: 150
tggatcggcg tttacaatgg tcacacaaaa tatgcacaga agttccaggg c        51

<210> SEQ ID NO 151
<211> LENGTH: 17
<212> TYPE: PRT
<213> ORGANISM: Homo sapiens

<400> SEQUENCE: 151

Trp Ile Gly Val Tyr Asn Gly His Thr Lys Tyr Ala Gln Lys Phe Gln
1               5                   10                  15

Gly

<210> SEQ ID NO 152
<211> LENGTH: 21
<212> TYPE: DNA
<213> ORGANISM: Homo sapiens

<400> SEQUENCE: 152
gaagtttcct accggttctc t        21

<210> SEQ ID NO 153
<211> LENGTH: 17
<212> TYPE: PRT
<213> ORGANISM: Homo sapiens

<400> SEQUENCE: 153

Val Ile Trp Tyr Asp Gly Ser His Lys Tyr Tyr Glu Asp Ser Val Lys
1               5                   10                  15

Gly

<210> SEQ ID NO 154
<211> LENGTH: 51
<212> TYPE: DNA
<213> ORGANISM: Homo sapiens

<400> SEQUENCE: 154
attatatggt ctgatggaat taacaaatac tatgcagact ccgtgaaggg c          51

<210> SEQ ID NO 155
<211> LENGTH: 17
<212> TYPE: PRT
<213> ORGANISM: Homo sapiens

<400> SEQUENCE: 155

Ile Ile Trp Ser Asp Gly Ile Asn Lys Tyr Tyr Ala Asp Ser Val Lys
1               5                   10                  15

Gly

<210> SEQ ID NO 156
<211> LENGTH: 51
<212> TYPE: DNA
<213> ORGANISM: Homo sapiens

<400> SEQUENCE: 156
aacattaata gtaggagtag tctcatatac tacacagact ctgtgaaggg c          51

<210> SEQ ID NO 157
<211> LENGTH: 17
<212> TYPE: PRT
<213> ORGANISM: Homo sapiens

<400> SEQUENCE: 157

Asn Ile Asn Ser Arg Ser Ser Leu Ile Tyr Tyr Thr Asp Ser Val Lys
1               5                   10                  15

Gly

<210> SEQ ID NO 158
<211> LENGTH: 51
<212> TYPE: DNA
<213> ORGANISM: Homo sapiens

<400> SEQUENCE: 158
tacattggta gtagtagtag tgccatatac tacggagact ctgtgaaggg c          51

<210> SEQ ID NO 159
<211> LENGTH: 17
<212> TYPE: PRT
<213> ORGANISM: Homo sapiens

<400> SEQUENCE: 159

Tyr Ile Gly Ser Ser Ser Ser Ala Ile Tyr Tyr Gly Asp Ser Val Lys
1               5                   10                  15

Gly

<210> SEQ ID NO 160
<211> LENGTH: 51
<212> TYPE: DNA
<213> ORGANISM: Homo sapiens

```
<400> SEQUENCE: 160
tctatatggt atgatggaag taataaatat tatgtagact ccgtgaaggg c          51

<210> SEQ ID NO 161
<211> LENGTH: 17
<212> TYPE: PRT
<213> ORGANISM: Homo sapiens

<400> SEQUENCE: 161

Ser Ile Trp Tyr Asp Gly Ser Asn Lys Tyr Tyr Val Asp Ser Val Lys
1               5                   10                  15
Gly

<210> SEQ ID NO 162
<211> LENGTH: 51
<212> TYPE: DNA
<213> ORGANISM: Homo sapiens

<400> SEQUENCE: 162
tacattggta gtagtagtag tgccatatac tacgcagact ctgtgaaggg c          51

<210> SEQ ID NO 163
<211> LENGTH: 17
<212> TYPE: PRT
<213> ORGANISM: Homo sapiens

<400> SEQUENCE: 163

Tyr Ile Gly Ser Ser Ser Ser Ala Ile Tyr Tyr Ala Asp Ser Val Lys
1               5                   10                  15
Gly

<210> SEQ ID NO 164
<211> LENGTH: 21
<212> TYPE: DNA
<213> ORGANISM: Homo sapiens

<400> SEQUENCE: 164
cttggtggtg gttttgacta c                                          21

<210> SEQ ID NO 165
<211> LENGTH: 7
<212> TYPE: PRT
<213> ORGANISM: Homo sapiens

<400> SEQUENCE: 165

Leu Gly Gly Gly Phe Asp Tyr
1               5

<210> SEQ ID NO 166
<211> LENGTH: 21
<212> TYPE: DNA
<213> ORGANISM: Homo sapiens

<400> SEQUENCE: 166
atgggaggcg gctttgacta c                                          21

<210> SEQ ID NO 167
<211> LENGTH: 7
<212> TYPE: PRT
<213> ORGANISM: Homo sapiens

<400> SEQUENCE: 167

Met Gly Gly Gly Phe Asp Tyr
```

<210> SEQ ID NO 168
<211> LENGTH: 57
<212> TYPE: DNA
<213> ORGANISM: Homo sapiens

<400> SEQUENCE: 168
gaaaaagatc attacgacat tttgactggt tataactact actacggtct ggacgtc    57

<210> SEQ ID NO 169
<211> LENGTH: 19
<212> TYPE: PRT
<213> ORGANISM: Homo sapiens

<400> SEQUENCE: 169

Glu Lys Asp His Tyr Asp Ile Leu Thr Gly Tyr Asn Tyr Tyr Tyr Gly
1               5                   10                  15

Leu Asp Val

<210> SEQ ID NO 170
<211> LENGTH: 57
<212> TYPE: DNA
<213> ORGANISM: Homo sapiens

<400> SEQUENCE: 170
gaggagacgt attacgatat tttgactggc tatcatcact actacggtat ggacgtc    57

<210> SEQ ID NO 171
<211> LENGTH: 19
<212> TYPE: PRT
<213> ORGANISM: Homo sapiens

<400> SEQUENCE: 171

Glu Glu Thr Tyr Tyr Asp Ile Leu Thr Gly Tyr His His Tyr Tyr Gly
1               5                   10                  15

Met Asp Val

<210> SEQ ID NO 172
<211> LENGTH: 57
<212> TYPE: DNA
<213> ORGANISM: Homo sapiens

<400> SEQUENCE: 172
gagcctcagt attacgatat tttgactggt tatgataact actacggtat ggacgtc    57

<210> SEQ ID NO 173
<211> LENGTH: 19
<212> TYPE: PRT
<213> ORGANISM: Homo sapiens

<400> SEQUENCE: 173

Glu Pro Gln Tyr Tyr Asp Ile Leu Thr Gly Tyr Asp Asn Tyr Tyr Gly
1               5                   10                  15

Met Asp Val

<210> SEQ ID NO 174
<211> LENGTH: 57
<212> TYPE: DNA
<213> ORGANISM: Homo sapiens

<400> SEQUENCE: 174
gaaaaaccgt attacgatat tttgactggt tatttctact actatggtat ggacgtc    57

<210> SEQ ID NO 175
<211> LENGTH: 19
<212> TYPE: PRT
<213> ORGANISM: Homo sapiens

<400> SEQUENCE: 175

Glu Lys Pro Tyr Tyr Asp Ile Leu Thr Gly Tyr Phe Tyr Tyr Tyr Gly
1               5                   10                  15

Met Asp Val

<210> SEQ ID NO 176
<211> LENGTH: 21
<212> TYPE: DNA
<213> ORGANISM: Homo sapiens

<400> SEQUENCE: 176
ttagcagtgg cctttgacta c                                         21

<210> SEQ ID NO 177
<211> LENGTH: 7
<212> TYPE: PRT
<213> ORGANISM: Homo sapiens

<400> SEQUENCE: 177

Leu Ala Val Ala Phe Asp Tyr
1               5

<210> SEQ ID NO 178
<211> LENGTH: 36
<212> TYPE: DNA
<213> ORGANISM: Homo sapiens

<400> SEQUENCE: 178
gaagatggca gtggctggta cggtgctttt gacatc                         36

<210> SEQ ID NO 179
<211> LENGTH: 12
<212> TYPE: PRT
<213> ORGANISM: Homo sapiens

<400> SEQUENCE: 179

Glu Asp Gly Ser Gly Trp Tyr Gly Ala Phe Asp Ile
1               5                   10

<210> SEQ ID NO 180
<211> LENGTH: 48
<212> TYPE: DNA
<213> ORGANISM: Homo sapiens

<400> SEQUENCE: 180
gatcaatacg atattttgac tggttattct tctgatgctt ttgatatc             48

<210> SEQ ID NO 181
<211> LENGTH: 16
<212> TYPE: PRT
<213> ORGANISM: Homo sapiens

<400> SEQUENCE: 181

Asp Gln Tyr Asp Ile Leu Thr Gly Tyr Ser Ser Asp Ala Phe Asp Ile
1               5                   10                  15

<210> SEQ ID NO 182
<211> LENGTH: 60

-continued

```
<212> TYPE: DNA
<213> ORGANISM: Homo sapiens

<400> SEQUENCE: 182
gcctattacg atattttgac tgattacccc cagtatgact actactacgg tatggacgtc        60

<210> SEQ ID NO 183
<211> LENGTH: 20
<212> TYPE: PRT
<213> ORGANISM: Homo sapiens

<400> SEQUENCE: 183

Ala Tyr Tyr Asp Ile Leu Thr Asp Tyr Pro Gln Tyr Asp Tyr Tyr Tyr
1               5                   10                  15

Gly Met Asp Val
            20

<210> SEQ ID NO 184
<211> LENGTH: 51
<212> TYPE: DNA
<213> ORGANISM: Homo sapiens

<400> SEQUENCE: 184
gatgggtatt acgatatttt gactggttat gaggatgatg cttttgatat c                 51

<210> SEQ ID NO 185
<211> LENGTH: 17
<212> TYPE: PRT
<213> ORGANISM: Homo sapiens

<400> SEQUENCE: 185

Asp Gly Tyr Tyr Asp Ile Leu Thr Gly Tyr Glu Asp Asp Ala Phe Asp
1               5                   10                  15

Ile

<210> SEQ ID NO 186
<211> LENGTH: 60
<212> TYPE: DNA
<213> ORGANISM: Homo sapiens

<400> SEQUENCE: 186
gaagggtttc attacgatat tttgactggt tcctacttct actactacgg tatggacgtc        60

<210> SEQ ID NO 187
<211> LENGTH: 20
<212> TYPE: PRT
<213> ORGANISM: Homo sapiens

<400> SEQUENCE: 187

Glu Gly Phe His Tyr Asp Ile Leu Thr Gly Ser Tyr Phe Tyr Tyr Tyr
1               5                   10                  15

Gly Met Asp Val
            20

<210> SEQ ID NO 188
<211> LENGTH: 30
<212> TYPE: DNA
<213> ORGANISM: Homo sapiens

<400> SEQUENCE: 188
agggtagcag tggctgggta cttttgactac                                        30

<210> SEQ ID NO 189
```

```
<211> LENGTH: 10
<212> TYPE: PRT
<213> ORGANISM: Homo sapiens

<400> SEQUENCE: 189

Arg Val Ala Val Ala Gly Tyr Phe Asp Tyr
1               5                   10

<210> SEQ ID NO 190
<211> LENGTH: 27
<212> TYPE: DNA
<213> ORGANISM: Homo sapiens

<400> SEQUENCE: 190
atgcaaaata tacagcctcc tctcacc                                          27

<210> SEQ ID NO 191
<211> LENGTH: 18
<212> TYPE: PRT
<213> ORGANISM: Homo sapiens

<400> SEQUENCE: 191

Val Gly Tyr Gly Ser Gly Trp Tyr Glu Tyr Tyr Tyr His Tyr Gly Met
1               5                   10                  15

Asp Val

<210> SEQ ID NO 192
<211> LENGTH: 57
<212> TYPE: DNA
<213> ORGANISM: Homo sapiens

<400> SEQUENCE: 192
gagagaggcc tctacgatat tttgactggt tattataact actacggtat tgacgtc        57

<210> SEQ ID NO 193
<211> LENGTH: 19
<212> TYPE: PRT
<213> ORGANISM: Homo sapiens

<400> SEQUENCE: 193

Glu Arg Gly Leu Tyr Asp Ile Leu Thr Gly Tyr Tyr Asn Tyr Tyr Gly
1               5                   10                  15

Ile Asp Val

<210> SEQ ID NO 194
<211> LENGTH: 39
<212> TYPE: DNA
<213> ORGANISM: Homo sapiens

<400> SEQUENCE: 194
gatcagtata actggaacta ctactacggt atggacgtc                             39

<210> SEQ ID NO 195
<211> LENGTH: 13
<212> TYPE: PRT
<213> ORGANISM: Homo sapiens

<400> SEQUENCE: 195

Asp Gln Tyr Asn Trp Asn Tyr Tyr Tyr Gly Met Asp Val
1               5                   10

<210> SEQ ID NO 196
<211> LENGTH: 33
<212> TYPE: DNA
```

```
<213> ORGANISM: Homo sapiens

<400> SEQUENCE: 196
tatagaagtg gctggtcccc cctctttgac ttc                                  33

<210> SEQ ID NO 197
<211> LENGTH: 11
<212> TYPE: PRT
<213> ORGANISM: Homo sapiens

<400> SEQUENCE: 197

Tyr Arg Ser Gly Trp Ser Pro Leu Phe Asp Phe
1               5                   10

<210> SEQ ID NO 198
<211> LENGTH: 33
<212> TYPE: DNA
<213> ORGANISM: Homo sapiens

<400> SEQUENCE: 198
tatagcagtg gctggtcccc cctctttgac tac                                  33

<210> SEQ ID NO 199
<211> LENGTH: 11
<212> TYPE: PRT
<213> ORGANISM: Homo sapiens

<400> SEQUENCE: 199

Tyr Ser Ser Gly Trp Ser Pro Leu Phe Asp Tyr
1               5                   10

<210> SEQ ID NO 200
<211> LENGTH: 17
<212> TYPE: PRT
<213> ORGANISM: Artificial Sequence
<220> FEATURE:
<223> OTHER INFORMATION: Description of Artificial Sequence:
      Synthetic consensus sequence
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (9)..(9)
<223> OTHER INFORMATION: Arg or Ser
<220> FEATURE:
<221> NAME/KEY: MOD_RES
<222> LOCATION: (10)..(10)
<223> OTHER INFORMATION: Asp or Ala

<400> SEQUENCE: 200

Arg Ser Xaa Gln Ser Leu Leu Asp Xaa Xaa Asp Gly Thr Tyr Thr Leu
1               5                   10                  15
Asp

<210> SEQ ID NO 201
<211> LENGTH: 11
<212> TYPE: PRT
<213> ORGANISM: Artificial Sequence
<220> FEATURE:
<223> OTHER INFORMATION: Description of Artificial Sequence:
      Synthetic consensus sequence
<220> FEATURE:
<221> NAME/KEY: MOD_RES
<222> LOCATION: (5)..(5)
<223> OTHER INFORMATION: Gly or Asp
<220> FEATURE:
<221> NAME/KEY: MOD_RES
```

```
<222> LOCATION: (10)..(10)
<223> OTHER INFORMATION: Leu or Phe

<400> SEQUENCE: 201

Arg Ala Ser Gln Xaa Ile Arg Asn Asp Xaa Gly
1               5                   10

<210> SEQ ID NO 202
<211> LENGTH: 11
<212> TYPE: PRT
<213> ORGANISM: Artificial Sequence
<220> FEATURE:
<223> OTHER INFORMATION: Description of Artificial Sequence:
      Synthetic consensus sequence
<220> FEATURE:
<221> NAME/KEY: MOD_RES
<222> LOCATION: (10)..(10)
<223> OTHER INFORMATION: Val or Ala

<400> SEQUENCE: 202

Ser Gly Asp Lys Leu Gly Asp Lys Tyr Xaa Cys
1               5                   10

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence:
      Synthetic consensus sequence
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (3)..(3)
<223> OTHER INFORMATION: Gly or Asp

<400> SEQUENCE: 203

Xaa Tyr Xaa Met His
1               5

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence:
      Synthetic consensus sequence
<220> FEATURE:
<221> NAME/KEY: MOD_RES
<222> LOCATION: (6)..(6)
<223> OTHER INFORMATION: Glu or Gln

<400> SEQUENCE: 204

Ala Ala Ser Ser Leu Xaa Ser
1               5

<210> SEQ ID NO 205
<211> LENGTH: 7
<212> TYPE: PRT
<213> ORGANISM: Artificial Sequence
<220> FEATURE:
<223> OTHER INFORMATION: Description of Artificial Sequence:
      Synthetic consensus sequence
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
```

```
<222> LOCATION: (3)..(3)
<223> OTHER INFORMATION: Thr or Ser

<400> SEQUENCE: 205

Gln Xaa Xaa Lys Arg Pro Ser
1               5

<210> SEQ ID NO 206
<211> LENGTH: 17
<212> TYPE: PRT
<213> ORGANISM: Artificial Sequence
<220> FEATURE:
<223> OTHER INFORMATION: Description of Artificial Sequence:
      Synthetic consensus sequence
<220> FEATURE:
<221> NAME/KEY: MOD_RES
<222> LOCATION: (1)..(1)
<223> OTHER INFORMATION: Ser, Phe, Val or Gln
<220> FEATURE:
<221> NAME/KEY: MOD_RES
<222> LOCATION: (4)..(4)
<223> OTHER INFORMATION: Tyr or Asn
<220> FEATURE:
<221> NAME/KEY: MOD_RES
<222> LOCATION: (8)..(8)
<223> OTHER INFORMATION: Asn or Gln
<220> FEATURE:
<221> NAME/KEY: MOD_RES
<222> LOCATION: (12)..(12)
<223> OTHER INFORMATION: Val or Ala

<400> SEQUENCE: 206

Xaa Ile Trp Xaa Asp Gly Ser Xaa Lys Tyr Tyr Xaa Asp Ser Val Lys
1               5                   10                  15

Gly

<210> SEQ ID NO 207
<211> LENGTH: 17
<212> TYPE: PRT
<213> ORGANISM: Artificial Sequence
<220> FEATURE:
<223> OTHER INFORMATION: Description of Artificial Sequence:
      Synthetic consensus sequence
<220> FEATURE:
<221> NAME/KEY: MOD_RES
<222> LOCATION: (1)..(1)
<223> OTHER INFORMATION: Val or Phe
<220> FEATURE:
<221> NAME/KEY: MOD_RES
<222> LOCATION: (4)..(4)
<223> OTHER INFORMATION: His, Asp or Tyr
<220> FEATURE:
<221> NAME/KEY: MOD_RES
<222> LOCATION: (8)..(8)
<223> OTHER INFORMATION: Asp, Asn or His
<220> FEATURE:
<221> NAME/KEY: MOD_RES
<222> LOCATION: (11)..(11)
<223> OTHER INFORMATION: Tyr or Ser
<220> FEATURE:
<221> NAME/KEY: MOD_RES
<222> LOCATION: (12)..(12)
<223> OTHER INFORMATION: Ala or Gly

<400> SEQUENCE: 207

Xaa Ile Ser Xaa Asp Gly Ser Xaa Lys Tyr Xaa Xaa Asp Ser Val Lys
1               5                   10                  15

Gly

<210> SEQ ID NO 208
<211> LENGTH: 9
<212> TYPE: PRT
```

```
<213> ORGANISM: Artificial Sequence
<220> FEATURE:
<223> OTHER INFORMATION: Description of Artificial Sequence:
      Synthetic consensus sequence
<220> FEATURE:
<221> NAME/KEY: MOD_RES
<222> LOCATION: (3)..(3)
<223> OTHER INFORMATION: His or Gln
<220> FEATURE:
<221> NAME/KEY: MOD_RES
<222> LOCATION: (6)..(6)
<223> OTHER INFORMATION: Asn, Asp or Tyr

<400> SEQUENCE: 208

Leu Gln Xaa Asn Ser Xaa Pro Leu Thr
1               5

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence:
      Synthetic consensus sequence
<220> FEATURE:
<221> NAME/KEY: MOD_RES
<222> LOCATION: (6)..(6)
<223> OTHER INFORMATION: Asn or Ser
<220> FEATURE:
<221> NAME/KEY: MOD_RES
<222> LOCATION: (9)..(9)
<223> OTHER INFORMATION: Ile or Val

<400> SEQUENCE: 209

Gln Ala Trp Asp Ser Xaa Thr Val Xaa
1               5

<210> SEQ ID NO 210
<211> LENGTH: 19
<212> TYPE: PRT
<213> ORGANISM: Artificial Sequence
<220> FEATURE:
<223> OTHER INFORMATION: Description of Artificial Sequence:
      Synthetic consensus sequence
<220> FEATURE:
<221> NAME/KEY: MOD_RES
<222> LOCATION: (2)..(2)
<223> OTHER INFORMATION: Lys, Glu or Pro
<220> FEATURE:
<221> NAME/KEY: MOD_RES
<222> LOCATION: (3)..(3)
<223> OTHER INFORMATION: Asp, Thr, Gln or Pro
<220> FEATURE:
<221> NAME/KEY: MOD_RES
<222> LOCATION: (4)..(4)
<223> OTHER INFORMATION: His or Tyr
<220> FEATURE:
<221> NAME/KEY: MOD_RES
<222> LOCATION: (12)..(12)
<223> OTHER INFORMATION: Asn, His, Asp or Phe
<220> FEATURE:
<221> NAME/KEY: MOD_RES
<222> LOCATION: (13)..(13)
<223> OTHER INFORMATION: Tyr, His or Asn
<220> FEATURE:
<221> NAME/KEY: MOD_RES
<222> LOCATION: (17)..(17)
<223> OTHER INFORMATION: Leu or Met

<400> SEQUENCE: 210

Glu Xaa Xaa Xaa Tyr Asp Ile Leu Thr Gly Tyr Xaa Xaa Tyr Tyr Gly
1               5                   10                  15

Xaa Asp Val
```

<210> SEQ ID NO 211
<211> LENGTH: 7
<212> TYPE: PRT
<213> ORGANISM: Artificial Sequence
<220> FEATURE:
<223> OTHER INFORMATION: Description of Artificial Sequence:
      Synthetic consensus sequence
<220> FEATURE:
<221> NAME/KEY: MOD_RES
<222> LOCATION: (1)..(1)
<223> OTHER INFORMATION: Leu or Met

<400> SEQUENCE: 211

Xaa Gly Gly Gly Phe Asp Tyr
1               5

<210> SEQ ID NO 212
<211> LENGTH: 339
<212> TYPE: DNA
<213> ORGANISM: Homo sapiens

<400> SEQUENCE: 212
gatattgtgc tgacccagac tccactctcc ctgcccgtca cccctggaga gccggcctcc      60
atctcctgca ggtctagtca gagcctcttg atagagatg atggagacac ctatttggac     120
tggtacctgc agaagccagg gcagtctcca cagctcctga tctatacgct ttcctatcgg     180
gcctctggag tcccagacag gttcagtggc agtgggtcag gcactgattt ctcactgaaa     240
atcagcaggg tggaggctga ggatgttgga gtttattact gcatgcaacg tatagagttt     300
ccattcactt tcggccctgg gaccaaagtg gatatcaaa                            339

<210> SEQ ID NO 213
<211> LENGTH: 113
<212> TYPE: PRT
<213> ORGANISM: Homo sapiens

<400> SEQUENCE: 213

Asp Ile Val Leu Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Arg
            20                  25                  30

Asp Asp Gly Asp Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Ser Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Phe Thr Phe Gly Pro Gly Thr Lys Val Asp Ile
            100                 105                 110

Lys

<210> SEQ ID NO 214
<211> LENGTH: 323
<212> TYPE: DNA
<213> ORGANISM: Homo sapiens

<400> SEQUENCE: 214
agactccact ctccctgccc gtcacccctg gagagccggc ctccatctcc tgcaggtcta      60
gtcagagcct cttggatagt gctgatggag acacctattt ggactggtac ctgcagaagc    120

```
cagggcagtc tccacagctc ctgatctata cgctttccta tcgggcctct ggagtcccag    180
acaggttcag tggcagtggg tcagacactg atttctcact gaaaatcagc agggtggagg    240
ctgaggatgt tggagtttat tactgcatgc aacgtataga gtttccattc actttcggcc    300
ctgggaccaa agtggatatc aaa                                            323
```

```
<210> SEQ ID NO 215
<211> LENGTH: 113
<212> TYPE: PRT
<213> ORGANISM: Homo sapiens

<400> SEQUENCE: 215
```

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Ala Asp Gly Asp Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Asp Thr Asp Phe Ser Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Phe Thr Phe Gly Pro Gly Thr Lys Val Asp Ile
            100                 105                 110

Lys

```
<210> SEQ ID NO 216
<211> LENGTH: 321
<212> TYPE: DNA
<213> ORGANISM: Homo sapiens
<400> SEQUENCE: 216
gacatccaga tgacccagtc tccatcctcc ctgtctgcat ctgtaggaga cagagtcacc     60
atcacttgcc gggcaagtca gggcattaga aatgatttag ctggtatca gcagaaacca    120 gggaaagccc ctaagcgcct gatctatgct gcatccagtt tgcaaagtgg ggtcccatca    180
aggttcagcg gcagtggatc tgggacagaa ttcactctca caatcagcag tgtgcagcct    240
gaagattttg taacttatta ctgtctacag cataatagta accctctcac tttcggcgga    300
gggaccaagg tggagatcaa a                                              321
```

```
<210> SEQ ID NO 217
<211> LENGTH: 107
<212> TYPE: PRT
<213> ORGANISM: Homo sapiens

<400> SEQUENCE: 217
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

-continued

Ser Gly Ser Gly Thr Glu Phe Thr Leu Thr Ile Ser Ser Val Gln Pro
65                  70                  75                  80

Glu Asp Phe Val Thr Tyr Tyr Cys Leu Gln His Asn Ser Asn Pro Leu
                85                  90                  95

Thr Phe Gly Gly Gly Thr Lys Val Glu Ile Lys
            100                 105

<210> SEQ ID NO 218
<211> LENGTH: 321
<212> TYPE: DNA
<213> ORGANISM: Homo sapiens

<400> SEQUENCE: 218

```
gacatccaga tgacccagtc tccatcctcc ctgtctgcat ctgtaggaga cagagtcacc    60
atcacttgcc gggcaagtca gggcattaga aatgatttag ctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag tctgcagcct   240
gaagattttg caacttatta ctgtctacag cataatagta accctctcac tttcggcgga   300
gggaccaagg tggagatcaa a                                             321
```

<210> SEQ ID NO 219
<211> LENGTH: 107
<212> TYPE: PRT
<213> ORGANISM: Homo sapiens

<400> SEQUENCE: 219

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Asn Pro Leu
                85                  90                  95

Thr Phe Gly Gly Gly Thr Lys Val Glu Ile Lys
            100                 105

<210> SEQ ID NO 220
<211> LENGTH: 321
<212> TYPE: DNA
<213> ORGANISM: Homo sapiens

<400> SEQUENCE: 220

```
gacatccaga tgacccagtc tccatcctcc ctgtctgcat ttgtaggaga cagagtcacc    60
atcacttgcc gggcaagtca gggcattaga aatgatttag ctggtatca gcagaaacca   120
gggaaagccc ctaagcgcct gctctatgct gcctccagtt tgcaaagtgg ggtcccatca   180
aggttcagcg gcagtgggtc tgggtcagaa ttcactctca caatcagcag cctgcagcct   240
gaagattttg caacttatta ctgtctacag cataatagtg acccgctcac cttcggccaa   300
gggacacgac tggagattaa a                                             321
```

<210> SEQ ID NO 221

```
<211> LENGTH: 107
<212> TYPE: PRT
<213> ORGANISM: Homo sapiens

<400> SEQUENCE: 221

Asp Ile Gln Met Thr Gln Ser Pro Ser Ser Leu Ser Ala Phe Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Leu
        35                  40                  45

Tyr Ala Ala Ser Ser Leu Gln Ser Gly Val Pro Ser Arg Phe Ser Gly
50                  55                  60

Ser Gly Ser Gly Ser Glu Phe Thr Leu Thr Ile Ser Ser Leu Gln Pro
65                  70                  75                  80

Glu Asp Phe Ala Thr Tyr Tyr Cys Leu Gln His Asn Ser Asp Pro Leu
                85                  90                  95

Thr Phe Gly Gln Gly Thr Arg Leu Glu Ile Lys
            100                 105

<210> SEQ ID NO 222
<211> LENGTH: 324
<212> TYPE: DNA
<213> ORGANISM: Homo sapiens

<400> SEQUENCE: 222
gaaattgtgt tgacgcagtc tccaggcacc ctgtctttgt ttccagggga aagagccacc      60
ctctcctgca gggccagtca gagtgttagc agcaactact tagcctggta ccagcagaaa     120
tctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcaa caatatggta actcaccatt cactttcggc    300
cctgggacca atgtggatat caaa                                            324

<210> SEQ ID NO 223
<211> LENGTH: 108
<212> TYPE: PRT
<213> ORGANISM: Homo sapiens

<400> SEQUENCE: 223

Glu Ile Val Leu Thr Gln Ser Pro Gly Thr Leu Ser Leu Phe Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Ser Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Phe Thr Phe Gly Pro Gly Thr Asn Val Asp Ile Lys
            100                 105

<210> SEQ ID NO 224
<211> LENGTH: 321
<212> TYPE: DNA
```

<213> ORGANISM: Homo sapiens

<400> SEQUENCE: 224

```
gacatccaga tgacccagtc tccatcctcc ctgtctgcat ctgtaggaga cagagtcacc    60
gtcacttgcc gggcaagtca ggacattaga aatgattttg ctggtatca gcaaaaacca   120
gggaaagccc ctaagcgcct gatctatgct gcatccagtt tacaaagtgg ggtcccatca   180
aggttcagcg gcagtggatc tgggacagaa ttcactctca caatcagcag cctgcagcct   240
gaagattttg caacttatta ctgtctacag caaaatagtt acccgctcac tttcggggga   300
gggaccaagg tggaaatcaa a                                             321
```

<210> SEQ ID NO 225
<211> LENGTH: 107
<212> TYPE: PRT
<213> ORGANISM: Homo sapiens

<400> SEQUENCE: 225

```
Asp Ile Gln Met Thr Gln Ser Pro Ser Ser Leu Ser Ala Ser Val Gly
 1               5                  10                  15
Asp Arg Val Thr Val Thr Cys Arg Ala Ser Gln Asp Ile Arg Asn Asp
             20                  25                  30
Phe Gly Trp Tyr Gln Gln Lys Pro Gly Lys Ala Pro Lys Arg Leu Ile
         35                  40                  45
Tyr Ala Ala Ser Ser Leu Gln Ser Gly Val Pro Ser Arg Phe Ser Gly
     50                  55                  60
Ser Gly Ser Gly Thr Glu Phe Thr Leu Thr Ile Ser Ser Leu Gln Pro
 65                  70                  75                  80
Glu Asp Phe Ala Thr Tyr Tyr Cys Leu Gln Gln Asn Ser Tyr Pro Leu
                 85                  90                  95
Thr Phe Gly Gly Gly Thr Lys Val Glu Ile Lys
            100                 105
```

<210> SEQ ID NO 226
<211> LENGTH: 339
<212> TYPE: DNA
<213> ORGANISM: Homo sapiens

<400> SEQUENCE: 226

```
gatattgtga tgacccagac tccactctcc ctgcccgtca cccctggaga gccggcctcc    60
atctcctgca ggtctactca gagcctcttg gatagtgatg atggagacac ctatttggac   120
tggtacctgc agaagccggg gcagtctcca cagctcctga tctatacgct ttcctatcgg   180
gcctctggag tcccagacag gttcagtggc agtgggtcag gcactgattt cacactgaaa   240
atcagcaggg tggaggctga ggatgttgga gtttattact gcatgcaacg tatagagttt   300
ccattcactt tcggccctgg gaccaaagtg gatatcaaa                          339
```

<210> SEQ ID NO 227
<211> LENGTH: 113
<212> TYPE: PRT
<213> ORGANISM: Homo sapiens

<400> SEQUENCE: 227

```
Asp Ile Val Met Thr Gln Thr Pro Leu Ser Leu Pro Val Thr Pro Gly
 1               5                  10                  15
Glu Pro Ala Ser Ile Ser Cys Arg Ser Thr Gln Ser Leu Leu Asp Ser
             20                  25                  30
Asp Asp Gly Asp Thr Tyr Leu Asp Trp Tyr Leu Gln Lys Pro Gly Gln
```

```
              35                  40                  45
Ser Pro Gln Leu Leu Ile Tyr Thr Leu Ser Tyr Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Arg Ile Glu Phe Pro Phe Thr Phe Gly Pro Gly Thr Lys Val Asp Ile
            100                 105                 110

Lys

<210> SEQ ID NO 228
<211> LENGTH: 321
<212> TYPE: DNA
<213> ORGANISM: Homo sapiens

<400> SEQUENCE: 228
gacatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagcgcct gatctatgct gcatccagtt tggaaagtgg ggtcccatca    180
aggttcagcg gcagtggatc tgggacagaa ttcactctca caatcagcag tgtgcagcct    240
gaagattttg taacttatta ctgtctacag cataatagta accctctcac tttcggcgga    300
gggaccaagg tggagatcaa a                                              321

<210> SEQ ID NO 229
<211> LENGTH: 107
<212> TYPE: PRT
<213> ORGANISM: Homo sapiens

<400> SEQUENCE: 229

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Arg Leu Ile
             35                  40                  45

Tyr Ala Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Val Gln Pro
 65                  70                  75                  80

Glu Asp Phe Val Thr Tyr Tyr Cys Leu Gln His Asn Ser Asn Pro Leu
                 85                  90                  95

Thr Phe Gly Gly Gly Thr Lys Val Glu Ile Lys
            100                 105

<210> SEQ ID NO 230
<211> LENGTH: 321
<212> TYPE: DNA
<213> ORGANISM: Homo sapiens

<400> SEQUENCE: 230
gacatccaga tgacccagtc tccatcctcc ctgtctgcat ctgtgggaga cagagtcacc      60
atcacttgcc aggcgagtca ggacattagt aagtattta attggtatca gcagaaacca     120
gggaaagccc ctaagctcct catctacgat gcatccaatt tggaaacagg ggtcccatca    180
aggttcagtg gaagtggatc tgggacagat tttactttca ccatcagcag cctgcagcct    240
```

```
gaagatattg caacatatta ctgtcaacag tatggtaatc tcccgatcac cttcggccaa    300
gggacacgac tggagagtaa a                                              321
```

<210> SEQ ID NO 231
<211> LENGTH: 107
<212> TYPE: PRT
<213> ORGANISM: Homo sapiens

<400> SEQUENCE: 231

```
Asp Ile Gln Met Thr Gln Ser Pro Ser Leu Ser Ala Ser Val Gly
1               5                   10                  15

Asp Arg Val Thr Ile Thr Cys Gln Ala Ser Gln Asp Ile Ser Lys Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Gly Asn Leu Pro Ile
                85                  90                  95

Thr Phe Gly Gln Gly Thr Arg Leu Glu Ser Lys
            100                 105
```

<210> SEQ ID NO 232
<211> LENGTH: 318
<212> TYPE: DNA
<213> ORGANISM: Homo sapiens

<400> SEQUENCE: 232

```
tcctatgagc tgactcagcc accctcagtg tccgtgtccc caggacagac agccagcatc     60
acctgctctg gagataaaat tggggataaa tatgtttgct ggtatcagca gaagccaggc    120
cagtcccctg tgctggtcat ctatcaaact tccaagcggc cctcagggat ccctgagcgg    180
ttctctggct ccaactctgg gaacacagcc actctgacca tcagcgggac ccaggctatg    240
gatgaggctg actattactg tcaggcgtgg gacagcaaca ctgtgatttt cggcggaggg    300
accaagctga ccgtccta                                                  318
```

<210> SEQ ID NO 233
<211> LENGTH: 106
<212> TYPE: PRT
<213> ORGANISM: Homo sapiens

<400> SEQUENCE: 233

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
                20                  25                  30

Cys Trp Tyr Gln Gln Lys Pro Gly Gln Ser Pro Val Leu Val Ile Tyr
            35                  40                  45

Gln Thr Ser Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Asn Thr Val Ile
                85                  90                  95
```

Phe Gly Gly Gly Thr Lys Leu Thr Val Leu
            100                 105

<210> SEQ ID NO 234
<211> LENGTH: 318
<212> TYPE: DNA
<213> ORGANISM: Homo sapiens

<400> SEQUENCE: 234
tcctatgagc tgactcagcc accctcagtg tccgtgtccc caggacagac agccagcatc      60
acctgctctg gagataaatt gggggataaa tatgtttgct ggtatcagca gaagccaggc     120
cagtcccctg tgctggtcat ctatcaaact tccaagcggc cctcagggat ccctgagcgg     180
ttctctggct ccaactctgg gaacacagcc actctgacca tcagcgggac ccaggctatg     240
gatgaggctg actattactg tcaggcgtgg gacagcagca ctgtggtttt cggcggaggg     300
accaagctga ccgtccta                                                    318

<210> SEQ ID NO 235
<211> LENGTH: 106
<212> TYPE: PRT
<213> ORGANISM: Homo sapiens

<400> SEQUENCE: 235

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Cys Trp Tyr Gln Gln Lys Pro Gly Gln Ser Pro Val Leu Val Ile Tyr
        35                  40                  45

Gln Thr Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105

<210> SEQ ID NO 236
<211> LENGTH: 318
<212> TYPE: DNA
<213> ORGANISM: Homo sapiens

<400> SEQUENCE: 236
tcctatgagc tgactcagcc accctcagtg tccgtgtccc caggacagac agccagcatc      60
acctgctctg gagataaatt gggggataaa tatgcttgct ggtatcagca gaagccaggc     120
cagtcccctg tactggtcat ctatcaatct accaagcggc cctcagggat ccctgagcgt     180
ttctctggct ccaactctgg gaacacagcc actctgacca tcagcgggac ccaggctatg     240
gatgaggctg actattactg tcaggcgtgg gacagcagca ctgtggtatt cggcggaggg     300
accaagctga ccgtccta                                                    318

<210> SEQ ID NO 237
<211> LENGTH: 106
<212> TYPE: PRT
<213> ORGANISM: Homo sapiens

<400> SEQUENCE: 237

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
                20                  25                  30

Cys Trp Tyr Gln Gln Lys Pro Gly Gln Ser Pro Val Leu Val Ile Tyr
            35                  40                  45

Gln Ser Thr Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105

<210> SEQ ID NO 238
<211> LENGTH: 330
<212> TYPE: DNA
<213> ORGANISM: Homo sapiens

<400> SEQUENCE: 238
aattttatgc tgactcagcc ccactctgtg tcggagtctc cggggaagac ggtaaccatc      60
tcctgcaccc gcagcagtgg cagcattgtc agcaactttg tgcaatggta ccagcagcgc     120
ccgggcagtt cccccaccac tgtgatctat gaggataacc aaagaccctc tggggtccct     180
gatcggttct ctggctccat cgacagctcc tccaactctg cctccctcac catctctgga     240
ctgaagactg aggacgaggc tgactactac tgtcagtctt atgataccag caatcaggtg     300
ttcggcggag ggaccaagct gaccgtcctg                                      330

<210> SEQ ID NO 239
<211> LENGTH: 110
<212> TYPE: PRT
<213> ORGANISM: Homo sapiens

<400> SEQUENCE: 239

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Val Ser Asn
                20                  25                  30

Phe Val Gln Trp Tyr Gln Gln Arg Pro Gly Ser Ser Pro Thr Thr Val
            35                  40                  45

Ile Tyr Glu Asp Asn Gln Arg Pro Ser Gly Val Pro Asp Arg Phe Ser
        50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Thr
                85                  90                  95

Ser Asn Gln Val Phe Gly Gly Gly Thr Lys Leu Thr Val Leu
            100                 105                 110

<210> SEQ ID NO 240
<211> LENGTH: 330
<212> TYPE: DNA
<213> ORGANISM: Homo sapiens

<400> SEQUENCE: 240
cagtctgtcc tgactcagcc accccagcg tctgggaccc ccgggcagag ggtcaccatc       60
```

-continued

```
tcgtgtactg gaatcacctc caacatcgga agcaatactg tacactggta ccagcagttc    120
ccaggaacgg cccccaaact cctcatctat agtaataatc agcggccctc aggggtccct    180
gaccgattct ctggctccaa gtctggcacc tcagcctccc tggccatcag tgggctccag    240
tctgaggatg aggctgatta ttactgtgca gcatgggatg acagcctgaa tggtccggtg    300
ttcggcggag ggaccaagct gaccgtccta                                     330
```

<210> SEQ ID NO 241
<211> LENGTH: 110
<212> TYPE: PRT
<213> ORGANISM: Homo sapiens

<400> SEQUENCE: 241

| Gln | Ser | Val | Leu | Thr | Gln | Pro | Pro | Ala | Ser | Gly | Thr | Pro | Gly | Gln |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Arg Val Thr Ile Ser Cys Thr Gly Ile Thr Ser Asn Ile Gly Ser Asn
            20                  25                  30

Thr Val His Trp Tyr Gln Gln Phe Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 242
<211> LENGTH: 330
<212> TYPE: DNA
<213> ORGANISM: Homo sapiens

<400> SEQUENCE: 242

```
cagtctgtgc tgactcagcc accctcagcg tctgggaccc ccgggcagag ggtcaccatc     60
tcttgttctg gaagcaggtc caacatcgga agtaattatg tatactggta ccaacagctc    120
ccaggaacgg cccccaaact cctcatctat aggaataatc agcggccctc aggggtccct    180
gaccgattct ctggctccaa gtctggcacc tcagcctccc tggccatcag tgggctccgg    240
tccgaggatg aggctgatta ttactgtgca gcatgggatg acagcctgag taggccggta    300
ttcggcggag ggaccaagct gaccgtccta                                     330
```

<210> SEQ ID NO 243
<211> LENGTH: 110
<212> TYPE: PRT
<213> ORGANISM: Homo sapiens

<400> SEQUENCE: 243

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg

```
                65                  70                  75                  80
Ser Glu Asp Glu Ala Asp Tyr Tyr Cys Ala Ala Trp Asp Asp Ser Leu
                    85                  90                  95

Ser Arg Pro Val Phe Gly Gly Gly Thr Lys Leu Thr Val Leu
                100                 105                 110
```

<210> SEQ ID NO 244
<211> LENGTH: 330
<212> TYPE: DNA
<213> ORGANISM: Homo sapiens

<400> SEQUENCE: 244

```
cagtctgtgc tgacgcagcc gccctcagtg tctggggccc cagggcagag ggtcaccatc    60
tcctgcactg ggagcagctc caacatcggg gcaggttatg ctgtacactg gtaccagcag   120
cttccaggaa cagcccccaa actcctcatc tatgataaca acaatcggcc ctcaggggtc   180
cctgaccgat tctctggctc caagtctggc acctcagcct ccctggccat cactgggctc   240
caggctgagg atgaggctga ttattactgc cagtcctatg acagcagcct gagtgctata   300
ttcggcggag ggaccaagct gaccgtccta                                     330
```

<210> SEQ ID NO 245
<211> LENGTH: 110
<212> TYPE: PRT
<213> ORGANISM: Homo sapiens

<400> SEQUENCE: 245

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Ala Val His Trp Tyr Gln Gln Leu Pro Gly Thr Ala Pro Lys Leu
            35                  40                  45

Leu Ile Tyr Asp Asn Asn Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Ile Phe Gly Gly Gly Thr Lys Leu Thr Val Leu
                100                 105                 110
```

<210> SEQ ID NO 246
<211> LENGTH: 336
<212> TYPE: DNA
<213> ORGANISM: Homo sapiens

<400> SEQUENCE: 246

```
aatattgtga tgacccagac tccactctct ctgtccgtca cccctggaca gccggcctcc    60
atctcctgca agtctagtca gagcctcctg catagtgatg gaaagaacta tttgttttgg   120
tacctacaga agccaggcca gtctccacag ctcctgatct atgaagtttc ctaccggttc   180
tctggagtgc cagataggtt cagtggcagc gggtcaggga cagatttctc attgaaaatc   240
agccgggtgg aggctgagga tgttggggtt tattactgca tgcaaaatat acagcctcct   300
ctcaccttcg gccaagggac acgactggag attaaa                              336
```

<210> SEQ ID NO 247
<211> LENGTH: 112

```
<212> TYPE: PRT
<213> ORGANISM: Homo sapiens

<400> SEQUENCE: 247

Asn Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Asn Tyr Leu Phe Trp Tyr Leu Gln Lys Pro Gly Gln Ser
        35                  40                  45

Pro Gln Leu Leu Ile Tyr Glu Val Ser Tyr Arg Phe Ser Gly Val Pro
    50                  55                  60

Asp Arg Phe Ser Gly Ser Gly Ser Gly Thr Asp Phe Ser Leu Lys Ile
65                  70                  75                  80

Ser Arg Val Glu Ala Glu Asp Val Gly Val Tyr Tyr Cys Met Gln Asn
                85                  90                  95

Ile Gln Pro Pro Leu Thr Phe Gly Gln Gly Thr Arg Leu Glu Ile Lys
            100                 105                 110

<210> SEQ ID NO 248
<211> LENGTH: 336
<212> TYPE: DNA
<213> ORGANISM: Homo sapiens

<400> SEQUENCE: 248
ggtattgtgc tgactcagtc tccactctcc ctgcccgtca cccctggaga gccggcctcc      60
atctcctgca ggtctagtca gagcctcctg catagtaatg gatacaacta tttggattgg    120
tacttgcaga agccagggca gtctccgcag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tggaagctct tcaaactatg    300
tgcagttttg gccaggggac caagctggag atcaag                              336

<210> SEQ ID NO 249
<211> LENGTH: 112
<212> TYPE: PRT
<213> ORGANISM: Homo sapiens

<400> SEQUENCE: 249

Gly Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Glu Ala
                85                  90                  95

Leu Gln Thr Met Cys Ser Phe Gly Gln Gly Thr Lys Leu Glu Ile Lys
            100                 105                 110

<210> SEQ ID NO 250
<211> LENGTH: 321
<212> TYPE: DNA
<213> ORGANISM: Homo sapiens
```

<400> SEQUENCE: 250

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatct   180
aggttcagcg gcagtggatc tgggacagaa ttcactctca caatcagcaa cctgcagcct   240
gaagattttg caacttatta ctgtctacag cataatagtt accctcgcag ttttggccag   300
gggaccaagc tggagatcaa a                                             321
```

<210> SEQ ID NO 251
<211> LENGTH: 107
<212> TYPE: PRT
<213> ORGANISM: Homo sapiens

<400> SEQUENCE: 251

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Leu Gln His Asn Ser Tyr Pro Arg
                85                  90                  95

Ser Phe Gly Gln Gly Thr Lys Leu Glu Ile Lys
            100                 105
```

<210> SEQ ID NO 252
<211> LENGTH: 321
<212> TYPE: DNA
<213> ORGANISM: Homo sapiens

<400> SEQUENCE: 252

```
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct aatctatgct gcatccagtt tgcaaagtgg ggtcccatca   180
cggttcagcg gcagtgggtc tgggacagat ttcactctca ccatcagcag cctgcagcct   240
gaagattttg caacttacta ttgtcaacag gctaacagtt cccgctcac tttcggcgga   300
gggaccaagg tggagatcaa a                                             321
```

<210> SEQ ID NO 253
<211> LENGTH: 107
<212> TYPE: PRT
<213> ORGANISM: Homo sapiens

<400> SEQUENCE: 253

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
                100                 105

<210> SEQ ID NO 254
<211> LENGTH: 339
<212> TYPE: DNA
<213> ORGANISM: Homo sapiens

<400> SEQUENCE: 254
gatattgtgc tgacccagac tccactctcc ctgcccgtca cccctggaga gccggcctcc      60
atctcctgca ggtctagtca gagcctcttg atagagatg atgggagacac ctatttggac     120 tggtacctgc agaagccagg gcagtctcca cagctcctga tctatacgct ttcctatcgg     180
gcctctggag tcccagacag gttcagtggc agtgggtcag gcactgattt ctcactgaaa     240
atcagcaggg tggaggctga ggatgttgga gtttattact gcatgcaacg tatagagttt     300
ccattcactt tcggccctgg gaccaaagtg gatatcaaa                            339

<210> SEQ ID NO 255
<211> LENGTH: 113
<212> TYPE: PRT
<213> ORGANISM: Homo sapiens

<400> SEQUENCE: 255

Asp Ile Val Leu Thr Gln Thr Pro Leu Ser Leu Pro Val Thr Pro Gly
 1               5                  10                  15

Glu Pro Ala Ser Ile Ser Cys Arg Ser Ser Gln Ser Leu Leu Asp Arg
                20                  25                  30

Asp Asp Gly Asp Thr Tyr Leu Asp Trp Tyr Leu Gln Lys Pro Gly Gln
            35                  40                  45

Ser Pro Gln Leu Leu Ile Tyr Thr Leu Ser Tyr Arg Ala Ser Gly Val
        50                  55                  60

Pro Asp Arg Phe Ser Gly Ser Gly Ser Gly Thr Asp Phe Ser Leu Lys
 65                  70                  75                  80

Ile Ser Arg Val Glu Ala Glu Asp Val Gly Val Tyr Tyr Cys Met Gln
                85                  90                  95

Arg Ile Glu Phe Pro Phe Thr Phe Gly Pro Gly Thr Lys Val Asp Ile
                100                 105                 110

Lys

<210> SEQ ID NO 256
<211> LENGTH: 321
<212> TYPE: DNA
<213> ORGANISM: Homo sapiens

<400> SEQUENCE: 256
gacatccaga tgacccagtc tccatcttcc gtgtctgcgt ctgtagggga cagagtcacc      60
atcacttgtc gggcgagtca gggtattagc agctggttag cctggtatca gcagaaacca    120
gggaaagccc ctaagctcct gatctatact gcatccactt tgcaaagtgg ggtcccatca    180
aggttcagcg gcagtggatc tgggacagat ttcactctca ccatcagcag cctgcagcct    240
```

```
gaagattttg caacttacta ttgtcaacag tctaacagtt tcccgctcac tttcggcgga      300
gggaccaagg tggagatcaa a                                                321
```

<210> SEQ ID NO 257
<211> LENGTH: 107
<212> TYPE: PRT
<213> ORGANISM: Homo sapiens

<400> SEQUENCE: 257

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Phe Pro Leu
                85                  90                  95

Thr Phe Gly Gly Gly Thr Lys Val Glu Ile Lys
            100                 105
```

<210> SEQ ID NO 258
<211> LENGTH: 348
<212> TYPE: DNA
<213> ORGANISM: Homo sapiens

<400> SEQUENCE: 258

```
caggtgcagc tggtggagtc tgggggaggc gtggtccagc ctggagggtc cctgagactc      60
tcctgtgcag cgtctggaat cacccttcagt agctatggca tgcactgggt ccgccaggct    120
ccaggcaagg ggctggagtg ggtggcatct atatggtatg atggaagtaa taaatattat    180
gtagactccg tgaagggccg attcaccatc ttcagagaca attccaagaa aacgctgtat    240
ctgcaaatga acaggctgag agccgaggac acggctgtgt attactgtgc gagacttggt    300
ggtggttttg actactgggg ccagggaacc ctggtcaccg tctcctca                 348
```

<210> SEQ ID NO 259
<211> LENGTH: 116
<212> TYPE: PRT
<213> ORGANISM: Homo sapiens

<400> SEQUENCE: 259

```
Gln Val Gln Leu Val Glu Ser Gly Gly Gly Val Val Gln Pro Gly Arg
1               5                   10                  15

Ser Leu Arg Leu Ser Cys Ala Ala Ser Gly Ile Thr Phe Ser Ser Tyr
            20                  25                  30

Gly Met His Trp Val Arg Gln Ala Pro Gly Lys Gly Leu Glu Trp Val
        35                  40                  45

Ala Ser Ile Trp Tyr Asp Gly Ser Asn Lys Tyr Tyr Val Asp Ser Val
    50                  55                  60

Lys Gly Arg Phe Thr Ile Phe Asp Asn Ser Lys Lys Thr Leu Tyr
65                  70                  75                  80

Leu Gln Met Asn Arg Leu Arg Ala Glu Asp Thr Ala Val Tyr Tyr Cys
                85                  90                  95

Ala Arg Leu Gly Gly Gly Phe Asp Tyr Trp Gly Gln Gly Thr Leu Val
```

Thr Val Ser Ser
        115

<210> SEQ ID NO 260
<211> LENGTH: 348
<212> TYPE: DNA
<213> ORGANISM: Homo sapiens

<400> SEQUENCE: 260
caggtgcaac tggtggagtc tgggggaggc gtggtccagc ctggaggtc cctgagactc      60 tcctgtgcag cgtctggaat caccttcagt agctatggca tgcactgggt ccgccagggt    120
ccaggcaagg ggctggagtg ggtggcattt atatggtatg atggaagtga aaaatattat    180
gtagactccg tgaagggccg attcaccatc tccagagaca attccaagaa cacgctgtat    240
ctgcaaatga acagtctgag agccgaggac acggctgtgt attactgtgc gagaatggga    300
ggcggctttg actactgggg ccagggaacc ctggtcaccg tctcctca                 348

<210> SEQ ID NO 261
<211> LENGTH: 116
<212> TYPE: PRT
<213> ORGANISM: Homo sapiens

<400> SEQUENCE: 261

Gln Val Gln Leu Val Glu Ser Gly Gly Gly Val Val Gln Pro Gly Arg
1               5                   10                  15

Ser Leu Arg Leu Ser Cys Ala Ala Ser Gly Ile Thr Phe Ser Ser Tyr
            20                  25                  30

Gly Met His Trp Val Arg Gln Gly Pro Gly Lys Gly Leu Glu Trp Val
        35                  40                  45

Ala Phe Ile Trp Tyr Asp Gly Ser Glu Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Gly Gly Phe Asp Tyr Trp Gly Gln Gly Thr Leu Val
            100                 105                 110

Thr Val Ser Ser
        115

<210> SEQ ID NO 262
<211> LENGTH: 384
<212> TYPE: DNA
<213> ORGANISM: Homo sapiens

<400> SEQUENCE: 262
caggtgcagc tggtggagtc tgggggaggc gtggtccagc ctggaggtc cctgagactc      60 tcctgtgcag cgtctggatt caccttcagt agctatggca tgcactgggt ccgccaggct    120
ccaggcaagg ggctggagtg ggtggcagtt atgtggtatg atggaagtaa taaagactat    180
gtagactccg tgaagggccg attcaccatc tccagagaca attccaagaa cacgctgtat    240
ctgcaaatga accgcctgag agccgaggac acggctgtgt attactgtgc gagagaaaaa    300
gatcattacg acattttgac tggttataac tactactacg gtctggacgt ctggggccaa    360
gggaccacgg tcaccgtctc ctca                                           384

<210> SEQ ID NO 263
<211> LENGTH: 128
<212> TYPE: PRT
<213> ORGANISM: Homo sapiens

<400> SEQUENCE: 263

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Met Trp Tyr Asp Gly Ser Asn Lys Asp Tyr Val Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Arg Leu Arg Ala Glu Asp Thr Ala Val Tyr Tyr Cys
                85                  90                  95
Ala Arg Glu Lys Asp His Tyr Asp Ile Leu Thr Gly Tyr Asn Tyr Tyr
            100                 105                 110
Tyr Gly Leu Asp Val Trp Gly Gln Gly Thr Thr Val Thr Val Ser Ser
        115                 120                 125
```

<210> SEQ ID NO 264
<211> LENGTH: 467
<212> TYPE: DNA
<213> ORGANISM: Homo sapiens

<400> SEQUENCE: 264

```
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atgtggtatg atggaagtaa taaagactat     180
gtagactccg tgaagggccg attcaccatc tccagagaca attccaagaa cacgctgtat     240
ctgcaaatga accgcctgag agccgaggac acggctgtgt attactgtgc gagagaaaaa     300
gatcattacg acattttgac tggttataac tactactacg gtctggacgt ctggggccaa     360
gggaccacgg tcaccgtctc ctcagcctcc accaagggcc catcggtctt ccccctggcg     420
ccctgctcca ggagcacctc cgagagcaca gcggccctgg gctgcct                   467
```

<210> SEQ ID NO 265
<211> LENGTH: 128
<212> TYPE: PRT
<213> ORGANISM: Homo sapiens

<400> SEQUENCE: 265

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Met Trp Tyr Asp Gly Ser Asn Lys Asp Tyr Val Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
```

```
Ala Arg Glu Lys Asp His Tyr Asp Ile Leu Thr Gly Tyr Asn Tyr Tyr
            100                 105                 110

Tyr Gly Leu Asp Val Trp Gly Gln Gly Thr Thr Val Thr Val Ser Ser
        115                 120                 125

<210> SEQ ID NO 266
<211> LENGTH: 384
<212> TYPE: DNA
<213> ORGANISM: Homo sapiens

<400> SEQUENCE: 266
caggtgcagc tggtggagtc tgggggaggc gtggtccagc ctggaggtc cctgagactc      60 tcctgtgcag cctctggatt caccttcagt acctatggga tgcactgggt ccgccaggct    120
ccaggcaagg gtctggagtg ggtggcagtt atatcagatg atggaagtca taaatactct    180
gcagactccg tgaagggccg attcaccatc tccagagaca attccaagaa cacgctgtat    240
ctgcaaatga acagcctgag aactgaggac tcggctgtgt attactgtgc gagagaggag    300
acgtattacg atattttgac tggctatcat cactactacg gtatggacgt ctggggccaa    360
gggaccacgg tcaccgtctc ctca                                           384

<210> SEQ ID NO 267
<211> LENGTH: 128
<212> TYPE: PRT
<213> ORGANISM: Homo sapiens

<400> SEQUENCE: 267

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Ser Asp Asp Gly Ser His Lys Tyr Ser Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Ser Ala Val Tyr Tyr Cys
                85                  90                  95

Ala Arg Glu Glu Thr Tyr Tyr Asp Ile Leu Thr Gly Tyr His His Tyr
            100                 105                 110

Tyr Gly Met Asp Val Trp Gly Gln Gly Thr Thr Val Thr Val Ser Ser
        115                 120                 125

<210> SEQ ID NO 268
<211> LENGTH: 384
<212> TYPE: DNA
<213> ORGANISM: Homo sapiens

<400> SEQUENCE: 268
caggtgcagc tggtggagtc tgggggaggc gtggtccagc ctggaggtc cctgagactc      60 tcctgtgcag cgtctggatt caccttcagt agctatggca tgcactgggt ccgccaggct    120
ccaggcaagg ggctggagtg ggtggcagaa atatggaatg atggaagtaa taatactat     180 gcagactccg tgaagggccg attcaccatc tccagagaca atcccaagaa cacgctgtat    240
ctgcaaatga acagcctgag agccgaggac acggctgtgt attattgtgc gagagagcct    300
cagtattacg atattttgac tggttatgat aactactacg gtatggacgt ctggggccaa    360
```
gggaccacgg tcaccgtctc ctca        384

<210> SEQ ID NO 269
<211> LENGTH: 128
<212> TYPE: PRT
<213> ORGANISM: Homo sapiens

<400> SEQUENCE: 269

```
Gln Val Gln Leu Val Glu Ser Gly Gly Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Glu Ile Trp Asn Asp Gly Ser Asn Lys Tyr Tyr Ala Asp Ser Val
        50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Gln Tyr Tyr Asp Ile Leu Thr Gly Tyr Asp Asn Tyr
            100                 105                 110

Tyr Gly Met Asp Val Trp Gly Gln Gly Thr Thr Val Thr Val Ser Ser
        115                 120                 125
```

<210> SEQ ID NO 270
<211> LENGTH: 384
<212> TYPE: DNA
<213> ORGANISM: Homo sapiens

<400> SEQUENCE: 270
caggtgcagc tggtggagtc tgggggaggc gtggtccagc ctgggaggtc cctgagactc      60
tcctgtgcag cctctggatt caccttcagt agctatggca tgcactgggt ccgccaggct     120
ccaggcaagg ggctggagtg ggtggcagtg atatcacatg atggaagtga taaatactat     180
gcagactccg tgaagggccg attcaccatc tccagagaca attccaagaa cacgctgtat     240
ctgcaaatga gcagtttgag agctgaggac acggctgtgt attactgtgc gagagaaaaa     300
ccgtattacg atattttgac tggttatttc tactactatg gtatggacgt ctggggccaa     360
gggaccacgg tcaccgtctc ctca        384

<210> SEQ ID NO 271
<211> LENGTH: 128
<212> TYPE: PRT
<213> ORGANISM: Homo sapiens

<400> SEQUENCE: 271

```
Gln Val Gln Leu Val Glu Ser Gly Gly Val Gln Pro Gly Arg
1               5                   10                  15

Ser Leu Arg Leu Ser Cys Ala Ala Ser Gly Phe Thr Phe Ser Ser Tyr
                20                  25                  30

Asp Met His Trp Val Arg Gln Ala Pro Gly Lys Gly Leu Glu Trp Val
            35                  40                  45

Ala Val Ile Ser His Asp Gly Ser Asp Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80
```

Leu Gln Met Ser Ser Leu Arg Ala Glu Asp Thr Ala Val Tyr Tyr Cys
                85                  90                  95

Ala Arg Glu Lys Pro Tyr Tyr Asp Ile Leu Thr Gly Tyr Phe Tyr Tyr
            100                 105                 110

Tyr Gly Met Asp Val Trp Gly Gln Gly Thr Thr Val Thr Val Ser Ser
        115                 120                 125

<210> SEQ ID NO 272
<211> LENGTH: 348
<212> TYPE: DNA
<213> ORGANISM: Homo sapiens

<400> SEQUENCE: 272
caggtgcagt tggcggagtc tgggggaggc gtggtccagc ctgggaggtc cctgagactc    60
tcctgtacag cgtctggaat caccttcagt agctatggca tgcactgggt ccgccaggct   120
ccaggcaagg ggctgagtg gtggcaggt atatggtatg atggaaggaa taaatactat    180
gtagactccg tgaagggccg attcaccatc tccagagaca attccaagaa aacgctgtat   240
ctgcaaatga acagcctgag agccgaggac acggctgtgt attactgtgc gaggttagca   300
gtggcctttg actactgggg ccagggaact ttggtcaccg tctcctca                348

<210> SEQ ID NO 273
<211> LENGTH: 116
<212> TYPE: PRT
<213> ORGANISM: Homo sapiens

<400> SEQUENCE: 273

Gln Val Gln Leu Ala Glu Ser Gly Gly Gly Val Val Gln Pro Gly Arg
1               5                   10                  15

Ser Leu Arg Leu Ser Cys Thr Ala Ser Gly Ile Thr Phe Ser Ser Tyr
            20                  25                  30

Gly Met His Trp Val Arg Gln Ala Pro Gly Lys Gly Leu Glu Trp Val
        35                  40                  45

Ala Gly Ile Trp Tyr Asp Gly Arg Asn Lys Tyr Tyr Val Asp Ser Val
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Val Ala Phe Asp Tyr Trp Gly Gln Gly Thr Leu Val
            100                 105                 110

Thr Val Ser Ser
        115

<210> SEQ ID NO 274
<211> LENGTH: 384
<212> TYPE: DNA
<213> ORGANISM: Homo sapiens

<400> SEQUENCE: 274
caggtgcagc tggtggagtc tgggggaggc gtggtccagc ctggggaggtc cctgagactc    60 tcctgtgcag cgtctggatt caccttcagt agctatggca tgcactgggt ccgccaggct   120
ccaggcaagg ggctggagtg gtggcagtt atgtggtatg atggaagtaa taaagactat    180
gtagactccg tgaagggccg attcaccatc tccagagaca attccaagaa cacgctgtat   240
ctgcaaatga accgcctgag agccgaggac acggctgtgt attactgtgc gagagaaaaa   300
gatcattacg acattttgac tggttataac tactactacg gtctggacgt ctggggccaa   360
gggaccacgg tcaccgtctc ctca                                                  384

<210> SEQ ID NO 275
<211> LENGTH: 128
<212> TYPE: PRT
<213> ORGANISM: Homo sapiens

<400> SEQUENCE: 275

Gln Val Gln Leu Val Glu Ser Gly Gly Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Trp Tyr Asp Gly Ser Asn Lys Asp Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Glu Lys Asp His Tyr Asp Ile Leu Thr Gly Tyr Asn Tyr Tyr
            100                 105                 110

Tyr Gly Leu Asp Val Trp Gly Gln Gly Thr Thr Val Thr Val Ser Ser
        115                 120                 125

<210> SEQ ID NO 276
<211> LENGTH: 372
<212> TYPE: DNA
<213> ORGANISM: Homo sapiens

<400> SEQUENCE: 276
caggtacagc tgcagcagtc aggtccagga ctggtgaggc cctcgcagac cctctcactc    60
acctgtgcca tctccgggga cagtgtctct agcaactatg ctgcttggaa ctggatcagg   120
cagtccccat cgagaggcct tgagtggctg gaaggacat  actacaggtc caagtggtat   180
aatgattatg cagtatctgt gagaagtcga acaaccatca acccagacac atccaagaac   240
cagttctccc tgcagttgaa ctctgtgact cccgaggaca cggctgtgta ttactgtaca   300
agagaagatg gcagtggctg gtacggtgct tttgacatct ggggccaagg gacaatggtc   360
accgtctctt ca                                                       372

<210> SEQ ID NO 277
<211> LENGTH: 124
<212> TYPE: PRT
<213> ORGANISM: Homo sapiens

<400> SEQUENCE: 277

Gln Val Gln Leu Gln Gln Ser Gly Pro Gly Leu Val Arg Pro Ser Gln
1               5                   10                  15

Thr Leu Ser Leu Thr Cys Ala Ile Ser Gly Asp Ser Val Ser Ser Asn
            20                  25                  30

Tyr Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Arg Ser Arg Thr Thr Ile Asn Pro Asp Thr Ser Lys Asn
65                  70                  75                  80

```
Gln Phe Ser Leu Gln Leu Asn Ser Val Thr Pro Glu Asp Thr Ala Val
                85                  90                  95
Tyr Tyr Cys Thr Arg Glu Asp Gly Ser Gly Trp Tyr Gly Ala Phe Asp
            100                 105                 110
Ile Trp Gly Gln Gly Thr Met Val Thr Val Ser Ser
        115                 120
```

<210> SEQ ID NO 278
<211> LENGTH: 374
<212> TYPE: DNA
<213> ORGANISM: Homo sapiens

<400> SEQUENCE: 278

```
caggtgcaac tggtggagtc tgggggaggc gtggtccagc ctggagggtc cctgagactc    60
tcctgtgcag cctctgggag caccttcaga agctatgaca tgcactgggt ccgccaggct   120
ccaggcaagg ggctggagtg ggtggcattt atatcagatg atggaagtaa taaatactat   180
ggagactccg tgaagggccg attgaccatc tccagagaca attccaagaa cacgctgtat   240
ctgcaaatga acagcctgag agctgaggac acggctgtgt attactgtgc gagagatcaa   300
tacgatattt tgactggtta ttcttctgat gcttttgata tctggggcca agggacaatg   360
gtcaccgtct cttc                                                     374
```

<210> SEQ ID NO 279
<211> LENGTH: 125
<212> TYPE: PRT
<213> ORGANISM: Homo sapiens

<400> SEQUENCE: 279

```
Gln Val Gln Leu Val Glu Ser Gly Gly Gly Val Val Gln Pro Gly Arg
1               5                   10                  15
Ser Leu Arg Leu Ser Cys Ala Ala Ser Gly Ser Thr Phe Arg Ser Tyr
            20                  25                  30
Asp Met His Trp Val Arg Gln Ala Pro Gly Lys Gly Leu Glu Trp Val
        35                  40                  45
Ala Phe Ile Ser Asp Asp Gly Ser Asn Lys Tyr Tyr Gly Asp Ser Val
    50                  55                  60
Lys Gly Arg Leu Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Gln Tyr Asp Ile Leu Thr Gly Tyr Ser Ser Asp Ala Phe
            100                 105                 110
Asp Ile Trp Gly Gln Gly Thr Met Val Thr Val Ser Ser
        115                 120                 125
```

<210> SEQ ID NO 280
<211> LENGTH: 375
<212> TYPE: DNA
<213> ORGANISM: Homo sapiens

<400> SEQUENCE: 280

```
caggtgcaac tggtggagtc tgggggaggc gtggtccagc ctggagggtc cctgagactc    60
tcctgtgcag cctctgggag caccttcaga agctatgaca tgcactgggt ccgccaggct   120
ccaggcaagg ggctggagtg ggtggcattt atatcagatg atggaagtaa taaatattat   180
ggagactccg tgaagggccg attgaccatc tccagagaca attccaagaa cacgctgtat   240
ctgcaaatga acagcctgag agctgaggac acggctgtgt attattgtgc gagagatcaa   300
```
tacgatattt tgactggtta ttcttctgat gcttttgata tctggggcca agggacaatg    360
gtcaccgtct cttca                                                    375

<210> SEQ ID NO 281
<211> LENGTH: 125
<212> TYPE: PRT
<213> ORGANISM: Homo sapiens

<400> SEQUENCE: 281

Gln Val Gln Leu Val Glu Ser Gly Gly Gly Val Val Gln Pro Gly Arg
1               5                   10                  15

Ser Leu Arg Leu Ser Cys Ala Ala Ser Gly Ser Thr Phe Arg Ser Tyr
            20                  25                  30

Asp Met His Trp Val Arg Gln Ala Pro Gly Lys Gly Leu Glu Trp Val
        35                  40                  45

Ala Phe Ile Ser Asp Asp Gly Ser Asn Lys Tyr Tyr Gly Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Tyr Asp Ile Leu Thr Gly Tyr Ser Ser Asp Ala Phe
            100                 105                 110

Asp Ile Trp Gly Gln Gly Thr Met Val Thr Val Ser Ser
        115                 120                 125

<210> SEQ ID NO 282
<211> LENGTH: 375
<212> TYPE: DNA
<213> ORGANISM: Homo sapiens

<400> SEQUENCE: 282
caggtgcagc tggtggagtc tgggggaggc gtggtccagc ctggagggtc cctgagactc    60
tcctgtgcag cctctggaag caccttcaga agctatgaca tgcactgggt ccgccaggct    120
ccaggcaagg ggctggagtg ggtggcagtt atatcatatg atggaagtaa taaatactat    180
ggagactccg tgaagggccg attgaccatc tccagagaca attccaagaa cacgctgtat    240
ctgcaaatga acagcctgag agctgaggac acggctgtgt attactgtgc gagagatcaa    300
tacgatattt tgactggtta ttcttctgat gcttttgata tctggggcca agggacaatg    360
gtcaccgtct cttca                                                    375

<210> SEQ ID NO 283
<211> LENGTH: 125
<212> TYPE: PRT
<213> ORGANISM: Homo sapiens

<400> SEQUENCE: 283

Gln Val Gln Leu Val Glu Ser Gly Gly Gly Val Val Gln Pro Gly Arg
1               5                   10                  15

Ser Leu Arg Leu Ser Cys Ala Ala Ser Gly Ser Thr Phe Arg Ser Tyr
            20                  25                  30

Asp Met His Trp Val Arg Gln Ala Pro Gly Lys Gly Leu Glu Trp Val
        35                  40                  45

Ala Val Ile Ser Tyr Asp Gly Ser Asn Lys Tyr Tyr Gly Asp Ser Val
    50                  55                  60

Lys Gly Arg Leu Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95

Ala Arg Asp Gln Tyr Asp Ile Leu Thr Gly Tyr Ser Ser Asp Ala Phe
                100                 105                 110

Asp Ile Trp Gly Gln Gly Thr Met Val Thr Val Ser Ser
            115                 120                 125

<210> SEQ ID NO 284
<211> LENGTH: 387
<212> TYPE: DNA
<213> ORGANISM: Homo sapiens

<400> SEQUENCE: 284
caggtgcagc tggtggagtc tgggggaggc gtggtccagc ctggagggtc cctgagactc      60
tcctgtgcag cgtctggatt caccttcagt aactatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagcctat     300
tacgatattt tgactgatta cccccagtat gactactact acggtatgga cgtctggggc     360
caagggacca cggtcaccgt ctcctca                                          387

<210> SEQ ID NO 285
<211> LENGTH: 129
<212> TYPE: PRT
<213> ORGANISM: Homo sapiens

<400> SEQUENCE: 285

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Tyr Tyr Asp Ile Leu Thr Asp Tyr Pro Gln Tyr Asp Tyr
                100                 105                 110

Tyr Tyr Gly Met Asp Val Trp Gly Gln Gly Thr Thr Val Thr Val Ser
            115                 120                 125

Ser

<210> SEQ ID NO 286
<211> LENGTH: 378
<212> TYPE: DNA
<213> ORGANISM: Homo sapiens

<400> SEQUENCE: 286
caggtgcagc tggtggagtc tgggggaggc gtggtccagc ctggaagtc cctgagactc       60 tcctgtgcag tctctggatt catcttcagt agctatggca tgcactgggt ccgccaggct     120
ccaggcaagg ggctggagtg ggtggcactt atatcatttg atggaagtaa taaatactat     180
```

```
gcagactccg tgaagggccg attcaccatc tccagagaca attccaagaa cacgctgtat    240
ctgcaaatga acagcctgag agctgaggac acggctgtgt attactgtgc gagagatggg    300
tattacgata ttttgactgg ttatgaggat gatgcttttg atatctgggg ccaagggaca    360
atggtcaccg tctcttca                                                  378
```

<210> SEQ ID NO 287
<211> LENGTH: 126
<212> TYPE: PRT
<213> ORGANISM: Homo sapiens

<400> SEQUENCE: 287

```
Gln Val Gln Leu Val Glu Ser Gly Gly Gly Val Val Gln Pro Gly Lys
1               5                   10                  15

Ser Leu Arg Leu Ser Cys Ala Val Ser Gly Phe Ile Phe Ser Ser Tyr
            20                  25                  30

Gly Met His Trp Val Arg Gln Ala Pro Gly Lys Gly Leu Glu Trp Val
        35                  40                  45

Ala Leu Ile Ser Phe Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Tyr Asp Ile Leu Thr Gly Tyr Glu Asp Asp Ala
            100                 105                 110

Phe Asp Ile Trp Gly Gln Gly Thr Met Val Thr Val Ser Ser
        115                 120                 125
```

<210> SEQ ID NO 288
<211> LENGTH: 387
<212> TYPE: DNA
<213> ORGANISM: Homo sapiens

<400> SEQUENCE: 288

```
caggtgcagc tggtgcagtc tggggctgag gtgaagaagc ctggggcctc agtgaaggtc    60
tcctgcaagg cttctggata caccttcacc ggctactatt tgcactgggt gcgacaggcc    120
cctggacaag gcttgagtg gatgggatgg atcatccctg acagtggtgg cacaaagtat    180
gcacagaagt tccagggcag ggtcaccatg accagggaca cgtccatcag cacagcctac    240
ttggagctga gcaggctgag atctgacgac acggccgtgt attactgtgc gagagaaggg    300
tttcattacg atattttgac tggttcctac ttctactact acggtatgga cgtctggggc    360
caagggacca cggtcaccgt ctcctca                                        387
```

<210> SEQ ID NO 289
<211> LENGTH: 129
<212> TYPE: PRT
<213> ORGANISM: Homo sapiens

<400> SEQUENCE: 289

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Leu His Trp Val Arg Gln Ala Pro Gly Gln Gly Leu Glu Trp Met
        35                  40                  45
```

Gly Trp Ile Ile Pro Asp Ser Gly Gly Thr Lys Tyr Ala Gln Lys Phe
            50                  55                  60

Gln Gly Arg Val Thr Met Thr Arg Asp Thr Ser Ile Ser Thr Ala Tyr
 65                  70                  75                  80

Leu Glu Leu Ser Arg Leu Arg Ser Asp Asp Thr Ala Val Tyr Tyr Cys
                 85                  90                  95

Ala Arg Glu Gly Phe His Tyr Asp Ile Leu Thr Gly Ser Tyr Phe Tyr
            100                 105                 110

Tyr Tyr Gly Met Asp Val Trp Gly Gln Gly Thr Thr Val Thr Val Ser
            115                 120                 125

Ser

<210> SEQ ID NO 290
<211> LENGTH: 357
<212> TYPE: DNA
<213> ORGANISM: Homo sapiens

<400> SEQUENCE: 290
caggttcagc tggtgcagtc tggagctgag gtgaagaagc ctggggcctc agtgaaggtc     60
tcctgcaagg cttctggtta cacctttacc agctatggta tcagttgggc gcgacaggcc    120
cctggacaag gcttgagtg atgggatgg atcggcgttt acaatggtca cacaaaatat      180
gcacagaagt tccagggcag agtcaccatg accacagaca catccacgag cacagcctac    240
atggagctga ggagcctgag atctgacgac acggccatat tttactgtgc gagaagggta    300
gcagtggctg gtactttga ctactgggc cagggaaccc tggtcaccgt ctcctca         357

<210> SEQ ID NO 291
<211> LENGTH: 119
<212> TYPE: PRT
<213> ORGANISM: Homo sapiens

<400> SEQUENCE: 291

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Gly Ile Ser Trp Ala Arg Gln Ala Pro Gly Gln Gly Leu Glu Trp Met
         35                  40                  45

Gly Trp Ile Gly Val Tyr Asn Gly His Thr Lys Tyr Ala Gln Lys Phe
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Ile Phe Tyr Cys
                 85                  90                  95

Ala Arg Arg Val Ala Val Ala Gly Tyr Phe Asp Tyr Trp Gly Gln Gly
            100                 105                 110

Thr Leu Val Thr Val Ser Ser
            115

<210> SEQ ID NO 292
<211> LENGTH: 381
<212> TYPE: DNA
<213> ORGANISM: Homo sapiens

<400> SEQUENCE: 292
caggtgcagc tggtgagtc tgggggaggc gtggtccagc ctggggaggtc cctgagactc     60 tcctgtgcag cgtctggatt cacctttcagt agatatggca tgcactgggt ccgccaggct   120

```
ccaggcaagg ggctggagtg ggtggcagtt atatggtatg atggaagtca taaatactat      180
gaagactccg tgaagggccg attcaccatc tccagagaca attctaagaa cacgctgtat      240
ctgcaaatga acagcctgag agccgacgac acgggtgtgt attactgtgc gagagtcggg      300
tatggcagtg gctggtacga gtactattac cactacggta tggacgtctg gggccaaggg      360
accacggtca ccgtctcctc a                                                381
```

<210> SEQ ID NO 293
<211> LENGTH: 127
<212> TYPE: PRT
<213> ORGANISM: Homo sapiens

<400> SEQUENCE: 293

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser His Lys Tyr Tyr Glu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Gly Val Tyr Tyr Cys
                85                  90                  95

Ala Arg Val Gly Tyr Gly Ser Gly Trp Tyr Glu Tyr Tyr Tyr His Tyr
            100                 105                 110

Gly Met Asp Val Trp Gly Gln Gly Thr Thr Val Thr Val Ser Ser
        115                 120                 125
```

<210> SEQ ID NO 294
<211> LENGTH: 384
<212> TYPE: DNA
<213> ORGANISM: Homo sapiens

<400> SEQUENCE: 294

```
caggtgcagc tggtggagtc tgggggaggc gtggtccagc ctgggaggtc cctgagactc      60
tcctgtgcag cgtctggatt caccttcagt agctatggca tgcactgggt ccgccaggct      120
ccaggcaagg ggctggagtg ggtgacaatt atatggtctg atggaattaa caaatactat      180
gcagactccg tgaagggccg attcaccata tccagagaca attccaagaa cacgctgaat      240
ctgcaaatga acagtttgag agccgaggac acggctgtgt attactgtgc gagagagaga      300
ggcctctacg atattttgac tggttattat aactactacg gtattgacgt ctggggccaa      360
gggaccacgg tcaccgtctc ctca                                             384
```

<210> SEQ ID NO 295
<211> LENGTH: 128
<212> TYPE: PRT
<213> ORGANISM: Homo sapiens

<400> SEQUENCE: 295

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
```

```
                  35                  40                  45
Thr Ile Ile Trp Ser Asp Gly Ile Asn Lys Tyr Tyr Ala Asp Ser Val
 50                  55                  60
Lys Gly Arg Phe Thr Ile Ser Arg Asp Asn Ser Lys Asn Thr Leu Asn
 65                  70                  75                  80
Leu Gln Met Asn Ser Leu Arg Ala Glu Asp Thr Ala Val Tyr Tyr Cys
                 85                  90                  95
Ala Arg Glu Arg Gly Leu Tyr Asp Ile Leu Thr Gly Tyr Tyr Asn Tyr
            100                 105                 110
Tyr Gly Ile Asp Val Trp Gly Gln Gly Thr Thr Val Thr Val Ser Ser
            115                 120                 125
```

<210> SEQ ID NO 296
<211> LENGTH: 366
<212> TYPE: DNA
<213> ORGANISM: Homo sapiens

<400> SEQUENCE: 296

```
gaggtgcagc tggtggagtc tgggggagac ttggtacagc ctgggggtc cctgagactc      60
tcctgtgcag cctctggatt caccttcagt ggctatacct tgaactgggt ccgccaggct     120
ccagggaagg gctggagtg gtttcaaac attaatagta ggagtagtct catatactac      180
acagactctg tgaagggccg attcaccatc tccagagaca tgccaagaa ctcactgtat     240
ctgcaaatga acagcctgag agacgaggac acggctgtgt atttctgtgc gagagatcag    300
tataactgga actactacta cggtatggac gtctggggcc aagggaccac ggtcaccgtc    360
tcctca                                                               366
```

<210> SEQ ID NO 297
<211> LENGTH: 122
<212> TYPE: PRT
<213> ORGANISM: Homo sapiens

<400> SEQUENCE: 297

```
Glu Val Gln Leu Val Glu Ser Gly Gly Asp Leu Val Gln Pro Gly Gly
  1               5                  10                  15
Ser Leu Arg Leu Ser Cys Ala Ala Ser Gly Phe Thr Phe Ser Gly Tyr
             20                  25                  30
Thr Leu Asn Trp Val Arg Gln Ala Pro Gly Lys Gly Leu Glu Trp Val
             35                  40                  45
Ser Asn Ile Asn Ser Arg Ser Ser Leu Ile Tyr Tyr Thr Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Asp Glu Asp Thr Ala Val Tyr Phe Cys
                 85                  90                  95
Ala Arg Asp Gln Tyr Asn Trp Asn Tyr Tyr Tyr Gly Met Asp Val Trp
            100                 105                 110
Gly Gln Gly Thr Thr Val Thr Val Ser Ser
            115                 120
```

<210> SEQ ID NO 298
<211> LENGTH: 360
<212> TYPE: DNA
<213> ORGANISM: Homo sapiens

<400> SEQUENCE: 298

```
gaggtgcggc tggtggagtc tgggggagac ttggtacagc ctgggggtc cctgagactc      60
```

```
tcctgtgcag cctctggatt caccttcagt agctatgcca tgaactgggt ccgccaggct    120
ccagggaagg ggctggagtg gatttcatac attggtagta gtagtagtgc catatactac    180
ggagactctg tgaagggccg attcaccatc tccagagaca atgccaagaa ctcactgtat    240
ctgcaaatga acagcctgag agacgaggac acggctgtgt attactgtgc gagatataga    300
agtggctggt ccccctctt tgacttctgg ggccagggaa gcctggtcac cgtctcctca     360
```

<210> SEQ ID NO 299
<211> LENGTH: 120
<212> TYPE: PRT
<213> ORGANISM: Homo sapiens

<400> SEQUENCE: 299

```
Glu Val Arg Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Ile
        35                  40                  45

Ser Tyr Ile Gly Ser Ser Ser Ala Ile Tyr Tyr Gly Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Tyr Arg Ser Gly Trp Ser Pro Leu Phe Asp Phe Trp Gly Gln
            100                 105                 110

Gly Ser Leu Val Thr Val Ser Ser
        115                 120
```

<210> SEQ ID NO 300
<211> LENGTH: 348
<212> TYPE: DNA
<213> ORGANISM: Homo sapiens

<400> SEQUENCE: 300

```
caggtgcagc tggtggagtc tgggggaggc gtggtccagc ctgggaggtc cctgagactc     60
tcctgtgcag cgtctggaat caccttcagt agctatggca tgcactgggt ccgccaggct    120
ccaggcaagg ggctggagtg ggtggcatct atatggtatg atggaagtaa taaatattat    180
gtagactccg tgaagggccg attcaccatc ttcagagaca attccaagaa aacgctgtat    240
ctgcaaatga acaggctgag agccgaggac acggctgtgt attactgtgc gagacttggt    300
ggtggttttg actactgggg ccagggaacc ctggtcaccg tctcctca                 348
```

<210> SEQ ID NO 301
<211> LENGTH: 116
<212> TYPE: PRT
<213> ORGANISM: Homo sapiens

<400> SEQUENCE: 301

```
Gln Val Gln Leu Val Glu Ser Gly Gly Gly Val Val Gln Pro Gly Arg
1               5                   10                  15

Ser Leu Arg Leu Ser Cys Ala Ala Ser Gly Ile Thr Phe Ser Ser Tyr
            20                  25                  30

Gly Met His Trp Val Arg Gln Ala Pro Gly Lys Gly Leu Glu Trp Val
        35                  40                  45
```

```
Ala Ser Ile Trp Tyr Asp Gly Ser Asn Lys Tyr Tyr Val Asp Ser Val
 50                  55                  60

Lys Gly Arg Phe Thr Ile Phe Arg Asp Asn Ser Lys Thr Leu Tyr
 65                  70                  75                  80

Leu Gln Met Asn Arg Leu Arg Ala Glu Asp Thr Ala Val Tyr Tyr Cys
                 85                  90                  95

Ala Arg Leu Gly Gly Gly Phe Asp Tyr Trp Gly Gln Gly Thr Leu Val
            100                 105                 110

Thr Val Ser Ser
        115

<210> SEQ ID NO 302
<211> LENGTH: 360
<212> TYPE: DNA
<213> ORGANISM: Homo sapiens

<400> SEQUENCE: 302
gaggtgcggc tggtggagtc tgggggaggc ttggtacagc ctggggggtc cctgagactc      60
tcctgtacag cctctggatt ccccttcaat agatatgcca tgaactgggt ccgccaggct    120
ccagggaagg ggctggagtg ggtttcatac attggtagta gtagtagtgc catatactac    180
gcagactctg tgaagggccg attcaccatc tccagagaca atgccaagaa ctcactgtat    240
ctgcaaatga acagcctgag agatgaagac acggctgtgt attactgtgc gagatatagc    300
agtggctggt ccccctcttt tgactactgg ggccagggaa ccctggtcac cgtctcctca    360

<210> SEQ ID NO 303
<211> LENGTH: 120
<212> TYPE: PRT
<213> ORGANISM: Homo sapiens

<400> SEQUENCE: 303

Glu Val Arg Leu Val Glu Ser Gly Gly Gly Leu Val Gln Pro Gly Gly
 1               5                  10                  15

Ser Leu Arg Leu Ser Cys Thr Ala Ser Gly Phe Pro Phe Asn Arg Tyr
                20                  25                  30

Ala Met Asn Trp Val Arg Gln Ala Pro Gly Lys Gly Leu Glu Trp Val
             35                  40                  45

Ser Tyr Ile Gly Ser Ser Ser Ala Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Tyr Ser Ser Gly Trp Ser Pro Leu Phe Asp Tyr Trp Gly Gln
            100                 105                 110

Gly Thr Leu Val Thr Val Ser Ser
        115                 120

<210> SEQ ID NO 304
<211> LENGTH: 321
<212> TYPE: DNA
<213> ORGANISM: Homo sapiens

<400> SEQUENCE: 304
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
```

```
agcaaggaca gcacctacag cctcagcagc accctgacgc tgagcaaagc agactacgag      240
aaacacaaag tctacgcctg cgaagtcacc catcagggcc tgagctcgcc cgtcacaaag      300
agcttcaaca ggggagagtg t                                                321
```

<210> SEQ ID NO 305
<211> LENGTH: 107
<212> TYPE: PRT
<213> ORGANISM: Homo sapiens

<400> SEQUENCE: 305

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 306
<211> LENGTH: 318
<212> TYPE: DNA
<213> ORGANISM: Homo sapiens

<400> SEQUENCE: 306

```
ggtcagccca aggctgcccc ctcggtcact ctgttcccgc cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca acaagtacgc ggccagcagc tatctgagcc tgacgcctga gcagtggaag     240
tcccacagaa gctacagctg ccaggtcacg catgaaggga gcaccgtgga agacagtg      300 gcccctacag aatgttca                                                   318
```

<210> SEQ ID NO 307
<211> LENGTH: 106
<212> TYPE: PRT
<213> ORGANISM: Homo sapiens

<400> SEQUENCE: 307

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95
```

Glu Lys Thr Val Ala Pro Thr Glu Cys Ser
            100                 105

<210> SEQ ID NO 308
<211> LENGTH: 978
<212> TYPE: DNA
<213> ORGANISM: Homo sapiens

<400> SEQUENCE: 308

```
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggaccctga ggtcacgtgc      420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt tgtgcaccag gactggctga acggcaagga gtacaagtgc     600
aaggtctcca acaaaggcct cccagccccc atcgagaaaa ccatctccaa aaccaaaggg     660
cagccccgag aaccacaggt gtacaccctg cccccatccc gggaggagat gaccaagaac     720
caggtcagcc tgacctgcct ggtcaaaggc ttctacccca gcgacatcgc cgtggagtgg     780
gagagcaatg ggcagccgga gaacaactac aagaccacac ctcccatgct ggactccgac     840
ggctccttct tcctctacag caagctcacc gtggacaaga gcaggtggca gcaggggaac     900
gtcttctcat gctccgtgat gcatgaggct ctgcacaacc actacacgca gaagagcctc     960
tccctgtctc cgggtaaa                                                   978
```

<210> SEQ ID NO 309
<211> LENGTH: 326
<212> TYPE: PRT
<213> ORGANISM: Homo sapiens

<400> SEQUENCE: 309

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

```
Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
        180                 185                 190

Leu Asn Gly Lys Glu Tyr Lys Cys Lys Val Ser Asn Lys Gly Leu Pro
    195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 310
<211> LENGTH: 236
<212> TYPE: PRT
<213> ORGANISM: Homo sapiens

<400> SEQUENCE: 310

Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Glu Ser Gly Val
65                  70                  75                  80

Pro Ser Arg Phe Ser Gly Ser Gly Ser Gly Thr Glu Phe Thr Leu Thr
            85                  90                  95

Ile Ser Ser Val Gln Pro Glu Asp Phe Val Thr Tyr Tyr Cys Leu Gln
        100                 105                 110

His Asn Ser Asn Pro Leu Thr Phe Gly Gly Gly Thr Lys Val Glu Ile
    115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
        180                 185                 190
```

```
Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 311
<211> LENGTH: 473
<212> TYPE: PRT
<213> ORGANISM: Homo sapiens

<400> SEQUENCE: 311

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Met Trp Tyr Asp Gly Ser Asn Lys Asp Tyr Val
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Arg Leu Arg Ala Glu Asp Thr Ala Val
            100                 105                 110

Tyr Tyr Cys Ala Arg Glu Lys Asp His Tyr Asp Ile Leu Thr Gly Tyr
        115                 120                 125

Asn Tyr Tyr Gly Leu Asp Val Trp Gly Gln Gly Thr Thr Val Thr
    130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Asn Phe Gly
    210                 215                 220

Thr Gln Thr Tyr Thr Cys Asn Val Asp His Lys Pro Ser Asn Thr Lys
225                 230                 235                 240

Val Asp Lys Thr Val Glu Arg Lys Cys Cys Val Glu Cys Pro Pro Cys
                245                 250                 255

Pro Ala Pro Pro Val Ala Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Gln Phe Asn Trp Tyr
    290                 295                 300

Val Asp Gly Val Glu Val His Asn Ala Lys Thr Lys Pro Arg Glu Glu
305                 310                 315                 320

Gln Phe Asn Ser Thr Phe Arg Val Val Ser Val Leu Thr Val Val His
                325                 330                 335
```

Gln Asp Trp Leu Asn Gly Lys Glu Tyr Lys Cys Lys Val Ser Asn Lys
                340                 345                 350

Gly Leu Pro Ala Pro Ile Glu Lys Thr Ile Ser Lys Thr Lys Gly Gln
                355                 360                 365

Pro Arg Glu Pro Gln Val Tyr Thr Leu Pro Pro Ser Arg Glu Glu Met
                370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Met Leu Asp Ser Asp Gly Ser Phe Phe Leu
                420                 425                 430

Tyr Ser Lys Leu Thr Val Asp Lys Ser Arg Trp Gln Gln Gly Asn Val
                435                 440                 445

Phe Ser Cys Ser Val Met His Glu Ala Leu His Asn His Tyr Thr Gln
                450                 455                 460

Lys Ser Leu Ser Leu Ser Pro Gly Lys
465                 470

<210> SEQ ID NO 312
<211> LENGTH: 236
<212> TYPE: PRT
<213> ORGANISM: Homo sapiens

<400> SEQUENCE: 312

Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
                20                  25                  30

Leu Ser Ala Ser Val Gly Asp Arg Val Thr Ile Thr Cys Arg Ala Ser
                35                  40                  45

Gln Gly Ile Arg Asn Asp Leu Gly Trp Tyr Gln Lys Pro Gly Lys
50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Val Gln Pro Glu Asp Phe Val Thr Tyr Tyr Cys Leu Gln
                100                 105                 110

His Asn Ser Asn Pro Leu Thr Phe Gly Gly Gly Thr Lys Val Glu Ile
                115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
                210                 215                 220

Ser Pro Val Thr Lys Ser Phe Asn Arg Gly Glu Cys
225                 230                 235

<210> SEQ ID NO 313
<211> LENGTH: 54
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 313
aagctcgagg tcgactagac caccatggac atgagggtcc ccgctcagct cctg        54

<210> SEQ ID NO 314
<211> LENGTH: 10
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 314

Met Asp Met Arg Val Pro Ala Gln Leu Leu
1               5                   10

<210> SEQ ID NO 315
<211> LENGTH: 41
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 315
aaccgtttaa acgcggccgc tcaacactct cccctgttga a                     41

<210> SEQ ID NO 316
<211> LENGTH: 6
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 316

Phe Asn Arg Gly Glu Cys
1               5

<210> SEQ ID NO 317
<211> LENGTH: 51
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 317
aagctcgagg tcgactagac caccatggag tttgggctga gctgggtttt c          51

<210> SEQ ID NO 318
<211> LENGTH: 9
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 318

Met Glu Phe Gly Leu Ser Trp Val Phe
1               5

<210> SEQ ID NO 319
<211> LENGTH: 48
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 319
gaccacggtc accgtctcct cagcctccac caagggccca tcggtctt                48

<210> SEQ ID NO 320
<211> LENGTH: 48
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 320
aagaccgatg ggcccttggt ggaggctgag gagacggtga ccgtggtc                48

<210> SEQ ID NO 321
<211> LENGTH: 17
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 321

Gly Thr Thr Val Thr Val Ser Ser Ala Ser Thr Lys Gly Pro Ser Val
1               5                   10                  15

Phe

<210> SEQ ID NO 322
<211> LENGTH: 41
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 322
aaccgtttaa acgcggccgc tcatttaccc ggagacaggg a                       41

<210> SEQ ID NO 323
<211> LENGTH: 6
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 323

Ser Leu Ser Pro Gly Lys
1               5

<210> SEQ ID NO 324
<211> LENGTH: 15
<212> TYPE: DNA
<213> ORGANISM: Homo sapiens

<400> SEQUENCE: 324
ggctatacct tgaac                                                    15